US009549912B2

(12) United States Patent
Milner et al.

(10) Patent No.: US 9,549,912 B2
(45) Date of Patent: Jan. 24, 2017

(54) METHODS FOR TREATING ATRIAL FIBRILLATION

(71) Applicant: Armetheon, Inc., Menlo Park, CA (US)

(72) Inventors: Peter G. Milner, Los Altos Hills, CA (US); David J. Ellis, Los Altos, CA (US)

(73) Assignee: Armetheon, Inc., Milpitas, CA (US)

( * ) Notice: Subject to any disclaimer, the term of this patent is extended or adjusted under 35 U.S.C. 154(b) by 390 days.

(21) Appl. No.: 13/758,687

(22) Filed: Feb. 4, 2013

(65) Prior Publication Data
US 2013/0143861 A1 Jun. 6, 2013

Related U.S. Application Data

(63) Continuation-in-part of application No. 12/952,683, filed on Nov. 23, 2010, now abandoned, which is a continuation-in-part of application No. 12/952,666, filed on Nov. 23, 2010, now abandoned, which is a continuation-in-part of application No. 12/952,696, filed on Nov. 23, 2010, now abandoned.

(60) Provisional application No. 61/263,564, filed on Nov. 23, 2009, provisional application No. 61/263,465, filed on Nov. 23, 2009, provisional application No. 61/263,567, filed on Nov. 23, 2009.

(51) Int. Cl.
| | |
|---|---|
| *A61K 31/343* | (2006.01) |
| *A61K 45/06* | (2006.01) |
| *A61K 31/37* | (2006.01) |
| *A61K 31/397* | (2006.01) |
| *A61K 31/40* | (2006.01) |
| *A61K 31/439* | (2006.01) |
| *A61K 31/4402* | (2006.01) |
| *A61K 31/4418* | (2006.01) |
| *A61K 31/4439* | (2006.01) |
| *A61K 31/444* | (2006.01) |
| *A61K 31/445* | (2006.01) |
| *A61K 31/4545* | (2006.01) |
| *A61K 31/4709* | (2006.01) |
| *A61K 31/5377* | (2006.01) |
| *A61K 31/4184* | (2006.01) |

(52) U.S. Cl.
CPC ............ *A61K 31/343* (2013.01); *A61K 31/37* (2013.01); *A61K 31/397* (2013.01); *A61K 31/40* (2013.01); *A61K 31/4184* (2013.01); *A61K 31/439* (2013.01); *A61K 31/4402* (2013.01); *A61K 31/444* (2013.01); *A61K 31/445* (2013.01); *A61K 31/4418* (2013.01); *A61K 31/4439* (2013.01); *A61K 31/4545* (2013.01); *A61K 31/4709* (2013.01); *A61K 31/5377* (2013.01); *A61K 45/06* (2013.01)

(58) Field of Classification Search
CPC .. A61K 31/343; A61K 45/06; A61K 31/5377; A61K 31/4709; A61K 31/4545; A61K 31/445; A61K 31/444; A61K 31/4184; A61K 31/37; A61K 31/397; A61K 31/40; A61K 31/439; A61K 31/4402; A61K 31/4418; A61K 31/4439; A61K 2300/00
See application file for complete search history.

(56) References Cited

U.S. PATENT DOCUMENTS

| | | |
|---|---|---|
| 5,364,880 A | 11/1994 | Druzgala |
| 5,440,054 A | 8/1995 | Druzgala |
| 5,849,788 A | 12/1998 | Druzgala |
| 6,130,240 A | 10/2000 | Druzgala |
| 6,316,487 B1 | 11/2001 | Druzgala et al. |
| 6,362,223 B1 | 3/2002 | Druzgala et al. |
| 6,372,783 B1 | 4/2002 | Druzgala et al. |
| 6,683,195 B2 | 1/2004 | Druzgala et al. |
| 6,864,279 B2 | 3/2005 | Druzgala et al. |
| 7,145,020 B2 | 12/2006 | Druzgala et al. |
| 7,220,553 B2 | 5/2007 | Chu |
| 7,253,208 B2 | 8/2007 | Druzgala et al. |
| 7,285,671 B2 | 10/2007 | Druzgala et al. |

(Continued)

OTHER PUBLICATIONS

Chun et al (1995) "Long-term Efficacy of Amiodarone for the Maintenance of Normal Sinus Rhythm in Patients with Refractory Atrial Fibrillation or Flutter." Am J Cardiol, 76: 47-50.*
Rietbrock et al (2008) "Chronic atrial fibrillation: Incidence, prevalence, and prediction of stroke using the Congestive heart failure, Hypertension, Age >75, Diabetes mellitus, and prior Stroke or transient ischemic attack (CHADS2) risk stratification scheme." Am Heart J., 156:57-64.*
Zimetbaum (2007) "Amiodarone for Atrial Fibrillation." N Eng J Med., 356:935-41.*
Peck (May 18, 2009). "HRS: Investigational Drug Offers Gentler Afib Remedy." Retrieved on Jul. 28, 2015. Retrieved from the Internet <URL: http://www.medpagetoday.com/MeetingCoverage/HRS/14252>.*

(Continued)

*Primary Examiner* — Anoop Singh
*Assistant Examiner* — Doan Phan
(74) *Attorney, Agent, or Firm* — Cooley LLP

(57) ABSTRACT

The subject invention provides methods for reducing stroke rate, methods for preventing atrial remodeling, and methods for reversing atrial remodeling by administering budiodarone to reduce atrial fibrillation (AF) episode duration and an anticoagulant (AC). According to some methods of the invention, the average AF episode duration can be reduced to less than about 24, 5, 3 or 1 hour(s), and the maximum AF episode duration may be reduced to less than about 20, 10 or 5 hours. According to some methods of the invention, the reduced stroke rate upon administration of budiodarone and AC is less than the age-adjusted overall stroke rate. Further, some methods provide that patients who were refractory to one or more anti-arrhythmic drugs prior to administration of budiodarone may also be treated. Some methods provide for prevention of atrial remodeling and others provide for the reversal of atrial remodeling, including methods to quantify the reversal of atrial remodeling. In some methods of the invention, budiodarone is administered 400 mg BID or more preferably 600 mg BID.

43 Claims, 7 Drawing Sheets

(56) References Cited

U.S. PATENT DOCUMENTS

| | | | |
|---|---|---|---|
| 7,498,449 B2 | 3/2009 | Druzgala et al. |
| 7,666,902 B2 | 2/2010 | Druzgala et al. |
| 7,932,405 B2 | 4/2011 | Druzgala et al. |
| 2011/0136779 A1 | 6/2011 | Milner et al. |
| 2011/0144199 A1 | 6/2011 | Milner et al. |
| 2011/0269762 A1 | 11/2011 | Milner et al. |
| 2014/0309296 A1 | 10/2014 | Druzgala |

OTHER PUBLICATIONS

Lee et al (2000). "Intravenous Amiodarone for Prevention of Atrial Fibrillation After Coronary Artery Bypass Grafting." The Society of Thoracic Surgeons, 70: 157-61.*

Horowitz et al (1985). "Use of Amiodarone in the Treatment of Persistent and Paroxysmal Atrial Fibrillation Resistant to Quinidine Therapy." JACC, 6(6): 1402-1407.*

Roy et al (2000). "Amiodarone to prevent recurrence of atrial fibrillation." The New England Journal of Medicine, 342(13): 913-920.*

Turpie (Dec. 19, 2007). "New oral anticogulants in atrial fibrillation." European Heart Journal, pp. 1-11.*

Arya, A. et al., (2009). "A Preliminary Assessment of the Effects of ATI-2042 in Subjects with Paroxysmal Atrial Fibrillation Using Implanted Pacemaker Methodology," *Europace*, 11 (4):458-464.

Business Wire. "ARYx Therapeutics Inc. Updates Progress with Tecarfarin EmbraceAC Study", located at <http://www.businesswire.com/news/home/20090616005465/en/ARYx-Therapeutics-Updates-Progress-Tecarfarin-EmraceAC-Study>, last visited Dec. 27, 2012, 3 pages.

Capucci, A. et al., (2005). "Monitored Atrial Fibrillation Duration Predicts Arterial Embolic Events in Patients Suffering From Bradycardia and Atrial Fibrillation Implanted With Antitachycardia Pacemakers," *Journal of American College of Cardiology*, 46(10):1913-1920.

Carlsson, J. et al., (2003). "Randomized Trial of Rate-Control Versus Rhythm-Control in Persistent Atrial Fibrillation," Journal of American College of Cardiology, 41 (1 0):1690-1696.

Connolly, S.J. et al., (Sep. 17, 2009). "Dabigatran Versus Warfarin in Patients with Atrial Fibrillation," *The New England Journal of Medicine*, 361(12)1139-1151.

Connolly, S.J. et al., (Sep. 29, 2009). "Analysis of Stroke in ATHENA: A Placebo-Controlled, Double-Blind, Parallel-Arm Trial to 21 Assess the Efficacy of Dronedarone 400 mg BID for the Prevention of Cardiovascular Hospitalization or Death From Any Cause in Patients With Atrial Fibrillation/Atrial Flutter," *Circulation*, 120:1174-1180.

Currie, C.J. et al., (2006). "Evaluation of Survival and Ischaemic and Thromboembolic Event Rates in Patients with Non-Valvar Atrial Fibrillation in the General Population when Treated and Untreated with Warfarin," *Heart*, 92:196-200.

Echt, D.S. et al., (1991). "Mortality and Morbidity in Patients Receiving Encainide, Flecainide or Placebo: The Cardiac Arrhythmia Suppression Trial," *The New England Journal of Medicine*, 324(12):781-788.

Ezekowitz, M. et al., (2009). "PASCAL: A Randomized, Double-Blind, Placebo-Controlled Study of Budiodarone (ATI-2042) in Patients with Paroxysmal Atrial Fibrillation and Pacemakers with Atrial Fibrillation Data Logging Capabilities," Abstract and Presentation, 22 pages.

Ezekowitz, M. et al., (Jun. 2012, e-published Dec. 29, 2011). "A Randomized Trial of Budiodarone in Paroxysmal Atrial Fibrillation," *J Interv Card Electrophysiol* 34(1):1-9.

Glotzer, T.V. et al. (Apr. 1, 2003, e-published Mar. 24, 2003). "Atrial High Rate Episodes Detected by Pacemaker Diagnostics Predict Death and Stroke: Report of the Atrial Diagnostics Ancillary Study of the MOde Selection Trial (MOST)," *Circulation* 107(12):1614-1619.

Glotzer, T.V. et al. (Oct. 2009, e-published Aug. 4, 2009). "The Relationship Between Daily Atrial Tachyarrhythmia Burden from Implantable Device Diagnostics and Stroke Risk: the TRENDS Study," *Circ Arrhythm Electrophysiol* 2(5):474-480.

Hart, R.G. et al., (2007). "Meta-Analysis: Antithrombotic Therapy to Prevent Stroke in Patients Who Have Nonvalvular Atrial Fibrillation," *Ann. Intern. Med.*, 146:857-867.

Healey, J.S. et al. (Jan. 12, 2012). "Subclinical Atrial Fibrillation and the Risk of Stroke," *N Engl J Med* 366(2):120-129.

Hobbs, W.J.C. et al., (Mar. 14, 2000). "Reversal of Atrial Electrical Remodeling After Cardioversion of Persistent Atrial Fibrillation in Humans," *Circulation* 101:1145-1151.

Hohnloser, S.H. et al., (Nov. 25, 2000) "Rhythm or Rate Control in Atrial Fibrillation-Pharmacological Intervention in Atrial Fibrillation (PIAF): a Randomised Trial," *Lancet*, 356:1789-1794.

Hohnloser, S.H. et al., (2007). "Incidence of Stroke in Paroxysmal Versus Sustained Atrial Fibrillation in Patients Taking Oral Anticoagulation or Combined Antiplatelet Therapy," *Journal of the American College of Cardiology*, 50 (22):2156-2161.

Hohnloser, S.H. et al., (Feb. 12, 2009). "Effect of Dronedarone on Cardiovascular Events in Atrial Fibrillation," *The New England Journal of Medicine*, 360(7):668-678.

Hohnloser, S.H. et al., (Feb. 12, 2009). "Effect of Dronedarone on Cardiovascular Events in Atrial Fibrillation," *The New England Journal of Medicine*, 360(7):668-678. Erratum in: N. Engl. J. Med., 360(23):2487 (Jun. 4, 2009).

Jones, M. et al. (2005)"Evaluation of the Pattern of Treatment, Level of Anticoagulation Control, and Outcome of Treatment with 23 Warfarin in Patients with Non-Valvar Atrial Fibrillation: a Record Linkage Study in a Large British Population," *Heart*, 91:472-477.

Lip, G.Y.H. et al., (1995). "Increased Markers of Thrombogenesis in Chronic Atrial Fibrillation: Effects of Warfarin Treatment," *Br. Heart J.*, 73:527-533.

Lip, G.Y.H. et al., (Apr. 1996). "Fibrinogen and Fibrin D-Dimer Levels in Paroxysmal Atrial Fibrillation: Evidence for Intermediate Elevated Levels of Intravascular Thrombogenesis," *American Heart Journal*, 131(4):724-730.

Lloyd-Jones, D. et al., (Jan. 27, 2009). "Heart Disease and Stroke Statistics—2009 Ipdate," *Circulation*, 119(3):480-486.

Marin, F. et al., (Oct. 2004). "Plasma Von Willebrand Factor, Soluble Thrombomodulin, and Fibrin D-Dimer Concentrations in Acute Onset Non-Rheumatic Atrial Fibrillation," *Heart*, 90(10):1162-1166.

Milner, P.G. et al., (2012). "Mean Duration of AF Episodes in the PASCAL (Paroxysmal Atrial Fibrillation Study with Continuous Atrial Fibrillation Logging) Study are Reduced by Treatment with Higher Doses of Budiodarone," Abstract and Presentation, 16 pages.

Opolski, G. et al., (Aug. 2004). "Rate Control vs Rhythm Control in Patients With Nonvalvular Persistent Atrial Fibrillation," *Chest*, 126(2):476-486.

Page, R.L. et al., (Jan. 1994). "Asymptomatic Arrhythmias in Patients With Symptomatic Paroxysmal Atrial Fibrillation and paroxysmal Supraventricular Tachycardia," *Circulation*, 89(1):224-227.

Roy, D. et al., (Jun. 19, 2008). "Rhythm Control versus Rate Control for Atrial Fibrillation and Heart Failure," *The New England Journal of Medicine*, 358(25):2667-2677.

Savelieva, I. et al., (2000). "Clincial Relevance of Silent Atrial Fibrillation: Prevalence, Prognosis, Quality of Life, and Management," *Journal of Interventional Cardiac Electrophysiology*, 4:369-382.

Singh, B.N. et al., (Sep. 6, 2007). "Drondarone for Maintenance of Sinus Rhythm in Atrial Fibrillation or Flutter," *The New England Journal of Medicine*, 357(10):987-999.

Tayal, A.H. et al., (2008). "Atrial Fibrillation Detected by Mobile Cardiac Outpatient Telemetry in Cryptogenic TIA or Stroke," *Neurology*, 71:1696-1701.

Van Gelder, I. C. et al., (Dec. 5, 2002). "A Comparison of Rate Control and Rhythm Control in Patients with Recurrent Persistent Atrial Fibrillation," *The New England Journal of Medicine*, 347(23):1834-1840.

Wolf, P.A. et al., (Sep. 1987). "Atrial Fibrillation: A Major Contributor to Stroke in the Elderly," *Arch Intern Med.*, 147:1561-1564.

(56) References Cited

OTHER PUBLICATIONS

Wolf, P. A. et al., (Aug. 1991). "Atrial Fibrillation as an Independent Risk Factor for Stroke: The Framingham Study," *Stroke*, 22 (8):983-988.

Wyse. D.G. et al., (Dec. 2002). "A Comparison of Rate Control and Rhythm Control in Patients with Atrial Fibrillation," *The New England Journal of Medicine*, 347(23):1825-1833.

Di Diego, J.M. et al. (Dec. 2011, e-published Jul. 6, 2011). "Ischemic Ventricular Arrhythmias: Experimental Models and Their Clinical Relevance," *Heart Rhythm* 8(12):1963-1968.

Elizari, M.V. et al. (Feb. 2000). "Morbidity and Mortality Following Early Administration of Amiodarone in Acute Myocardial Infarction," *European Heart Journal* 21(3):198-205.

Hu, K. et al. (Dec. 2004). "Effects of High- and Low-Dose Amiodarone on Mortality, Left Ventricular Remodeling, and Hemodynamics in Rats with Experimental Myocardial Infarction," *J. Cardiovasc. Pharmacol.* 44(6):627-630.

Kodama, I. et al. (Jul. 1997). "Cellular Electropharmacology of Amiodarone," *Cardiovascular Research* 35(1):13-29.

Vassallo, P. et al. (Sep. 19, 2007). "Prescribing Amiodarone: An Evidence-Based Review of Clinical Indications," *JAMA* 298(11):1312-1322.

Altman, R. (2011). "Battle of Oral Anticoagulants in the Field of Atrial Fibrillation Scrutinized from a Clinical Practice (the Real World) Perspective," *Thrombosis Journal* 9(12)1-8.

Choppin, A. (2009, e-published Oct. 20, 2009). "Effect of Tecarfarin, a Novel Vitamin K Epoxide Reductase Inhibitor, on Coagulation in Beagle Dogs," *British Journal of Pharmacology* 158:1536-1547.

Ellis, D.J. (Sep. 22, 2009). The First Evaluation of a Novel Vitamin K Antagonist, Tecarfin (ATI-5923), in Patients With Atrial Fibrillation, *Circulation* 120:1029-1035.

Ezekowitz, M.D. et al. (Oct. 2010). "The Evolving Field of Stroke Prevention in Patients With Atrial Fibrillation," *Stroke* 41(Supp. 1):S17-S20.

Freedman, J.E (Sep. 22, 2009, e-published Sep. 8, 2009). "New Therapies for Stroke Prevention in Atrial Fibrillation: The Long Road to Enhanced Efficacy," *Circulation* 120:1024-1026.

Amr, Y.M. et al. (Jul.-Dec. 2010) "Intraoperative Loading Dose of Amiodarone for Prophylaxis Against Atrial Fibrillation After Valvular Heart Surgery" *Anesth Essays Res* 4:96-101.

Chen, W.C. et al. (May 2015) "Amiodarone Use is Associated with Increased Risk of Stroke in Patients with Nonvalvular Atrial Fibrillation," *Medicine* 94(19):e849 pp. 1-6.

\* cited by examiner

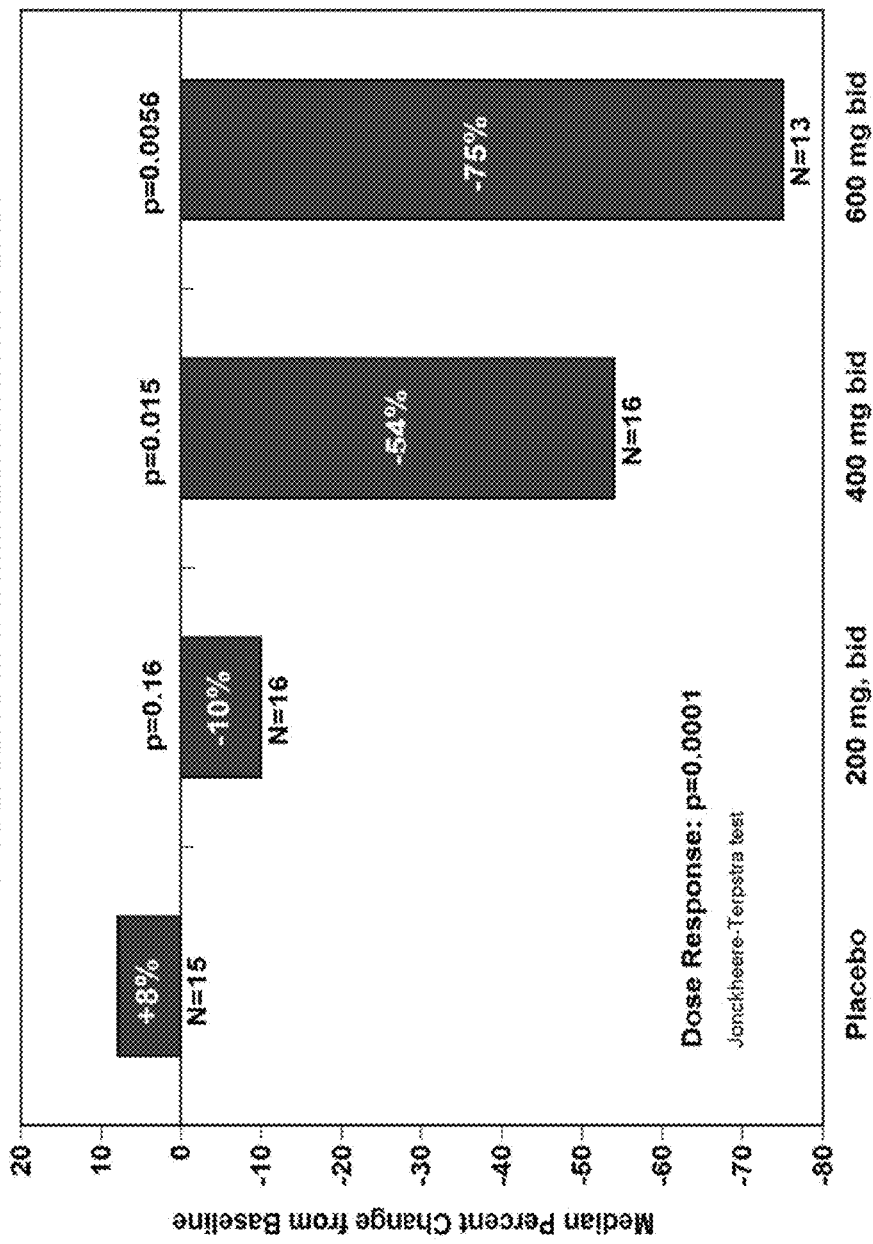
FIGURE 1: Dose Dependent Decrease in AFIB Burden

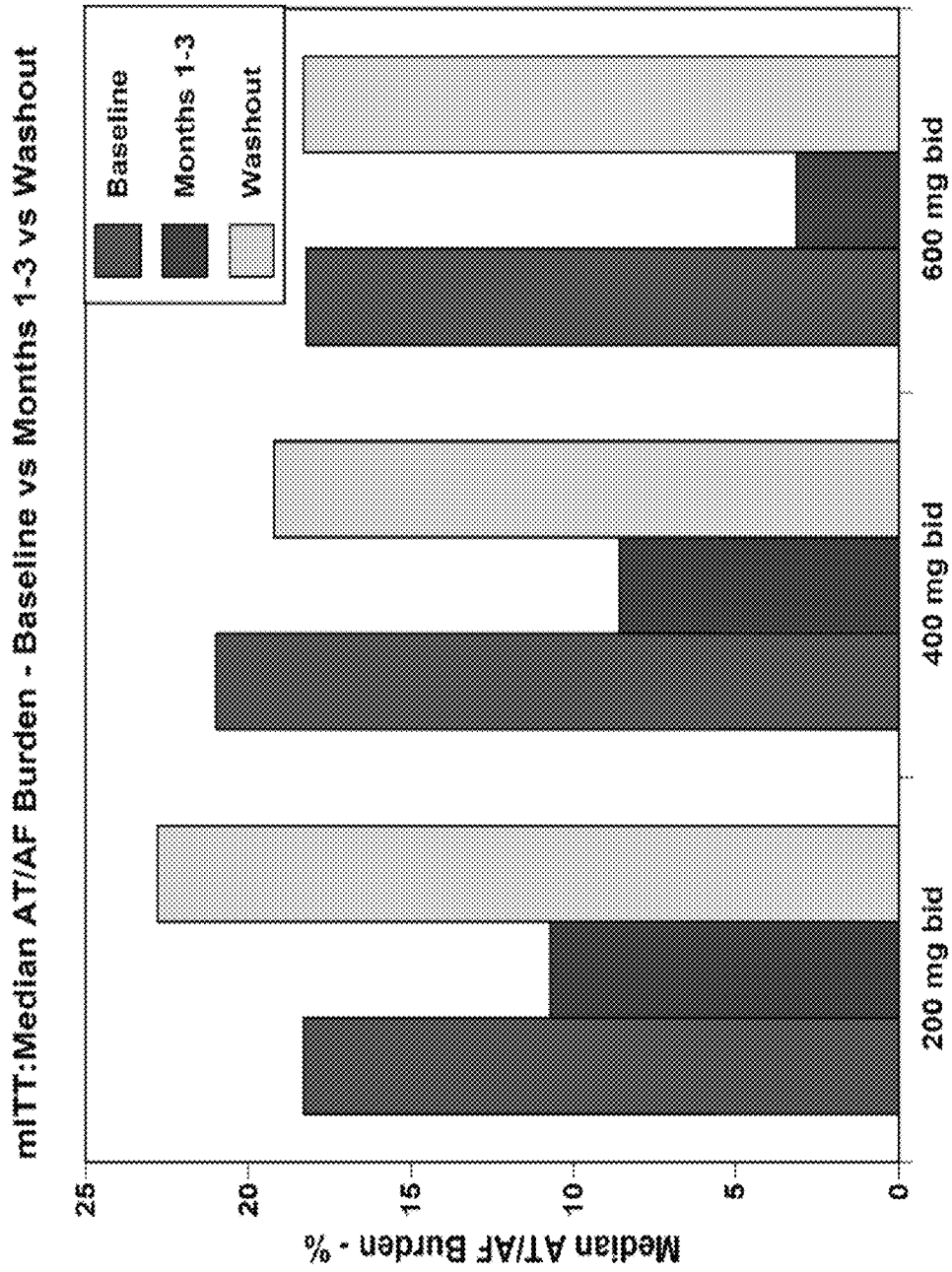
FIGURE 2: Burden Returns to Baseline After Treatment Period

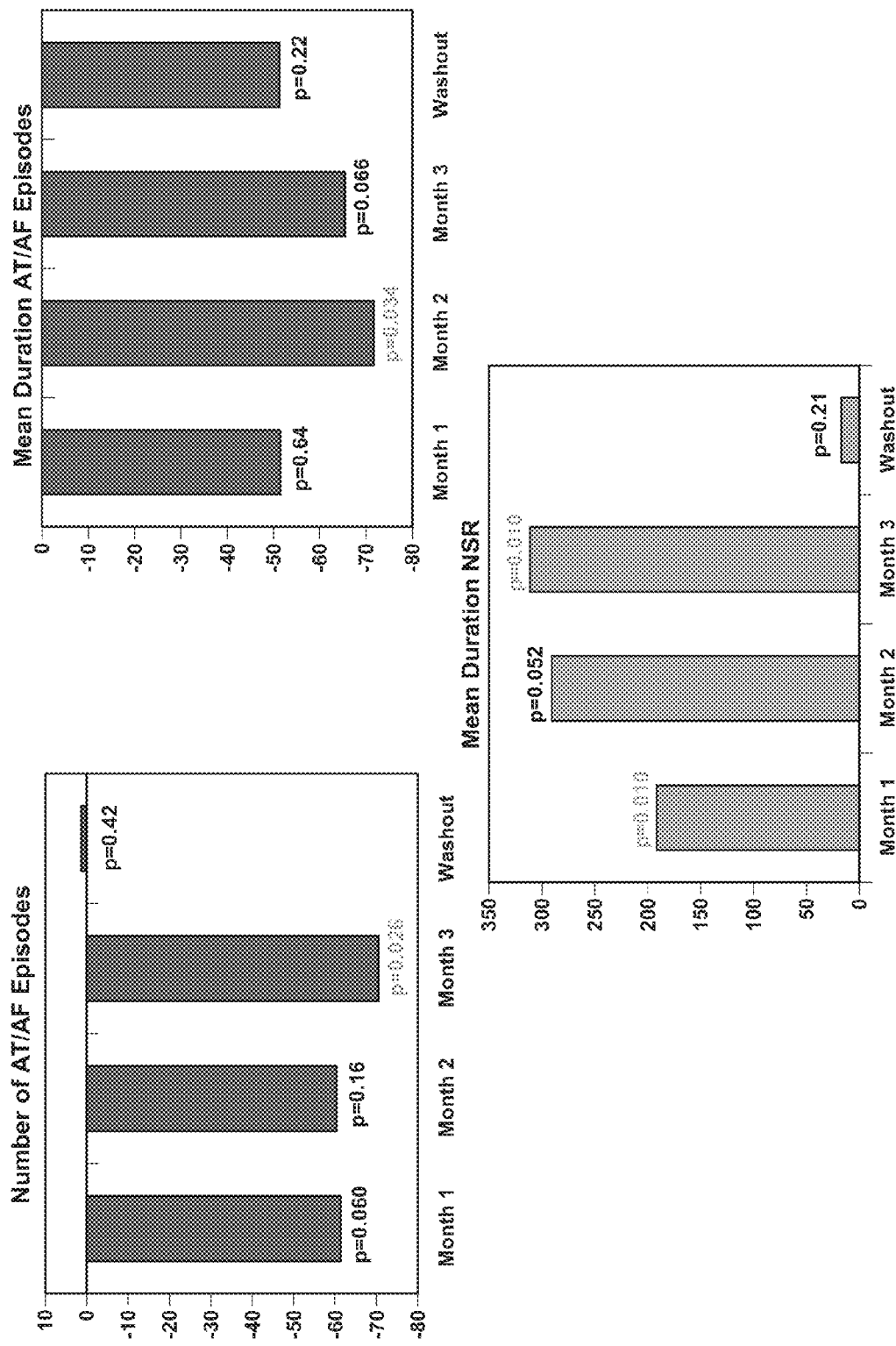
FIGURE 3: Median Percent Change from Baseline

FIGURE 4: Duration (hours) of AF Episodes

| | Duration of AF episodes in hours | Duration of AF episodes in hours | Duration of AF episodes in hours | Duration of AF episodes in hours | Duration of AF episodes in hours |
|---|---|---|---|---|---|
| | Baseline | Month 1 | Month 2 | Month 3 | Washout |
| Placebo | | | | | |
| N | 13 | 13 | 11 | 11 | 11 |
| Mean (SD) | 8.5 (19.9) | 17.2 (56.8) | 63.4 (202.8) | 15.2 (39.7) | 13.1 (33.0) |
| Median | 3.1 | 1.0 | 2.3 | 2.3 | 2.2 |
| Max | 74.2 | 206.3 | 674.9 | 133.9 | 112.0 |
| 600 mg bid | | | | | |
| N | 10 | 10 | 9 | 8 | 8 |
| Mean (SD) | 23.4 (69.6) | 1.4 (2.5) | 0.4 (0.7) | 0.7 (1.1) | 1.0 (1.6) |
| Median | 1.1 | 0.1 | 0.1 | 0.0 | 0.3 |
| Max | 221.4 | 7.1 | 2.2 | 3.1 | 4.9 |
| 400 mg bid | | | | | |
| N | 15 | 14 | 15 | 15 | 12 |
| Mean (SD) | 2.3 (2.0) | 1.2 (2.4) | 2.1 (3.7) | 1.3 (1.8) | 4.2 (6.6) |
| Median | 1.8 | 0.5 | 0.4 | 0.3 | 1.2 |
| Max | 6.0 | 9.3 | 13.5 | 4.9 | 23.2 |
| 200 mg bid | | | | | |
| N | 11 | 12 | 11 | 11 | 10 |
| Mean (SD) | 2.4 (2.0) | 4.1 (3.6) | 3.3 (4.4) | 2.5 (2.5) | 5.7 (6.8) |
| Median | 2.1 | 3.7 | 1.4 | 1.4 | 2.4 |
| Max | 5.9 | 11.5 | 15.2 | 7.9 | 20.5 |

FIGURE 5: Median Duration (hours) of AF Episodes

|            | Baseline | Month 1 | Month 2 | Month 3 | Washout |
|------------|----------|---------|---------|---------|---------|
| Placebo    | 3.1      | 1.0     | 2.3     | 2.3     | 2.2     |
| 200 mg bid | 2.1      | 3.7     | 1.4     | 1.4     | 2.4     |
| 400 mg bid | 1.8      | 0.5     | 0.4     | 0.3     | 1.2     |
| 600 mg bid | 1.1      | 0.1     | 0.1     | 0.0     | 0.3     |
| P-Value[1] | 0.68     | 0.05    | 0.01    | 0.017   | 0.20    |

FIGURE 6: Cumulative Time of All AF Episodes Lasting > 24 hours

| Treatment Group | Screening & Baseline – hrs | 1 – 3 Months hrs | Washout – hrs |
|---|---|---|---|
| Placebo | 333 | 2009 | 60 |
| 200 mg bid | 734 | 120 | 477 |
| 400 mg bid | 305 | 24 | 0 |
| 600 mg bid | 609 | 0 | 0 |

FIGURE 7: Results from Phase 2a Pilot Study

(CLN-208)

Table 2 Mean (SD) absolute atrial fibrillation burden, relative reductions (RR), and changes in episode number and episode duration per study period

| N | p1 | p2 | p3 | p4 | p5 | p6 |
|---|---|---|---|---|---|---|
|  | 6 | 6 | 6 | 5 | 5 | 6 |
| Dose (bid) of ATI-2042 | Baseline | 200 mg | 400 mg | 600 mg | 800 mg | Washout |
| AFB (%) | 20.4 ± 14.6 | 5.2 ± 4.2* | 5.2 ± 5.2* | 2.8 ± 3.4* | 1.5 ± 0.5* | 11.7 ± 14.0 |
| P-value vs. p1 | --- | 0.0045 | 0.0047 | 0.0023 | 0.0013 | 0.1880 |
| RR-AFB (%) | --- | 71.2 ± 31.3 | 71.7 ± 20.6 | 79.9 ± 26.4 | 86.8 ± 9.8 | 27.4 ± 78.3 |
| Episodes (no.) | 19.3 ± 22.1 | 31.4 ± 38.0 | 31.9 ± 42.3 | 41.6 ± 66.2 | 22.1 ± 27.8 | 30.9 ± 46.3 |
| Episode duration (hrs) | 4.8 ± 5.2 | 1.7 ± 2.5* | 0.6 ± 0.7* | 0.1 ± 0.2* | 0.5 ± 0.7* | 2.4 ± 3.0 |
| Trough PK level (ng/mL) | 0.0 ± 0.0 | 2.4 ± 0.9 | 5.2 ± 1.7 | 13.1 ± 5.6 | 19.8 ± 17.9 | 0.3 ± 0.4 | p1 is baseline, p2 200 mg bid, p3 400 mg bid, p4 600 mg bid, p5 800 mg bid, and p6 is the washout period. *p < 0.05 when compared with p1

METHODS FOR TREATING ATRIAL FIBRILLATION

CROSS-REFERENCE TO RELATED APPLICATIONS

This application is a continuation-in-part of U.S. patent application Ser. No. 12/952,683, filed Nov. 23, 2010, which claims priority to U.S. Provisional Application No. 61/263,564, filed Nov. 23, 2009; this application is also a continuation-in-part of U.S. patent application Ser. No. 12/952,666, filed Nov. 23, 2010, which claims priority to U.S. Provisional Application No. 61/263,465, filed Nov. 23, 2009; and this application is also a continuation-in-part of U.S. patent application Ser. No. 12/952,696, filed Nov. 23, 2010, which claims priority to U.S. Provisional Application No. 61/263,567, filed Nov. 23, 2009; the contents of each of which are incorporated herein by reference in their entirety.

BACKGROUND

Atrial fibrillation (AF) is a common cardiac disorder characterized transient to permanent replacement of the normal, coordinated electrical impulses generated by the sinoatrial (SA) node by disorganized electrical impulses originating in the atria and pulmonary veins. An irregular heartbeat results.

AF is classified into three classes after the first detected AF event, each with a greater proportion of time spent in AF. Paroxysmal atrial fibrillation (PAF) patients have multiple self-terminating episodes of arrhythmia that can span from >30 seconds to days, but they must self-terminate in less than seven days. PAF is typically responsive to chemical or electrical cardioversion, or the reestablishment of sinus rhythm. Persistent AF is characterized by episodes that can last more than 7 days, but are generally still responsive to cardioversion. Permanent AF is characterized by continuous AF that is unresponsive to efforts to reestablish sinus rhythm. The natural tendency of AF is to become a chronic condition, advancing from PAF to persistent and eventually to permanent AF.

The process whereby AF advances from first event to PAF to persistent and finally permanent AF is called atrial remodeling. Remodeling is broadly comprised of electrical remodeling and structural remodeling though thrombotic remodeling is often considered a separate part of the progression and dependent upon electrical remodeling. Electrical remodeling refers to the changes primarily affecting the excitability and electrical activity of the atrial myocytes. Such remodeling is fairly rapid, happening on the hours to days timescale. Structural remodeling refers to the changes in myocyte number, chamber size, interstitial collagen deposition, and fibroblast proliferation, which is a slower process that occurs on the months to years timescale. All types of remodeling have adverse medical consequences such as an increased risk of clot formation and stroke. Remodeling can lead to loss of the primary mechanical function of the atrium, the properly coordinated diastolic filling of the left and right ventricles, which in turn can lead to congestive heart failure.

Thrombotic remodeling refers to increase in thrombogenicity of the atria in AF patients. AF is associated with the upregulation of thrombogenic factors, for example fibrinogen, fibrin D-dimer, and von Willebrand factor, that, when combined with decreased blood flow and left atrial stasis in AF, promotes thrombogenesis (Marin, F, et al., Heart. 2004 October; 90(10):1162-6; Lip G Y, et al., Br Heart J. 1995 June; 73(6):527-33). Patients with first onset AF, PAF, as well as persistent and permanent AF exhibit such upregulation (Marin, F, et al., supra; Lip, G Y, et al., Am Heart J. 1996 April; 131(4):724-30). The presence of such upregulation for first onset AF suggests that thrombogenic remodeling takes place in the hours timescale, similar to electrical remodeling. It is thought that these are important early biomarkers of increased risk of clot formation and stroke. It has only recently been recognized, counter to prior conventional wisdom, that PAF or new onset AF carries a significant stroke risk.

Remodeling, particularly electrical remodeling, appears to be reversible, and the greater the time a patient spends in normal sinus rhythm after some atrial remodeling has occurred, the greater the reversal of remodeling, and the lower the probability of AF recurrence (Hobbs et al., Circulation Hobbs et al. 101(10): 1145. (2000)). Several parameters can be measured to determine the level of remodeling or reversal of remodeling, including atrial fibrillation cycle length (AFCL). AFCL decreases as a patient spends more time in AF and, conversely, AFCL increases with increased time spent in normal sinus rhythm. Longer AFCLs reflect greater atrial refractoriness and, in general, resistance to AF. It is accepted in clinical practice that "AF begets AF". This may be because increased time in AF is associated with decreased AFCL making it more difficult over time for the AF to either terminate spontaneously, or be to cardioverted back to normal sinus rhythm by direct current or drugs. Hobbs et al., (supra) found that AFCL at the right atrial appendage increased an average of 6 milliseconds when a patient was cardioverted from AF and spent time in NSR, which was a statistically significant change in AFCL (and atrial refractoriness) that represented greater resistance to AF. At the distal coronary sinus, a statistically significant increase in AFCL of 6 milliseconds was observed after the first cardioversion and time spent in NSR. Thus, measurement of a patient's AFCL before treatment and over time can reflect the extent of reversal of electrical remodeling. Similarly, other measures of refractoriness, such as the shortest coupling interval of atrial premature beats and directly measured refractory periods after cardioversion, can indicate the extent of electrical remodeling and remodeling reversal.

While there are many factors that influence stroke risk, such as age, heredity, race, sex, prior stroke, hypertension, cardiac failure, diabetes, and others, a significant risk factor for stroke is AF. The characteristic lack of coordinated atrial contraction can result in clot formation in the atrium, and particularly the left atrial appendage (assisted by the localized prothrombotic state due to thrombotic remodeling). The increased stasis of blood in the atrium due to loss of mechanical function (i.e. contraction), combined with poorly understood changes in the thrombogenicity of the atrial endocardial surface in AF is thought to be the primary basis for clot formation in the left atrium and left atrial appendage in AF. There is good precedent for this. For example the combination of stasis and increased thromogenicity of the underlying surface when they occur in the veins of the calf are well accepted to be the eitiology of clot formation in the legs known as deep venous thrombosis (DVT).

If the blood clot leaves the atria and becomes lodged in an artery in the brain, a stroke results. This is known as an embolic or more precisely as a thromboembolic cerebrovascular accident (CVA). If the clot travels to the periphery, other damage can occur, such as bowel ischemia. This event is known as systemic thromboembolic event. Approximately 15% of strokes occur in people with AF, a number that is likely artificially low due to cryptogenic stroke, or stroke whose cause is indeterminate, actually being caused by formerly undiagnosed or unrecognized AF. Approximately one third of strokes are classified as cryptogenic, of which nearly one quarter were associated with undiagnosed AF (Tayal, et al., Neurology. 2008 Nov. 18; 71(21):1696-701). Diagnosed AF is associated with a four- to five-fold increase in stroke risk (Wolf P A, Abbott R D, Kannel W B, Arch Intern Med. 1987 September; 147(9):1561-4; Stroke. 1991 August; 22(8):983-8).

Regarding the relative risk of the subtypes of AF, the benchmark study is known as ACTIVE W (Hohnloser S H, et al., J Am Coll Cardiol. 2007 Nov. 27; 50(22):2156-61). ACTIVE W investigated the incidence of stroke in 1202 paroxysmal AF patients versus a combined group of 5495 patients with either persistent or permanent (i.e., "sustained") AF. The investigators found that patients with paroxysmal AF have a similar risk of stroke as those with sustained AF, and that despite the statistically significantly lower $CHADS_2$ score in the paroxysmal AF population ($CHADS_2$ of 1.79 versus 2.04, p<0.00001). $CHADS_2$ is a clinical prediction rule for estimating the risk of stroke in AF patients comprising Cardiac failure, Hypertension, Age, Diabetes, and Stroke or transient ischemic event (TIA) [doubled], wherein the higher a patient's score, the greater their risk of stroke. In an observational study, Capucci et al (J Am Coll Cardiol. 2005 Nov. 15; 46(10):1913-20) reported in PAF an increased risk of stroke for patients with episodes longer than 24 hours and suggested that such information be used to guide anticoagulation regimen. The reference fails to offer any teaching or suggestion that a drug could or should intervene and modulate AF episode duration thereby offering therapeutic intervention for stroke as with the instant invention. Again, Capucci's teaching relates to guiding anticoagulation therapy in AF not antiarrhythmic therapy. In fact the conventional accepted medical belief, as a result of multiple antiarrhythmic drug studies over many years that failed to shown any reduction in stroke rate with antiarrhythmic drug therapy, has been that, an antiarrhythmic drug would have no benefit or role in reducing stroke risk in AF.

Atrial fibrillation can be symptomatic or asymptomatic. Symptomatic AF can be characterized by, for example, palpitations, dyspnea, chest discomfort, fatigue, dizziness, syncope, exercise intolerance, and transient ischemic attack (TIA), and is often found upon examination for such symptoms. Asymptomatic AF, due to its lack of symptoms, is generally found by happenstance, such as during a routine examination or preoperative assessment. Page et al. (Circulation. 1994 January; 89(1):224-7), found that asymptomatic AF is more than 12-fold more prevalent than symptomatic AF, which is particularly significant given that asymptomatic AF is thought to confer no less risk than symptomatic AF with regard AF-related complications (Savelieva, I. Camm, I. John, J Intery Card Electrophysiol. 2000 June; 4(2):369-82). From the results of Tayal et al on the etiology of cryptogenic stroke described above (Tayal, et al., Neurology. 2008 Nov. 18; 71(21):1696-701) it is clear that asymptomatic PAF or undiagnosed PAF can prose a major threat of stroke in often otherwise seemingly health people.

Two primary chemotherapeutic paradigms are utilized to treat AF, one to address the AF itself, and the other addresses stroke. Chemotherapeutic treatment of AF includes heart rate control drugs (such as digoxin), beta-blockers, and calcium channel blockers (such as verapamil and diltiazem), which seek to reduce the heart rate to one that is closer to normal to reduce symptoms, and rhythm control drugs (such as amiodarone, dronedarone, budiodarone, vernakalant, celivarone and AZD-1305), which seek to restore and maintain the regular heart rhythm. It has been widely accepted for many years that these treatment strategies offer no protection from stroke in AF, and that the only effective stroke prevention treatment for patients with AF is to administer an effective dose of an (oral) anticoagulant (blood thinner) on a chronic basis as described later.

Regarding the relative effectiveness of rhythm control and rate control drugs on AF, the benchmark study is known as AFFIRM (Wyse D G, et al., N Engl J. Med. 2002 Dec. 5; 347(23):1825-33). AFFIRM compared rhythm control and rate control in 4060 AF patients with an endpoint of overall mortality. The study demonstrated that management of AF with rhythm control offers no survival advantage over rate control, and that rate control potentially offers advantages, such as a lower risk of adverse events. Regarding stroke, the AFFIRM study showed similar numbers (rate control: 77 events among 2027 patients; rhythm control: 80 events among 2033 patients), indicating, like ACTIVE W, that more time spent in AF does not correlate with a greater risk of stroke and that antiarrhythmic drug therapy failes to prevent strokes in AF. Additional studies came to the same conclusion, such as PIAF (Hohnloser S H, et al. Lancet 2000; 356:1789-94), STAF (Carlsson J, et al. J Am Coll Cardiol 2003; 41:1690-6), RACE (Van Gelder I C, et al., N Engl J Med 2002; 347:1834-40), HOT CAFÉ (Opolski G., et al, Chest 2004; 126: 476-86) and AF-CHF (Roy D, et al., N Engl J Med 2008; 358:2667-77).

A standard study design for new anti-arrhythmic drugs involves TTFR, or time to first recurrence of AF. Two examples of such a study are EURIDIS and ADONIS for dronedarone (Singh B N, et al., N Engl J. Med. 2007 Sep. 6; 357(10):987-99). In EURIDIS and ADONIS, 1237 (combined) AF patients were given placebo (409) or dronedarone (828), and followed for a year. Follow-up consisted of two 12-lead electrocardiograms, 10 minutes apart on days 2, 3, and 5, as well as at months 3, 5, 7, and 10 post-randomization, or whenever they had symptomatic AF. The primary end point was the time from randomization to the first documented recurrence of AF, defined as an episode lasting for at least 10 minutes and confirmed by two consecutive recordings taken 10 minutes apart. EURIDIS and ADONIS demonstrated a significant increase in TTFR compared to placebo.

Nevertheless, EURIDIS and ADONIS, as well as other TTFR trials, have weaknesses. Increased TTFR assumes less overall AF, but detection still occurs by chance, i.e., on preplanned days 2, 3, and 5, after months 3, 5, 7, and 10, or when AF is symptomatic (the only non-chance identification of AF). However, asymptomatic AF accounts for at least 12× more AF than symptomatic AF, and stroke risk of both is thought to be the same. Thus, TTFR trials like EURIDIS and ADONIS may quantify an increase in TTFR, but they significantly under represent the amount of time a patient spends in AF. That is, they fail, except by chance, to identify and account for the significant amount of asymptomatic AF, and they fail to characterize AF and how AF might change under influence of study drug or comparator. As a consequence, one of ordinary skill in the art has no guidance regarding the present invention.

A recent outcome study, ATHENA, followed the EURIDIS and ADONIS TTFR studies on dronedarone (Hohnloser S H, et al., N Engl J. Med. 2009 Feb. 12; 360(7):668-78. Erratum in: N Engl J. Med. 2009 Jun. 4; 360(23):2487; Connolly S J, et al., Circulation. 2009 Sep. 29; 120(13):1174-80). In ATHENA, of 4628 total patients, 2327 were given placebo and 2301 were given dronedarone, and the primary study outcome was time to first hospitalization due to cardiovascular events or death from any cause. Contrary to the vast body of clinical studies and literature, treatment with an anti-arrhythmic was correlated with a reduction in stroke. However, confounding that observation was the inexplicable finding in ATHENA that patients with only AF or atrial flutter on all ECGs through out the 2 years of the study (i.e., those who had degraded into permanent AF, which is unresponsive to anti-arrhythmics), experienced 2 strokes versus 8 for the placebo, suggesting a possible undetermined imbalance between the treatment groups. Moreover, the study authors describe how study drug reduced blood pressure and that reductions in blood pressure are correlated with decreased stroke. It is well known that blood pressure reduction reduces stroke risk due to non-embolic cerebrovascular accidents. The failure to properly ajudicate the cause of these strokes in AF in the ATHENA study fails to teach or suggest whether the cause of the reduction in strokes was due to preventing embolic strokes from the left atrium, hypertensive strokes, strokes due to in situ thrombosis in the cerebral arteries, some other cause, or a combination of some or all of the above. The study authors also describe that study drug reduced heart rate and that such an effect could directly reduce stroke risk by preventing hypotension. To the extent that the study authors say that a reduction in overall AF could have influenced stroke risk, they provide no teaching or suggestion regarding how reduced AF may exert this effect (which is contrary to the vast body of knowledge in the art that anti-arrhythmics have no effect on stroke, e.g., AFFIRM), or how their drug may specifically affect AF. They even summarize their study by stating "the results of the present study should not be interpreted to indicate that dronedarone might be a replacement for AC therapy or a treatment for stroke prevention." (supra). Thus, ATHENA provides no teaching or suggestion regarding how an anti-arrhythmic could affect stroke risk, beyond blood pressure and heart rate, and in particular no teaching or suggestion of the present invention.

The other primary AF treatment paradigm is anticoagulation as a means to reduce stroke risk. Anticoagulation is the only proven and currently accepted drug therapy known to reduce stoke risk in AF. In patients with AF, warfarin prevents 64% of strokes (Hart R G, Pearce L A, Aguilar M I. Ann Intern Med. 2007 Jun. 19; 146(12):857-67). Warfarin, despite being effective, is inconvenient to use and is susceptible to a significant number of drug-drug interactions, which complicate its use. As a consequence, other anticoagulants are being developed that are vitamin-K epoxide reductase inhibitors (for example, tecarfarin), direct thrombin inhibitors (for example, AZD-0837; dabigatran etexilate, dabigatran, ximelagatran; melagatran, and argatroban), or Factor Xa inhibitors (for example, apixaban, rivaroxaban, YM466, betrixaban, and edoxaban).

In a phase 2 clinical trial, tecarfarin (ATI-5923) demonstrated an statistically significant increase in time in therapeutic range (TTR), defined as an International Normalized Ratio (INR) of between 2.0 and 3.0, as compared to warfarin (p=0.0009). TTR was 71.5% versus 59.3% for the same exact patient population when they were previously on warfarin. The proportion of time spent in more thrombogenic INR ranges were also reduced compared to warfarin. On warfarin, patients had INR ratios between 1.5 and 1.9 22.4% of the time versus 14.2% for tecarfarin. On warfarin, patients had INR ratios below 1.5 3.9% of the time versus 1.2% for tecarfarin. Similar results were seen for higher INR ratios, which are representative of higher risk of hemorrhage. Greater time in therapeutic range correlates with increased life expectancy, from approximately 50% life expectancy at 5 years for 32% TTR, to about 65% at 59% TTR, to about 75% at 72% TTR and about 85% at 84% TTR (Currie et al., Heart 2006(92)196-200). Regarding outcomes, a 10% decrease in TTR results in a 29% increase in mortality, a 10% increase in ischemic stroke risk and a 12% increase in all thromboembolic events (Jones et al., Heart 2005(91)472-477). Thus, tecarfarin should be an important AC for use in AF patients to reduce stroke.

The results of an outcome trial for a direct thrombin inhibitor (DTI), dabigatran etexilate, were recently published (Connolly S J, et al., N Engl J. Med. 2009 Sep. 17; 361(12):1139-51; Gage BF, N Engl J. Med. 2009 Sep. 17; 361(12):1139-51). The RE-LY trial followed over 18000 patients for an average of two years, with a primary outcome of systemic embolism or stroke. Dabigatran at 150 mg proved superior to warfarin with respect to stroke and noninferior with respect to major bleeding; whereas, dabigatran at 110 mg proved noninferior to warfarin with respect to stroke and superior with respect to major bleeding. Amiodarone was being used concomitantly in approximately 2000 of the 18000 enrolled patients, and those patients appeared to show a trend toward lower stroke risk in contrast to other trials, but the trend was not statistically significant. Moreover, dabigatran is a P-glycoprotein (P-gp) substrate, and amiodarone is a P-gp inhibitor, so the trend was attributed to a pharmacokinetic interaction between amiodarone and dabigatran through P-gp resulting in an increased serum concentration of dabigatran and hence greater efficacy in reducing stroke risk in AF. Further bolstering this explanation is the fact that quinidine, another anti-arrhythmic that was originally permitted in the study, was later removed because the combination of dabigatran and quinidine was unfavorable to patient health. Quinidine is a particularly potent P-gp inhibitor and because it is a more potent inhibitor of P-gp than amiodarone, it raised dabigatran blood levels to unacceptably high levels. Quinidine is now specifically contraindicated in dabigatran product literature.

Clarfication of the recommended and accepted current treatments for preventing stroke in AF can be found in practice guidelines. There are three professional bodies in the US that issue guidelines to physicians on how to reduce stroke risk in AF; the ACC (American College of Cardiology), the AHA (American Heart Association), and the ACCP (American College of Chest Physicians). All three concur that an anticoagulant can, and should be used to prevent stroke in AF especially in patients who have a $CHADS_2$ score of 1 or greater. As of the date of application none of the current guidelines from these three professional bodies recommend, or even suggest that, an antiarrhythmic drug can be used to reduce stroke risk in AF.

Given the above, the prior art fails to teach or suggest that budiodarone can serve as a therapeutic intervention for stroke by reducing AF episode duration. Likewise, there is no teaching or suggestion than AF episode duration can be lowered as substantially as described herein, or that budiodarone can prevent or reverse atrial remodeling through reduction in AF episode duration.

Given the above, the prior art fails to teach or suggest that the administration of an anti-arrhythmic and an anticoagulant can serve as a synergistic therapeutic intervention for stroke by reducing AF episode duration and inhibiting thrombogenesis. Likewise, there is no teaching or suggestion than AF episode duration can be lowered as substantially as described herein, or that the administration of an anti-arrhythmic and an anticoagulant can prevent or reverse atrial remodeling through reduction in AF episode duration.

Given the above, the prior art fails to teach or suggest that the administration of budiodarone and an anticoagulant can serve as a synergistic therapeutic intervention for stroke by reducing AF episode duration and inhibiting thrombogenesis. Likewise, there is no teaching or suggestion than AF episode duration can be lowered as substantially as described herein, or that the administration of budiodarone and an anticoagulant can prevent or reverse atrial remodeling through reduction in AF episode duration.

SUMMARY OF THE INVENTION

The present invention provides methods for reducing atrial fibrillation (AF) episode duration comprising administering an amount of budiodarone effective to reduce AF episode duration. Average AF episode duration can be reduced to less than about 24 hours, less than about 5 hours, less than about 3 hours and less than about 1 hour. The invention also provides methods for reducing maximum AF episode duration to less than about 20 hours, less than about 10 hours and less than about 5 hours.

The subject invention provides methods for reducing atrial fibrillation (AF) episode duration, methods for reducing stroke rate, methods for increasing time in normal sinus rhythm (NSR), methods for preventing atrial remodeling, and methods for reversing atrial remodeling, all comprising administering an amount of budiodarone effective to reduce AF episode duration.

The subject invention provides methods for reducing stroke rate, methods for preventing atrial remodeling, and methods for reversing atrial remodeling by administering a multiple ion channel blocker anti-arrhythmic to reduce atrial fibrillation (AF) episode duration and an anticoagulant (AC). According to some methods of the invention, the average AF episode duration can be reduced to less than about 24, 5, 3 or 1 hour(s), and the maximum AF episode duration may be reduced to less than about 20, 10 or 5 hours. According to some methods of the invention, the reduced stroke rate upon administration of multiple ion channel blocker and AC is less than the age-adjusted overall stroke rate. Further, some methods provide that patients who were refractory to one or more anti-arrhythmic drugs prior to administration of the multiple ion channel blocker may also be treated. Some methods provide for prevention of atrial remodeling and others provide for the reversal of atrial remodeling, including methods to quantify the reversal of atrial remodeling. In some methods of the invention, budiodarone is administered 400 mg BID or more preferably 600 mg BID.

The present invention provides methods for reducing stroke rate comprising administering an amount of multiple ion channel blocker selected from the group consisting of amiodarone, dronedarone, budiodarone, vernakalant, celivarone, and AZD1305 effective to reduce atrial fibrillation (AF) episode duration and an effective amount of anticoagulant (AC) selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin. According to the invention, the average AF episode duration can be reduced to less than about 24 hours, less than about 5 hours, less than about 3 hours, and less than about 1 hour. The methods of the invention also provide for the reduction of maximum AF episode duration to less than about 20 hours, less than about 10 hours and less than about 5 hours.

The present invention provides methods for reducing stroke rate comprising administering an amount of budiodarone effective to reduce atrial fibrillation (AF) episode duration and an effective amount of anticoagulant (AC) selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin. According to the invention, the average AF episode duration can be reduced to less than about 24 hours, less than about 5 hours, less than about 3 hours, and less than about 1 hour. The methods of the invention also provide for the reduction of maximum AF episode duration to less than about 20 hours, less than about 10 hours and less than about 5 hours.

The present invention also provides methods for reducing stroke rate comprising administering an amount of budiodarone effective to reduce AF episode duration. As above, average AF episode duration can be reduced to less than about 24, 5, 3, and 1 hours, as well as reducing maximum AF episode duration to less than about 20, 10 and 5 hours.

The invention also provides methods for increasing time in normal sinus rhythm (NSR) comprising administering an amount of budiodarone effective to reduce AF episode duration. Certain methods provide for the reduction of average and maximum AF episode duration according to the time spans recited above.

According to certain methods of the invention, the reduced stroke rate upon administration of multiple ion channel blocker and AC is less than the age-adjusted overall stroke rate. Certain other methods of the invention provide for the administration of multiple ion channel blocker and AC in patients who were refractory to one or more anti-arrhythmic drugs prior to administration of budiodarone.

According to certain methods of the invention, the reduced stroke rate upon administration of budiodarone and AC is less than the age-adjusted overall stroke rate. Certain other methods of the invention provide for the administration of budiodarone and AC in patients who were refractory to one or more anti-arrhythmic drugs prior to administration of budiodarone.

The invention also provides methods for preventing atrial remodeling comprising administering an amount of budiodarone effective to reduce AF episode duration. Again, certain methods of the invention provide for the reduction of average and maximum AF episode duration according to the time spans recited above.

The invention also provides methods for preventing atrial remodeling comprising administering an amount of multiple ion channel blocker effective to reduce atrial fibrillation (AF) episode duration and an effective amount of anticoagulant (AC) selected from the group listed above. Some methods provide for the reduction in average and maximum AF episode duration according to the times recited above. Certain methods also provide for the administration of multiple ion channel blocker and AC in patients who were refractory to one or more anti-arrhythmic drugs prior to administration of budiodarone.

The invention also provides methods for preventing atrial remodeling comprising administering an amount of budiodarone effective to reduce atrial fibrillation (AF) episode duration and an effective amount of anticoagulant (AC) selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin. Some methods provide for the reduction in average and maximum AF episode duration according to the times recited above. Certain methods also provide for the administration of budiodarone and AC in patients who were refractory to one or more anti-arrhythmic drugs prior to administration of budiodarone.

The invention further provides methods for reversing atrial remodeling comprising administering an amount of budiodarone effective to reduce AF episode duration. Some methods provide for reductions in average and maximum AF episode duration as recited above. Further some methods provide for quantifying the reversal of remodeling.

The present invention also provides methods for reversing atrial remodeling comprising administering an amount of multiple ion channel blocker effective to reduce atrial fibrillation (AF) episode duration and an effective amount of anticoagulant (AC) selected from the group listed above. Some methods also provide for the reduction in average and maximum AF episode duration according to the times recited above. Some methods also provide for the administration of multiple ion channel blocker and AC in patients who were refractory to one or more anti-arrhythmic drugs prior to administration of multiple ion channel blocker. Additional methods provide for quantifying the reversal of atrial remodeling.

The present invention also provides methods for reversing atrial remodeling comprising administering an amount of budiodarone effective to reduce atrial fibrillation (AF) episode duration and an effective amount of anticoagulant (AC) selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin. Some methods also provide for the reduction in average and maximum AF episode duration according to the times recited above. Some methods also provide for the administration of budiodarone and AC in patients who were refractory to one or more anti-arrhythmic drugs prior to administration of budiodarone. Additional methods provide for quantifying the reversal of atrial remodeling.

In each case above, the invention also provides methods wherein the patient was refractory to one or more anti-arrhythmic drugs prior to the administration of budiodarone. Further methods are provided wherein budiodarone is administered 400 mg or 600 mg BID.

In each case above, the invention also provides methods wherein budiodarone is administered 400 mg or 600 mg BID.

BRIEF DESCRIPTION OF THE DRAWINGS

FIG. 1 shows a dose-dependent decrease in atrial fibrillation burden (AFB) on budiodarone, with overall burden decreasing 54% on 400 mg and 75% on 600 mg. AFB is the duration of time a subject's cardiac rhythm was AF divided by the total time recorded for the study period, expressed as a percent.

FIG. 2 shows the reduction of AFB on budiodarone, as well as a return to pre-treatment burden state after washout.

FIG. 3 shows the median percent change from baseline for three parameters on 600 mg budiodarone. Top left graph: number of AT/AF episodes decrease by more than 60% in all three treatment months. Top right: duration of episodes decreases by more than 50% in treatment month 1, followed by a decrease of more than 70% in treatment month 2 and nearly 70% in treatment month 3.

FIG. 4 shows the duration of AF episodes at baseline, after treatment months 1, 2 and 3, and after washout for placebo and for 200, 400 and 600 mg of budiodarone.

FIG. 5 shows the median duration of AF episodes in hours for placebo and budiodarone at 200, 400 and 600 mg at baseline, after treatment months 1, 2 and 3, and after washout.

FIG. 6 shows the cumulative time of all episodes over 24 hours for placebo and budiodarone at 200, 400 and 600 mg, at baseline, after treatment months 1-3, and after washout.

FIG. 7 shows the results of a Phase 2 pilot study of budiodarone. Mean absolute AFB, relative reductions in burden and changes in episode number and duration are described. Significant reductions in AFB and episode duration were observed on drug.

DETAILED DESCRIPTION OF THE INVENTION

In one aspect, the invention provides methods for reducing atrial fibrillation (AF) episode duration comprising administering an amount of budiodarone effective to reduce AF episode duration.

In another aspect, the invention provides methods for reducing AF episode duration comprising administering an amount of budiodarone effective to reduce average AF episode duration to less than about 24 hours.

In another aspect, the invention provides methods for reducing AF episode duration comprising administering an amount of budiodarone effective to reduce average AF episode duration to less than about 5 hours.

In another aspect, the invention provides methods for reducing AF episode duration comprising administering an amount of budiodarone effective to reduce average AF episode duration to less than about 3 hours.

In another aspect, the invention provides methods for reducing AF episode duration comprising administering an amount of budiodarone effective to reduce average AF episode duration to less than about 1 hour.

In another aspect, the invention provides methods for reducing AF episode duration comprising administering an amount of budiodarone effective to reduce the maximum AF episode duration to less than about 20 hours.

In another aspect, the invention provides methods for reducing AF episode duration comprising administering an amount of budiodarone effective to reduce the maximum AF episode duration to less than about 10 hours.

In another aspect, the invention provides methods for reducing AF episode duration comprising administering an amount of budiodarone effective to reduce the maximum AF episode duration to less than about 5 hours.

In another aspect, the invention provides methods for reducing stroke rate comprising administering an amount of budiodarone effective to reduce AF episode duration.

In another aspect, the invention provides methods for reducing stroke rate comprising administering an amount of budiodarone effective to reduce AF average episode duration to less than about 24 hours.

In another aspect, the invention provides methods for reducing stroke rate comprising administering an amount of budiodarone effective to reduce AF average episode duration to less than about 5 hours.

In another aspect, the invention provides methods for reducing stroke rate comprising administering an amount of budiodarone effective to reduce AF average episode duration to less than 3 hours.

In another aspect, the invention provides methods for reducing stroke rate comprising administering an amount of budiodarone effective to reduce AF average episode duration to less than about 1 hour.

In another aspect, the invention provides methods for reducing stroke rate comprising administering an amount of budiodarone effective to reduce maximum AF episode duration to less than about 20 hours.

In another aspect, the invention provides methods for reducing stroke rate comprising administering an amount of budiodarone effective to reduce maximum AF episode duration to less than about 10 hours.

In another aspect, the invention provides methods for reducing stroke rate comprising administering an amount of budiodarone effective to reduce maximum AF episode duration to less than about 5 hours.

In yet another aspect, the invention provides methods for increasing time in normal sinus rhythm (NSR) comprising administering an amount of budiodarone effective to reduce AF episode duration.

In another aspect, the invention provides methods for increasing time in NSR comprising administering an amount of budiodarone effective to reduce average AF episode duration to less than about 24 hours.

In another aspect, the invention provides methods for increasing time in NSR comprising administering an amount of budiodarone effective to reduce average AF episode duration to less than about 5 hours.

In another aspect, the invention provides methods for increasing time in NSR comprising administering an amount of budiodarone effective to reduce average AF episode duration to less than 3 hours.

In another aspect, the invention provides methods for increasing time in NSR comprising administering an amount of budiodarone effective to reduce average AF episode duration to less than about 1 hour.

In another aspect, the invention provides methods for increasing time in NSR comprising administering an amount of budiodarone effective to reduce the maximum AF episode duration to less than about 20 hours.

In another aspect, the invention provides methods for increasing time in NSR comprising administering an amount of budiodarone effective to reduce the maximum AF episode duration to less than about 10 hours.

In another aspect, the invention provides methods for increasing time in NSR comprising administering an amount of budiodarone effective to reduce the maximum AF episode duration to less than about 5 hours.

In yet another aspect, the invention provides methods for preventing atrial remodeling comprising administering an amount of budiodarone effective to reduce AF episode duration.

In another aspect, the invention provides methods for preventing atrial remodeling comprising administering an amount of budiodarone effective to reduce average AF episode duration to less than about 24 hours.

In another aspect, the invention provides methods for preventing atrial remodeling comprising administering an amount of budiodarone effective to reduce average AF episode duration to less than about 5 hours.

In another aspect, the invention provides methods for preventing atrial remodeling comprising administering an amount of budiodarone effective to reduce average AF episode duration to less than 3 hours.

In another aspect, the invention provides methods for preventing atrial remodeling comprising administering an amount of budiodarone effective to reduce average AF episode duration to less than about 1 hour.

In another aspect, the invention provides methods for preventing atrial remodeling comprising administering an amount of budiodarone effective to reduce the maximum AF episode duration to less than about 20 hours.

In another aspect, the invention provides methods for preventing atrial remodeling comprising administering an amount of budiodarone effective to reduce the maximum AF episode duration to less than about 10 hours.

In another aspect, the invention provides methods for preventing atrial remodeling comprising administering an amount of budiodarone effective to reduce the maximum AF episode duration to less than about 5 hours.

In yet another aspect, the invention provides methods for reversing atrial remodeling comprising administering an amount of budiodarone effective to reduce AF episode duration.

In another aspect, the invention provides methods for reversing atrial remodeling comprising administering an amount of budiodarone effective to reduce average AF episode duration to less than about 24 hours.

In another aspect, the invention provides methods for reversing atrial remodeling comprising administering an amount of budiodarone effective to reduce average AF episode duration to less than about 5 hours.

In another aspect, the invention provides methods for reversing atrial remodeling comprising administering an amount of budiodarone effective to reduce average AF episode duration to less than 3 hours.

In another aspect, the invention provides methods for reversing atrial remodeling comprising administering an amount of budiodarone effective to reduce average AF episode duration to less than about 1 hour.

In another aspect, the invention provides methods for reversing atrial remodeling comprising administering an amount of budiodarone effective to reduce the maximum AF episode duration to less than about 20 hours.

In another aspect, the invention provides methods for reversing atrial remodeling comprising administering an amount of budiodarone effective to reduce the maximum AF episode duration to less than about 10 hours.

In another aspect, the invention provides methods for reversing atrial remodeling comprising administering an amount of budiodarone effective to reduce the maximum AF episode duration to less than about 5 hours.

In yet another aspect, the invention provides methods for reversing atrial remodeling comprising administering an amount of budiodarone effective to reduce AF episode duration, wherein the reversal of atrial remodeling is defined as a measured increase in AFCL at the right atrial appendage or distal coronary sinus of at least 6 milliseconds.

In another aspect, the invention provides methods for reversing atrial remodeling comprising administering an amount of budiodarone effective to reduce average AF episode duration to less than about 24 hours, wherein the reversal of atrial remodeling is defined as a measured increase in AFCL at the right atrial appendage or distal coronary sinus of at least 6 milliseconds.

In another aspect, the invention provides methods for reversing atrial remodeling comprising administering an amount of budiodarone effective to reduce average AF episode duration to less than about 5 hours, wherein the reversal of atrial remodeling is defined as a measured increase in AFCL at the right atrial appendage or distal coronary sinus of at least 6 milliseconds.

In another aspect, the invention provides methods for reversing atrial remodeling comprising administering an amount of budiodarone effective to reduce average AF episode duration to less than 3 hours, wherein the reversal of atrial remodeling is defined as a measured increase in AFCL at the right atrial appendage or distal coronary sinus of at least 6 milliseconds.

In another aspect, the invention provides methods for reversing atrial remodeling comprising administering an amount of budiodarone effective to reduce average AF episode duration to less than about 1 hour, wherein the reversal of atrial remodeling is defined as a measured increase in AFCL at the right atrial appendage or distal coronary sinus of at least 6 milliseconds.

In another aspect, the invention provides methods for reversing atrial remodeling comprising administering an amount of budiodarone effective to reduce the maximum AF episode duration to less than about 20 hours, wherein the reversal of atrial remodeling is defined as a measured increase in AFCL at the right atrial appendage or distal coronary sinus of at least 6 milliseconds.

In another aspect, the invention provides methods for reversing atrial remodeling comprising administering an amount of budiodarone effective to reduce the maximum AF episode duration to less than about 10 hours, wherein the reversal of atrial remodeling is defined as a measured increase in AFCL at the right atrial appendage or distal coronary sinus of at least 6 milliseconds.

In another aspect, the invention provides methods for reversing atrial remodeling comprising administering an amount of budiodarone effective to reduce the maximum AF episode duration to less than about 5 hours, wherein the reversal of atrial remodeling is defined as a measured increase in AFCL at the right atrial appendage or distal coronary sinus of at least 6 milliseconds.

In yet another aspect, the invention provides methods for reducing atrial fibrillation (AF) episode duration comprising administering an amount of budiodarone effective to reduce average AF episode duration, wherein the patient was refractory to one or more anti-arrhythmic drugs.

In another aspect, the invention provides methods for reducing stroke rate comprising administering an amount of budiodarone effective to reduce average AF episode duration, wherein the patient was refractory to one or more anti-arrhythmic drugs.

In yet another aspect, the invention provides methods for increasing time in NSR comprising administering an amount of budiodarone effective to reduce average AF episode duration, wherein the patient was refractory to one or more anti-arrhythmic drugs.

In yet another aspect, the invention provides methods for preventing atrial remodeling comprising administering an amount of budiodarone effective to reduce average AF episode duration, wherein the patient was refractory to one or more anti-arrhythmic drugs.

In yet another aspect, the invention provides methods for reversing atrial remodeling comprising administering an amount of budiodarone effective to reduce average AF episode duration, wherein the patient was refractory to one or more anti-arrhythmic drugs.

In yet another aspect, the invention provides methods for reversing atrial remodeling comprising administering an amount of budiodarone effective to reduce average AF episode duration, wherein the reversal of atrial remodeling is defined as a measured increase in AFCL at the right atrial appendage or distal coronary sinus of at least 6 milliseconds, and wherein the patient was refractory to one or more anti-arrhythmic drugs.

In yet another aspect, the invention provides methods for reducing AF episode duration comprising administering an amount of budiodarone effective to reduce average AF episode duration, wherein the effective amount of budiodarone is 400 mg BID or more preferably 600 mg BID.

In yet another aspect, the invention provides methods for reducing AF episode duration comprising administering an amount of budiodarone effective to reduce average AF episode duration, wherein the effective amount of budiodarone is 600 mg BID.

In another aspect, the invention provides methods for reducing stroke rate comprising administering an amount of budiodarone effective to reduce average AF episode duration, wherein the effective amount of budiodarone is 400 mg BID or more preferably 600 mg BID.

In another aspect, the invention provides methods for reducing stroke rate comprising administering an amount of budiodarone effective to reduce average AF episode duration, wherein the effective amount of budiodarone is 600 mg BID.

In yet another aspect, the invention provides methods for increasing time in NSR comprising administering an amount of budiodarone effective to reduce average AF episode duration, wherein the effective amount of budiodarone is 400 mg BID or more preferably 600 mg BID.

In yet another aspect, the invention provides methods for increasing time in NSR comprising administering an amount of budiodarone effective to reduce average AF episode duration, wherein the effective amount of budiodarone is 600 mg BID.

In yet another aspect, the invention provides methods for preventing atrial remodeling comprising administering an amount of budiodarone effective to reduce average AF episode duration, wherein the effective amount of budiodarone is 400 mg BID or more preferably 600 mg BID.

In yet another aspect, the invention provides methods for preventing atrial remodeling comprising administering an amount of budiodarone effective to reduce average AF episode duration, wherein the effective amount of budiodarone is 600 mg BID.

In yet another aspect, the invention provides methods for reversing atrial remodeling comprising administering an amount of budiodarone effective to reduce average AF episode duration, wherein the effective amount of budiodarone is 400 mg BID or more preferably 600 mg BID.

In yet another aspect, the invention provides methods for reversing atrial remodeling comprising administering an amount of budiodarone effective to reduce average AF episode duration, wherein the effective amount of budiodarone is 600 mg BID.

In yet other aspects, the invention provides for all of the above methods in patients with severe heart failure.

In one aspect, the invention provides methods for reducing stroke rate comprising administering an amount of multiple ion channel blocker anti-arrhythmic selected from the group consisting of amiodarone, dronedarone, budiodarone, vernakalant, celivarone, and AZD1305 effective to reduce atrial fibrillation (AF) episode duration and an effective amount of anticoagulant (AC) selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin.

In another aspect, the invention provides methods for reducing stroke rate comprising administering an amount of multiple ion channel blocker selected from the group consisting of amiodarone, dronedarone, budiodarone, vernakalant, celivarone, and AZD1305 effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the average AF episode duration is reduced to less than about 24 hours, less than about 5 hours, less than about 3 hours, or less than about 1 hour.

In another aspect, the invention provides methods for reducing stroke rate comprising administering an amount of multiple ion channel blocker selected from the group consisting of amiodarone, dronedarone, budiodarone, vernakalant, celivarone, and AZD1305 effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the maximum AF episode duration is reduced to less than about 20 hours, less than about 10 hours, or less than about 5 hours.

In another aspect, the invention provides methods for reducing stroke rate comprising administering an amount of multiple ion channel blocker selected from the group consisting of budiodarone, dronedarone, celivarone, AZD1305 or vernakalant effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin.

In another aspect, the invention provides methods for reducing stroke rate comprising administering an amount of multiple ion channel blocker selected from the group consisting of dronedarone, budiodarone, vernakalant, celivarone, and AZD1305 effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the average AF episode duration is reduced to less than about 24 hours, less than about 5 hours, less than about 3 hours, or less than about 1 hour.

In another aspect, the invention provides methods for reducing stroke rate comprising administering an amount of multiple ion channel blocker selected from the group consisting of dronedarone, budiodarone, vernakalant, celivarone, and AZD1305 effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the maximum AF episode duration is reduced to less than about 20 hours, less than about 10 hours, or less than about 5 hours.

In one aspect, the invention provides methods for reducing stroke rate comprising administering an amount of budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin.

In another aspect, the invention provides methods for reducing stroke rate comprising administering an amount of budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the average AF episode duration is reduced to less than about 24 hours, less than about 5 hours, less than about 3 hours, or less than about 1 hour.

In another aspect, the invention provides methods for reducing stroke rate comprising administering an amount budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the maximum AF episode duration is reduced to less than about 20 hours, less than about 10 hours, or less than about 5 hours.

In one aspect, the invention provides methods for reducing stroke rate comprising administering an amount of multiple ion channel blocker selected from the group consisting of amiodarone, dronedarone, budiodarone, vernakalant, celivarone, and AZD1305 effective to reduce AF episode duration and an effective amount of AC selected from the group consisting of tecarfarin, dabigatran etexilate, ximelagatran, AZD0837, apixaban and rivaroxaban.

In another aspect, the invention provides methods for reducing stroke rate comprising administering an amount of multiple ion channel blocker selected from the group consisting of amiodarone, dronedarone, budiodarone, vernakalant, celivarone, and AZD1305 effective to reduce AF episode duration and an effective amount of AC selected from the group consisting of tecarfarin, dabigatran etexilate, ximelagatran, AZD0837, apixaban and rivaroxaban, wherein the average AF episode duration is reduced to less than about 24 hours, less than about 5 hours, less than about 3 hours, or less than about 1 hour.

In another aspect, the invention provides methods for reducing stroke rate comprising administering an amount of multiple ion channel blocker selected from the group consisting of amiodarone, dronedarone, budiodarone, vernakalant, celivarone, and AZD1305 effective to reduce AF episode duration and an effective amount of AC selected from the group consisting of tecarfarin, dabigatran etexilate, ximelagatran, AZD0837, apixaban and rivaroxaban, wherein the maximum AF episode duration is reduced to less than about 20 hours, less than about 10 hours, or less than about 5 hours.

In another aspect, the invention provides methods for reducing stroke rate comprising administering an amount of multiple ion channel blocker selected from the group consisting of budiodarone, dronedarone, celivarone, AZD1305 or vernakalant effective to reduce AF episode duration and an effective amount of AC selected from the group consisting of tecarfarin, dabigatran etexilate, ximelagatran, AZD0837, apixaban and rivaroxaban.

In another aspect, the invention provides methods for reducing stroke rate comprising administering an amount of multiple ion channel blocker selected from the group consisting of dronedarone, budiodarone, vernakalant, celivarone, and AZD1305 effective to reduce AF episode duration and an effective amount of AC selected from the group consisting of tecarfarin, dabigatran etexilate, ximelagatran, AZD0837, apixaban and rivaroxaban, wherein the average AF episode duration is reduced to less than about 24 hours, less than about 5 hours, less than about 3 hours, or less than about 1 hour.

In another aspect, the invention provides methods for reducing stroke rate comprising administering an amount of multiple ion channel blocker selected from the group consisting of dronedarone, budiodarone, vernakalant, celivarone, and AZD1305 effective to reduce AF episode duration and an effective amount of AC selected from the group consisting of tecarfarin, dabigatran etexilate, ximelagatran, AZD0837, apixaban and rivaroxaban, wherein the maximum AF episode duration is reduced to less than about 20 hours, less than about 10 hours, or less than about 5 hours.

In one aspect, the invention provides methods for reducing stroke rate comprising administering an amount of budiodarone effective to reduce AF episode duration and an effective amount of AC selected from the group consisting of tecarfarin, dabigatran etexilate, ximelagatran, AZD0837, apixaban and rivaroxaban.

In another aspect, the invention provides methods for reducing stroke rate comprising administering an amount of budiodarone effective to reduce AF episode duration and an effective amount of AC selected from the group consisting of tecarfarin, dabigatran etexilate, ximelagatran, AZD0837, apixaban and rivaroxaban, wherein the average AF episode duration is reduced to less than about 24 hours, less than about 5 hours, less than about 3 hours, or less than about 1 hour.

In another aspect, the invention provides methods for reducing stroke rate comprising administering an amount of budiodarone effective to reduce AF episode duration and an effective amount of AC selected from the group consisting of tecarfarin, dabigatran etexilate, ximelagatran, AZD0837, apixaban and rivaroxaban, wherein the maximum AF episode duration is reduced to less than about 20 hours, less than about 10 hours, or less than about 5 hours.

In another aspect, the invention provides methods for reducing stroke rate comprising administering an amount of multiple ion channel blocker selected from the group consisting of amiodarone, dronedarone, budiodarone, vernakalant, celivarone, and AZD1305 effective to reduce AF episode duration and an effective amount of dabigatran etexilate, wherein the average AF episode duration is reduced to less than about 24 hours, less than about 5 hours, less than about 3 hours, or less than about 1 hour.

In another aspect, the invention provides methods for reducing stroke rate comprising administering an amount of multiple ion channel blocker selected from the group consisting of amiodarone, dronedarone, budiodarone, vernakalant, celivarone, and AZD1305 effective to reduce AF episode duration and an effective amount of dabigatran etexilate, wherein the maximum AF episode duration is reduced to less than about 20 hours, less than about 10 hours, or less than about 5 hours.

In another aspect, the invention provides methods for reducing stroke rate comprising administering an amount of multiple ion channel blocker selected from the group consisting of dronedarone, budiodarone, vernakalant, celivarone, and AZD1305 effective to reduce AF episode duration and an effective amount of dabigatran etexilate, wherein the average AF episode duration is reduced to less than about 24 hours, less than about 5 hours, less than about 3 hours, or less than about 1 hour.

In another aspect, the invention provides methods for reducing stroke rate comprising administering an amount of multiple ion channel blocker selected from the group consisting of dronedarone, budiodarone, vernakalant, celivarone, and AZD1305 effective to reduce AF episode duration and an effective amount of dabigatran etexilate, wherein the maximum AF episode duration is reduced to less than about 20 hours, less than about 10 hours, or less than about 5 hours.

In another aspect, the invention provides methods for reducing stroke rate comprising administering an amount of budiodarone effective to reduce AF episode duration and an effective amount of dabigatran etexilate, wherein the average AF episode duration is reduced to less than about 24 hours, less than about 5 hours, less than about 3 hours, or less than about 1 hour.

In another aspect, the invention provides methods for reducing stroke rate comprising administering an amount budiodarone effective to reduce AF episode duration and an effective amount of dabigatran etexilate, wherein the maximum AF episode duration is reduced to less than about 20 hours, less than about 10 hours, or less than about 5 hours.

In another aspect, the invention provides methods for reducing stroke rate comprising administering an amount of multiple ion channel blocker selected from the group consisting of amiodarone, dronedarone, budiodarone, vernakalant, celivarone, and AZD1305 effective to reduce AF episode duration and an effective amount of AC selected from the group consisting of ximelagatran and AZD0837, wherein the average AF episode duration is reduced to less than about 24 hours, less than about 5 hours, less than about 3 hours, or less than about 1 hour.

In another aspect, the invention provides methods for reducing stroke rate comprising administering an amount of multiple ion channel blocker selected from the group consisting of amiodarone, dronedarone, budiodarone, vernakalant, celivarone, and AZD1305 effective to reduce AF episode duration and an effective amount of AC selected from the group consisting of ximelagatran and AZD0837, wherein the maximum AF episode duration is reduced to less than about 20 hours, less than about 10 hours, or less than about 5 hours.

In another aspect, the invention provides methods for reducing stroke rate comprising administering an amount of multiple ion channel blocker selected from the group consisting of dronedarone, budiodarone, vernakalant, celivarone, and AZD1305 effective to reduce AF episode duration and an effective amount of AC selected from the group consisting of ximelagatran and AZD0837, wherein the average AF episode duration is reduced to less than about 24 hours, less than about 5 hours, less than about 3 hours, or less than about 1 hour.

In another aspect, the invention provides methods for reducing stroke rate comprising administering an amount of multiple ion channel blocker selected from the group consisting of dronedarone, budiodarone, vernakalant, celivarone, and AZD1305 effective to reduce AF episode duration and an effective amount of AC selected from the group consisting of ximelagatran and AZD0837, wherein the maximum AF episode duration is reduced to less than about 20 hours, less than about 10 hours, or less than about 5 hours.

In another aspect, the invention provides methods for reducing stroke rate comprising administering an amount of budiodarone effective to reduce AF episode duration and an effective amount of AC selected from the group consisting of ximelagatran and AZD0837, wherein the average AF episode duration is reduced to less than about 24 hours, less than about 5 hours, less than about 3 hours, or less than about 1 hour.

In another aspect, the invention provides methods for reducing stroke rate comprising administering an amount budiodarone effective to reduce AF episode duration and an effective amount of AC selected from the group consisting of ximelagatran and AZD0837, wherein the maximum AF episode duration is reduced to less than about 20 hours, less than about 10 hours, or less than about 5 hours.

In another aspect, the invention provides methods for reducing stroke rate comprising administering an amount of multiple ion channel blocker selected from the group consisting of amiodarone, dronedarone, budiodarone, vernakalant, celivarone, and AZD1305 effective to reduce AF episode duration and an effective amount of apixaban, wherein the average AF episode duration is reduced to less than about 24 hours, less than about 5 hours, less than about 3 hours, or less than about 1 hour.

In another aspect, the invention provides methods for reducing stroke rate comprising administering an amount of multiple ion channel blocker selected from the group consisting of amiodarone, dronedarone, budiodarone, vernakalant, celivarone, and AZD1305 effective to reduce AF episode duration and an effective amount of apixaban, wherein the maximum AF episode duration is reduced to less than about 20 hours, less than about 10 hours, or less than about 5 hours.

In another aspect, the invention provides methods for reducing stroke rate comprising administering an amount of multiple ion channel blocker selected from the group consisting of dronedarone, budiodarone, vernakalant, celivarone, and AZD1305 effective to reduce AF episode duration and an effective amount of apixaban, wherein the average AF episode duration is reduced to less than about 24 hours, less than about 5 hours, less than about 3 hours, or less than about 1 hour.

In another aspect, the invention provides methods for reducing stroke rate comprising administering an amount of multiple ion channel blocker selected from the group consisting of dronedarone, budiodarone, vernakalant, celivarone, and AZD1305 effective to reduce AF episode duration and an effective amount of apixaban, wherein the maximum AF episode duration is reduced to less than about 20 hours, less than about 10 hours, or less than about 5 hours.

In another aspect, the invention provides methods for reducing stroke rate comprising administering an amount of budiodarone effective to reduce AF episode duration and an effective amount of apixaban, wherein the average AF episode duration is reduced to less than about 24 hours, less than about 5 hours, less than about 3 hours, or less than about 1 hour.

In another aspect, the invention provides methods for reducing stroke rate comprising administering an amount budiodarone effective to reduce AF episode duration and an effective amount of apixaban, wherein the maximum AF episode duration is reduced to less than about 20 hours, less than about 10 hours, or less than about 5 hours.

In another aspect, the invention provides methods for reducing stroke rate comprising administering an amount of multiple ion channel blocker selected from the group consisting of amiodarone, dronedarone, budiodarone, vernakalant, celivarone, and AZD1305 effective to reduce AF episode duration and an effective amount of rivaroxaban, wherein the average AF episode duration is reduced to less than about 24 hours, less than about 5 hours, less than about 3 hours, or less than about 1 hour.

In another aspect, the invention provides methods for reducing stroke rate comprising administering an amount of multiple ion channel blocker selected from the group consisting of amiodarone, dronedarone, budiodarone, vernakalant, celivarone, and AZD1305 effective to reduce AF episode duration and an effective amount of rivaroxaban, wherein the maximum AF episode duration is reduced to less than about 20 hours, less than about 10 hours, or less than about 5 hours.

In another aspect, the invention provides methods for reducing stroke rate comprising administering an amount of multiple ion channel blocker selected from the group consisting of dronedarone, budiodarone, vernakalant, celivarone, and AZD1305 effective to reduce AF episode duration and an effective amount of rivaroxaban, wherein the average AF episode duration is reduced to less than about 24 hours, less than about 5 hours, less than about 3 hours, or less than about 1 hour.

In another aspect, the invention provides methods for reducing stroke rate comprising administering an amount of multiple ion channel blocker selected from the group consisting of dronedarone, budiodarone, vernakalant, celivarone, and AZD1305 effective to reduce AF episode duration and an effective amount of rivaroxaban, wherein the maximum AF episode duration is reduced to less than about 20 hours, less than about 10 hours, or less than about 5 hours.

In another aspect, the invention provides methods for reducing stroke rate comprising administering an amount of budiodarone effective to reduce AF episode duration and an effective amount of rivaroxaban, wherein the average AF episode duration is reduced to less than about 24 hours, less than about 5 hours, less than about 3 hours, or less than about 1 hour.

In another aspect, the invention provides methods for reducing stroke rate comprising administering an amount budiodarone effective to reduce AF episode duration and an effective amount of rivaroxaban, wherein the maximum AF episode duration is reduced to less than about 20 hours, less than about 10 hours, or less than about 5 hours.

In another aspect, the invention provides methods for reducing stroke rate comprising administering an amount of multiple ion channel blocker selected from the group consisting of amiodarone, dronedarone, budiodarone, vernakalant, celivarone, and AZD1305 effective to reduce AF episode duration and an effective amount of tecarfarin, wherein the average AF episode duration is reduced to less than about 24 hours, less than about 5 hours, less than about 3 hours, or less than about 1 hour.

In another aspect, the invention provides methods for reducing stroke rate comprising administering an amount of multiple ion channel blocker selected from the group consisting of amiodarone, dronedarone, budiodarone, vernakalant, celivarone, and AZD1305 effective to reduce AF episode duration and an effective amount of tecarfarin, wherein the maximum AF episode duration is reduced to less than about 20 hours, less than about 10 hours, or less than about 5 hours.

In another aspect, the invention provides methods for reducing stroke rate comprising administering an amount of multiple ion channel blocker selected from the group consisting of dronedarone, budiodarone, vernakalant, celivarone, and AZD1305 effective to reduce AF episode duration and an effective amount of tecarfarin, wherein the average AF episode duration is reduced to less than about 24 hours, less than about 5 hours, less than about 3 hours, or less than about 1 hour.

In another aspect, the invention provides methods for reducing stroke rate comprising administering an amount of multiple ion channel blocker selected from the group consisting of dronedarone, budiodarone, vernakalant, celivarone, and AZD1305 effective to reduce AF episode duration and an effective amount of tecarfarin, wherein the maximum AF episode duration is reduced to less than about 20 hours, less than about 10 hours, or less than about 5 hours.

In another aspect, the invention provides methods for reducing stroke rate comprising administering an amount of budiodarone effective to reduce AF episode duration and an effective amount of tecarfarin, wherein the average AF episode duration is reduced to less than about 24 hours, less than about 5 hours, less than about 3 hours, or less than about 1 hour.

In another aspect, the invention provides methods for reducing stroke rate comprising administering an amount budiodarone effective to reduce AF episode duration and an effective amount of tecarfarin, wherein the maximum AF episode duration is reduced to less than about 20 hours, less than about 10 hours, or less than about 5 hours.

In one aspect, the invention provides methods for reducing stroke rate comprising administering an amount of multiple ion channel blocker selected from the group consisting of amiodarone, dronedarone, budiodarone, vernakalant, celivarone, and AZD1305 effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the reduced stroke rate is less than the age-adjusted overall stroke rate.

In another aspect, the invention provides methods for reducing stroke rate comprising administering an amount of multiple ion channel blocker selected from the group consisting of amiodarone, dronedarone, budiodarone, vernakalant, celivarone, and AZD1305 effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the average AF episode duration is reduced to less than about 24 hours, less than about 5 hours, less than about 3 hours, or less than about 1 hour, and wherein the reduced stroke rate is less than the age-adjusted overall stroke rate.

In another aspect, the invention provides methods for reducing stroke rate comprising administering an amount of multiple ion channel blocker selected from the group consisting of amiodarone, dronedarone, budiodarone, vernakalant, celivarone, and AZD1305 effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the maximum AF episode duration is reduced to less than about 20 hours, less than about 10 hours, or less than about 5 hours, and wherein the reduced stroke rate is less than the age-adjusted overall stroke rate.

In another aspect, the invention provides methods for reducing stroke rate comprising administering an amount of multiple ion channel blocker selected from the group consisting of dronedarone, budiodarone, vernakalant, celivarone, and AZD1305 effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the average AF episode duration is reduced to less than about 24 hours, less than about 5 hours, less than about 3 hours, or less than about 1 hour, and wherein the reduced stroke rate is less than the age-adjusted overall stroke rate.

In another aspect, the invention provides methods for reducing stroke rate comprising administering an amount of multiple ion channel blocker selected from the group consisting of dronedarone, budiodarone, vernakalant, celivarone, and AZD1305 effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the maximum AF episode duration is reduced to less than about 20 hours, less than about 10 hours, or less than about 5 hours, and wherein the reduced stroke rate is less than the age-adjusted overall stroke rate.

In another aspect, the invention provides methods for reducing stroke rate comprising administering an amount of budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the average AF episode duration is reduced to less than about 24 hours, less than about 5 hours, less than about 3 hours, or less than about 1 hour, and wherein the reduced stroke rate is less than the age-adjusted overall stroke rate.

In another aspect, the invention provides methods for reducing stroke rate comprising administering an amount of budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the maximum AF episode duration is reduced to less than about 20 hours, less than about 10 hours, or less than about 5 hours, and wherein the reduced stroke rate is less than the age-adjusted overall stroke rate.

In one aspect, the invention provides methods for reducing stroke rate comprising administering an amount of multiple ion channel blocker selected from the group consisting of amiodarone, dronedarone, budiodarone, vernakalant, celivarone, and AZD1305 effective to reduce AF episode duration and an effective amount of AC selected from the group consisting of tecarfarin, dabigatran etexilate, ximelagatran, AZD0837, apixaban and rivaroxaban, wherein the reduced stroke rate is less than the age-adjusted overall stroke rate.

In another aspect, the invention provides methods for reducing stroke rate comprising administering an amount of multiple ion channel blocker selected from the group consisting of amiodarone, dronedarone, budiodarone, vernakalant, celivarone, and AZD1305 effective to reduce AF episode duration and an effective amount of AC selected from the group consisting of tecarfarin, dabigatran etexilate, ximelagatran, AZD0837, apixaban and rivaroxaban, wherein the average AF episode duration is reduced to less than about 24 hours, less than about 5 hours, less than about 3 hours, or less than about 1 hour, and wherein the reduced stroke rate is less than the age-adjusted overall stroke rate.

In another aspect, the invention provides methods for reducing stroke rate comprising administering an amount of multiple ion channel blocker selected from the group consisting of amiodarone, dronedarone, budiodarone, vernakalant, celivarone, and AZD1305 effective to reduce AF episode duration and an effective amount of AC selected from the group consisting of tecarfarin, dabigatran etexilate, ximelagatran, AZD0837, apixaban and rivaroxaban, wherein the maximum AF episode duration is reduced to less than about 20 hours, less than about 10 hours, or less than about 5 hours, and wherein the reduced stroke rate is less than the age-adjusted overall stroke rate.

In another aspect, the invention provides methods for reducing stroke rate comprising administering an amount of multiple ion channel blocker selected from the group consisting of budiodarone, dronedarone, celivarone, AZD1305 or vernakalant effective to reduce AF episode duration and an effective amount of AC selected from the group consisting of tecarfarin, dabigatran etexilate, ximelagatran, AZD0837, apixaban and rivaroxaban, wherein the reduced stroke rate is less than the age-adjusted overall stroke rate.

In another aspect, the invention provides methods for reducing stroke rate comprising administering an amount of multiple ion channel blocker selected from the group consisting of dronedarone, budiodarone, vernakalant, celivarone, and AZD1305 effective to reduce AF episode duration and an effective amount of AC selected from the group consisting of tecarfarin, dabigatran etexilate, ximelagatran, AZD0837, apixaban and rivaroxaban, wherein the average AF episode duration is reduced to less than about 24 hours, less than about 5 hours, less than about 3 hours, or less than about 1 hour, and wherein the reduced stroke rate is less than the age-adjusted overall stroke rate.

In another aspect, the invention provides methods for reducing stroke rate comprising administering an amount of multiple ion channel blocker selected from the group consisting of dronedarone, budiodarone, vernakalant, celivarone, and AZD1305 effective to reduce AF episode duration and an effective amount of AC selected from the group consisting of tecarfarin, dabigatran etexilate, ximelagatran, AZD0837, apixaban and rivaroxaban, wherein the maximum AF episode duration is reduced to less than about 20 hours, less than about 10 hours, or less than about 5 hours, and wherein the reduced stroke rate is less than the age-adjusted overall stroke rate.

In one aspect, the invention provides methods for reducing stroke rate comprising administering an amount of budiodarone effective to reduce AF episode duration and an effective amount of AC selected from the group consisting of tecarfarin, dabigatran etexilate, ximelagatran, AZD0837, apixaban and rivaroxaban, wherein the reduced stroke rate is less than the age-adjusted overall stroke rate.

In another aspect, the invention provides methods for reducing stroke rate comprising administering an amount of budiodarone effective to reduce AF episode duration and an effective amount of AC selected from the group consisting of tecarfarin, dabigatran etexilate, ximelagatran, AZD0837, apixaban and rivaroxaban, wherein the average AF episode duration is reduced to less than about 24 hours, less than about 5 hours, less than about 3 hours, or less than about 1 hour, and wherein the reduced stroke rate is less than the age-adjusted overall stroke rate.

In another aspect, the invention provides methods for reducing stroke rate comprising administering an amount budiodarone effective to reduce AF episode duration and an effective amount of AC selected from the group consisting of tecarfarin, dabigatran etexilate, ximelagatran, AZD0837, apixaban and rivaroxaban, wherein the maximum AF episode duration is reduced to less than about 20 hours, less than about 10 hours, or less than about 5 hours, and wherein the reduced stroke rate is less than the age-adjusted overall stroke rate.

In another aspect, the invention provides methods for reducing stroke rate comprising administering an amount of multiple ion channel blocker selected from the group consisting of amiodarone, dronedarone, budiodarone, vernakalant, celivarone, and AZD1305 effective to reduce AF episode duration and an effective amount of dabigatran etexilate, wherein the average AF episode duration is reduced to less than about 24 hours, less than about 5 hours, less than about 3 hours, or less than about 1 hour, wherein the reduced stroke rate is less than the age-adjusted overall stroke rate.

In another aspect, the invention provides methods for reducing stroke rate comprising administering an amount of multiple ion channel blocker selected from the group consisting of amiodarone, dronedarone, budiodarone, vernakalant, celivarone, and AZD1305 effective to reduce AF episode duration and an effective amount of dabigatran etexilate, wherein the maximum AF episode duration is reduced to less than about 20 hours, less than about 10 hours, or less than about hours, and wherein the reduced stroke rate is less than the age-adjusted overall stroke rate.

In another aspect, the invention provides methods for reducing stroke rate comprising administering an amount of multiple ion channel blocker selected from the group consisting of dronedarone, budiodarone, vernakalant, celivarone, and AZD1305 effective to reduce AF episode duration and an effective amount of dabigatran etexilate, wherein the average AF episode duration is reduced to less than about 24 hours, less than about 5 hours, less than about 3 hours, or less than about 1 hour, and wherein the reduced stroke rate is less than the age-adjusted overall stroke rate.

In another aspect, the invention provides methods for reducing stroke rate comprising administering an amount of multiple ion channel blocker selected from the group consisting of dronedarone, budiodarone, vernakalant, celivarone, and AZD1305 effective to reduce AF episode duration and an effective amount of dabigatran etexilate, wherein the maximum AF episode duration is reduced to less than about 20 hours, less than about 10 hours, or less than about 5 hours, and wherein the reduced stroke rate is less than the age-adjusted overall stroke rate.

In another aspect, the invention provides methods for reducing stroke rate comprising administering an amount of budiodarone effective to reduce AF episode duration and an effective amount of dabigatran etexilate, wherein the average AF episode duration is reduced to less than about 24 hours, less than about 5 hours, less than about 3 hours, or less than about 1 hour, and wherein the reduced stroke rate is less than the age-adjusted overall stroke rate.

In another aspect, the invention provides methods for reducing stroke rate comprising administering an amount of budiodarone effective to reduce AF episode duration and an effective amount of dabigatran etexilate, wherein the maximum AF episode duration is reduced to less than about 20 hours, less than about 10 hours, or less than about 5 hours, and wherein the reduced stroke rate is less than the age-adjusted overall stroke rate.

In another aspect, the invention provides methods for reducing stroke rate comprising administering an amount of multiple ion channel blocker selected from the group consisting of amiodarone, dronedarone, budiodarone, vernakalant, celivarone, and AZD1305 effective to reduce AF episode duration and an effective amount of AC selected from the group consisting of ximelagatran and AZD0837, wherein the average AF episode duration is reduced to less than about 24 hours, less than about 5 hours, less than about 3 hours, or less than about 1 hour, and wherein the reduced stroke rate is less than the age-adjusted overall stroke rate.

In another aspect, the invention provides methods for reducing stroke rate comprising administering an amount of multiple ion channel blocker selected from the group consisting of amiodarone, dronedarone, budiodarone, vernakalant, celivarone, and AZD1305 effective to reduce AF episode duration and an effective amount of AC selected from the group consisting of ximelagatran and AZD0837, wherein the maximum AF episode duration is reduced to less than about 20 hours, less than about 10 hours, or less than about 5 hours, and wherein the reduced stroke rate is less than the age-adjusted overall stroke rate.

In another aspect, the invention provides methods for reducing stroke rate comprising administering an amount of multiple ion channel blocker selected from the group consisting of dronedarone, budiodarone, vernakalant, celivarone, and AZD1305 effective to reduce AF episode duration and an effective amount of AC selected from the group consisting of ximelagatran and AZD0837, wherein the average AF episode duration is reduced to less than about 24 hours, less than about 5 hours, less than about 3 hours, or less than about 1 hour, and wherein the reduced stroke rate is less than the age-adjusted overall stroke rate.

In another aspect, the invention provides methods for reducing stroke rate comprising administering an amount of multiple ion channel blocker selected from the group consisting of dronedarone, budiodarone, vernakalant, celivarone, and AZD1305 effective to reduce AF episode duration and an effective amount of AC selected from the group consisting of ximelagatran and AZD0837, wherein the maximum AF episode duration is reduced to less than about 20 hours, less than about 10 hours, or less than about 5 hours, and wherein the reduced stroke rate is less than the age-adjusted overall stroke rate.

In another aspect, the invention provides methods for reducing stroke rate comprising administering an amount of budiodarone effective to reduce AF episode duration and an effective amount of AC selected from the group consisting of ximelagatran and AZD0837, wherein the average AF episode duration is reduced to less than about 24 hours, less than about 5 hours, less than about 3 hours, or less than about 1 hour, and wherein the reduced stroke rate is less than the age-adjusted overall stroke rate.

In another aspect, the invention provides methods for reducing stroke rate comprising administering an amount budiodarone effective to reduce AF episode duration and an effective amount of AC selected from the group consisting of ximelagatran and AZD0837, wherein the maximum AF episode duration is reduced to less than about 20 hours, less than about 10 hours, or less than about 5 hours, and wherein the reduced stroke rate is less than the age-adjusted overall stroke rate.

In another aspect, the invention provides methods for reducing stroke rate comprising administering an amount of multiple ion channel blocker selected from the group consisting of amiodarone, dronedarone, budiodarone, vernakalant, celivarone, and AZD1305 effective to reduce AF episode duration and an effective amount of apixaban, wherein the average AF episode duration is reduced to less than about 24 hours, less than about 5 hours, less than about 3 hours, or less than about 1 hour, and wherein the reduced stroke rate is less than the age-adjusted overall stroke rate.

In another aspect, the invention provides methods for reducing stroke rate comprising administering an amount of multiple ion channel blocker selected from the group consisting of amiodarone, dronedarone, budiodarone, vernakalant, celivarone, and AZD1305 effective to reduce AF episode duration and an effective amount of apixaban, wherein the maximum AF episode duration is reduced to less than about 20 hours, less than about 10 hours, or less than about 5 hours, and wherein the reduced stroke rate is less than the age-adjusted overall stroke rate.

In another aspect, the invention provides methods for reducing stroke rate comprising administering an amount of multiple ion channel blocker selected from the group consisting of dronedarone, budiodarone, vernakalant, celivarone, and AZD1305 effective to reduce AF episode duration and an effective amount of apixaban, wherein the average AF episode duration is reduced to less than about 24 hours, less than about 5 hours, less than about 3 hours, or less than about 1 hour, and wherein the reduced stroke rate is less than the age-adjusted overall stroke rate.

In another aspect, the invention provides methods for reducing stroke rate comprising administering an amount of multiple ion channel blocker selected from the group consisting of dronedarone, budiodarone, vernakalant, celivarone, and AZD1305 effective to reduce AF episode duration and an effective amount of apixaban, wherein the maximum AF episode duration is reduced to less than about 20 hours, less than about 10 hours, or less than about 5 hours, and wherein the reduced stroke rate is less than the age-adjusted overall stroke rate.

In another aspect, the invention provides methods for reducing stroke rate comprising administering an amount of budiodarone effective to reduce AF episode duration and an effective amount of apixaban, wherein the average AF episode duration is reduced to less than about 24 hours, less than about 5 hours, less than about 3 hours, or less than about 1 hour, and wherein the reduced stroke rate is less than the age-adjusted overall stroke rate.

In another aspect, the invention provides methods for reducing stroke rate comprising administering an amount budiodarone effective to reduce AF episode duration and an effective amount of apixaban, wherein the maximum AF episode duration is reduced to less than about 20 hours, less than about 10 hours, or less than about 5 hours, and wherein the reduced stroke rate is less than the age-adjusted overall stroke rate.

In another aspect, the invention provides methods for reducing stroke rate comprising administering an amount of multiple ion channel blocker selected from the group consisting of amiodarone, dronedarone, budiodarone, vernakalant, celivarone, and AZD1305 effective to reduce AF episode duration and an effective amount of rivaroxaban, wherein the average AF episode duration is reduced to less than about 24 hours, less than about 5 hours, less than about 3 hours, or less than about 1 hour, and wherein the reduced stroke rate is less than the age-adjusted overall stroke rate.

In another aspect, the invention provides methods for reducing stroke rate comprising administering an amount of multiple ion channel blocker selected from the group consisting of amiodarone, dronedarone, budiodarone, vernakalant, celivarone, and AZD1305 effective to reduce AF episode duration and an effective amount of rivaroxaban, wherein the maximum AF episode duration is reduced to less than about 20 hours, less than about 10 hours, or less than about 5 hours, and wherein the reduced stroke rate is less than the age-adjusted overall stroke rate.

In another aspect, the invention provides methods for reducing stroke rate comprising administering an amount of multiple ion channel blocker selected from the group consisting of dronedarone, budiodarone, vernakalant, celivarone, and AZD1305 effective to reduce AF episode duration and an effective amount of rivaroxaban, wherein the average AF episode duration is reduced to less than about 24 hours, less than about 5 hours, less than about 3 hours, or less than about 1 hour, and wherein the reduced stroke rate is less than the age-adjusted overall stroke rate.

In another aspect, the invention provides methods for reducing stroke rate comprising administering an amount of multiple ion channel blocker selected from the group consisting of dronedarone, budiodarone, vernakalant, celivarone, and AZD1305 effective to reduce AF episode duration and an effective amount of rivaroxaban, wherein the maximum AF episode duration is reduced to less than about 20 hours, less than about 10 hours, or less than about 5 hours, and wherein the reduced stroke rate is less than the age-adjusted overall stroke rate.

In another aspect, the invention provides methods for reducing stroke rate comprising administering an amount of budiodarone effective to reduce AF episode duration and an effective amount of rivaroxaban, wherein the average AF episode duration is reduced to less than about 24 hours, less than about 5 hours, less than about 3 hours, or less than about 1 hour, and wherein the reduced stroke rate is less than the age-adjusted overall stroke rate.

In another aspect, the invention provides methods for reducing stroke rate comprising administering an amount budiodarone effective to reduce AF episode duration and an effective amount of rivaroxaban, wherein the maximum AF episode duration is reduced to less than about 20 hours, less than about 10 hours, or less than about 5 hours, and wherein the reduced stroke rate is less than the age-adjusted overall stroke rate.

In another aspect, the invention provides methods for reducing stroke rate comprising administering an amount of multiple ion channel blocker selected from the group consisting of amiodarone, dronedarone, budiodarone, vernakalant, celivarone, and AZD1305 effective to reduce AF episode duration and an effective amount of tecarfarin, wherein the average AF episode duration is reduced to less than about 24 hours, less than about 5 hours, less than about 3 hours, or less than about 1 hour, and wherein the reduced stroke rate is less than the age-adjusted overall stroke rate.

In another aspect, the invention provides methods for reducing stroke rate comprising administering an amount of multiple ion channel blocker selected from the group consisting of amiodarone, dronedarone, budiodarone, vernakalant, celivarone, and AZD1305 effective to reduce AF episode duration and an effective amount of tecarfarin, wherein the maximum AF episode duration is reduced to less than about 20 hours, less than about 10 hours, or less than about 5 hours, and wherein the reduced stroke rate is less than the age-adjusted overall stroke rate.

In another aspect, the invention provides methods for reducing stroke rate comprising administering an amount of multiple ion channel blocker selected from the group consisting of dronedarone, budiodarone, vernakalant, celivarone, and AZD1305 effective to reduce AF episode duration and an effective amount of tecarfarin, wherein the average AF episode duration is reduced to less than about 24 hours, less than about 5 hours, less than about 3 hours, or less than about 1 hour, and wherein the reduced stroke rate is less than the age-adjusted overall stroke rate.

In another aspect, the invention provides methods for reducing stroke rate comprising administering an amount of multiple ion channel blocker selected from the group consisting of dronedarone, budiodarone, vernakalant, celivarone, and AZD1305 effective to reduce AF episode duration and an effective amount of tecarfarin, wherein the maximum AF episode duration is reduced to less than about 20 hours, less than about 10 hours, or less than about 5 hours, and wherein the reduced stroke rate is less than the age-adjusted overall stroke rate.

In another aspect, the invention provides methods for reducing stroke rate comprising administering an amount of budiodarone effective to reduce AF episode duration and an effective amount of tecarfarin, wherein the average AF episode duration is reduced to less than about 24 hours, less than about 5 hours, less than about 3 hours, or less than about 1 hour, and wherein the reduced stroke rate is less than the age-adjusted overall stroke rate.

In another aspect, the invention provides methods for reducing stroke rate comprising administering an amount budiodarone effective to reduce AF episode duration and an effective amount of tecarfarin, wherein the maximum AF episode duration is reduced to less than about 20 hours, less than about 10 hours, or less than about 5 hours, and wherein the reduced stroke rate is less than the age-adjusted overall stroke rate.

In another aspect, the invention provides methods for reducing stroke rate comprising administering an amount of multiple ion channel blocker selected from the group consisting of amiodarone, dronedarone, budiodarone, vernakalant, celivarone, and AZD1305 effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the average AF episode duration is reduced to less than about 24 hours, less than about 5 hours, less than about 3 hours, or less than about 1 hour, and wherein the patient was refractory to one or more anti-arrhythmic drugs.

In another aspect, the invention provides methods for reducing stroke rate comprising administering an amount of multiple ion channel blocker selected from the group consisting of amiodarone, dronedarone, budiodarone, vernakalant, celivarone, and AZD1305 effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the maximum AF episode duration is reduced to less than about 20 hours, less than about 10 hours, or less than about 5 hours, and wherein the patient was refractory to one or more anti-arrhythmic drugs.

In another aspect, the invention provides methods for reducing stroke rate comprising administering an amount of multiple ion channel blocker selected from the group consisting of dronedarone, budiodarone, vernakalant, celivarone, and AZD1305 effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the average AF episode duration is reduced to less than about 24 hours, less than about 5 hours, less than about 3 hours, or less than about 1 hour, and wherein the patient was refractory to one or more anti-arrhythmic drugs.

In another aspect, the invention provides methods for reducing stroke rate comprising administering an amount of multiple ion channel blocker selected from the group consisting of dronedarone, budiodarone, vernakalant, celivarone, and AZD1305 effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the maximum AF episode duration is reduced to less than about 20 hours, less than about 10 hours, or less than about 5 hours, and wherein the patient was refractory to one or more anti-arrhythmic drugs.

In another aspect, the invention provides methods for reducing stroke rate comprising administering an amount of budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the average AF episode duration is reduced to less than about 24 hours, less than about 5 hours, less than about 3 hours, or less than about 1 hour, and wherein the patient was refractory to one or more anti-arrhythmic drugs.

In another aspect, the invention provides methods for reducing stroke rate comprising administering an amount budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the maximum AF episode duration is reduced to less than about 20 hours, less than about 10 hours, or less than about 5 hours, and wherein the patient was refractory to one or more anti-arrhythmic drugs.

In another aspect, the invention provides methods for reducing stroke rate comprising administering an amount of multiple ion channel blocker selected from the group consisting of amiodarone, dronedarone, budiodarone, vernakalant, celivarone, and AZD1305 effective to reduce AF episode duration and an effective amount of dabigatran etexilate, wherein the average AF episode duration is reduced to less than about 24 hours, less than about 5 hours, less than about 3 hours, or less than about 1 hour, and wherein the patient was refractory to one or more anti-arrhythmic drugs.

In another aspect, the invention provides methods for reducing stroke rate comprising administering an amount of multiple ion channel blocker selected from the group consisting of amiodarone, dronedarone, budiodarone, vernakalant, celivarone, and AZD1305 effective to reduce AF episode duration and an effective amount of dabigatran etexilate, wherein the maximum AF episode duration is reduced to less than about 20 hours, less than about 10 hours, or less than about 5 hours, and wherein the patient was refractory to one or more anti-arrhythmic drugs.

In another aspect, the invention provides methods for reducing stroke rate comprising administering an amount of multiple ion channel blocker selected from the group consisting of dronedarone, budiodarone, vernakalant, celivarone, and AZD1305 effective to reduce AF episode duration and an effective amount of dabigatran etexilate, wherein the average AF episode duration is reduced to less than about 24 hours, less than about 5 hours, less than about 3 hours, or less than about 1 hour, and wherein the patient was refractory to one or more anti-arrhythmic drugs.

In another aspect, the invention provides methods for reducing stroke rate comprising administering an amount of multiple ion channel blocker selected from the group consisting of dronedarone, budiodarone, vernakalant, celivarone, and AZD1305 effective to reduce AF episode duration and an effective amount of dabigatran etexilate, wherein the maximum AF episode duration is reduced to less than about 20 hours, less than about 10 hours, or less than about 5 hours, and wherein the patient was refractory to one or more anti-arrhythmic drugs.

In another aspect, the invention provides methods for reducing stroke rate comprising administering an amount of budiodarone effective to reduce AF episode duration and an effective amount of dabigatran etexilate, wherein the average AF episode duration is reduced to less than about 24 hours, less than about 5 hours, less than about 3 hours, or less than about 1 hour, and wherein the patient was refractory to one or more anti-arrhythmic drugs.

In another aspect, the invention provides methods for reducing stroke rate comprising administering an amount budiodarone effective to reduce AF episode duration and an effective amount of dabigatran etexilate, wherein the maximum AF episode duration is reduced to less than about 20 hours, less than about 10 hours, or less than about 5 hours, and wherein the patient was refractory to one or more anti-arrhythmic drugs.

In another aspect, the invention provides methods for reducing stroke rate comprising administering an amount of multiple ion channel blocker selected from the group consisting of amiodarone, dronedarone, budiodarone, vernakalant, celivarone, and AZD1305 effective to reduce AF episode duration and an effective amount of AC selected from the group consisting of ximelagatran and AZD0837, wherein the average AF episode duration is reduced to less than about 24 hours, less than about 5 hours, less than about 3 hours, or less than about 1 hour, and wherein the patient was refractory to one or more anti-arrhythmic drugs.

In another aspect, the invention provides methods for reducing stroke rate comprising administering an amount of multiple ion channel blocker selected from the group consisting of amiodarone, dronedarone, budiodarone, vernakalant, celivarone, and AZD1305 effective to reduce AF episode duration and an effective amount of AC selected from the group consisting of ximelagatran and AZD0837, wherein the maximum AF episode duration is reduced to less than about 20 hours, less than about 10 hours, or less than about 5 hours, and wherein the patient was refractory to one or more anti-arrhythmic drugs.

In another aspect, the invention provides methods for reducing stroke rate comprising administering an amount of multiple ion channel blocker selected from the group consisting of dronedarone, budiodarone, vernakalant, celivarone, and AZD1305 effective to reduce AF episode duration and an effective amount of AC selected from the group consisting of ximelagatran and AZD0837, wherein the average AF episode duration is reduced to less than about 24 hours, less than about 5 hours, less than about 3 hours, or less than about 1 hour, and wherein the patient was refractory to one or more anti-arrhythmic drugs.

In another aspect, the invention provides methods for reducing stroke rate comprising administering an amount of multiple ion channel blocker selected from the group consisting of dronedarone, budiodarone, vernakalant, celivarone, and AZD1305 effective to reduce AF episode duration and an effective amount of AC selected from the group consisting of ximelagatran and AZD0837, wherein the maximum AF episode duration is reduced to less than about 20 hours, less than about 10 hours, or less than about 5 hours, and wherein the patient was refractory to one or more anti-arrhythmic drugs.

In another aspect, the invention provides methods for reducing stroke rate comprising administering an amount of budiodarone effective to reduce AF episode duration and an effective amount of AC selected from the group consisting of ximelagatran and AZD0837, wherein the average AF episode duration is reduced to less than about 24 hours, less than about 5 hours, less than about 3 hours, or less than about 1 hour, and wherein the patient was refractory to one or more anti-arrhythmic drugs.

In another aspect, the invention provides methods for reducing stroke rate comprising administering an amount budiodarone effective to reduce AF episode duration and an effective amount of AC selected from the group consisting of ximelagatran and AZD0837, wherein the maximum AF episode duration is reduced to less than about 20 hours, less than about 10 hours, or less than about 5 hours, and wherein the patient was refractory to one or more anti-arrhythmic drugs.

In another aspect, the invention provides methods for reducing stroke rate comprising administering an amount of multiple ion channel blocker selected from the group consisting of amiodarone, dronedarone, budiodarone, vernakalant, celivarone, and AZD1305 effective to reduce AF episode duration and an effective amount of apixaban, wherein the average AF episode duration is reduced to less than about 24 hours, less than about 5 hours, less than about 3 hours, or less than about 1 hour, and wherein the patient was refractory to one or more anti-arrhythmic drugs.

In another aspect, the invention provides methods for reducing stroke rate comprising administering an amount of multiple ion channel blocker selected from the group consisting of amiodarone, dronedarone, budiodarone, vernakalant, celivarone, and AZD1305 effective to reduce AF episode duration and an effective amount of apixaban, wherein the maximum AF episode duration is reduced to less than about 20 hours, less than about 10 hours, or less than about 5 hours, and wherein the patient was refractory to one or more anti-arrhythmic drugs.

In another aspect, the invention provides methods for reducing stroke rate comprising administering an amount of multiple ion channel blocker selected from the group consisting of dronedarone, budiodarone, vernakalant, celivarone, and AZD1305 effective to reduce AF episode duration and an effective amount of apixaban, wherein the average AF episode duration is reduced to less than about 24 hours, less than about 5 hours, less than about 3 hours, or less than about 1 hour, and wherein the patient was refractory to one or more anti-arrhythmic drugs.

In another aspect, the invention provides methods for reducing stroke rate comprising administering an amount of multiple ion channel blocker selected from the group consisting of dronedarone, budiodarone, vernakalant, celivarone, and AZD1305 effective to reduce AF episode duration and an effective amount of apixaban, wherein the maximum AF episode duration is reduced to less than about 20 hours, less than about 10 hours, or less than about 5 hours, and wherein the patient was refractory to one or more anti-arrhythmic drugs.

In another aspect, the invention provides methods for reducing stroke rate comprising administering an amount of budiodarone effective to reduce AF episode duration and an effective amount of apixaban, wherein the average AF episode duration is reduced to less than about 24 hours, less than about 5 hours, less than about 3 hours, or less than about 1 hour, and wherein the patient was refractory to one or more anti-arrhythmic drugs.

In another aspect, the invention provides methods for reducing stroke rate comprising administering an amount budiodarone effective to reduce AF episode duration and an effective amount of apixaban, wherein the maximum AF episode duration is reduced to less than about 20 hours, less than about 10 hours, or less than about 5 hours, and wherein the patient was refractory to one or more anti-arrhythmic drugs.

In another aspect, the invention provides methods for reducing stroke rate comprising administering an amount of multiple ion channel blocker selected from the group consisting of amiodarone, dronedarone, budiodarone, vernakalant, celivarone, and AZD1305 effective to reduce AF episode duration and an effective amount of rivaroxaban, wherein the average AF episode duration is reduced to less than about 24 hours, less than about 5 hours, less than about 3 hours, or less than about 1 hour, and wherein the patient was refractory to one or more anti-arrhythmic drugs.

In another aspect, the invention provides methods for reducing stroke rate comprising administering an amount of multiple ion channel blocker selected from the group consisting of amiodarone, dronedarone, budiodarone, vernakalant, celivarone, and AZD1305 effective to reduce AF episode duration and an effective amount of rivaroxaban, wherein the maximum AF episode duration is reduced to less than about 20 hours, less than about 10 hours, or less than about 5 hours, and wherein the patient was refractory to one or more anti-arrhythmic drugs.

In another aspect, the invention provides methods for reducing stroke rate comprising administering an amount of multiple ion channel blocker selected from the group consisting of dronedarone, budiodarone, vernakalant, celivarone, and AZD1305 effective to reduce AF episode duration and an effective amount of rivaroxaban, wherein the average AF episode duration is reduced to less than about 24 hours, less than about 5 hours, less than about 3 hours, or less than about 1 hour, and wherein the patient was refractory to one or more anti-arrhythmic drugs.

In another aspect, the invention provides methods for reducing stroke rate comprising administering an amount of multiple ion channel blocker selected from the group consisting of dronedarone, budiodarone, vernakalant, celivarone, and AZD1305 effective to reduce AF episode duration and an effective amount of rivaroxaban, wherein the maximum AF episode duration is reduced to less than about 20 hours, less than about 10 hours, or less than about 5 hours, and wherein the patient was refractory to one or more anti-arrhythmic drugs.

In another aspect, the invention provides methods for reducing stroke rate comprising administering an amount of budiodarone effective to reduce AF episode duration and an effective amount of rivaroxaban, wherein the average AF episode duration is reduced to less than about 24 hours, less than about 5 hours, less than about 3 hours, or less than about 1 hour, and wherein the patient was refractory to one or more anti-arrhythmic drugs.

In another aspect, the invention provides methods for reducing stroke rate comprising administering an amount budiodarone effective to reduce AF episode duration and an effective amount of rivaroxaban, wherein the maximum AF episode duration is reduced to less than about 20 hours, less than about 10 hours, or less than about 5 hours, and wherein the patient was refractory to one or more anti-arrhythmic drugs.

In another aspect, the invention provides methods for reducing stroke rate comprising administering an amount of multiple ion channel blocker selected from the group consisting of amiodarone, dronedarone, budiodarone, vernakalant, celivarone, and AZD1305 effective to reduce AF episode duration and an effective amount of tecarfarin, wherein the average AF episode duration is reduced to less than about 24 hours, less than about 5 hours, less than about 3 hours, or less than about 1 hour, and wherein the patient was refractory to one or more anti-arrhythmic drugs.

In another aspect, the invention provides methods for reducing stroke rate comprising administering an amount of multiple ion channel blocker selected from the group consisting of amiodarone, dronedarone, budiodarone, vernakalant, celivarone, and AZD1305 effective to reduce AF episode duration and an effective amount of tecarfarin, wherein the maximum AF episode duration is reduced to less than about 20 hours, less than about 10 hours, or less than about 5 hours, and wherein the patient was refractory to one or more anti-arrhythmic drugs.

In another aspect, the invention provides methods for reducing stroke rate comprising administering an amount of multiple ion channel blocker selected from the group consisting of dronedarone, budiodarone, vernakalant, celivarone, and AZD1305 effective to reduce AF episode duration and an effective amount of tecarfarin, wherein the average AF episode duration is reduced to less than about 24 hours, less than about 5 hours, less than about 3 hours, or less than about 1 hour, and wherein the patient was refractory to one or more anti-arrhythmic drugs.

In another aspect, the invention provides methods for reducing stroke rate comprising administering an amount of multiple ion channel blocker selected from the group consisting of dronedarone, budiodarone, vernakalant, celivarone, and AZD1305 effective to reduce AF episode duration and an effective amount of tecarfarin, wherein the maximum AF episode duration is reduced to less than about 20 hours, less than about 10 hours, or less than about 5 hours, and wherein the patient was refractory to one or more anti-arrhythmic drugs.

In another aspect, the invention provides methods for reducing stroke rate comprising administering an amount of budiodarone effective to reduce AF episode duration and an effective amount of tecarfarin, wherein the average AF episode duration is reduced to less than about 24 hours, less than about 5 hours, less than about 3 hours, or less than about 1 hour, and wherein the patient was refractory to one or more anti-arrhythmic drugs.

In another aspect, the invention provides methods for reducing stroke rate comprising administering an amount budiodarone effective to reduce AF episode duration and an effective amount of tecarfarin, wherein the maximum AF episode duration is reduced to less than about 20 hours, less than about 10 hours, or less than about 5 hours, and wherein the patient was refractory to one or more anti-arrhythmic drugs.

In one aspect, the invention provides methods for reducing stroke rate comprising administering an amount of multiple ion channel blocker selected from the group consisting of amiodarone, dronedarone, budiodarone, vernakalant, celivarone, and AZD1305 effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the reduced stroke rate is less than the age-adjusted overall stroke rate, and wherein the patient was refractory to one or more anti-arrhythmic drugs.

In another aspect, the invention provides methods for reducing stroke rate comprising administering an amount of multiple ion channel blocker selected from the group consisting of amiodarone, dronedarone, budiodarone, vernakalant, celivarone, and AZD1305 effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the average AF episode duration is reduced to less than about 24 hours, less than about 5 hours, less than about 3 hours, or less than about 1 hour, and wherein the reduced stroke rate is less than the age-adjusted overall stroke rate, and wherein the patient was refractory to one or more anti-arrhythmic drugs.

In another aspect, the invention provides methods for reducing stroke rate comprising administering an amount of multiple ion channel blocker selected from the group consisting of amiodarone, dronedarone, budiodarone, vernakalant, celivarone, and AZD1305 effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the maximum AF episode duration is reduced to less than about 20 hours, less than about 10 hours, or less than about 5 hours, and wherein the reduced stroke rate is less than the age-adjusted overall stroke rate, and wherein the patient was refractory to one or more anti-arrhythmic drugs.

In another aspect, the invention provides methods for reducing stroke rate comprising administering an amount of multiple ion channel blocker selected from the group consisting of dronedarone, budiodarone, vernakalant, celivarone, and AZD1305 effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the average AF episode duration is reduced to less than about 24 hours, less than about 5 hours, less than about 3 hours, or less than about 1 hour, and wherein the reduced stroke rate is less than the age-adjusted overall stroke rate, and wherein the patient was refractory to one or more anti-arrhythmic drugs.

In another aspect, the invention provides methods for reducing stroke rate comprising administering an amount of multiple ion channel blocker selected from the group consisting of dronedarone, budiodarone, vernakalant, celivarone, and AZD1305 effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the maximum AF episode duration is reduced to less than about 20 hours, less than about 10 hours, or less than about 5 hours, and wherein the reduced stroke rate is less than the age-adjusted overall stroke rate, and wherein the patient was refractory to one or more anti-arrhythmic drugs.

In another aspect, the invention provides methods for reducing stroke rate comprising administering an amount of budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the average AF episode duration is reduced to less than about 24 hours, less than about 5 hours, less than about 3 hours, or less than about 1 hour, and wherein the reduced stroke rate is less than the age-adjusted overall stroke rate, and wherein the patient was refractory to one or more anti-arrhythmic drugs.

In another aspect, the invention provides methods for reducing stroke rate comprising administering an amount budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the maximum AF episode duration is reduced to less than about 20 hours, less than about 10 hours, or less than about 5 hours, and wherein the reduced stroke rate is less than the age-adjusted overall stroke rate, and wherein the patient was refractory to one or more anti-arrhythmic drugs.

In another aspect, the invention provides methods for reducing stroke rate comprising administering an amount of multiple ion channel blocker selected from the group consisting of amiodarone, dronedarone, budiodarone, vernakalant, celivarone, and AZD1305 effective to reduce AF episode duration and an effective amount of AC selected from the group consisting of tecarfarin, dabigatran etexilate, ximelagatran, AZD0837, apixaban and rivaroxaban, wherein the average AF episode duration is reduced to less than about 24 hours, less than about 5 hours, less than about 3 hours, or less than about 1 hour, and wherein the reduced stroke rate is less than the age-adjusted overall stroke rate, and wherein the patient was refractory to one or more anti-arrhythmic drugs.

In another aspect, the invention provides methods for reducing stroke rate comprising administering an amount of multiple ion channel blocker selected from the group consisting of amiodarone, dronedarone, budiodarone, vernakalant, celivarone, and AZD1305 effective to reduce AF episode duration and an effective amount of AC selected from the group consisting of tecarfarin, dabigatran etexilate, ximelagatran, AZD0837, apixaban and rivaroxaban, wherein the maximum AF episode duration is reduced to less than about 20 hours, less than about 10 hours, or less than about 5 hours, and wherein the reduced stroke rate is less than the age-adjusted overall stroke rate, and wherein the patient was refractory to one or more anti-arrhythmic drugs.

In another aspect, the invention provides methods for reducing stroke rate comprising administering an amount of multiple ion channel blocker selected from the group consisting of dronedarone, budiodarone, vernakalant, celivarone, and AZD1305 effective to reduce AF episode duration and an effective amount of AC selected from the group consisting of tecarfarin, dabigatran etexilate, ximelagatran, AZD0837, apixaban and rivaroxaban, wherein the average AF episode duration is reduced to less than about 24 hours, less than about 5 hours, less than about 3 hours, or less than about 1 hour, and wherein the reduced stroke rate is less than the age-adjusted overall stroke rate, and wherein the patient was refractory to one or more anti-arrhythmic drugs.

In another aspect, the invention provides methods for reducing stroke rate comprising administering an amount of multiple ion channel blocker selected from the group consisting of dronedarone, budiodarone, vernakalant, celivarone, and AZD1305 effective to reduce AF episode duration and an effective amount of AC selected from the group consisting of tecarfarin, dabigatran etexilate, ximelagatran, AZD0837, apixaban and rivaroxaban, wherein the maximum AF episode duration is reduced to less than about 20 hours, less than about 10 hours, or less than about 5 hours, and wherein the reduced stroke rate is less than the age-adjusted overall stroke rate, and wherein the patient was refractory to one or more anti-arrhythmic drugs.

In another aspect, the invention provides methods for reducing stroke rate comprising administering an amount of budiodarone effective to reduce AF episode duration and an effective amount of AC selected from the group consisting of tecarfarin, dabigatran etexilate, ximelagatran, AZD0837, apixaban and rivaroxaban, wherein the average AF episode duration is reduced to less than about 24 hours, less than about 5 hours, less than about 3 hours, or less than about 1 hour, and wherein the reduced stroke rate is less than the age-adjusted overall stroke rate, and wherein the patient was refractory to one or more anti-arrhythmic drugs.

In another aspect, the invention provides methods for reducing stroke rate comprising administering an amount budiodarone effective to reduce AF episode duration and an effective amount of AC selected from the group consisting of tecarfarin, dabigatran etexilate, ximelagatran, AZD0837, apixaban and rivaroxaban, wherein the maximum AF episode duration is reduced to less than about 20 hours, less than about 10 hours, or less than about 5 hours, and wherein the reduced stroke rate is less than the age-adjusted overall stroke rate, and wherein the patient was refractory to one or more anti-arrhythmic drugs.

In another aspect, the invention provides methods for reducing stroke rate comprising administering an amount of multiple ion channel blocker selected from the group consisting of amiodarone, dronedarone, budiodarone, vernakalant, celivarone, and AZD1305 effective to reduce AF episode duration and an effective amount of dabigatran etexilate, wherein the average AF episode duration is reduced to less than about 24 hours, less than about 5 hours, less than about 3 hours, or less than about 1 hour, wherein the reduced stroke rate is less than the age-adjusted overall stroke rate, and wherein the patient was refractory to one or more anti-arrhythmic drugs.

In another aspect, the invention provides methods for reducing stroke rate comprising administering an amount of multiple ion channel blocker selected from the group consisting of amiodarone, dronedarone, budiodarone, vernakalant, celivarone, and AZD1305 effective to reduce AF episode duration and an effective amount of dabigatran etexilate, wherein the maximum AF episode duration is reduced to less than about 20 hours, less than about 10 hours, or less than about 5 hours, and wherein the reduced stroke rate is less than the age-adjusted overall stroke rate, and wherein the patient was refractory to one or more anti-arrhythmic drugs.

In another aspect, the invention provides methods for reducing stroke rate comprising administering an amount of multiple ion channel blocker selected from the group consisting of dronedarone, budiodarone, vernakalant, celivarone, and AZD1305 effective to reduce AF episode duration and an effective amount of dabigatran etexilate, wherein the maximum AF episode duration is reduced to less than about 20 hours, less than about 10 hours, or less than about 5 hours, and wherein the reduced stroke rate is less than the age-adjusted overall stroke rate, and wherein the patient was refractory to one or more anti-arrhythmic drugs.

In another aspect, the invention provides methods for reducing stroke rate comprising administering an amount of multiple ion channel blocker selected from the group consisting of dronedarone, budiodarone, vernakalant, celivarone, and AZD1305 effective to reduce AF episode duration and an effective amount of dabigatran etexilate, wherein the average AF episode duration is reduced to less than about 24 hours, less than about 5 hours, less than about 3 hours, or less than about 1 hour, and wherein the reduced stroke rate is less than the age-adjusted overall stroke rate, and wherein the patient was refractory to one or more anti-arrhythmic drugs.

In another aspect, the invention provides methods for reducing stroke rate comprising administering an amount of budiodarone effective to reduce AF episode duration and an effective amount of dabigatran etexilate, wherein the average AF episode duration is reduced to less than about 24 hours, less than about 5 hours, less than about 3 hours, or less than about 1 hour, and wherein the reduced stroke rate is less than the age-adjusted overall stroke rate, and wherein the patient was refractory to one or more anti-arrhythmic drugs.

In another aspect, the invention provides methods for reducing stroke rate comprising administering an amount budiodarone effective to reduce AF episode duration and an effective amount of dabigatran etexilate, wherein the maximum AF episode duration is reduced to less than about 20 hours, less than about 10 hours, or less than about 5 hours, and wherein the reduced stroke rate is less than the age-adjusted overall stroke rate, and wherein the patient was refractory to one or more anti-arrhythmic drugs.

In another aspect, the invention provides methods for reducing stroke rate comprising administering an amount of multiple ion channel blocker selected from the group consisting of amiodarone, dronedarone, budiodarone, vernakalant, celivarone, and AZD1305 effective to reduce AF episode duration and an effective amount of AC selected from the group consisting of ximelagatran and AZD0837, wherein the average AF episode duration is reduced to less than about 24 hours, less than about 5 hours, less than about 3 hours, or less than about 1 hour, and wherein the reduced stroke rate is less than the age-adjusted overall stroke rate, and wherein the patient was refractory to one or more anti-arrhythmic drugs.

In another aspect, the invention provides methods for reducing stroke rate comprising administering an amount of multiple ion channel blocker selected from the group consisting of amiodarone, dronedarone, budiodarone, vernakalant, celivarone, and AZD1305 effective to reduce AF episode duration and an effective amount of AC selected from the group consisting of ximelagatran and AZD0837, wherein the maximum AF episode duration is reduced to less than about 20 hours, less than about 10 hours, or less than about 5 hours, and wherein the reduced stroke rate is less than the age-adjusted overall stroke rate, and wherein the patient was refractory to one or more anti-arrhythmic drugs.

In another aspect, the invention provides methods for reducing stroke rate comprising administering an amount of multiple ion channel blocker selected from the group consisting of dronedarone, budiodarone, vernakalant, celivarone, and AZD1305 effective to reduce AF episode duration and an effective amount of AC selected from the group consisting of ximelagatran and AZD0837, wherein the average AF episode duration is reduced to less than about 24 hours, less than about 5 hours, less than about 3 hours, or less than about 1 hour, and wherein the reduced stroke rate is less than the age-adjusted overall stroke rate, and wherein the patient was refractory to one or more anti-arrhythmic drugs.

In another aspect, the invention provides methods for reducing stroke rate comprising administering an amount of multiple ion channel blocker selected from the group consisting of dronedarone, budiodarone, vernakalant, celivarone, and AZD1305 effective to reduce AF episode duration and an effective amount of AC selected from the group consisting of ximelagatran and AZD0837, wherein the maximum AF episode duration is reduced to less than about 20 hours, less than about 10 hours, or less than about 5 hours, and wherein the reduced stroke rate is less than the age-adjusted overall stroke rate, and wherein the patient was refractory to one or more anti-arrhythmic drugs.

In another aspect, the invention provides methods for reducing stroke rate comprising administering an amount budiodarone effective to reduce AF episode duration and an effective amount of AC selected from the group consisting of ximelagatran and AZD0837, wherein the average AF episode duration is reduced to less than about 24 hours, less than about 5 hours, less than about 3 hours, or less than about 1 hour, and wherein the reduced stroke rate is less than the age-adjusted overall stroke rate, and wherein the patient was refractory to one or more anti-arrhythmic drugs.

In another aspect, the invention provides methods for reducing stroke rate comprising administering an amount budiodarone effective to reduce AF episode duration and an effective amount of AC selected from the group consisting of ximelagatran and AZD0837, wherein the maximum AF episode duration is reduced to less than about 20 hours, less than about 10 hours, or less than about 5 hours, and wherein the reduced stroke rate is less than the age-adjusted overall stroke rate, and wherein the patient was refractory to one or more anti-arrhythmic drugs.

In another aspect, the invention provides methods for reducing stroke rate comprising administering an amount of multiple ion channel blocker selected from the group consisting of amiodarone, dronedarone, budiodarone, vernakalant, celivarone, and AZD1305 effective to reduce AF episode duration and an effective amount of apixaban, wherein the average AF episode duration is reduced to less than about 24 hours, less than about 5 hours, less than about 3 hours, or less than about 1 hour, and wherein the reduced stroke rate is less than the age-adjusted overall stroke rate, and wherein the patient was refractory to one or more anti-arrhythmic drugs.

In another aspect, the invention provides methods for reducing stroke rate comprising administering an amount of multiple ion channel blocker selected from the group consisting of amiodarone, dronedarone, budiodarone, vernakalant, celivarone, and AZD1305 effective to reduce AF episode duration and an effective amount of apixaban, wherein the maximum AF episode duration is reduced to less than about 20 hours, less than about 10 hours, or less than about 5 hours, and wherein the reduced stroke rate is less than the age-adjusted overall stroke rate, and wherein the patient was refractory to one or more anti-arrhythmic drugs.

In another aspect, the invention provides methods for reducing stroke rate comprising administering an amount of multiple ion channel blocker selected from the group consisting of dronedarone, budiodarone, vernakalant, celivarone, and AZD1305 effective to reduce AF episode duration and an effective amount of apixaban, wherein the average AF episode duration is reduced to less than about 24 hours, less than about 5 hours, less than about 3 hours, or less than about 1 hour, and wherein the reduced stroke rate is less than the age-adjusted overall stroke rate, and wherein the patient was refractory to one or more anti-arrhythmic drugs.

In another aspect, the invention provides methods for reducing stroke rate comprising administering an amount of multiple ion channel blocker selected from the group consisting of dronedarone, budiodarone, vernakalant, celivarone, and AZD1305 effective to reduce AF episode duration and an effective amount of apixaban, wherein the maximum AF episode duration is reduced to less than about 20 hours, less than about 10 hours, or less than about 5 hours, and wherein the reduced stroke rate is less than the age-adjusted overall stroke rate, and wherein the patient was refractory to one or more anti-arrhythmic drugs.

In another aspect, the invention provides methods for reducing stroke rate comprising administering an amount of budiodarone effective to reduce AF episode duration and an effective amount of apixaban, wherein the average AF episode duration is reduced to less than about 24 hours, less than about 5 hours, less than about 3 hours, or less than about 1 hour, and wherein the reduced stroke rate is less than the age-adjusted overall stroke rate, and wherein the patient was refractory to one or more anti-arrhythmic drugs.

In another aspect, the invention provides methods for reducing stroke rate comprising administering an amount budiodarone effective to reduce AF episode duration and an effective amount of apixaban, wherein the maximum AF episode duration is reduced to less than about 20 hours, less than about 10 hours, or less than about 5 hours, and wherein the reduced stroke rate is less than the age-adjusted overall stroke rate, and wherein the patient was refractory to one or more anti-arrhythmic drugs.

In another aspect, the invention provides methods for reducing stroke rate comprising administering an amount of multiple ion channel blocker selected from the group consisting of amiodarone, dronedarone, budiodarone, vernakalant, celivarone, and AZD1305 effective to reduce AF episode duration and an effective amount of rivaroxaban, wherein the average AF episode duration is reduced to less than about 24 hours, less than about 5 hours, less than about 3 hours, or less than about 1 hour, and wherein the reduced stroke rate is less than the age-adjusted overall stroke rate, and wherein the patient was refractory to one or more anti-arrhythmic drugs.

In another aspect, the invention provides methods for reducing stroke rate comprising administering an amount of multiple ion channel blocker selected from the group consisting of amiodarone, dronedarone, budiodarone, vernakalant, celivarone, and AZD1305 effective to reduce AF episode duration and an effective amount of rivaroxaban, wherein the maximum AF episode duration is reduced to less than about 20 hours, less than about 10 hours, or less than about 5 hours, and wherein the reduced stroke rate is less than the age-adjusted overall stroke rate, and wherein the patient was refractory to one or more anti-arrhythmic drugs.

In another aspect, the invention provides methods for reducing stroke rate comprising administering an amount of multiple ion channel blocker selected from the group consisting of dronedarone, budiodarone, vernakalant, celivarone, and AZD1305 effective to reduce AF episode duration and an effective amount of rivaroxaban, wherein the average AF episode duration is reduced to less than about 24 hours, less than about 5 hours, less than about 3 hours, or less than about 1 hour, and wherein the reduced stroke rate is less than the age-adjusted overall stroke rate, and wherein the patient was refractory to one or more anti-arrhythmic drugs.

In another aspect, the invention provides methods for reducing stroke rate comprising administering an amount of multiple ion channel blocker selected from the group consisting of dronedarone, budiodarone, vernakalant, celivarone, and AZD1305 effective to reduce AF episode duration and an effective amount of rivaroxaban, wherein the maximum AF episode duration is reduced to less than about 20 hours, less than about 10 hours, or less than about 5 hours, and wherein the reduced stroke rate is less than the age-adjusted overall stroke rate, and wherein the patient was refractory to one or more anti-arrhythmic drugs.

In another aspect, the invention provides methods for reducing stroke rate comprising administering an amount of budiodarone effective to reduce AF episode duration and an effective amount of rivaroxaban, wherein the average AF episode duration is reduced to less than about 24 hours, less than about 5 hours, less than about 3 hours, or less than about 1 hour, and wherein the reduced stroke rate is less than the age-adjusted overall stroke rate, and wherein the patient was refractory to one or more anti-arrhythmic drugs.

In another aspect, the invention provides methods for reducing stroke rate comprising administering an amount budiodarone effective to reduce AF episode duration and an effective amount of rivaroxaban, wherein the maximum AF episode duration is reduced to less than about 20 hours, less than about 10 hours, or less than about 5 hours, and wherein the reduced stroke rate is less than the age-adjusted overall stroke rate, and wherein the patient was refractory to one or more anti-arrhythmic drugs.

In another aspect, the invention provides methods for reducing stroke rate comprising administering an amount of multiple ion channel blocker selected from the group consisting of amiodarone, dronedarone, budiodarone, vernakalant, celivarone, and AZD1305 effective to reduce AF episode duration and an effective amount of tecarfarin, wherein the average AF episode duration is reduced to less than about 24 hours, less than about 5 hours, less than about 3 hours, or less than about 1 hour, and wherein the reduced stroke rate is less than the age-adjusted overall stroke rate, and wherein the patient was refractory to one or more anti-arrhythmic drugs.

In another aspect, the invention provides methods for reducing stroke rate comprising administering an amount of multiple ion channel blocker selected from the group consisting of amiodarone, dronedarone, budiodarone, vernakalant, celivarone, and AZD1305 effective to reduce AF episode duration and an effective amount of tecarfarin, wherein the maximum AF episode duration is reduced to less than about 20 hours, less than about 10 hours, or less than about 5 hours, and wherein the reduced stroke rate is less than the age-adjusted overall stroke rate, and wherein the patient was refractory to one or more anti-arrhythmic drugs.

In another aspect, the invention provides methods for reducing stroke rate comprising administering an amount of multiple ion channel blocker selected from the group consisting of dronedarone, budiodarone, vernakalant, celivarone, and AZD1305 effective to reduce AF episode duration and an effective amount of tecarfarin, wherein the average AF episode duration is reduced to less than about 24 hours, less than about 5 hours, less than about 3 hours, or less than about 1 hour, and wherein the reduced stroke rate is less than the age-adjusted overall stroke rate, and wherein the patient was refractory to one or more anti-arrhythmic drugs.

In another aspect, the invention provides methods for reducing stroke rate comprising administering an amount of multiple ion channel blocker selected from the group consisting of dronedarone, budiodarone, vernakalant, celivarone, and AZD1305 effective to reduce AF episode duration and an effective amount of tecarfarin, wherein the maximum AF episode duration is reduced to less than about 20 hours, less than about 10 hours, or less than about 5 hours, and wherein the reduced stroke rate is less than the age-adjusted overall stroke rate, and wherein the patient was refractory to one or more anti-arrhythmic drugs.

In another aspect, the invention provides methods for reducing stroke rate comprising administering an amount of budiodarone effective to reduce AF episode duration and an effective amount of tecarfarin, wherein the average AF episode duration is reduced to less than about 24 hours, less than about 5 hours, less than about 3 hours, or less than about 1 hour, and wherein the reduced stroke rate is less than the age-adjusted overall stroke rate, and wherein the patient was refractory to one or more anti-arrhythmic drugs.

In another aspect, the invention provides methods for reducing stroke rate comprising administering an amount budiodarone effective to reduce AF episode duration and an effective amount of tecarfarin, wherein the maximum AF episode duration is reduced to less than about 20 hours, less than about 10 hours, or less than about 5 hours, and wherein the reduced stroke rate is less than the age-adjusted overall stroke rate, and wherein the patient was refractory to one or more anti-arrhythmic drugs.

In yet another aspect, the invention provides methods for preventing atrial remodeling comprising administering an amount of multiple ion channel blocker selected from the group consisting of amiodarone, dronedarone, budiodarone, vernakalant, celivarone, and AZD1305 effective to reduce atrial fibrillation (AF) episode duration and an effective amount of anticoagulant (AC) selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin.

In yet another aspect, the invention provides methods for preventing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the average AF episode duration is reduced to less than about 24 hours, less than about 5 hours, less than about 3 hours, or less than about 1 hour.

In yet another aspect, the invention provides methods for preventing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the maximum AF episode duration is reduced to less than about 20 hours, less than about 10 hours, or less than about 5 hours.

In yet another aspect, the invention provides methods for preventing atrial remodeling comprising administering an amount of multiple ion channel blocker selected from the group consisting of budiodarone, dronedarone, celivarone, AZD1305 and vernakalant effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin.

In yet another aspect, the invention provides methods for preventing atrial remodeling comprising administering an amount of multiple ion channel blocker selected from the group consisting of dronedarone, budiodarone, vernakalant, celivarone, and AZD1305 effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the average AF episode duration is reduced to less than about 24 hours, less than about 5 hours, less than about 3 hours, or less than about 1 hour.

In yet another aspect, the invention provides methods for preventing atrial remodeling comprising administering an amount of multiple ion channel blocker selected from the group consisting of dronedarone, budiodarone, vernakalant, celivarone, and AZD1305 effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the maximum AF episode duration is reduced to less than about 20 hours, less than about 10 hours, or less than about 5 hours.

In yet another aspect, the invention provides methods for preventing atrial remodeling comprising administering an amount of budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin.

In yet another aspect, the invention provides methods for preventing atrial remodeling comprising administering an amount of budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the average AF episode duration is reduced to less than about 24 hours, less than about 5 hours, less than about 3 hours, or less than about 1 hour.

In yet another aspect, the invention provides methods for preventing atrial remodeling comprising administering an amount of budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the maximum AF episode duration is reduced to less than about 20 hours, less than about 10 hours, or less than about 5 hours.

In yet another aspect, the invention provides methods for preventing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of AC selected from the group consisting of tecarfarin, dabigatran etexilate, ximelagatran, AZD0837, apixaban and rivaroxaban.

In yet another aspect, the invention provides methods for preventing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of AC selected from the group consisting of tecarfarin, dabigatran etexilate, ximelagatran, AZD0837, apixaban and rivaroxaban, wherein the average AF episode duration is reduced to less than about 24 hours, less than about 5 hours, less than about 3 hours, or less than about 1 hour.

In yet another aspect, the invention provides methods for preventing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of AC selected from the group consisting of tecarfarin, dabigatran etexilate, ximelagatran, AZD0837, apixaban and rivaroxaban, wherein the maximum AF episode duration is reduced to less than about 20 hours, less than about 10 hours, or less than about 5 hours.

In yet another aspect, the invention provides methods for preventing atrial remodeling comprising administering an amount of multiple ion channel blocker selected from the group consisting of budiodarone, dronedarone, celivarone, AZD1305 and vernakalant effective to reduce AF episode duration and an effective amount of AC selected from the group consisting of tecarfarin, dabigatran etexilate, ximelagatran, AZD0837, apixaban and rivaroxaban.

In yet another aspect, the invention provides methods for preventing atrial remodeling comprising administering an amount of multiple ion channel blocker selected from the group consisting of dronedarone, budiodarone, vernakalant, celivarone, and AZD1305 effective to reduce AF episode duration and an effective amount of AC selected from the group consisting of tecarfarin, dabigatran etexilate, ximelagatran, AZD0837, apixaban and rivaroxaban, wherein the average AF episode duration is reduced to less than about 24 hours, less than about 5 hours, less than about 3 hours, or less than about 1 hour.

In yet another aspect, the invention provides methods for preventing atrial remodeling comprising administering an amount of multiple ion channel blocker selected from the group consisting of dronedarone, budiodarone, vernakalant, celivarone, and AZD1305 effective to reduce AF episode duration and an effective amount of AC selected from the group consisting of tecarfarin, dabigatran etexilate, ximelagatran, AZD0837, apixaban and rivaroxaban, wherein the maximum AF episode duration is reduced to less than about 20 hours, less than about 10 hours, or less than about 5 hours.

In yet another aspect, the invention provides methods for preventing atrial remodeling comprising administering an amount of budiodarone effective to reduce AF episode duration and an effective amount of AC selected from the group consisting of tecarfarin, dabigatran etexilate, ximelagatran, AZD0837, apixaban and rivaroxaban.

In yet another aspect, the invention provides methods for preventing atrial remodeling comprising administering an amount of budiodarone effective to reduce AF episode duration and an effective amount of AC selected from the group consisting of tecarfarin, dabigatran etexilate, ximelagatran, AZD0837, apixaban and rivaroxaban, wherein the average AF episode duration is reduced to less than about 24 hours, less than about 5 hours, less than about 3 hours, or less than about 1 hour.

In yet another aspect, the invention provides methods for preventing atrial remodeling comprising administering an amount of budiodarone effective to reduce AF episode duration and an effective amount of AC selected from the group consisting of tecarfarin, dabigatran etexilate, ximelagatran, AZD0837, apixaban and rivaroxaban, wherein the maximum AF episode duration is reduced to less than about 20 hours, less than about 10 hours, or less than about 5 hours.

In yet another aspect, the invention provides methods for preventing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of dabigatran etexilate wherein the average AF episode duration is reduced to less than about 24 hours, less than about 5 hours, less than about 3 hours, or less than about 1 hour.

In yet another aspect, the invention provides methods for preventing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of dabigatran etexilate, wherein the maximum AF episode duration is reduced to less than about 20 hours, less than about 10 hours, or less than about 5 hours.

In yet another aspect, the invention provides methods for preventing atrial remodeling comprising administering an amount of multiple ion channel blocker selected from the group consisting of dronedarone, budiodarone, vernakalant, celivarone, and AZD1305 effective to reduce AF episode duration and an effective amount of dabigatran etexilate, wherein the average AF episode duration is reduced to less than about 24 hours, less than about 5 hours, less than about 3 hours, or less than about 1 hour.

In yet another aspect, the invention provides methods for preventing atrial remodeling comprising administering an amount of multiple ion channel blocker selected from the group consisting of dronedarone, budiodarone, vernakalant, celivarone, and AZD1305 effective to reduce AF episode duration and an effective amount of dabigatran etexilate, wherein the maximum AF episode duration is reduced to less than about 20 hours, less than about 10 hours, or less than about 5 hours.

In yet another aspect, the invention provides methods for preventing atrial remodeling comprising administering an amount of budiodarone effective to reduce AF episode duration and an effective amount of dabigatran etexilate, wherein the average AF episode duration is reduced to less than about 24 hours, less than about 5 hours, less than about 3 hours, or less than about 1 hour.

In yet another aspect, the invention provides methods for preventing atrial remodeling comprising administering an amount of budiodarone effective to reduce AF episode duration and an effective amount of dabigatran etexilate, wherein the maximum AF episode duration is reduced to less than about 20 hours, less than about 10 hours, or less than about 5 hours.

In yet another aspect, the invention provides methods for preventing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of AZD0837 or ximelagatran, wherein the average AF episode duration is reduced to less than about 24 hours, less than about 5 hours, less than about 3 hours, or less than about 1 hour.

In yet another aspect, the invention provides methods for preventing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of AZD0837 or ximelagatran, wherein the maximum AF episode duration is reduced to less than about 20 hours, less than about 10 hours, or less than about 5 hours.

In yet another aspect, the invention provides methods for preventing atrial remodeling comprising administering an amount of multiple ion channel blocker selected from the group consisting of dronedarone, budiodarone, vernakalant, celivarone, and AZD1305 effective to reduce AF episode duration and an effective amount of AZD0837 or ximelagatran, wherein the average AF episode duration is reduced to less than about 24 hours, less than about 5 hours, less than about 3 hours, or less than about 1 hour.

In yet another aspect, the invention provides methods for preventing atrial remodeling comprising administering an amount of multiple ion channel blocker selected from the group consisting of dronedarone, budiodarone, vernakalant, celivarone, and AZD1305 effective to reduce AF episode duration and an effective amount of AZD0837 or ximelagatran, wherein the maximum AF episode duration is reduced to less than about 20 hours, less than about 10 hours, or less than about 5 hours.

In yet another aspect, the invention provides methods for preventing atrial remodeling comprising administering an amount of budiodarone effective to reduce AF episode duration and an effective amount of AZD0837 or ximelagatran, wherein the average AF episode duration is reduced to less than about 24 hours, less than about 5 hours, less than about 3 hours, or less than about 1 hour.

In yet another aspect, the invention provides methods for preventing atrial remodeling comprising administering an amount of budiodarone effective to reduce AF episode duration and an effective amount of AZD0837 or ximelagatran, wherein the maximum AF episode duration is reduced to less than about 20 hours, less than about 10 hours, or less than about 5 hours.

In yet another aspect, the invention provides methods for preventing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of apixaban, wherein the average AF episode duration is reduced to less than about 24 hours, less than about 5 hours, less than about 3 hours, or less than about 1 hour.

In yet another aspect, the invention provides methods for preventing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of apixaban, wherein the maximum AF episode duration is reduced to less than about 20 hours, less than about 10 hours, or less than about 5 hours.

In yet another aspect, the invention provides methods for preventing atrial remodeling comprising administering an amount of multiple ion channel blocker selected from the group consisting of dronedarone, budiodarone, vernakalant, celivarone, and AZD1305 effective to reduce AF episode duration and an effective amount of apixaban, wherein the average AF episode duration is reduced to less than about 24 hours, less than about 5 hours, less than about 3 hours, or less than about 1 hour.

In yet another aspect, the invention provides methods for preventing atrial remodeling comprising administering an amount of multiple ion channel blocker selected from the group consisting of dronedarone, budiodarone, vernakalant, celivarone, and AZD1305 effective to reduce AF episode duration and an effective amount of apixaban, wherein the maximum AF episode duration is reduced to less than about 20 hours, less than about 10 hours, or less than about 5 hours.

In yet another aspect, the invention provides methods for preventing atrial remodeling comprising administering an amount of budiodarone effective to reduce AF episode duration and an effective amount of apixaban, wherein the average AF episode duration is reduced to less than about 24 hours, less than about 5 hours, less than about 3 hours, or less than about 1 hour.

In yet another aspect, the invention provides methods for preventing atrial remodeling comprising administering an amount of budiodarone effective to reduce AF episode duration and an effective amount of apixaban, wherein the maximum AF episode duration is reduced to less than about 20 hours, less than about 10 hours, or less than about 5 hours.

In yet another aspect, the invention provides methods for preventing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of rivaroxaban, wherein the average AF episode duration is reduced to less than about 24 hours, less than about 5 hours, less than about 3 hours, or less than about 1 hour.

In yet another aspect, the invention provides methods for preventing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of rivaroxaban, wherein the maximum AF episode duration is reduced to less than about 20 hours, less than about 10 hours, or less than about 5 hours.

In yet another aspect, the invention provides methods for preventing atrial remodeling comprising administering an amount of multiple ion channel blocker selected from the group consisting of dronedarone, budiodarone, vernakalant, celivarone, and AZD1305 effective to reduce AF episode duration and an effective amount of rivaroxaban, wherein the average AF episode duration is reduced to less than about 24 hours, less than about 5 hours, less than about 3 hours, or less than about 1 hour.

In yet another aspect, the invention provides methods for preventing atrial remodeling comprising administering an amount of multiple ion channel blocker selected from the group consisting of dronedarone, budiodarone, vernakalant, celivarone, and AZD1305 effective to reduce AF episode duration and an effective amount of rivaroxaban, wherein the maximum AF episode duration is reduced to less than about 20 hours, less than about 10 hours, or less than about 5 hours.

In yet another aspect, the invention provides methods for preventing atrial remodeling comprising administering an amount of budiodarone effective to reduce AF episode duration and an effective amount of rivaroxaban, wherein the average AF episode duration is reduced to less than about 24 hours, less than about 5 hours, less than about 3 hours, or less than about 1 hour.

In yet another aspect, the invention provides methods for preventing atrial remodeling comprising administering an amount of budiodarone effective to reduce AF episode duration and an effective amount of rivaroxaban, wherein the maximum AF episode duration is reduced to less than about 20 hours, less than about 10 hours, or less than about 5 hours.

In yet another aspect, the invention provides methods for preventing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of tecarfarin, wherein the average AF episode duration is reduced to less than about 24 hours, less than about 5 hours, less than about 3 hours, or less than about 1 hour.

In yet another aspect, the invention provides methods for preventing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of tecarfarin, wherein the maximum AF episode duration is reduced to less than about 20 hours, less than about 10 hours, or less than about 5 hours.

In yet another aspect, the invention provides methods for preventing atrial remodeling comprising administering an amount of multiple ion channel blocker selected from the group consisting of dronedarone, budiodarone, vernakalant, celivarone, and AZD1305 effective to reduce AF episode duration and an effective amount of tecarfarin, wherein the average AF episode duration is reduced to less than about 24 hours, less than about 5 hours, less than about 3 hours, or less than about 1 hour.

In yet another aspect, the invention provides methods for preventing atrial remodeling comprising administering an amount of multiple ion channel blocker selected from the group consisting of dronedarone, budiodarone, vernakalant, celivarone, and AZD1305 effective to reduce AF episode duration and an effective amount of tecarfarin, wherein the maximum AF episode duration is reduced to less than about 20 hours, less than about 10 hours, or less than about 5 hours.

In yet another aspect, the invention provides methods for preventing atrial remodeling comprising administering an amount of budiodarone effective to reduce AF episode duration and an effective amount of tecarfarin, wherein the average AF episode duration is reduced to less than about 24 hours, less than about 5 hours, less than about 3 hours, or less than about 1 hour.

In yet another aspect, the invention provides methods for preventing atrial remodeling comprising administering an amount of budiodarone effective to reduce AF episode duration and an effective amount of tecarfarin, wherein the maximum AF episode duration is reduced to less than about 20 hours, less than about 10 hours, or less than about 5 hours.

In yet another aspect, the invention provides methods for preventing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the average AF episode duration is reduced to less than about 24 hours, less than about 5 hours, less than about 3 hours, or less than about 1 hour, and wherein the patient was refractory to one or more anti-arrhythmic drugs.

In yet another aspect, the invention provides methods for preventing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the maximum AF episode duration is reduced to less than about 20 hours, less than about 10 hours, or less than about 5 hours, and wherein the patient was refractory to one or more anti-arrhythmic drugs.

In yet another aspect, the invention provides methods for preventing atrial remodeling comprising administering an amount of multiple ion channel blocker selected from the group consisting of dronedarone, budiodarone, vernakalant, celivarone, and AZD1305 effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the average AF episode duration is reduced to less than about 24 hours, less than about 5 hours, less than about 3 hours, or less than about 1 hour, and wherein the patient was refractory to one or more anti-arrhythmic drugs.

In yet another aspect, the invention provides methods for preventing atrial remodeling comprising administering an amount of multiple ion channel blocker selected from the group consisting of dronedarone, budiodarone, vernakalant, celivarone, and AZD1305 effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the maximum AF episode duration is reduced to less than about 20 hours, less than about 10 hours, or less than about 5 hours, and wherein the patient was refractory to one or more anti-arrhythmic drugs.

In yet another aspect, the invention provides methods for preventing atrial remodeling comprising administering an amount of budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the average AF episode duration is reduced to less than about 24 hours, less than about 5 hours, less than about 3 hours, or less than about 1 hour, and wherein the patient was refractory to one or more anti-arrhythmic drugs.

In yet another aspect, the invention provides methods for preventing atrial remodeling comprising administering an amount of budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the maximum AF episode duration is reduced to less than about 20 hours, less than about 10 hours, or less than about 5 hours, and wherein the patient was refractory to one or more anti-arrhythmic drugs.

In yet another aspect, the invention provides methods for preventing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of dabigatran etexilate wherein the average AF episode duration is reduced to less than about 24 hours, less than about 5 hours, less than about 3 hours, or less than about 1 hour, and wherein the patient was refractory to one or more anti-arrhythmic drugs.

In yet another aspect, the invention provides methods for preventing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of dabigatran etexilate, wherein the maximum AF episode duration is reduced to less than about 20 hours, less than about 10 hours, or less than about 5 hours, and wherein the patient was refractory to one or more anti-arrhythmic drugs.

In yet another aspect, the invention provides methods for preventing atrial remodeling comprising administering an amount of multiple ion channel blocker selected from the group consisting of dronedarone, budiodarone, vernakalant, celivarone, and AZD1305 effective to reduce AF episode duration and an effective amount of dabigatran etexilate, wherein the average AF episode duration is reduced to less than about 24 hours, less than about 5 hours, less than about 3 hours, or less than about 1 hour, and wherein the patient was refractory to one or more anti-arrhythmic drugs.

In yet another aspect, the invention provides methods for preventing atrial remodeling comprising administering an amount of multiple ion channel blocker selected from the group consisting of dronedarone, budiodarone, vernakalant, celivarone, and AZD1305 effective to reduce AF episode duration and an effective amount of dabigatran etexilate, wherein the maximum AF episode duration is reduced to less than about 20 hours, less than about 10 hours, or less than about 5 hours, and wherein the patient was refractory to one or more anti-arrhythmic drugs.

In yet another aspect, the invention provides methods for preventing atrial remodeling comprising administering an amount of budiodarone effective to reduce AF episode duration and an effective amount of dabigatran etexilate, wherein the average AF episode duration is reduced to less than about 24 hours, less than about 5 hours, less than about 3 hours, or less than about 1 hour, and wherein the patient was refractory to one or more anti-arrhythmic drugs.

In yet another aspect, the invention provides methods for preventing atrial remodeling comprising administering an amount of budiodarone effective to reduce AF episode duration and an effective amount of dabigatran etexilate, wherein the maximum AF episode duration is reduced to less than about 20 hours, less than about 10 hours, or less than about 5 hours, and wherein the patient was refractory to one or more anti-arrhythmic drugs.

In yet another aspect, the invention provides methods for preventing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of AZD0837 or ximelagatran, wherein the average AF episode duration is reduced to less than about 24 hours, less than about 5 hours, less than about 3 hours, or less than about 1 hour, and wherein the patient was refractory to one or more anti-arrhythmic drugs.

In yet another aspect, the invention provides methods for preventing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of AZD0837 or ximelagatran, wherein the maximum AF episode duration is reduced to less than about 20 hours, less than about 10 hours, or less than about 5 hours, and wherein the patient was refractory to one or more anti-arrhythmic drugs.

In yet another aspect, the invention provides methods for preventing atrial remodeling comprising administering an amount of multiple ion channel blocker selected from the group consisting of dronedarone, budiodarone, vernakalant, celivarone, and AZD1305 effective to reduce AF episode duration and an effective amount of AZD0837 or ximelagatran, wherein the average AF episode duration is reduced to less than about 24 hours, less than about 5 hours, less than about 3 hours, or less than about 1 hour, and wherein the patient was refractory to one or more anti-arrhythmic drugs.

In yet another aspect, the invention provides methods for preventing atrial remodeling comprising administering an amount of multiple ion channel blocker selected from the group consisting of dronedarone, budiodarone, vernakalant, celivarone, and AZD1305 effective to reduce AF episode duration and an effective amount of AZD0837 or ximelagatran, wherein the maximum AF episode duration is reduced to less than about 20 hours, less than about 10 hours, or less than about 5 hours, and wherein the patient was refractory to one or more anti-arrhythmic drugs.

In yet another aspect, the invention provides methods for preventing atrial remodeling comprising administering an amount of budiodarone effective to reduce AF episode duration and an effective amount of AZD0837 or ximelagatran, wherein the average AF episode duration is reduced to less than about 24 hours, less than about 5 hours, less than about 3 hours, or less than about 1 hour, and wherein the patient was refractory to one or more anti-arrhythmic drugs.

In yet another aspect, the invention provides methods for preventing atrial remodeling comprising administering an amount of budiodarone effective to reduce AF episode duration and an effective amount of AZD0837 or ximelagatran, wherein the maximum AF episode duration is reduced to less than about 20 hours, less than about 10 hours, or less than about 5 hours, and wherein the patient was refractory to one or more anti-arrhythmic drugs.

In yet another aspect, the invention provides methods for preventing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of apixaban, wherein the average AF episode duration is reduced to less than about 24 hours, less than about 5 hours, less than about 3 hours, or less than about 1 hour, and wherein the patient was refractory to one or more anti-arrhythmic drugs.

In yet another aspect, the invention provides methods for preventing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of apixaban, wherein the maximum AF episode duration is reduced to less than about 20 hours, less than about 10 hours, or less than about 5 hours, and wherein the patient was refractory to one or more anti-arrhythmic drugs.

In yet another aspect, the invention provides methods for preventing atrial remodeling comprising administering an amount of multiple ion channel blocker selected from the group consisting of dronedarone, budiodarone, vernakalant, celivarone, and AZD1305 effective to reduce AF episode duration and an effective amount of apixaban, wherein the average AF episode duration is reduced to less than about 24 hours, less than about 5 hours, less than about 3 hours, or less than about 1 hour, and wherein the patient was refractory to one or more anti-arrhythmic drugs.

In yet another aspect, the invention provides methods for preventing atrial remodeling comprising administering an amount of multiple ion channel blocker selected from the group consisting of dronedarone, budiodarone, vernakalant, celivarone, and AZD1305 effective to reduce AF episode duration and an effective amount of apixaban, wherein the maximum AF episode duration is reduced to less than about 20 hours, less than about 10 hours, or less than about 5 hours, and wherein the patient was refractory to one or more anti-arrhythmic drugs.

In yet another aspect, the invention provides methods for preventing atrial remodeling comprising administering an amount of budiodarone effective to reduce AF episode duration and an effective amount of apixaban, wherein the average AF episode duration is reduced to less than about 24 hours, less than about 5 hours, less than about 3 hours, or less than about 1 hour, and wherein the patient was refractory to one or more anti-arrhythmic drugs.

In yet another aspect, the invention provides methods for preventing atrial remodeling comprising administering an amount of budiodarone effective to reduce AF episode duration and an effective amount of apixaban, wherein the maximum AF episode duration is reduced to less than about 20 hours, less than about 10 hours, or less than about 5 hours, and wherein the patient was refractory to one or more anti-arrhythmic drugs.

In yet another aspect, the invention provides methods for preventing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of rivaroxaban, wherein the average AF episode duration is reduced to less than about 24 hours, less than about 5 hours, less than about 3 hours, or less than about 1 hour, and wherein the patient was refractory to one or more anti-arrhythmic drugs.

In yet another aspect, the invention provides methods for preventing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of rivaroxaban, wherein the maximum AF episode duration is reduced to less than about 20 hours, less than about 10 hours, or less than about 5 hours, and wherein the patient was refractory to one or more anti-arrhythmic drugs.

In yet another aspect, the invention provides methods for preventing atrial remodeling comprising administering an amount of multiple ion channel blocker selected from the group consisting of dronedarone, budiodarone, vernakalant, celivarone, and AZD1305 effective to reduce AF episode duration and an effective amount of rivaroxaban, wherein the average AF episode duration is reduced to less than about 24 hours, less than about 5 hours, less than about 3 hours, or less than about 1 hour, and wherein the patient was refractory to one or more anti-arrhythmic drugs.

In yet another aspect, the invention provides methods for preventing atrial remodeling comprising administering an amount of multiple ion channel blocker selected from the group consisting of dronedarone, budiodarone, vernakalant, celivarone, and AZD1305 effective to reduce AF episode duration and an effective amount of rivaroxaban, wherein the maximum AF episode duration is reduced to less than about 20 hours, less than about 10 hours, or less than about 5 hours, and wherein the patient was refractory to one or more anti-arrhythmic drugs.

In yet another aspect, the invention provides methods for preventing atrial remodeling comprising administering an amount of budiodarone effective to reduce AF episode duration and an effective amount of rivaroxaban, wherein the average AF episode duration is reduced to less than about 24 hours, less than about 5 hours, less than about 3 hours, or less than about 1 hour, and wherein the patient was refractory to one or more anti-arrhythmic drugs.

In yet another aspect, the invention provides methods for preventing atrial remodeling comprising administering an amount of budiodarone effective to reduce AF episode duration and an effective amount of rivaroxaban, wherein the maximum AF episode duration is reduced to less than about 20 hours, less than about 10 hours, or less than about 5 hours, and wherein the patient was refractory to one or more anti-arrhythmic drugs.

In yet another aspect, the invention provides methods for preventing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of tecarfarin, wherein the average AF episode duration is reduced to less than about 24 hours, less than about 5 hours, less than about 3 hours, or less than about 1 hour, and wherein the patient was refractory to one or more anti-arrhythmic drugs.

In yet another aspect, the invention provides methods for preventing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of tecarfarin, wherein the maximum AF episode duration is reduced to less than about 20 hours, less than about 10 hours, or less than about 5 hours, and wherein the patient was refractory to one or more anti-arrhythmic drugs.

In yet another aspect, the invention provides methods for preventing atrial remodeling comprising administering an amount of multiple ion channel blocker selected from the group consisting of dronedarone, budiodarone, vernakalant, celivarone, and AZD1305 effective to reduce AF episode duration and an effective amount of tecarfarin, wherein the average AF episode duration is reduced to less than about 24 hours, less than about 5 hours, less than about 3 hours, or less than about 1 hour, and wherein the patient was refractory to one or more anti-arrhythmic drugs.

In yet another aspect, the invention provides methods for preventing atrial remodeling comprising administering an amount of multiple ion channel blocker selected from the group consisting of dronedarone, budiodarone, vernakalant, celivarone, and AZD1305 effective to reduce AF episode duration and an effective amount of tecarfarin, wherein the maximum AF episode duration is reduced to less than about 20 hours, less than about 10 hours, or less than about 5 hours, and wherein the patient was refractory to one or more anti-arrhythmic drugs.

In yet another aspect, the invention provides methods for preventing atrial remodeling comprising administering an amount of budiodarone effective to reduce AF episode duration and an effective amount of tecarfarin, wherein the average AF episode duration is reduced to less than about 24 hours, less than about 5 hours, less than about 3 hours, or less than about 1 hour, and wherein the patient was refractory to one or more anti-arrhythmic drugs.

In yet another aspect, the invention provides methods for preventing atrial remodeling comprising administering an amount of budiodarone effective to reduce AF episode duration and an effective amount of tecarfarin, wherein the maximum AF episode duration is reduced to less than about 20 hours, less than about 10 hours, or less than about 5 hours, and wherein the patient was refractory to one or more anti-arrhythmic drugs.

In yet another aspect, the invention provides methods for reversing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin.

In yet another aspect, the invention provides methods for reversing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the average AF episode duration is reduced to less than about 24 hours, less than about 5 hours, less than about 3 hours, or less than about 1 hour.

In yet another aspect, the invention provides methods for reversing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the maximum AF episode duration is reduced to less than about 20 hours, less than about 10 hours, or less than about 5 hours.

In yet another aspect, the invention provides methods for reversing atrial remodeling comprising administering an amount of multiple ion channel blocker selected from the group consisting of dronedarone, budiodarone, vernakalant, celivarone, and AZD1305 effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin.

In yet another aspect, the invention provides methods for reversing atrial remodeling comprising administering an amount of multiple ion channel blocker selected from the group consisting of dronedarone, budiodarone, vernakalant, celivarone, and AZD1305 effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the average AF episode duration is reduced to less than about 24 hours, less than about 5 hours, less than about 3 hours, or less than about 1 hour.

In yet another aspect, the invention provides methods for reversing atrial remodeling comprising administering an amount of multiple ion channel blocker selected from the group consisting of dronedarone, budiodarone, vernakalant, celivarone, and AZD1305 effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the maximum AF episode duration is reduced to less than about 20 hours, less than about 10 hours, or less than about 5 hours.

In yet another aspect, the invention provides methods for reversing atrial remodeling comprising administering an amount of multiple ion channel blocker selected from the group consisting of budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin.

In yet another aspect, the invention provides methods for reversing atrial remodeling comprising administering an amount of multiple ion channel blocker selected from the group consisting of budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the average AF episode duration is reduced to less than about 24 hours, less than about 5 hours, less than about 3 hours, or less than about 1 hour.

In yet another aspect, the invention provides methods for reversing atrial remodeling comprising administering an amount of multiple ion channel blocker selected from the group consisting of budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the maximum AF episode duration is reduced to less than about 20 hours, less than about 10 hours, or less than about 5 hours.

In yet another aspect, the invention provides methods for reversing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of AC selected from the group consisting of tecarfarin, dabigatran etexilate, ximelagatran, AZD0837, apixaban and rivaroxaban.

In yet another aspect, the invention provides methods for reversing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of AC selected from the group consisting of tecarfarin, dabigatran etexilate, ximelagatran, AZD0837, apixaban and rivaroxaban, wherein the average AF episode duration is reduced to less than about 24 hours, less than about 5 hours, less than about 3 hours, or less than about 1 hour.

In yet another aspect, the invention provides methods for reversing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of AC selected from the group consisting of tecarfarin, dabigatran etexilate, ximelagatran, AZD0837, apixaban and rivaroxaban, wherein the maximum AF episode duration is reduced to less than about 20 hours, less than about 10 hours, or less than about 5 hours.

In yet another aspect, the invention provides methods for reversing atrial remodeling comprising administering an amount of multiple ion channel blocker selected from the group consisting of dronedarone, budiodarone, vernakalant, celivarone, and AZD1305 effective to reduce AF episode duration and an effective amount of AC selected from the group consisting of tecarfarin, dabigatran etexilate, ximelagatran, AZD0837, apixaban and rivaroxaban.

In yet another aspect, the invention provides methods for reversing atrial remodeling comprising administering an amount of multiple ion channel blocker selected from the group consisting of dronedarone, budiodarone, vernakalant, celivarone, and AZD1305 effective to reduce AF episode duration and an effective amount of AC selected from the group consisting of tecarfarin, dabigatran etexilate, ximelagatran, AZD0837, apixaban and rivaroxaban, wherein the average AF episode duration is reduced to less than about 24 hours, less than about 5 hours, less than about 3 hours, or less than about 1 hour.

In yet another aspect, the invention provides methods for reversing atrial remodeling comprising administering an amount of multiple ion channel blocker selected from the group consisting of dronedarone, budiodarone, vernakalant, celivarone, and AZD1305 effective to reduce AF episode duration and an effective amount of AC selected from the group consisting of tecarfarin, dabigatran etexilate, ximelagatran, AZD0837, apixaban and rivaroxaban, wherein the maximum AF episode duration is reduced to less than about 20 hours, less than about 10 hours, or less than about 5 hours.

In yet another aspect, the invention provides methods for reversing atrial remodeling comprising administering an amount of multiple ion channel blocker selected from the group consisting of budiodarone effective to reduce AF episode duration and an effective amount of AC selected from the group consisting of tecarfarin, dabigatran etexilate, ximelagatran, AZD0837, apixaban and rivaroxaban.

In yet another aspect, the invention provides methods for reversing atrial remodeling comprising administering an amount of multiple ion channel blocker selected from the group consisting of budiodarone effective to reduce AF episode duration and an effective amount of AC selected from the group consisting of tecarfarin, dabigatran etexilate, ximelagatran, AZD0837, apixaban and rivaroxaban, wherein the average AF episode duration is reduced to less than about 24 hours, less than about 5 hours, less than about 3 hours, or less than about 1 hour.

In yet another aspect, the invention provides methods for reversing atrial remodeling comprising administering an amount of multiple ion channel blocker selected from the group consisting of budiodarone effective to reduce AF episode duration and an effective amount of AC selected from the group consisting of tecarfarin, dabigatran etexilate, ximelagatran, AZD0837, apixaban and rivaroxaban, wherein the maximum AF episode duration is reduced to less than about 20 hours, less than about 10 hours, or less than about 5 hours.

In yet another aspect, the invention provides methods for reversing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of dabigatran etexilate, wherein the average AF episode duration is reduced to less than about 24 hours, less than about 5 hours, less than about 3 hours, or less than about 1 hour.

In yet another aspect, the invention provides methods for reversing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of dabigatran etexilate, wherein the maximum AF episode duration is reduced to less than about 20 hours, less than about 10 hours, or less than about 5 hours.

In yet another aspect, the invention provides methods for reversing atrial remodeling comprising administering an amount of multiple ion channel blocker selected from the group consisting of dronedarone, budiodarone, vernakalant, celivarone, and AZD1305 effective to reduce AF episode duration and an effective amount of dabigatran etexilate, wherein the average AF episode duration is reduced to less than about 24 hours, less than about 5 hours, less than about 3 hours, or less than about 1 hour.

In yet another aspect, the invention provides methods for reversing atrial remodeling comprising administering an amount of multiple ion channel blocker selected from the group consisting of dronedarone, budiodarone, vernakalant, celivarone, and AZD1305 effective to reduce AF episode duration and an effective amount of dabigatran etexilate, wherein the maximum AF episode duration is reduced to less than about 20 hours, less than about 10 hours, or less than about 5 hours.

In yet another aspect, the invention provides methods for reversing atrial remodeling comprising administering an amount of multiple ion channel blocker selected from the group consisting of budiodarone effective to reduce AF episode duration and an effective amount of dabigatran etexilate, wherein the average AF episode duration is reduced to less than about 24 hours, less than about 5 hours, less than about 3 hours, or less than about 1 hour.

In yet another aspect, the invention provides methods for reversing atrial remodeling comprising administering an amount of multiple ion channel blocker selected from the group consisting of budiodarone effective to reduce AF episode duration and an effective amount of dabigatran etexilate, wherein the maximum AF episode duration is reduced to less than about 20 hours, less than about 10 hours, or less than about 5 hours.

In yet another aspect, the invention provides methods for reversing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of ximelagatran or AZD0837, wherein the average AF episode duration is reduced to less than about 24 hours, less than about 5 hours, less than about 3 hours, or less than about 1 hour.

In yet another aspect, the invention provides methods for reversing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of ximelagatran or AZD0837, wherein the maximum AF episode duration is reduced to less than about 20 hours, less than about 10 hours, or less than about 5 hours.

In yet another aspect, the invention provides methods for reversing atrial remodeling comprising administering an amount of multiple ion channel blocker selected from the group consisting of dronedarone, budiodarone, vernakalant, celivarone, and AZD1305 effective to reduce AF episode duration and an effective amount of ximelagatran or AZD0837, wherein the average AF episode duration is reduced to less than about 24 hours, less than about 5 hours, less than about 3 hours, or less than about 1 hour.

In yet another aspect, the invention provides methods for reversing atrial remodeling comprising administering an amount of multiple ion channel blocker selected from the group consisting of dronedarone, budiodarone, vernakalant, celivarone, and AZD1305 effective to reduce AF episode duration and an effective amount of ximelagatran or AZD0837, wherein the maximum AF episode duration is reduced to less than about 20 hours, less than about 10 hours, or less than about 5 hours.

In yet another aspect, the invention provides methods for reversing atrial remodeling comprising administering an amount of multiple ion channel blocker selected from the group consisting of budiodarone effective to reduce AF episode duration and an effective amount of ximelagatran or AZD0837, wherein the average AF episode duration is reduced to less than about 24 hours, less than about 5 hours, less than about 3 hours, or less than about 1 hour.

In yet another aspect, the invention provides methods for reversing atrial remodeling comprising administering an amount of multiple ion channel blocker selected from the group consisting of budiodarone effective to reduce AF episode duration and an effective amount of ximelagatran or AZD0837, wherein the maximum AF episode duration is reduced to less than about 20 hours, less than about 10 hours, or less than about 5 hours.

In yet another aspect, the invention provides methods for reversing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of apixaban, wherein the average AF episode duration is reduced to less than about 24 hours, less than about 5 hours, less than about 3 hours, or less than about 1 hour.

In yet another aspect, the invention provides methods for reversing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of apixaban, wherein the maximum AF episode duration is reduced to less than about 20 hours, less than about 10 hours, or less than about 5 hours.

In yet another aspect, the invention provides methods for reversing atrial remodeling comprising administering an amount of multiple ion channel blocker selected from the group consisting of dronedarone, budiodarone, vernakalant, celivarone, and AZD1305 effective to reduce AF episode duration and an effective amount of apixaban, wherein the average AF episode duration is reduced to less than about 24 hours, less than about 5 hours, less than about 3 hours, or less than about 1 hour.

In yet another aspect, the invention provides methods for reversing atrial remodeling comprising administering an amount of multiple ion channel blocker selected from the group consisting of dronedarone, budiodarone, vernakalant, celivarone, and AZD1305 effective to reduce AF episode duration and an effective amount of apixaban, wherein the maximum AF episode duration is reduced to less than about 20 hours, less than about 10 hours, or less than about 5 hours.

In yet another aspect, the invention provides methods for reversing atrial remodeling comprising administering an amount of multiple ion channel blocker selected from the group consisting of budiodarone effective to reduce AF episode duration and an effective amount of apixaban, wherein the average AF episode duration is reduced to less than about 24 hours, less than about 5 hours, less than about 3 hours, or less than about 1 hour.

In yet another aspect, the invention provides methods for reversing atrial remodeling comprising administering an amount of multiple ion channel blocker selected from the group consisting of budiodarone effective to reduce AF episode duration and an effective amount of apixaban, wherein the maximum AF episode duration is reduced to less than about 20 hours, less than about 10 hours, or less than about 5 hours.

In yet another aspect, the invention provides methods for reversing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of rivaroxaban, wherein the average AF episode duration is reduced to less than about 24 hours, less than about 5 hours, less than about 3 hours, or less than about 1 hour.

In yet another aspect, the invention provides methods for reversing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of rivaroxaban, wherein the maximum AF episode duration is reduced to less than about 20 hours, less than about 10 hours, or less than about 5 hours.

In yet another aspect, the invention provides methods for reversing atrial remodeling comprising administering an amount of multiple ion channel blocker selected from the group consisting of dronedarone, budiodarone, vernakalant, celivarone, and AZD1305 effective to reduce AF episode duration and an effective amount of rivaroxaban, wherein the average AF episode duration is reduced to less than about 24 hours, less than about 5 hours, less than about 3 hours, or less than about 1 hour.

In yet another aspect, the invention provides methods for reversing atrial remodeling comprising administering an amount of multiple ion channel blocker selected from the group consisting of dronedarone, budiodarone, vernakalant, celivarone, and AZD1305 effective to reduce AF episode duration and an effective amount of rivaroxaban, wherein the maximum AF episode duration is reduced to less than about 20 hours, less than about 10 hours, or less than about 5 hours.

In yet another aspect, the invention provides methods for reversing atrial remodeling comprising administering an amount of multiple ion channel blocker selected from the group consisting of budiodarone effective to reduce AF episode duration and an effective amount of rivaroxaban, wherein the average AF episode duration is reduced to less than about 24 hours, less than about 5 hours, less than about 3 hours, or less than about 1 hour.

In yet another aspect, the invention provides methods for reversing atrial remodeling comprising administering an amount of multiple ion channel blocker selected from the group consisting of budiodarone effective to reduce AF episode duration and an effective amount of rivaroxaban, wherein the maximum AF episode duration is reduced to less than about 20 hours, less than about 10 hours, or less than about 5 hours.

In yet another aspect, the invention provides methods for reversing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of tecarfarin, wherein the average AF episode duration is reduced to less than about 24 hours, less than about 5 hours, less than about 3 hours, or less than about 1 hour.

In yet another aspect, the invention provides methods for reversing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of tecarfarin, wherein the maximum AF episode duration is reduced to less than about 20 hours, less than about 10 hours, or less than about 5 hours.

In yet another aspect, the invention provides methods for reversing atrial remodeling comprising administering an amount of multiple ion channel blocker selected from the group consisting of dronedarone, budiodarone, vernakalant, celivarone, and AZD1305 effective to reduce AF episode duration and an effective amount of tecarfarin, wherein the average AF episode duration is reduced to less than about 24 hours, less than about 5 hours, less than about 3 hours, or less than about 1 hour.

In yet another aspect, the invention provides methods for reversing atrial remodeling comprising administering an amount of multiple ion channel blocker selected from the group consisting of dronedarone, budiodarone, vernakalant, celivarone, and AZD1305 effective to reduce AF episode duration and an effective amount of tecarfarin, wherein the maximum AF episode duration is reduced to less than about 20 hours, less than about 10 hours, or less than about 5 hours.

In yet another aspect, the invention provides methods for reversing atrial remodeling comprising administering an amount of multiple ion channel blocker selected from the group consisting of budiodarone effective to reduce AF episode duration and an effective amount of tecarfarin, wherein the average AF episode duration is reduced to less than about 24 hours, less than about 5 hours, less than about 3 hours, or less than about 1 hour.

In yet another aspect, the invention provides methods for reversing atrial remodeling comprising administering an amount of multiple ion channel blocker selected from the group consisting of budiodarone effective to reduce AF episode duration and an effective amount of tecarfarin, wherein the maximum AF episode duration is reduced to less than about 20 hours, less than about 10 hours, or less than about 5 hours.

In yet another aspect, the invention provides methods for reversing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the average AF episode duration is reduced to less than about 24 hours, less than about 5 hours, less than about 3 hours, or less than about 1 hour, and wherein the patient was refractory to one or more anti-arrhythmic drugs.

In yet another aspect, the invention provides methods for reversing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the maximum AF episode duration is reduced to less than about 20 hours, less than about 10 hours, or less than about 5 hours, and wherein the patient was refractory to one or more anti-arrhythmic drugs.

In yet another aspect, the invention provides methods for reversing atrial remodeling comprising administering an amount of multiple ion channel blocker selected from the group consisting of dronedarone, budiodarone, vernakalant, celivarone, and AZD1305 effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the average AF episode duration is reduced to less than about 24 hours, less than about 5 hours, less than about 3 hours, or less than about 1 hour, and wherein the patient was refractory to one or more anti-arrhythmic drugs.

In yet another aspect, the invention provides methods for reversing atrial remodeling comprising administering an amount of multiple ion channel blocker selected from the group consisting of dronedarone, budiodarone, vernakalant, celivarone, and AZD1305 effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the maximum AF episode duration is reduced to less than about 20 hours, less than about 10 hours, or less than about 5 hours, and wherein the patient was refractory to one or more anti-arrhythmic drugs.

In yet another aspect, the invention provides methods for reversing atrial remodeling comprising administering an amount of multiple ion channel blocker selected from the group consisting of budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the average AF episode duration is reduced to less than about 24 hours, less than about 5 hours, less than about 3 hours, or less than about 1 hour, and wherein the patient was refractory to one or more anti-arrhythmic drugs.

In yet another aspect, the invention provides methods for reversing atrial remodeling comprising administering an amount of multiple ion channel blocker selected from the group consisting of budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the maximum AF episode duration is reduced to less than about 20 hours, less than about 10 hours, or less than about 5 hours, and wherein the patient was refractory to one or more anti-arrhythmic drugs.

In yet another aspect, the invention provides methods for reversing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of dabigatran etexilate, wherein the maximum AF episode duration is reduced to less than about 20 hours, less than about 10 hours, or less than about 5 hours, and wherein the patient was refractory to one or more anti-arrhythmic drugs.

In yet another aspect, the invention provides methods for reversing atrial remodeling comprising administering an amount of multiple ion channel blocker selected from the group consisting of dronedarone, budiodarone, vernakalant, celivarone, and AZD1305 effective to reduce AF episode duration and an effective amount of dabigatran etexilate, wherein the average AF episode duration is reduced to less than about 24 hours, less than about 5 hours, less than about 3 hours, or less than about 1 hour, and wherein the patient was refractory to one or more anti-arrhythmic drugs.

In yet another aspect, the invention provides methods for reversing atrial remodeling comprising administering an amount of multiple ion channel blocker selected from the group consisting of dronedarone, budiodarone, vernakalant, celivarone, and AZD1305 effective to reduce AF episode duration and an effective amount of dabigatran etexilate, wherein the maximum AF episode duration is reduced to less than about 20 hours, less than about 10 hours, or less than about 5 hours, and wherein the patient was refractory to one or more anti-arrhythmic drugs.

In yet another aspect, the invention provides methods for reversing atrial remodeling comprising administering an amount of multiple ion channel blocker selected from the group consisting of budiodarone effective to reduce AF episode duration and an effective amount of dabigatran etexilate, wherein the average AF episode duration is reduced to less than about 24 hours, less than about 5 hours, less than about 3 hours, or less than about 1 hour, and wherein the patient was refractory to one or more anti-arrhythmic drugs.

In yet another aspect, the invention provides methods for reversing atrial remodeling comprising administering an amount of multiple ion channel blocker selected from the group consisting of budiodarone effective to reduce AF episode duration and an effective amount of dabigatran etexilate, wherein the maximum AF episode duration is reduced to less than about 20 hours, less than about 10 hours, or less than about 5 hours, wherein the patient was refractory to one or more anti-arrhythmic drugs.

In yet another aspect, the invention provides methods for reversing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of ximelagatran or AZD0837, wherein the average AF episode duration is reduced to less than about 24 hours, less than about 5 hours, less than about 3 hours, or less than about 1 hour, and wherein the patient was refractory to one or more anti-arrhythmic drugs.

In yet another aspect, the invention provides methods for reversing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of ximelagatran or AZD0837, wherein the maximum AF episode duration is reduced to less than about 20 hours, less than about 10 hours, or less than about 5 hours, and wherein the patient was refractory to one or more anti-arrhythmic drugs.

In yet another aspect, the invention provides methods for reversing atrial remodeling comprising administering an amount of multiple ion channel blocker selected from the group consisting of dronedarone, budiodarone, vernakalant, celivarone, and AZD1305 effective to reduce AF episode duration and an effective amount of ximelagatran or AZD0837, wherein the average AF episode duration is reduced to less than about 24 hours, less than about 5 hours, less than about 3 hours, or less than about 1 hour, and wherein the patient was refractory to one or more anti-arrhythmic drugs.

In yet another aspect, the invention provides methods for reversing atrial remodeling comprising administering an amount of multiple ion channel blocker selected from the group consisting of dronedarone, budiodarone, vernakalant, celivarone, and AZD1305 effective to reduce AF episode duration and an effective amount of ximelagatran or AZD0837, wherein the maximum AF episode duration is reduced to less than about 20 hours, less than about 10 hours, or less than about 5 hours, and wherein the patient was refractory to one or more anti-arrhythmic drugs.

In yet another aspect, the invention provides methods for reversing atrial remodeling comprising administering an amount of multiple ion channel blocker selected from the group consisting of budiodarone effective to reduce AF episode duration and an effective amount of ximelagatran or AZD0837, wherein the average AF episode duration is reduced to less than about 24 hours, less than about 5 hours, less than about 3 hours, or less than about 1 hour, and wherein the patient was refractory to one or more anti-arrhythmic drugs.

In yet another aspect, the invention provides methods for reversing atrial remodeling comprising administering an amount of multiple ion channel blocker selected from the group consisting of budiodarone effective to reduce AF episode duration and an effective amount of ximelagatran or AZD0837, wherein the maximum AF episode duration is reduced to less than about 20 hours, less than about 10 hours, or less than about 5 hours, and wherein the patient was refractory to one or more anti-arrhythmic drugs.

In yet another aspect, the invention provides methods for reversing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of apixaban, wherein the average AF episode duration is reduced to less than about 24 hours, less than about 5 hours, less than about 3 hours, or less than about 1 hour, and wherein the patient was refractory to one or more anti-arrhythmic drugs.

In yet another aspect, the invention provides methods for reversing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of apixaban, wherein the maximum AF episode duration is reduced to less than about 20 hours, less than about 10 hours, or less than about 5 hours, and wherein the patient was refractory to one or more anti-arrhythmic drugs.

In yet another aspect, the invention provides methods for reversing atrial remodeling comprising administering an amount of multiple ion channel blocker selected from the group consisting of dronedarone, budiodarone, vernakalant, celivarone, and AZD1305 effective to reduce AF episode duration and an effective amount of apixaban, wherein the average AF episode duration is reduced to less than about 24 hours, less than about 5 hours, less than about 3 hours, or less than about 1 hour, and wherein the patient was refractory to one or more anti-arrhythmic drugs.

In yet another aspect, the invention provides methods for reversing atrial remodeling comprising administering an amount of multiple ion channel blocker selected from the group consisting of dronedarone, budiodarone, vernakalant, celivarone, and AZD1305 effective to reduce AF episode duration and an effective amount of apixaban, wherein the maximum AF episode duration is reduced to less than about 20 hours, less than about 10 hours, or less than about 5 hours, and wherein the patient was refractory to one or more anti-arrhythmic drugs.

In yet another aspect, the invention provides methods for reversing atrial remodeling comprising administering an amount of multiple ion channel blocker selected from the group consisting of budiodarone effective to reduce AF episode duration and an effective amount of apixaban, wherein the average AF episode duration is reduced to less than about 24 hours, less than about 5 hours, less than about 3 hours, or less than about 1 hour, and wherein the patient was refractory to one or more anti-arrhythmic drugs.

In yet another aspect, the invention provides methods for reversing atrial remodeling comprising administering an amount of multiple ion channel blocker selected from the group consisting of budiodarone effective to reduce AF episode duration and an effective amount of apixaban, wherein the maximum AF episode duration is reduced to less than about 20 hours, less than about 10 hours, or less than about 5 hours, and wherein the patient was refractory to one or more anti-arrhythmic drugs.

In yet another aspect, the invention provides methods for reversing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of rivaroxaban, wherein the average AF episode duration is reduced to less than about 24 hours, less than about 5 hours, less than about 3 hours, or less than about 1 hour, and wherein the patient was refractory to one or more anti-arrhythmic drugs.

In yet another aspect, the invention provides methods for reversing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of rivaroxaban, wherein the maximum AF episode duration is reduced to less than about 20 hours, less than about 10 hours, or less than about 5 hours, and wherein the patient was refractory to one or more anti-arrhythmic drugs.

In yet another aspect, the invention provides methods for reversing atrial remodeling comprising administering an amount of multiple ion channel blocker selected from the group consisting of dronedarone, budiodarone, vernakalant, celivarone, and AZD1305 effective to reduce AF episode duration and an effective amount of rivaroxaban, wherein the average AF episode duration is reduced to less than about 24 hours, less than about 5 hours, less than about 3 hours, or less than about 1 hour, and wherein the patient was refractory to one or more anti-arrhythmic drugs.

In yet another aspect, the invention provides methods for reversing atrial remodeling comprising administering an amount of multiple ion channel blocker selected from the group consisting of dronedarone, budiodarone, vernakalant, celivarone, and AZD1305 effective to reduce AF episode duration and an effective amount of rivaroxaban, wherein the maximum AF episode duration is reduced to less than about 20 hours, less than about 10 hours, or less than about 5 hours, and wherein the patient was refractory to one or more anti-arrhythmic drugs.

In yet another aspect, the invention provides methods for reversing atrial remodeling comprising administering an amount of multiple ion channel blocker selected from the group consisting of budiodarone effective to reduce AF episode duration and an effective amount of rivaroxaban, wherein the average AF episode duration is reduced to less than about 24 hours, less than about 5 hours, less than about 3 hours, or less than about 1 hour, and wherein the patient was refractory to one or more anti-arrhythmic drugs.

In yet another aspect, the invention provides methods for reversing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of tecarfarin, wherein the average AF episode duration is reduced to less than about 24 hours, less than about 5 hours, less than about 3 hours, or less than about 1 hour, and wherein the patient was refractory to one or more anti-arrhythmic drugs.

In yet another aspect, the invention provides methods for reversing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of tecarfarin, wherein the maximum AF episode duration is reduced to less than about 20 hours, less than about 10 hours, or less than about 5 hours, and wherein the patient was refractory to one or more anti-arrhythmic drugs.

In yet another aspect, the invention provides methods for reversing atrial remodeling comprising administering an amount of multiple ion channel blocker selected from the group consisting of dronedarone, budiodarone, vernakalant, celivarone, and AZD1305 effective to reduce AF episode duration and an effective amount of tecarfarin, wherein the average AF episode duration is reduced to less than about 24 hours, less than about 5 hours, less than about 3 hours, or less than about 1 hour, and wherein the patient was refractory to one or more anti-arrhythmic drugs.

In yet another aspect, the invention provides methods for reversing atrial remodeling comprising administering an amount of multiple ion channel blocker selected from the group consisting of dronedarone, budiodarone, vernakalant, celivarone, and AZD1305 effective to reduce AF episode duration and an effective amount of tecarfarin, wherein the maximum AF episode duration is reduced to less than about 20 hours, less than about 10 hours, or less than about 5 hours, and wherein the patient was refractory to one or more anti-arrhythmic drugs.

In yet another aspect, the invention provides methods for reversing atrial remodeling comprising administering an amount of multiple ion channel blocker selected from the group consisting of budiodarone effective to reduce AF episode duration and an effective amount of tecarfarin, wherein the average AF episode duration is reduced to less than about 24 hours, less than about 5 hours, less than about 3 hours, or less than about 1 hour, and wherein the patient was refractory to one or more anti-arrhythmic drugs.

In yet another aspect, the invention provides methods for reversing atrial remodeling comprising administering an amount of multiple ion channel blocker selected from the group consisting of budiodarone effective to reduce AF episode duration and an effective amount of tecarfarin, wherein the maximum AF episode duration is reduced to less than about 20 hours, less than about 10 hours, or less than about 5 hours, and wherein the patient was refractory to one or more anti-arrhythmic drugs.

In yet another aspect, the invention provides methods for reversing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the average AF episode duration is reduced to less than about 24 hours, less than about 5 hours, less than about 3 hours, or less than about 1 hour, and wherein the reversal of atrial remodeling is defined as a measured increase in AFCL at the right atrial appendage or distal coronary sinus of at least 6 milliseconds.

In yet another aspect, the invention provides methods for reversing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the maximum AF episode duration is reduced to less than about 20 hours, less than about 10 hours, or less than about 5 hours, and wherein the reversal of atrial remodeling is defined as a measured increase in AFCL at the right atrial appendage or distal coronary sinus of at least 6 milliseconds.

In yet another aspect, the invention provides methods for reversing atrial remodeling comprising administering an amount of multiple ion channel blocker selected from the group consisting of dronedarone, budiodarone, vernakalant, celivarone, and AZD1305 effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the average AF episode duration is reduced to less than about 24 hours, less than about 5 hours, less than about 3 hours, or less than about 1 hour, and wherein the reversal of atrial remodeling is defined as a measured increase in AFCL at the right atrial appendage or distal coronary sinus of at least 6 milliseconds.

In yet another aspect, the invention provides methods for reversing atrial remodeling comprising administering an amount of multiple ion channel blocker selected from the group consisting of dronedarone, budiodarone, vernakalant, celivarone, and AZD1305 effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the maximum AF episode duration is reduced to less than about 20 hours, less than about 10 hours, or less than about 5 hours, and wherein the reversal of atrial remodeling is defined as a measured increase in AFCL at the right atrial appendage or distal coronary sinus of at least 6 milliseconds.

In yet another aspect, the invention provides methods for reversing atrial remodeling comprising administering an amount of multiple ion channel blocker selected from the group consisting of budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the average AF episode duration is reduced to less than about 24 hours, less than about 5 hours, less than about 3 hours, or less than about 1 hour, and wherein the reversal of atrial remodeling is defined as a measured increase in AFCL at the right atrial appendage or distal coronary sinus of at least 6 milliseconds.

In yet another aspect, the invention provides methods for reversing atrial remodeling comprising administering an amount of multiple ion channel blocker selected from the group consisting of budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the maximum AF episode duration is reduced to less than about 20 hours, less than about 10 hours, or less than about 5 hours, and wherein the reversal of atrial remodeling is defined as a measured increase in AFCL at the right atrial appendage or distal coronary sinus of at least 6 milliseconds.

In yet another aspect, the invention provides methods for reversing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of dabigatran etexilate, wherein the average AF episode duration is reduced to less than about 24 hours, less than about 5 hours, less than about 3 hours, or less than about 1 hour, and wherein the reversal of atrial remodeling is defined as a measured increase in AFCL at the right atrial appendage or distal coronary sinus of at least 6 milliseconds.

In yet another aspect, the invention provides methods for reversing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of dabigatran etexilate, wherein the maximum AF episode duration is reduced to less than about 20 hours, less than about 10 hours, or less than about 5 hours, and wherein the reversal of atrial remodeling is defined as a measured increase in AFCL at the right atrial appendage or distal coronary sinus of at least 6 milliseconds.

In yet another aspect, the invention provides methods for reversing atrial remodeling comprising administering an amount of multiple ion channel blocker selected from the group consisting of dronedarone, budiodarone, vernakalant, celivarone, and AZD1305 effective to reduce AF episode duration and an effective amount of dabigatran etexilate, wherein the average AF episode duration is reduced to less than about 24 hours, less than about 5 hours, less than about 3 hours, or less than about 1 hour, and wherein the reversal of atrial remodeling is defined as a measured increase in AFCL at the right atrial appendage or distal coronary sinus of at least 6 milliseconds.

In yet another aspect, the invention provides methods for reversing atrial remodeling comprising administering an amount of multiple ion channel blocker selected from the group consisting of dronedarone, budiodarone, vernakalant, celivarone, and AZD1305 effective to reduce AF episode duration and an effective amount of dabigatran etexilate, wherein the maximum AF episode duration is reduced to less than about 20 hours, less than about 10 hours, or less than about 5 hours, and wherein the reversal of atrial remodeling is defined as a measured increase in AFCL at the right atrial appendage or distal coronary sinus of at least 6 milliseconds.

In yet another aspect, the invention provides methods for reversing atrial remodeling comprising administering an amount of multiple ion channel blocker selected from the group consisting of budiodarone effective to reduce AF episode duration and an effective amount of dabigatran etexilate, wherein the average AF episode duration is reduced to less than about 24 hours, less than about 5 hours, less than about 3 hours, or less than about 1 hour, and wherein the reversal of atrial remodeling is defined as a measured increase in AFCL at the right atrial appendage or distal coronary sinus of at least 6 milliseconds.

In yet another aspect, the invention provides methods for reversing atrial remodeling comprising administering an amount of multiple ion channel blocker selected from the group consisting of budiodarone effective to reduce AF episode duration and an effective amount of dabigatran etexilate, wherein the maximum AF episode duration is reduced to less than about 20 hours, less than about 10 hours, or less than about 5 hours, and wherein the reversal of atrial remodeling is defined as a measured increase in AFCL at the right atrial appendage or distal coronary sinus of at least 6 milliseconds.

In yet another aspect, the invention provides methods for reversing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of ximelagatran or AZD0837, wherein the average AF episode duration is reduced to less than about 24 hours, less than about 5 hours, less than about 3 hours, or less than about 1 hour, and wherein the reversal of atrial remodeling is defined as a measured increase in AFCL at the right atrial appendage or distal coronary sinus of at least 6 milliseconds.

In yet another aspect, the invention provides methods for reversing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of ximelagatran or AZD0837, wherein the maximum AF episode duration is reduced to less than about 20 hours, less than about 10 hours, or less than about 5 hours, and wherein the reversal of atrial remodeling is defined as a measured increase in AFCL at the right atrial appendage or distal coronary sinus of at least 6 milliseconds.

In yet another aspect, the invention provides methods for reversing atrial remodeling comprising administering an amount of multiple ion channel blocker selected from the group consisting of dronedarone, budiodarone, vernakalant, celivarone, and AZD1305 effective to reduce AF episode duration and an effective amount of ximelagatran or AZD0837, wherein the average AF episode duration is reduced to less than about 24 hours, less than about 5 hours, less than about 3 hours, or less than about 1 hour, and wherein the reversal of atrial remodeling is defined as a measured increase in AFCL at the right atrial appendage or distal coronary sinus of at least 6 milliseconds.

In yet another aspect, the invention provides methods for reversing atrial remodeling comprising administering an amount of multiple ion channel blocker selected from the group consisting of dronedarone, budiodarone, vernakalant, celivarone, and AZD1305 effective to reduce AF episode duration and an effective amount of ximelagatran or AZD0837, wherein the maximum AF episode duration is reduced to less than about 20 hours, less than about 10 hours, or less than about 5 hours, and wherein the reversal of atrial remodeling is defined as a measured increase in AFCL at the right atrial appendage or distal coronary sinus of at least 6 milliseconds.

In yet another aspect, the invention provides methods for reversing atrial remodeling comprising administering an amount of multiple ion channel blocker selected from the group consisting of budiodarone effective to reduce AF episode duration and an effective amount of ximelagatran or AZD0837, wherein the average AF episode duration is reduced to less than about 24 hours, less than about 5 hours, less than about 3 hours, or less than about 1 hour, and wherein the reversal of atrial remodeling is defined as a measured increase in AFCL at the right atrial appendage or distal coronary sinus of at least 6 milliseconds.

In yet another aspect, the invention provides methods for reversing atrial remodeling comprising administering an amount of multiple ion channel blocker selected from the group consisting of budiodarone effective to reduce AF episode duration and an effective amount of ximelagatran or AZD0837, wherein the maximum AF episode duration is reduced to less than about 20 hours, less than about 10 hours, or less than about 5 hours, and wherein the reversal of atrial remodeling is defined as a measured increase in AFCL at the right atrial appendage or distal coronary sinus of at least 6 milliseconds.

In yet another aspect, the invention provides methods for reversing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of apixaban, wherein the average AF episode duration is reduced to less than about 24 hours, less than about 5 hours, less than about 3 hours, or less than about 1 hour, and wherein the reversal of atrial remodeling is defined as a measured increase in AFCL at the right atrial appendage or distal coronary sinus of at least 6 milliseconds.

In yet another aspect, the invention provides methods for reversing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of apixaban, wherein the maximum AF episode duration is reduced to less than about 20 hours, less than about 10 hours, or less than about 5 hours, and wherein the reversal of atrial remodeling is defined as a measured increase in AFCL at the right atrial appendage or distal coronary sinus of at least 6 milliseconds.

In yet another aspect, the invention provides methods for reversing atrial remodeling comprising administering an amount of multiple ion channel blocker selected from the group consisting of dronedarone, budiodarone, vernakalant, celivarone, and AZD1305 effective to reduce AF episode duration and an effective amount of apixaban, wherein the average AF episode duration is reduced to less than about 24 hours, less than about 5 hours, less than about 3 hours, or less than about 1 hour, and wherein the reversal of atrial remodeling is defined as a measured increase in AFCL at the right atrial appendage or distal coronary sinus of at least 6 milliseconds.

In yet another aspect, the invention provides methods for reversing atrial remodeling comprising administering an amount of multiple ion channel blocker selected from the group consisting of dronedarone, budiodarone, vernakalant, celivarone, and AZD1305 effective to reduce AF episode duration and an effective amount of apixaban, wherein the maximum AF episode duration is reduced to less than about 20 hours, less than about 10 hours, or less than about 5 hours, and wherein the reversal of atrial remodeling is defined as a measured increase in AFCL at the right atrial appendage or distal coronary sinus of at least 6 milliseconds.

In yet another aspect, the invention provides methods for reversing atrial remodeling comprising administering an amount of multiple ion channel blocker selected from the group consisting of budiodarone effective to reduce AF episode duration and an effective amount of apixaban, wherein the average AF episode duration is reduced to less than about 24 hours, less than about 5 hours, less than about 3 hours, or less than about 1 hour, and wherein the reversal of atrial remodeling is defined as a measured increase in AFCL at the right atrial appendage or distal coronary sinus of at least 6 milliseconds.

In yet another aspect, the invention provides methods for reversing atrial remodeling comprising administering an amount of multiple ion channel blocker selected from the group consisting of budiodarone effective to reduce AF episode duration and an effective amount of apixaban, wherein the maximum AF episode duration is reduced to less than about 20 hours, less than about 10 hours, or less than about 5 hours, and wherein the reversal of atrial remodeling is defined as a measured increase in AFCL at the right atrial appendage or distal coronary sinus of at least 6 milliseconds.

In yet another aspect, the invention provides methods for reversing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of rivaroxaban, wherein the average AF episode duration is reduced to less than about 24 hours, less than about 5 hours, less than about 3 hours, or less than about 1 hour, and wherein the reversal of atrial remodeling is defined as a measured increase in AFCL at the right atrial appendage or distal coronary sinus of at least 6 milliseconds.

In yet another aspect, the invention provides methods for reversing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of rivaroxaban, wherein the maximum AF episode duration is reduced to less than about 20 hours, less than about 10 hours, or less than about 5 hours, and wherein the reversal of atrial remodeling is defined as a measured increase in AFCL at the right atrial appendage or distal coronary sinus of at least 6 milliseconds.

In yet another aspect, the invention provides methods for reversing atrial remodeling comprising administering an amount of multiple ion channel blocker selected from the group consisting of dronedarone, budiodarone, vernakalant, celivarone, and AZD1305 effective to reduce AF episode duration and an effective amount of rivaroxaban, wherein the average AF episode duration is reduced to less than about 24 hours, less than about 5 hours, less than about 3 hours, or less than about 1 hour, and wherein the reversal of atrial remodeling is defined as a measured increase in AFCL at the right atrial appendage or distal coronary sinus of at least 6 milliseconds.

In yet another aspect, the invention provides methods for reversing atrial remodeling comprising administering an amount of multiple ion channel blocker selected from the group consisting of dronedarone, budiodarone, vernakalant, celivarone, and AZD1305 effective to reduce AF episode duration and an effective amount of rivaroxaban, wherein the maximum AF episode duration is reduced to less than about 20 hours, less than about 10 hours, or less than about 5 hours, and wherein the reversal of atrial remodeling is defined as a measured increase in AFCL at the right atrial appendage or distal coronary sinus of at least 6 milliseconds.

In yet another aspect, the invention provides methods for reversing atrial remodeling comprising administering an amount of multiple ion channel blocker selected from the group consisting of budiodarone effective to reduce AF episode duration and an effective amount of rivaroxaban, wherein the average AF episode duration is reduced to less than about 24 hours, less than about 5 hours, less than about 3 hours, or less than about 1 hour, and wherein the reversal of atrial remodeling is defined as a measured increase in AFCL at the right atrial appendage or distal coronary sinus of at least 6 milliseconds.

In yet another aspect, the invention provides methods for reversing atrial remodeling comprising administering an amount of multiple ion channel blocker selected from the group consisting of budiodarone effective to reduce AF episode duration and an effective amount of rivaroxaban, wherein the maximum AF episode duration is reduced to less than about 20 hours, less than about 10 hours, or less than about 5 hours, and wherein the reversal of atrial remodeling is defined as a measured increase in AFCL at the right atrial appendage or distal coronary sinus of at least 6 milliseconds.

In yet another aspect, the invention provides methods for reversing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of tecarfarin, wherein the average AF episode duration is reduced to less than about 24 hours, less than about 5 hours, less than about 3 hours, or less than about 1 hour, and wherein the reversal of atrial remodeling is defined as a measured increase in AFCL at the right atrial appendage or distal coronary sinus of at least 6 milliseconds.

In yet another aspect, the invention provides methods for reversing atrial remodeling comprising administering an amount of multiple ion channel blocker selected from the group consisting of amiodarone, dronedarone, budiodarone, vernakalant, celivarone, and AZD1305 effective to reduce AF episode duration and an effective amount of tecarfarin, wherein the maximum AF episode duration is reduced to less than about 20 hours, less than about 10 hours, or less than about 5 hours, and wherein the reversal of atrial remodeling is defined as a measured increase in AFCL at the right atrial appendage or distal coronary sinus of at least 6 milliseconds.

In yet another aspect, the invention provides methods for reversing atrial remodeling comprising administering an amount of multiple ion channel blocker selected from the group consisting of dronedarone, budiodarone, vernakalant, celivarone, and AZD1305 effective to reduce AF episode duration and an effective amount of tecarfarin, wherein the average AF episode duration is reduced to less than about 24 hours, less than about 5 hours, less than about 3 hours, or less than about 1 hour, and wherein the reversal of atrial remodeling is defined as a measured increase in AFCL at the right atrial appendage or distal coronary sinus of at least 6 milliseconds.

In yet another aspect, the invention provides methods for reversing atrial remodeling comprising administering an amount of multiple ion channel blocker selected from the group consisting of dronedarone, budiodarone, vernakalant, celivarone, and AZD1305 effective to reduce AF episode duration and an effective amount of tecarfarin, wherein the maximum AF episode duration is reduced to less than about 20 hours, less than about 10 hours, or less than about 5 hours, and wherein the reversal of atrial remodeling is defined as a measured increase in AFCL at the right atrial appendage or distal coronary sinus of at least 6 milliseconds.

In yet another aspect, the invention provides methods for reversing atrial remodeling comprising administering an amount of multiple ion channel blocker selected from the group consisting of budiodarone effective to reduce AF episode duration and an effective amount of tecarfarin, wherein the average AF episode duration is reduced to less than about 24 hours, less than about 5 hours, less than about 3 hours, or less than about 1 hour, and wherein the reversal of atrial remodeling is defined as a measured increase in AFCL at the right atrial appendage or distal coronary sinus of at least 6 milliseconds.

In yet another aspect, the invention provides methods for reversing atrial remodeling comprising administering an amount of multiple ion channel blocker selected from the group consisting of budiodarone effective to reduce AF episode duration and an effective amount of tecarfarin, wherein the maximum AF episode duration is reduced to less than about 20 hours, less than about 10 hours, or less than about 5 hours, and wherein the reversal of atrial remodeling is defined as a measured increase in AFCL at the right atrial appendage or distal coronary sinus of at least 6 milliseconds.

In one aspect, the invention provides methods for reducing stroke rate comprising administering an amount of budiodarone effective to reduce atrial fibrillation (AF) episode duration and an effective amount of anticoagulant (AC) selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin.

In another aspect, the invention provides methods for reducing stroke rate comprising administering an amount of budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the average AF episode duration is reduced to less than about 24 hours, less than about 5 hours, less than about 3 hours, or less than about 1 hour, comprising administering an amount of budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the maximum AF episode duration is reduced to less than about 20 hours, less than about 10 hours, or less than about 5 hours.

In another aspect, the invention provides methods for reducing stroke rate comprising administering an amount of budiodarone effective to reduce AF episode duration and an effective amount of AC selected from the group consisting of tecarfarin, dabigatran etexilate, ximelagatran, AZD0837, apixaban or rivaroxaban.

In another aspect, the invention provides methods for reducing stroke rate comprising administering an amount of budiodarone effective to reduce AF episode duration and an effective amount of AC selected from the group consisting of tecarfarin, dabigatran etexilate, ximelagatran, AZD0837, apixaban or rivaroxaban, wherein the average AF episode duration is reduced to less than about 24 hours, less than about 5 hours, less than about 3 hours, or less than about 1 hour.

In another aspect, the invention provides methods for reducing stroke rate comprising administering an amount of budiodarone effective to reduce AF episode duration and an effective amount of AC selected from the group consisting of tecarfarin, dabigatran etexilate, ximelagatran, AZD0837, apixaban or rivaroxaban, wherein the maximum AF episode duration is reduced to less than about 20 hours, less than about 10 hours, or less than about 5 hours.

In another aspect, the invention provides methods for reducing stroke rate comprising administering an amount of budiodarone effective to reduce AF episode duration and an effective amount of dabigatran etexilate, wherein the average AF episode duration is reduced to less than about 24 hours, less than about 5 hours, less than about 3 hours, or less than about 1 hour.

In another aspect, the invention provides methods for reducing stroke rate comprising administering an amount of budiodarone effective to reduce AF episode duration and an effective amount of dabigatran etexilate, wherein the maximum AF episode duration is reduced to less than about 20 hours, less than about 10 hours, or less than about 5 hours.

In another aspect, the invention provides methods for reducing stroke rate comprising administering an amount of budiodarone effective to reduce AF episode duration and an effective amount of AC selected from the group consisting of ximelagatran and AZD0837, wherein the average AF episode duration is reduced to less than about 24 hours, less than about 5 hours, less than about 3 hours, or less than about 1 hour.

In another aspect, the invention provides methods for reducing stroke rate comprising administering an amount of budiodarone effective to reduce AF episode duration and an effective amount of AC selected from the group consisting of ximelagatran and AZD0837, wherein the maximum AF episode duration is reduced to less than about 20 hours, less than about 10 hours, or less than about 5 hours.

In another aspect, the invention provides methods for reducing stroke rate comprising administering an amount of budiodarone effective to reduce AF episode duration and an effective amount of apixaban, wherein the average AF episode duration is reduced to less than about 24 hours, less than about 5 hours, less than about 3 hours, or less than about 1 hour.

In another aspect, the invention provides methods for reducing stroke rate comprising administering an amount of budiodarone effective to reduce AF episode duration and an effective amount of apixaban, wherein the maximum AF episode duration is reduced to less than about 20 hours, less than about 10 hours, or less than about 5 hours.

In another aspect, the invention provides methods for reducing stroke rate comprising administering an amount of budiodarone effective to reduce AF episode duration and an effective amount of rivaroxaban, wherein the average AF episode duration is reduced to less than about 24 hours, less than about 5 hours, less than about 3 hours, or less than about 1 hour.

In another aspect, the invention provides methods for reducing stroke rate comprising administering an amount of budiodarone effective to reduce AF episode duration and an effective amount of rivaroxaban, wherein the maximum AF episode duration is reduced to less than about 20 hours, less than about 10 hours, or less than about 5 hours.

In another aspect, the invention provides methods for reducing stroke rate comprising administering an amount of budiodarone effective to reduce AF episode duration and an effective amount of tecarfarin, wherein the average AF episode duration is reduced to less than about 24 hours, less than about 5 hours, less than about 3 hours, or less than about 1 hour.

In another aspect, the invention provides methods for reducing stroke rate comprising administering an amount of budiodarone effective to reduce AF episode duration and an effective amount of tecarfarin, wherein the maximum AF episode duration is reduced to less than about 20 hours, less than about 10 hours, or less than about 5 hours.

In another aspect, the invention provides methods for reducing stroke rate comprising administering an amount of budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the reduced stroke rate is less than the age-adjusted overall stroke rate.

In another aspect, the invention provides methods for reducing stroke rate comprising administering an amount of budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the average AF episode duration is reduced to less than about 24 hours, less than about 5 hours, less than about 3 hours, or less than about 1 hour, and wherein the reduced stroke rate is less than the age-adjusted overall stroke rate.

In another aspect, the invention provides methods for reducing stroke rate comprising administering an amount of budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the maximum AF episode duration is reduced to less than about 20 hours, less than about 10 hours or less than about 5 hours, and wherein the reduced stroke rate is less than the age-adjusted overall stroke rate.

In another aspect, the invention provides methods for reducing stroke rate comprising administering an amount of budiodarone effective to reduce AF episode duration and an effective amount of AC selected from the group consisting of tecarfarin, dabigatran etexilate, ximelagatran, AZD0837, apixaban or rivaroxaban, wherein the average AF episode duration is reduced to less than about 24 hours, less than about 5 hours, less than about 3 hours, or less than about 1 hour, and wherein the reduced stroke rate is less than the age-adjusted overall stroke rate.

In another aspect, the invention provides methods for reducing stroke rate comprising administering an amount of budiodarone effective to reduce AF episode duration and an effective amount of AC selected from the group consisting of tecarfarin, dabigatran etexilate, ximelagatran, AZD0837, apixaban or rivaroxaban, wherein the maximum AF episode duration is reduced to less than about 20 hours, less than about 10 hours or less than about 5 hours, and wherein the reduced stroke rate is less than the age-adjusted overall stroke rate.

In another aspect, the invention provides methods for reducing stroke rate comprising administering an amount of budiodarone effective to reduce AF episode duration and an effective amount of dabigatran etexilate, wherein the average AF episode duration is reduced to less than about 24 hours, less than about 5 hours, less than about 3 hours or less than about 1 hour, and wherein the reduced stroke rate is less than the age-adjusted overall stroke rate.

In another aspect, the invention provides methods for reducing stroke rate comprising administering an amount of budiodarone effective to reduce AF episode duration and an effective amount of dabigatran etexilate, wherein the maximum AF episode duration is reduced to less than about 20 hours, less than about 10 hours, or less than about 5 hours, and wherein the reduced stroke rate is less than the age-adjusted overall stroke rate.

In another aspect, the invention provides methods for reducing stroke rate comprising administering an amount of budiodarone effective to reduce AF episode duration and an effective amount of AC selected from the group consisting of ximelagatran and AZD0837, wherein the average AF episode duration is reduced to less than about 24 hours, less than about 5 hours, less than about 3 hours, or less than about 1 hour, and wherein the reduced stroke rate is less than the age-adjusted overall stroke rate.

In another aspect, the invention provides methods for reducing stroke rate comprising administering an amount of budiodarone effective to reduce AF episode duration and an effective amount of AC selected from the group consisting of ximelagatran and AZD0837, wherein the maximum AF episode duration is reduced to less than about 20 hours, less than about 10 hours, or less than about 5 hours, and wherein the reduced stroke rate is less than the age-adjusted overall stroke rate.

In another aspect, the invention provides methods for reducing stroke rate comprising administering an amount of budiodarone effective to reduce AF episode duration and an effective amount of apixaban, wherein the average AF episode duration is reduced to less than about 24 hours, less than about 5 hours, less than about 3 hours, or less than about 1 hour, and wherein the reduced stroke rate is less than the age-adjusted overall stroke rate.

In another aspect, the invention provides methods for reducing stroke rate comprising administering an amount of budiodarone effective to reduce AF episode duration and an effective amount of apixaban, wherein the maximum AF episode duration is reduced to less than about 20 hours, less than about 10 hours, or less than about 5 hours, and wherein the reduced stroke rate is less than the age-adjusted overall stroke rate.

In another aspect, the invention provides methods for reducing stroke rate comprising administering an amount of budiodarone effective to reduce AF episode duration and an effective amount of rivaroxaban, wherein the average AF episode duration is reduced to less than about 24 hours, less than about 5 hours, less than about 3 hours, or less than about 1 hour, and wherein the reduced stroke rate is less than the age-adjusted overall stroke rate.

In another aspect, the invention provides methods for reducing stroke rate comprising administering an amount of budiodarone effective to reduce AF episode duration and an effective amount of rivaroxaban, wherein the maximum AF episode duration is reduced to less than about 20 hours, less than about 10 hours, or less than about 5 hours, and wherein the reduced stroke rate is less than the age-adjusted overall stroke rate.

In another aspect, the invention provides methods for reducing stroke rate comprising administering an amount of budiodarone effective to reduce AF episode duration and an effective amount of tecarfarin, wherein the average AF episode duration is reduced to less than about 24 hours, less than about 5 hours, less than about 3 hours, or less than about 1 hour, and wherein the reduced stroke rate is less than the age-adjusted overall stroke rate.

In another aspect, the invention provides methods for reducing stroke rate comprising administering an amount of budiodarone effective to reduce AF episode duration and an effective amount of tecarfarin, wherein the maximum AF episode duration is reduced to less than about 20 hours, less than about 10 hours, or less than about 5 hours, and wherein the reduced stroke rate is less than the age-adjusted overall stroke rate.

In one aspect, the invention provides methods for reducing stroke rate comprising administering an amount of budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the patient was refractory to one or more anti-arrhythmic drugs.

In another aspect, the invention provides methods for reducing stroke rate comprising administering an amount of budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the average AF episode duration is reduced to less than about 24 hours, less than about 5 hours, less than about 3 hours, or less than about 1 hour, and wherein the patient was refractory to one or more anti-arrhythmic drugs.

In another aspect, the invention provides methods for reducing stroke rate comprising administering an amount of budiodarone effective to reduce AF episode duration and an effective amount of AC selected from the group consisting of tecarfarin, dabigatran etexilate, ximelagatran, AZD0837, apixaban or rivaroxaban, wherein the average AF episode duration is reduced to less than about 24 hours, less than about 5 hours, less than about 3 hours, or less than about 1 hour, and wherein the patient was refractory to one or more anti-arrhythmic drugs.

In another aspect, the invention provides methods for reducing stroke rate comprising administering an amount of budiodarone effective to reduce AF episode duration and an effective amount of dabigatran etexilate, wherein the average AF episode duration is reduced to less than about 24 hours, less than about 5 hours, less than about 3 hours or less than about 1 hour, and wherein the patient was refractory to one or more anti-arrhythmic drugs.

In another aspect, the invention provides methods for reducing stroke rate comprising administering an amount of budiodarone effective to reduce AF episode duration and an effective amount of dabigatran etexilate, wherein the maximum AF episode duration is reduced to less than about 20 hours, less than about 10 hours, or less than about 5 hours, and wherein the patient was refractory to one or more anti-arrhythmic drugs.

In another aspect, the invention provides methods for reducing stroke rate comprising administering an amount of budiodarone effective to reduce AF episode duration and an effective amount of AZD0837, wherein the average AF episode duration is reduced to less than about 24 hours, less than about 5 hours, less than about 3 hours or less than about 1 hour, and wherein the patient was refractory to one or more anti-arrhythmic drugs.

In another aspect, the invention provides methods for reducing stroke rate comprising administering an amount of budiodarone effective to reduce AF episode duration and an effective amount of AZD0837, wherein the maximum AF episode duration is reduced to less than about 20 hours, less than about 10 hours, or less than about 5 hours, and wherein the patient was refractory to one or more anti-arrhythmic drugs.

In another aspect, the invention provides methods for reducing stroke rate comprising administering an amount of budiodarone effective to reduce AF episode duration and an effective amount of apixaban, wherein the average AF episode duration is reduced to less than about 24 hours, less than about 5 hours, less than about 3 hours or less than about 1 hour, and wherein the patient was refractory to one or more anti-arrhythmic drugs.

In another aspect, the invention provides methods for reducing stroke rate comprising administering an amount of budiodarone effective to reduce AF episode duration and an effective amount of apixaban, wherein the maximum AF episode duration is reduced to less than about 20 hours, less than about 10 hours, or less than about 5 hours, and wherein the patient was refractory to one or more anti-arrhythmic drugs.

In another aspect, the invention provides methods for reducing stroke rate comprising administering an amount of budiodarone effective to reduce AF episode duration and an effective amount of rivaroxaban, wherein the average AF episode duration is reduced to less than about 24 hours, less than about 5 hours, less than about 3 hours or less than about 1 hour, and wherein the patient was refractory to one or more anti-arrhythmic drugs.

In another aspect, the invention provides methods for reducing stroke rate comprising administering an amount of budiodarone effective to reduce AF episode duration and an effective amount of rivaroxaban, wherein the maximum AF episode duration is reduced to less than about 20 hours, less than about 10 hours, or less than about 5 hours, and wherein the patient was refractory to one or more anti-arrhythmic drugs.

In another aspect, the invention provides methods for reducing stroke rate comprising administering an amount of budiodarone effective to reduce AF episode duration and an effective amount of tecarfarin, wherein the average AF episode duration is reduced to less than about 24 hours, less than about 5 hours, less than about 3 hours or less than about 1 hour, and wherein the patient was refractory to one or more anti-arrhythmic drugs.

In another aspect, the invention provides methods for reducing stroke rate comprising administering an amount of budiodarone effective to reduce AF episode duration and an effective amount of tecarfarin, wherein the maximum AF episode duration is reduced to less than about 20 hours, less than about 10 hours, or less than about 5 hours, and wherein the patient was refractory to one or more anti-arrhythmic drugs.

In yet another aspect, the invention provides methods for preventing atrial remodeling comprising administering an amount of budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin.

In yet another aspect, the invention provides methods for preventing atrial remodeling comprising administering an amount of budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the average AF episode duration is reduced to less than about 24 hours, less than about 5 hours, less than about 3 hours, or less than about 1 hour.

In yet another aspect, the invention provides methods for preventing atrial remodeling comprising administering an amount of budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the maximum AF episode duration is reduced to less than about 20 hours, less than about 10 hours, or less than about 5 hours.

In yet another aspect, the invention provides methods for preventing atrial remodeling comprising administering an amount of budiodarone effective to reduce AF episode duration and an effective amount of AC selected from the group consisting of is tecarfarin, dabigatran etexilate, ximelagatran, AZD0837, apixaban or rivaroxaban.

In yet another aspect, the invention provides methods for preventing atrial remodeling comprising administering an amount of budiodarone effective to reduce AF episode duration and an effective amount of AC selected from the group consisting of is tecarfarin, dabigatran etexilate, ximelagatran, AZD0837, apixaban or rivaroxaban, wherein the average AF episode duration is reduced to less than about 24 hours, less than about 5 hours, less than about 3 hours, or less than about 1 hour.

In yet another aspect, the invention provides methods for preventing atrial remodeling comprising administering an amount of budiodarone effective to reduce AF episode duration and an effective amount of AC selected from the group consisting of is tecarfarin, dabigatran etexilate, ximelagatran, AZD0837, apixaban or rivaroxaban, wherein the maximum AF episode duration is reduced to less than about 20 hours, less than about 10 hours, or less than about 5 hours.

In yet another aspect, the invention provides methods for preventing atrial remodeling comprising administering an amount of budiodarone effective to reduce AF episode duration and an effective amount of AC that is dabigatran etexilate.

In yet another aspect, the invention provides methods for preventing atrial remodeling comprising administering an amount of budiodarone effective to reduce AF episode duration and an effective amount of AC that is dabigatran etexilate, wherein the average AF episode duration is reduced to less than about 24 hours, less than about 5 hours, less than about 3 hours, or less than about 1 hour.

In yet another aspect, the invention provides methods for preventing atrial remodeling comprising administering an amount of budiodarone effective to reduce AF episode duration and an effective amount of AC that is dabigatran etexilate, wherein the maximum AF episode duration is reduced to less than about 20 hours, less than about 10 hours, or less than about 5 hours.

In yet another aspect, the invention provides methods for preventing atrial remodeling comprising administering an amount of budiodarone effective to reduce AF episode duration and an effective amount of AC selected from the group consisting of AZD0837 and ximelagatran.

In yet another aspect, the invention provides methods for preventing atrial remodeling comprising administering an amount of budiodarone effective to reduce AF episode duration and an effective amount of AC selected from the group consisting of AZD0837 and ximelagatran, wherein the average AF episode duration is reduced to less than about 24 hours, less than about 5 hours, less than about 3 hours, or less than about 1 hour.

In yet another aspect, the invention provides methods for preventing atrial remodeling comprising administering an amount of budiodarone effective to reduce AF episode duration and an effective amount of AC selected from the group consisting of AZD0837 and ximelagatran, wherein the maximum AF episode duration is reduced to less than about 20 hours, less than about 10 hours, or less than about 5 hours.

In yet another aspect, the invention provides methods for preventing atrial remodeling comprising administering an amount of budiodarone effective to reduce AF episode duration and an effective amount of AC that is apixaban.

In yet another aspect, the invention provides methods for preventing atrial remodeling comprising administering an amount of budiodarone effective to reduce AF episode duration and an effective amount of AC that is apixaban, wherein the average AF episode duration is reduced to less than about 24 hours, less than about 5 hours, less than about 3 hours, or less than about 1 hour.

In yet another aspect, the invention provides methods for preventing atrial remodeling comprising administering an amount of budiodarone effective to reduce AF episode duration and an effective amount of AC that is apixaban, wherein the maximum AF episode duration is reduced to less than about 20 hours, less than about 10 hours, or less than about 5 hours.

In yet another aspect, the invention provides methods for preventing atrial remodeling comprising administering an amount of budiodarone effective to reduce AF episode duration and an effective amount of AC that is rivaroxaban.

In yet another aspect, the invention provides methods for preventing atrial remodeling comprising administering an amount of budiodarone effective to reduce AF episode duration and an effective amount of AC that is rivaroxaban, wherein the average AF episode duration is reduced to less than about 24 hours, less than about 5 hours, less than about 3 hours, or less than about 1 hour.

In yet another aspect, the invention provides methods for preventing atrial remodeling comprising administering an amount of budiodarone effective to reduce AF episode duration and an effective amount of AC that is rivaroxaban, wherein the maximum AF episode duration is reduced to less than about 20 hours, less than about 10 hours, or less than about 5 hours.

In yet another aspect, the invention provides methods for preventing atrial remodeling comprising administering an amount of budiodarone effective to reduce AF episode duration and an effective amount of AC that is tecarfarin.

In yet another aspect, the invention provides methods for preventing atrial remodeling comprising administering an amount of budiodarone effective to reduce AF episode duration and an effective amount of AC that is tecarfarin, wherein the average AF episode duration is reduced to less than about 24 hours, less than about 5 hours, less than about 3 hours, or less than about 1 hour.

In yet another aspect, the invention provides methods for preventing atrial remodeling comprising administering an amount of budiodarone effective to reduce AF episode duration and an effective amount of AC that is tecarfarin, wherein the maximum AF episode duration is reduced to less than about 20 hours, less than about 10 hours, or less than about 5 hours.

In yet another aspect, the invention provides methods for preventing atrial remodeling comprising administering an amount of budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the patient was refractory to one or more anti-arrhythmic drugs.

In yet another aspect, the invention provides methods for preventing atrial remodeling comprising administering an amount of budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the average AF episode duration is reduced to less than about 24 hours, less than about 5 hours, less than about 3 hours, or less than about 1 hour, and wherein the patient was refractory to one or more anti-arrhythmic drugs.

In yet another aspect, the invention provides methods for preventing atrial remodeling comprising administering an amount of budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the maximum AF episode duration is reduced to less than about 20 hours, less than about 10 hours, or less than about 5 hours, and wherein the patient was refractory to one or more anti-arrhythmic drugs.

In yet another aspect, the invention provides methods for preventing atrial remodeling comprising administering an amount of budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the AC is tecarfarin, dabigatran etexilate, ximelagatran, AZD0837, apixaban or rivaroxaban, wherein the patient was refractory to one or more anti-arrhythmic drugs.

In yet another aspect, the invention provides methods for preventing atrial remodeling comprising administering an amount of budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the average AF episode duration is reduced to less than about 24 hours, less than about 5 hours, less than about 3 hours, or less than about 1 hour, and wherein the AC is tecarfarin, dabigatran etexilate, ximelagatran, AZD0837, apixaban or rivaroxaban, and wherein the patient was refractory to one or more anti-arrhythmic drugs.

In yet another aspect, the invention provides methods for preventing atrial remodeling comprising administering an amount of budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the maximum AF episode duration is reduced to less than about 20 hours, less than about 10 hours, or less than about 5 hours, and wherein the AC is tecarfarin, dabigatran etexilate, ximelagatran, AZD0837, apixaban or rivaroxaban, and wherein the patient was refractory to one or more anti-arrhythmic drugs.

In yet another aspect, the invention provides methods for preventing atrial remodeling comprising administering an amount of budiodarone effective to reduce AF episode duration and an effective amount of AC selected from the group consisting of is tecarfarin, dabigatran etexilate, ximelagatran, AZD0837, apixaban or rivaroxaban, wherein the patient was refractory to one or more anti-arrhythmic drugs.

In yet another aspect, the invention provides methods for preventing atrial remodeling comprising administering an amount of budiodarone effective to reduce AF episode duration and an effective amount of AC selected from the group consisting of is tecarfarin, dabigatran etexilate, ximelagatran, AZD0837, apixaban or rivaroxaban, wherein the average AF episode duration is reduced to less than about 24 hours, less than about 5 hours, less than about 3 hours, or less than about 1 hour, wherein the patient was refractory to one or more anti-arrhythmic drugs.

In yet another aspect, the invention provides methods for preventing atrial remodeling comprising administering an amount of budiodarone effective to reduce AF episode duration and an effective amount of AC selected from the group consisting of is tecarfarin, dabigatran etexilate, ximelagatran, AZD0837, apixaban or rivaroxaban, wherein the maximum AF episode duration is reduced to less than about 20 hours, less than about 10 hours, or less than about 5 hours, wherein the patient was refractory to one or more anti-arrhythmic drugs.

In yet another aspect, the invention provides methods for preventing atrial remodeling comprising administering an amount of budiodarone effective to reduce AF episode duration and an effective amount of AC that is dabigatran etexilate, wherein the average AF episode duration is reduced to less than about 24 hours, less than about 5 hours, less than about 3 hours, or less than about 1 hour, and wherein the patient was refractory to one or more anti-arrhythmic drugs.

In yet another aspect, the invention provides methods for preventing atrial remodeling comprising administering an amount of budiodarone effective to reduce AF episode duration and an effective amount of AC that is dabigatran etexilate, wherein the maximum AF episode duration is reduced to less than about 20 hours, less than about 10 hours, or less than about 5 hours, and wherein the patient was refractory to one or more anti-arrhythmic drugs.

In yet another aspect, the invention provides methods for preventing atrial remodeling comprising administering an amount of budiodarone effective to reduce AF episode duration and an effective amount of AC selected from the group consisting of AZD0837 and ximelagatran, wherein the average AF episode duration is reduced to less than about 24 hours, less than about 5 hours, less than about 3 hours, or less than about 1 hour, and wherein the patient was refractory to one or more anti-arrhythmic drugs.

In yet another aspect, the invention provides methods for preventing atrial remodeling comprising administering an amount of budiodarone effective to reduce AF episode duration and an effective amount of AC selected from the group consisting of AZD0837 and ximelagatran, wherein the maximum AF episode duration is reduced to less than about 20 hours, less than about 10 hours, or less than about 5 hours, and wherein the patient was refractory to one or more anti-arrhythmic drugs.

In yet another aspect, the invention provides methods for preventing atrial remodeling comprising administering an amount of budiodarone effective to reduce AF episode duration and an effective amount of AC that is apixaban, wherein the average AF episode duration is reduced to less than about 24 hours, less than about 5 hours, less than about 3 hours, or less than about 1 hour, and wherein the patient was refractory to one or more anti-arrhythmic drugs.

In yet another aspect, the invention provides methods for preventing atrial remodeling comprising administering an amount of budiodarone effective to reduce AF episode duration and an effective amount of AC that is apixaban, wherein the maximum AF episode duration is reduced to less than about 20 hours, less than about 10 hours, or less than about 5 hours, and wherein the patient was refractory to one or more anti-arrhythmic drugs.

In yet another aspect, the invention provides methods for preventing atrial remodeling comprising administering an amount of budiodarone effective to reduce AF episode duration and an effective amount of AC that is rivaroxaban, wherein the average AF episode duration is reduced to less than about 24 hours, less than about 5 hours, less than about 3 hours, or less than about 1 hour, and wherein the patient was refractory to one or more anti-arrhythmic drugs.

In yet another aspect, the invention provides methods for preventing atrial remodeling comprising administering an amount of budiodarone effective to reduce AF episode duration and an effective amount of AC that is rivaroxaban, wherein the maximum AF episode duration is reduced to less than about 20 hours, less than about 10 hours, or less than about 5 hours, and wherein the patient was refractory to one or more anti-arrhythmic drugs.

In yet another aspect, the invention provides methods for preventing atrial remodeling comprising administering an amount of budiodarone effective to reduce AF episode duration and an effective amount of AC that is tecarfarin, wherein the average AF episode duration is reduced to less than about 24 hours, less than about 5 hours, less than about 3 hours, or less than about 1 hour, and wherein the patient was refractory to one or more anti-arrhythmic drugs.

In yet another aspect, the invention provides methods for preventing atrial remodeling comprising administering an amount of budiodarone effective to reduce AF episode duration and an effective amount of AC that is tecarfarin, wherein the maximum AF episode duration is reduced to less than about 20 hours, less than about 10 hours, or less than about 5 hours, and wherein the patient was refractory to one or more anti-arrhythmic drugs.

In another aspect, the invention provides methods for reversing atrial remodeling comprising administering an amount of budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin.

In another aspect, the invention provides methods for reversing atrial remodeling comprising administering an amount of budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the average AF episode duration is reduced to less than about 24 hours, less than about 5 hours, less than about 3 hours, or less than about 1 hour.

In another aspect, the invention provides methods for reversing atrial remodeling comprising administering an amount of budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the maximum AF episode duration is reduced to less than about 20 hours, less than about 10 hours, or less than about 5 hours.

In another aspect, the invention provides methods for reversing atrial remodeling comprising administering an amount of budiodarone effective to reduce AF episode duration and an effective amount of AC selected from the group consisting of tecarfarin, dabigatran etexilate, ximelagatran, AZD0837, apixaban and rivaroxaban.

In another aspect, the invention provides methods for reversing atrial remodeling comprising administering an amount of budiodarone effective to reduce AF episode duration and an effective amount of AC selected from the group consisting of tecarfarin, dabigatran etexilate, ximelagatran, AZD0837, apixaban or rivaroxaban, wherein the average AF episode duration is reduced to less than about 24 hours, less than about 5 hours, less than about 3 hours, or less than about 1 hour.

In another aspect, the invention provides methods for reversing atrial remodeling comprising administering an amount of budiodarone effective to reduce AF episode duration and an effective amount of AC selected from the group consisting of tecarfarin, dabigatran etexilate, ximelagatran, AZD0837, apixaban or rivaroxaban, wherein the maximum AF episode duration is reduced to less than about 20 hours, less than about 10 hours, or less than about 5 hours.

A method for reversing atrial remodeling comprising administering an amount of budiodarone effective to reduce AF episode duration and an effective amount of AC that is dabigatran etexilate.

In another aspect, the invention provides methods for reversing atrial remodeling comprising administering an amount of budiodarone effective to reduce AF episode duration and an effective amount of AC that is dabigatran etexilate, wherein the average AF episode duration is reduced to less than about 24 hours, less than about 5 hours, less than about 3 hours, or less than about 1 hour.

In another aspect, the invention provides methods for reversing atrial remodeling comprising administering an amount of budiodarone effective to reduce AF episode duration and an effective amount of AC that is dabigatran etexilate, wherein the maximum AF episode duration is reduced to less than about 20 hours, less than about 10 hours, or less than about 5 hours.

In another aspect, the invention provides methods for reversing atrial remodeling comprising administering an amount of budiodarone effective to reduce AF episode duration and an effective amount of AC selected from the group consisting of ximelagatran and AZD0837.

In another aspect, the invention provides methods for reversing atrial remodeling comprising administering an amount of budiodarone effective to reduce AF episode duration and an effective amount of AC selected from the group consisting of ximelagatran and AZD0837, wherein the average AF episode duration is reduced to less than about 24 hours, less than about 5 hours, less than about 3 hours, or less than about 1 hour.

In another aspect, the invention provides methods for reversing atrial remodeling comprising administering an amount of budiodarone effective to reduce AF episode duration and an effective amount of AC selected from the group consisting of ximelagatran and AZD0837, wherein the maximum AF episode duration is reduced to less than about 20 hours, less than about 10 hours, or less than about 5 hours.

In another aspect, the invention provides methods for reversing atrial remodeling comprising administering an amount of budiodarone effective to reduce AF episode duration and an effective amount of AC that is apixaban.

In another aspect, the invention provides methods for reversing atrial remodeling comprising administering an amount of budiodarone effective to reduce AF episode duration and an effective amount of AC that is apixaban, wherein the average AF episode duration is reduced to less than about 24 hours, less than about 5 hours, less than about 3 hours, or less than about 1 hour.

In another aspect, the invention provides methods for reversing atrial remodeling comprising administering an amount of budiodarone effective to reduce AF episode duration and an effective amount of AC that is apixaban, wherein the maximum AF episode duration is reduced to less than about 20 hours, less than about 10 hours, or less than about 5 hours.

In another aspect, the invention provides methods for reversing atrial remodeling comprising administering an amount of budiodarone effective to reduce AF episode duration and an effective amount of AC that is rivaroxaban.

In another aspect, the invention provides methods for reversing atrial remodeling comprising administering an amount of budiodarone effective to reduce AF episode duration and an effective amount of AC that is rivaroxaban, wherein the average AF episode duration is reduced to less than about 24 hours, less than about 5 hours, less than about 3 hours, or less than about 1 hour.

In another aspect, the invention provides methods for reversing atrial remodeling comprising administering an amount of budiodarone effective to reduce AF episode duration and an effective amount of AC that is rivaroxaban, wherein the maximum AF episode duration is reduced to less than about 20 hours, less than about 10 hours, or less than about 5 hours.

In another aspect, the invention provides methods for reversing atrial remodeling comprising administering an amount of budiodarone effective to reduce AF episode duration and an effective amount of AC that is tecarfarin.

In another aspect, the invention provides methods for reversing atrial remodeling comprising administering an amount of budiodarone effective to reduce AF episode duration and an effective amount of AC that is tecarfarin, wherein the average AF episode duration is reduced to less than about 24 hours, less than about 5 hours, less than about 3 hours, or less than about 1 hour.

In another aspect, the invention provides methods for reversing atrial remodeling comprising administering an amount of budiodarone effective to reduce AF episode duration and an effective amount of AC that is tecarfarin, wherein the maximum AF episode duration is reduced to less than about 20 hours, less than about 10 hours, or less than about 5 hours.

In another aspect, the invention provides methods for reversing atrial remodeling comprising administering an amount of budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the patient was refractory to one or more anti-arrhythmic drugs.

In another aspect, the invention provides methods for reversing atrial remodeling comprising administering an amount of budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the average AF episode duration is reduced to less than about 24 hours, less than about 5 hours, less than about 3 hours, or less than about 1 hour, and wherein the patient was refractory to one or more anti-arrhythmic drugs.

In another aspect, the invention provides methods for reversing atrial remodeling comprising administering an amount of budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the maximum AF episode duration is reduced to less than about 20 hours, less than about 10 hours, or less than about 5 hours, and wherein the patient was refractory to one or more anti-arrhythmic drugs.

In another aspect, the invention provides methods for reversing atrial remodeling comprising administering an amount of budiodarone effective to reduce AF episode duration and an effective amount of AC selected from the group consisting of tecarfarin, dabigatran etexilate, ximelagatran, AZD0837, apixaban and rivaroxaban, wherein the patient was refractory to one or more anti-arrhythmic drugs.

In another aspect, the invention provides methods for reversing atrial remodeling comprising administering an amount of budiodarone effective to reduce AF episode duration and an effective amount of AC selected from the group consisting of tecarfarin, dabigatran etexilate, ximelagatran, AZD0837, apixaban or rivaroxaban, wherein the average AF episode duration is reduced to less than about 24 hours, less than about 5 hours, less than about 3 hours, or less than about 1 hour, and wherein the patient was refractory to one or more anti-arrhythmic drugs.

In another aspect, the invention provides methods for reversing atrial remodeling comprising administering an amount of budiodarone effective to reduce AF episode duration and an effective amount of AC selected from the group consisting of tecarfarin, dabigatran etexilate, ximelagatran, AZD0837, apixaban or rivaroxaban, wherein the maximum AF episode duration is reduced to less than about 20 hours, less than about 10 hours, or less than about 5 hours, and wherein the patient was refractory to one or more anti-arrhythmic drugs.

A method for reversing atrial remodeling comprising administering an amount of budiodarone effective to reduce AF episode duration and an effective amount of AC that is dabigatran etexilate, wherein the patient was refractory to one or more anti-arrhythmic drugs.

In another aspect, the invention provides methods for reversing atrial remodeling comprising administering an amount of budiodarone effective to reduce AF episode duration and an effective amount of AC that is dabigatran etexilate, wherein the average AF episode duration is reduced to less than about 24 hours, less than about 5 hours, less than about 3 hours, or less than about 1 hour, and wherein the patient was refractory to one or more anti-arrhythmic drugs.

In another aspect, the invention provides methods for reversing atrial remodeling comprising administering an amount of budiodarone effective to reduce AF episode duration and an effective amount of AC that is dabigatran etexilate, wherein the maximum AF episode duration is reduced to less than about 20 hours, less than about 10 hours, or less than about 5 hours, and wherein the patient was refractory to one or more anti-arrhythmic drugs.

In another aspect, the invention provides methods for reversing atrial remodeling comprising administering an amount of budiodarone effective to reduce AF episode duration and an effective amount of AC selected from the group consisting of ximelagatran and AZD0837, wherein the patient was refractory to one or more anti-arrhythmic drugs.

In another aspect, the invention provides methods for reversing atrial remodeling comprising administering an amount of budiodarone effective to reduce AF episode duration and an effective amount of AC selected from the group consisting of ximelagatran and AZD0837, wherein the average AF episode duration is reduced to less than about 24 hours, less than about 5 hours, less than about 3 hours, or less than about 1 hour, and wherein the patient was refractory to one or more anti-arrhythmic drugs.

In another aspect, the invention provides methods for reversing atrial remodeling comprising administering an amount of budiodarone effective to reduce AF episode duration and an effective amount of AC selected from the group consisting of ximelagatran and AZD0837, wherein the maximum AF episode duration is reduced to less than about 20 hours, less than about 10 hours, or less than about 5 hours, and wherein the patient was refractory to one or more anti-arrhythmic drugs.

In another aspect, the invention provides methods for reversing atrial remodeling comprising administering an amount of budiodarone effective to reduce AF episode duration and an effective amount of AC that is apixaban, wherein the patient was refractory to one or more anti-arrhythmic drugs.

In another aspect, the invention provides methods for reversing atrial remodeling comprising administering an amount of budiodarone effective to reduce AF episode duration and an effective amount of AC that is apixaban, wherein the average AF episode duration is reduced to less than about 24 hours, less than about 5 hours, less than about 3 hours, or less than about 1 hour, and wherein the patient was refractory to one or more anti-arrhythmic drugs.

In another aspect, the invention provides methods for reversing atrial remodeling comprising administering an amount of budiodarone effective to reduce AF episode duration and an effective amount of AC that is apixaban, wherein the maximum AF episode duration is reduced to less than about 20 hours, less than about 10 hours, or less than about 5 hours, and wherein the patient was refractory to one or more anti-arrhythmic drugs.

In another aspect, the invention provides methods for reversing atrial remodeling comprising administering an amount of budiodarone effective to reduce AF episode duration and an effective amount of AC that is rivaroxaban, wherein the patient was refractory to one or more anti-arrhythmic drugs.

In another aspect, the invention provides methods for reversing atrial remodeling comprising administering an amount of budiodarone effective to reduce AF episode duration and an effective amount of AC that is rivaroxaban, wherein the average AF episode duration is reduced to less than about 24 hours, less than about 5 hours, less than about 3 hours, or less than about 1 hour, and wherein the patient was refractory to one or more anti-arrhythmic drugs.

In another aspect, the invention provides methods for reversing atrial remodeling comprising administering an amount of budiodarone effective to reduce AF episode duration and an effective amount of AC that is rivaroxaban, wherein the maximum AF episode duration is reduced to less than about 20 hours, less than about 10 hours, or less than about 5 hours, and wherein the patient was refractory to one or more anti-arrhythmic drugs.

In another aspect, the invention provides methods for reversing atrial remodeling comprising administering an amount of budiodarone effective to reduce AF episode duration and an effective amount of AC that is tecarfarin, wherein the patient was refractory to one or more anti-arrhythmic drugs.

In another aspect, the invention provides methods for reversing atrial remodeling comprising administering an amount of budiodarone effective to reduce AF episode duration and an effective amount of AC that is tecarfarin, wherein the average AF episode duration is reduced to less than about 24 hours, less than about 5 hours, less than about 3 hours, or less than about 1 hour, and wherein the patient was refractory to one or more anti-arrhythmic drugs.

In another aspect, the invention provides methods for reversing atrial remodeling comprising administering an amount of budiodarone effective to reduce AF episode duration and an effective amount of AC that is tecarfarin, wherein the maximum AF episode duration is reduced to less than about 20 hours, less than about 10 hours, or less than about 5 hours, and wherein the patient was refractory to one or more anti-arrhythmic drugs.

In one aspect, the invention provides methods for reducing stroke rate comprising administering an amount of budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the effective amount of budiodarone is 400 mg BID or more preferably 600 mg BID.

In another aspect, the invention provides methods for reducing stroke rate comprising administering an amount of budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the average AF episode duration is reduced to less than about 24 hours, less than about 5 hours, less than about 3 hours, or less than about 1 hour, and wherein the effective amount of budiodarone is 600 mg BID.

In another aspect, the invention provides methods for reducing stroke rate comprising administering an amount of budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the maximum AF episode duration is reduced to less than about 20 hours, less than about 10 hours, or less than about 5 hours, and wherein the effective amount of budiodarone is 400 mg BID or more preferably 600 mg BID.

In another aspect, the invention provides methods for reducing stroke rate comprising administering an amount of budiodarone effective to reduce AF episode duration and an effective amount of AC selected from the group consisting of tecarfarin, dabigatran etexilate, ximelagatran, AZD0837, apixaban or rivaroxaban, and wherein the effective amount of budiodarone is 400 mg BID or more preferably 600 mg BID.

In another aspect, the invention provides methods for reducing stroke rate comprising administering an amount of budiodarone effective to reduce AF episode duration and an effective amount of AC selected from the group consisting of tecarfarin, dabigatran etexilate, ximelagatran, AZD0837, apixaban or rivaroxaban, wherein the average AF episode duration is reduced to less than about 24 hours, less than about 5 hours, less than about 3 hours, or less than about 1 hour, and wherein the effective amount of budiodarone is 400 mg BID or more preferably 600 mg BID.

In another aspect, the invention provides methods for reducing stroke rate comprising administering an amount of budiodarone effective to reduce AF episode duration and an effective amount of AC selected from the group consisting of tecarfarin, dabigatran etexilate, ximelagatran, AZD0837, apixaban or rivaroxaban, wherein the maximum AF episode duration is reduced to less than about 20 hours, less than about 10 hours, or less than about 5 hours, and wherein the effective amount of budiodarone is 400 mg BID or more preferably 600 mg BID.

In another aspect, the invention provides methods for reducing stroke rate comprising administering an amount of budiodarone effective to reduce AF episode duration and an effective amount of dabigatran etexilate, wherein the average AF episode duration is reduced to less than about 24 hours, less than about 5 hours, less than about 3 hours, or less than about 1 hour, and wherein the effective amount of budiodarone is 400 mg BID or more preferably 600 mg BID.

In another aspect, the invention provides methods for reducing stroke rate comprising administering an amount of budiodarone effective to reduce AF episode duration and an effective amount of dabigatran etexilate, wherein the maximum AF episode duration is reduced to less than about 20 hours, less than about 10 hours, or less than about 5 hours, and wherein the effective amount of budiodarone is 400 mg BID or more preferably 600 mg BID.

In another aspect, the invention provides methods for reducing stroke rate comprising administering an amount of budiodarone effective to reduce AF episode duration and an effective amount of AC selected from the group consisting of ximelagatran and AZD0837, wherein the average AF episode duration is reduced to less than about 24 hours, less than about 5 hours, less than about 3 hours, or less than about 1 hour, and wherein the effective amount of budiodarone is 400 mg BID or more preferably 600 mg BID.

In another aspect, the invention provides methods for reducing stroke rate comprising administering an amount of budiodarone effective to reduce AF episode duration and an effective amount of AC selected from the group consisting of ximelagatran and AZD0837, wherein the maximum AF episode duration is reduced to less than about 20 hours, less than about 10 hours, or less than about 5 hours, and wherein the effective amount of budiodarone is 400 mg BID or more preferably 600 mg BID.

In another aspect, the invention provides methods for reducing stroke rate comprising administering an amount of budiodarone effective to reduce AF episode duration and an effective amount of apixaban, wherein the average AF episode duration is reduced to less than about 24 hours, less than about 5 hours, less than about 3 hours, or less than about 1 hour, and wherein the effective amount of budiodarone is 400 mg BID or more preferably 600 mg BID.

In another aspect, the invention provides methods for reducing stroke rate comprising administering an amount of budiodarone effective to reduce AF episode duration and an effective amount of apixaban, wherein the maximum AF episode duration is reduced to less than about 20 hours, less than about 10 hours, or less than about 5 hours, and wherein the effective amount of budiodarone is 400 mg BID or more preferably 600 mg BID.

In another aspect, the invention provides methods for reducing stroke rate comprising administering an amount of budiodarone effective to reduce AF episode duration and an effective amount of rivaroxaban, wherein the average AF episode duration is reduced to less than about 24 hours, less than about 5 hours, less than about 3 hours, or less than about 1 hour, and wherein the effective amount of budiodarone is 400 mg BID or more preferably 600 mg BID.

In another aspect, the invention provides methods for reducing stroke rate comprising administering an amount of budiodarone effective to reduce AF episode duration and an effective amount of rivaroxaban, wherein the maximum AF episode duration is reduced to less than about 20 hours, less than about 10 hours, or less than about 5 hours, and wherein the effective amount of budiodarone is 400 mg BID or more preferably 600 mg BID.

In another aspect, the invention provides methods for reducing stroke rate comprising administering an amount of budiodarone effective to reduce AF episode duration and an effective amount of tecarfarin, wherein the average AF episode duration is reduced to less than about 24 hours, less than about 5 hours, less than about 3 hours, or less than about 1 hour, and wherein the effective amount of budiodarone is 400 mg BID or more preferably 600 mg BID.

In another aspect, the invention provides methods for reducing stroke rate comprising administering an amount of budiodarone effective to reduce AF episode duration and an effective amount of tecarfarin, wherein the maximum AF episode duration is reduced to less than about 20 hours, less than about 10 hours, or less than about 5 hours, and wherein the effective amount of budiodarone is 400 mg BID or more preferably 600 mg BID.

In another aspect, the invention provides methods for reducing stroke rate comprising administering an amount of budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the reduced stroke rate is less than the age-adjusted overall stroke rate, and wherein the effective amount of budiodarone is 400 mg BID or more preferably 600 mg BID.

In another aspect, the invention provides methods for reducing stroke rate comprising administering an amount of budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the average AF episode duration is reduced to less than about 24 hours, less than about 5 hours, less than about 3 hours, or less than about 1 hour, and wherein the reduced stroke rate is less than the age-adjusted overall stroke rate, and wherein the effective amount of budiodarone is 400 mg BID or more preferably 600 mg BID.

In another aspect, the invention provides methods for reducing stroke rate comprising administering an amount of budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the maximum AF episode duration is reduced to less than about 20 hours, less than about 10 hours or less than about 5 hours, and wherein the reduced stroke rate is less than the age-adjusted overall stroke rate, and wherein the effective amount of budiodarone is 400 mg BID or more preferably 600 mg BID.

In another aspect, the invention provides methods for reducing stroke rate comprising administering an amount of budiodarone effective to reduce AF episode duration and an effective amount of AC selected from the group consisting of tecarfarin, dabigatran etexilate, ximelagatran, AZD0837, apixaban or rivaroxaban, wherein the average AF episode duration is reduced to less than about 24 hours, less than about 5 hours, less than about 3 hours, or less than about 1 hour, and wherein the reduced stroke rate is less than the age-adjusted overall stroke rate, and wherein the effective amount of budiodarone is 400 mg BID or more preferably 600 mg BID.

In another aspect, the invention provides methods for reducing stroke rate comprising administering an amount of budiodarone effective to reduce AF episode duration and an effective amount of AC selected from the group consisting of tecarfarin, dabigatran etexilate, ximelagatran, AZD0837, apixaban or rivaroxaban, wherein the maximum AF episode duration is reduced to less than about 20 hours, less than about 10 hours or less than about 5 hours, and wherein the reduced stroke rate is less than the age-adjusted overall stroke rate, and wherein the effective amount of budiodarone is 400 mg BID or more preferably 600 mg BID.

In another aspect, the invention provides methods for reducing stroke rate comprising administering an amount of budiodarone effective to reduce AF episode duration and an effective amount of dabigatran etexilate, wherein the average AF episode duration is reduced to less than about 24 hours, less than about 5 hours, less than about 3 hours or less than about 1 hour, and wherein the reduced stroke rate is less than the age-adjusted overall stroke rate, and wherein the effective amount of budiodarone is 400 mg BID or more preferably 600 mg BID.

In another aspect, the invention provides methods for reducing stroke rate comprising administering an amount of budiodarone effective to reduce AF episode duration and an effective amount of dabigatran etexilate, wherein the maximum AF episode duration is reduced to less than about 20 hours, less than about 10 hours, or less than about 5 hours, and wherein the reduced stroke rate is less than the age-adjusted overall stroke rate, and wherein the effective amount of budiodarone is 400 mg BID or more preferably 600 mg BID.

In another aspect, the invention provides methods for reducing stroke rate comprising administering an amount of budiodarone effective to reduce AF episode duration and an effective amount of AC selected from the group consisting of ximelagatran and AZD0837, wherein the average AF episode duration is reduced to less than about 24 hours, less than about 5 hours, less than about 3 hours, or less than about 1 hour, and wherein the reduced stroke rate is less than the age-adjusted overall stroke rate, and wherein the effective amount of budiodarone is 400 mg BID or more preferably 600 mg BID.

In another aspect, the invention provides methods for reducing stroke rate comprising administering an amount of budiodarone effective to reduce AF episode duration and an effective amount of AC selected from the group consisting of ximelagatran and AZD0837, wherein the maximum AF episode duration is reduced to less than about 20 hours, less than about 10 hours, or less than about 5 hours, and wherein the reduced stroke rate is less than the age-adjusted overall stroke rate, wherein the effective amount of budiodarone is 400 mg BID or more preferably 600 mg BID.

In another aspect, the invention provides methods for reducing stroke rate comprising administering an amount of budiodarone effective to reduce AF episode duration and an effective amount of apixaban, wherein the average AF episode duration is reduced to less than about 24 hours, less than about 5 hours, less than about 3 hours, or less than about 1 hour, and wherein the reduced stroke rate is less than the age-adjusted overall stroke rate, and wherein the effective amount of budiodarone is 400 mg BID or more preferably 600 mg BID.

In another aspect, the invention provides methods for reducing stroke rate comprising administering an amount of budiodarone effective to reduce AF episode duration and an effective amount of apixaban, wherein the maximum AF episode duration is reduced to less than about 20 hours, less than about 10 hours, or less than about 5 hours, and wherein the reduced stroke rate is less than the age-adjusted overall stroke rate, and wherein the effective amount of budiodarone is 400 mg BID or more preferably 600 mg BID.

In another aspect, the invention provides methods for reducing stroke rate comprising administering an amount of budiodarone effective to reduce AF episode duration and an effective amount of rivaroxaban, wherein the average AF episode duration is reduced to less than about 24 hours, less than about 5 hours, less than about 3 hours, or less than about 1 hour, and wherein the reduced stroke rate is less than the age-adjusted overall stroke rate, and wherein the effective amount of budiodarone is 400 mg BID or more preferably 600 mg BID.

In another aspect, the invention provides methods for reducing stroke rate comprising administering an amount of budiodarone effective to reduce AF episode duration and an effective amount of rivaroxaban, wherein the maximum AF episode duration is reduced to less than about 20 hours, less than about 10 hours, or less than about 5 hours, and wherein the reduced stroke rate is less than the age-adjusted overall stroke rate, and wherein the effective amount of budiodarone is 400 mg BID or more preferably 600 mg BID.

In another aspect, the invention provides methods for reducing stroke rate comprising administering an amount of budiodarone effective to reduce AF episode duration and an effective amount of tecarfarin, wherein the average AF episode duration is reduced to less than about 24 hours, less than about 5 hours, less than about 3 hours, or less than about 1 hour, and wherein the reduced stroke rate is less than the age-adjusted overall stroke rate, and wherein the effective amount of budiodarone is 400 mg BID or more preferably 600 mg BID.

In another aspect, the invention provides methods for reducing stroke rate comprising administering an amount of budiodarone effective to reduce AF episode duration and an effective amount of tecarfarin, wherein the maximum AF episode duration is reduced to less than about 20 hours, less than about 10 hours, or less than about 5 hours, and wherein the reduced stroke rate is less than the age-adjusted overall stroke rate, and wherein the effective amount of budiodarone is 400 mg BID or more preferably 600 mg BID.

In other aspects, the invention provides methods wherein the patient was refractory to one or more anti-arrhythmic drugs prior to treating with each above recited 400 mgBID or more preferably 600 mg BID dose of budiodarone.

In yet another aspect, the invention provides methods for preventing atrial remodeling comprising administering an amount of budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the effective amount of budiodarone is 400 mg BID or more preferably 600 mg BID.

In yet another aspect, the invention provides methods for preventing atrial remodeling comprising administering an amount of budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, and wherein the effective amount of budiodarone is 400 mg BID or more preferably 600 mg BID.

In yet another aspect, the invention provides methods for preventing atrial remodeling comprising administering an amount of budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the average AF episode duration is reduced to less than about 24 hours, less than about 5 hours, less than about 3 hours, or less than about 1 hour, and wherein the effective amount of budiodarone is 400 mg BID or more preferably 600 mg BID. In yet another aspect, the invention provides methods for preventing atrial remodeling comprising administering an amount of budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the maximum AF episode duration is reduced to less than about 20 hours, less than about 10 hours, or less than about 5 hours, and wherein the effective amount of budiodarone is 400 mg BID or more preferably 600 mg BID.

In yet another aspect, the invention provides methods for preventing atrial remodeling comprising administering an amount of budiodarone effective to reduce AF episode duration and an effective amount of AC selected from the group consisting of is tecarfarin, dabigatran etexilate, ximelagatran, AZD0837, apixaban or rivaroxaban, wherein the average AF episode duration is reduced to less than about 24 hours, less than about 5 hours, less than about 3 hours, or less than about 1 hour, and wherein the effective amount of budiodarone is 400 mg BID or more preferably 600 mg BID.

In yet another aspect, the invention provides methods for preventing atrial remodeling comprising administering an amount of budiodarone effective to reduce AF episode duration and an effective amount of AC selected from the group consisting of is tecarfarin, dabigatran etexilate, ximelagatran, AZD0837, apixaban or rivaroxaban, wherein the maximum AF episode duration is reduced to less than about 20 hours, less than about 10 hours, or less than about 5 hours, and wherein the effective amount of budiodarone is 400 mg BID or more preferably 600 mg BID.

In yet another aspect, the invention provides methods for preventing atrial remodeling comprising administering an amount of budiodarone effective to reduce AF episode duration and an effective amount of AC that is dabigatran etexilate, wherein the effective amount of budiodarone is 400 mg BID or more preferably 600 mg BID.

In yet another aspect, the invention provides methods for preventing atrial remodeling comprising administering an amount of budiodarone effective to reduce AF episode duration and an effective amount of AC that is dabigatran etexilate, wherein the average AF episode duration is reduced to less than about 24 hours, less than about 5 hours, less than about 3 hours, or less than about 1 hour, and wherein the effective amount of budiodarone is 400 mg BID or more preferably 600 mg BID.

In yet another aspect, the invention provides methods for preventing atrial remodeling comprising administering an amount of budiodarone effective to reduce AF episode duration and an effective amount of AC that is dabigatran etexilate, wherein the maximum AF episode duration is reduced to less than about 20 hours, less than about 10 hours, or less than about 5 hours, and wherein the effective amount of budiodarone is 400 mg BID or more preferably 600 mg BID.

In yet another aspect, the invention provides methods for preventing atrial remodeling comprising administering an amount of budiodarone effective to reduce AF episode duration and an effective amount of AC selected from the group consisting of AZD0837 and ximelagatran, wherein the effective amount of budiodarone is 400 mg BID or more preferably 600 mg BID.

In yet another aspect, the invention provides methods for preventing atrial remodeling comprising administering an amount of budiodarone effective to reduce AF episode duration and an effective amount of AC selected from the group consisting of AZD0837 and ximelagatran, wherein the average AF episode duration is reduced to less than about 24 hours, less than about 5 hours, less than about 3 hours, or less than about 1 hour, and wherein the effective amount of budiodarone is 400 mg BID or more preferably 600 mg BID.

In yet another aspect, the invention provides methods for preventing atrial remodeling comprising administering an amount of budiodarone effective to reduce AF episode duration and an effective amount of AC selected from the group consisting of AZD0837 and ximelagatran, wherein the maximum AF episode duration is reduced to less than about 20 hours, less than about 10 hours, or less than about 5 hours, and wherein the effective amount of budiodarone is 400 mg BID or more preferably 600 mg BID.

In yet another aspect, the invention provides methods for preventing atrial remodeling comprising administering an amount of budiodarone effective to reduce AF episode duration and an effective amount of AC that is apixaban, wherein the effective amount of budiodarone is 400 mg BID or more preferably 600 mg BID.

In yet another aspect, the invention provides methods for preventing atrial remodeling comprising administering an amount of budiodarone effective to reduce AF episode duration and an effective amount of AC that is apixaban, wherein the average AF episode duration is reduced to less than about 24 hours, less than about 5 hours, less than about 3 hours, or less than about 1 hour, and wherein the effective amount of budiodarone is 400 mg BID or more preferably 600 mg BID.

In yet another aspect, the invention provides methods for preventing atrial remodeling comprising administering an amount of budiodarone effective to reduce AF episode duration and an effective amount of AC that is apixaban, wherein the maximum AF episode duration is reduced to less than about 20 hours, less than about 10 hours, or less than about 5 hours, and wherein the effective amount of budiodarone is 400 mg BID or more preferably 600 mg BID.

In yet another aspect, the invention provides methods for preventing atrial remodeling comprising administering an amount of budiodarone effective to reduce AF episode duration and an effective amount of AC that is rivaroxaban, wherein the effective amount of budiodarone is 400 mg BID or more preferably 600 mg BID.

In yet another aspect, the invention provides methods for preventing atrial remodeling comprising administering an amount of budiodarone effective to reduce AF episode duration and an effective amount of AC that is rivaroxaban, wherein the average AF episode duration is reduced to less than about 24 hours, less than about 5 hours, less than about 3 hours, or less than about 1 hour, and wherein the effective amount of budiodarone is 400 mg BID or more preferably 600 mg BID.

In yet another aspect, the invention provides methods for preventing atrial remodeling comprising administering an amount of budiodarone effective to reduce AF episode duration and an effective amount of AC that is rivaroxaban, wherein the maximum AF episode duration is reduced to less than about 20 hours, less than about 10 hours, or less than about 5 hours, and wherein the effective amount of budiodarone is 400 mg BID or more preferably 600 mg BID.

In yet another aspect, the invention provides methods for preventing atrial remodeling comprising administering an amount of budiodarone effective to reduce AF episode duration and an effective amount of AC that is tecarfarin, wherein the effective amount of budiodarone is 400 mg BID or more preferably 600 mg BID.

In yet another aspect, the invention provides methods for preventing atrial remodeling comprising administering an amount of budiodarone effective to reduce AF episode duration and an effective amount of AC that is tecarfarin, wherein the average AF episode duration is reduced to less than about 24 hours, less than about 5 hours, less than about 3 hours, or less than about 1 hour, and wherein the effective amount of budiodarone is 400 mg BID or more preferably 600 mg BID.

In yet another aspect, the invention provides methods for preventing atrial remodeling comprising administering an amount of budiodarone effective to reduce AF episode duration and an effective amount of AC that is tecarfarin, wherein the maximum AF episode duration is reduced to less than about 20 hours, less than about 10 hours, or less than about 5 hours, and wherein the effective amount of budiodarone is 400 mg BID or more preferably 600 mg BID.

In another aspect, the invention provides methods for reversing atrial remodeling comprising administering an amount of budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the effective amount of budiodarone is 400 mg BID or more preferably 600 mg BID.

In another aspect, the invention provides methods for reversing atrial remodeling comprising administering an amount of budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the average AF episode duration is reduced to less than about 24 hours, less than about 5 hours, less than about 3 hours, or less than about 1 hour, and wherein the effective amount of budiodarone is 400 mg BID or more preferably 600 mg BID.

In another aspect, the invention provides methods for reversing atrial remodeling comprising administering an amount of budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the maximum AF episode duration is reduced to less than about 20 hours, less than about 10 hours, or less than about 5 hours, and wherein the effective amount of budiodarone is 400 mg BID or more preferably 600 mg BID.

In another aspect, the invention provides methods for reversing atrial remodeling comprising administering an amount of budiodarone effective to reduce AF episode duration and an effective amount of AC selected from the group consisting of tecarfarin, dabigatran etexilate, ximelagatran, AZD0837, apixaban and rivaroxaban, wherein the effective amount of budiodarone is 400 mg BID or more preferably 600 mg BID.

In another aspect, the invention provides methods for reversing atrial remodeling comprising administering an amount of budiodarone effective to reduce AF episode duration and an effective amount of AC selected from the group consisting of tecarfarin, dabigatran etexilate, ximelagatran, AZD0837, apixaban or rivaroxaban, wherein the average AF episode duration is reduced to less than about 24 hours, less than about 5 hours, less than about 3 hours, or less than about 1 hour, and wherein the effective amount of budiodarone is 400 mg BID or more preferably 600 mg BID.

In another aspect, the invention provides methods for reversing atrial remodeling comprising administering an amount of budiodarone effective to reduce AF episode duration and an effective amount of AC selected from the group consisting of tecarfarin, dabigatran etexilate, ximelagatran, AZD0837, apixaban or rivaroxaban, wherein the maximum AF episode duration is reduced to less than about 20 hours, less than about 10 hours, or less than about 5 hours, and wherein the effective amount of budiodarone is 400 mg BID or more preferably 600 mg BID.

A method for reversing atrial remodeling comprising administering an amount of budiodarone effective to reduce AF episode duration and an effective amount of AC that is dabigatran etexilate, wherein the effective amount of budiodarone is 400 mg BID or more preferably 600 mg BID.

In another aspect, the invention provides methods for reversing atrial remodeling comprising administering an amount of budiodarone effective to reduce AF episode duration and an effective amount of AC that is dabigatran etexilate, wherein the average AF episode duration is reduced to less than about 24 hours, less than about 5 hours, less than about 3 hours, or less than about 1 hour, and wherein the effective amount of budiodarone is 400 mg BID or more preferably 600 mg BID.

In another aspect, the invention provides methods for reversing atrial remodeling comprising administering an amount of budiodarone effective to reduce AF episode duration and an effective amount of AC that is dabigatran etexilate, wherein the maximum AF episode duration is reduced to less than about 20 hours, less than about 10 hours, or less than about 5 hours, and wherein the effective amount of budiodarone is 400 mg BID or more preferably 600 mg BID.

In another aspect, the invention provides methods for reversing atrial remodeling comprising administering an amount of budiodarone effective to reduce AF episode duration and an effective amount of AC selected from the group consisting of ximelagatran and AZD0837, wherein the effective amount of budiodarone is 400 mg BID or more preferably 600 mg BID.

In another aspect, the invention provides methods for reversing atrial remodeling comprising administering an amount of budiodarone effective to reduce AF episode duration and an effective amount of AC selected from the group consisting of ximelagatran and AZD0837, wherein the average AF episode duration is reduced to less than about 24 hours, less than about 5 hours, less than about 3 hours, or less than about 1 hour, and wherein the effective amount of budiodarone is 400 mg BID or more preferably 600 mg BID.

In another aspect, the invention provides methods for reversing atrial remodeling comprising administering an amount of budiodarone effective to reduce AF episode duration and an effective amount of AC selected from the group consisting of ximelagatran and AZD0837, wherein the maximum AF episode duration is reduced to less than about 20 hours, less than about 10 hours, or less than about 5 hours, and wherein the effective amount of budiodarone is 400 mg BID or more preferably 600 mg BID.

In another aspect, the invention provides methods for reversing atrial remodeling comprising administering an amount of budiodarone effective to reduce AF episode duration and an effective amount of AC that is apixaban, wherein the effective amount of budiodarone is 400 mg BID or more preferably 600 mg BID.

In another aspect, the invention provides methods for reversing atrial remodeling comprising administering an amount of budiodarone effective to reduce AF episode duration and an effective amount of AC that is apixaban, wherein the average AF episode duration is reduced to less than about 24 hours, less than about 5 hours, less than about 3 hours, or less than about 1 hour, and wherein the effective amount of budiodarone is 400 mg BID or more preferably 600 mg BID.

In another aspect, the invention provides methods for reversing atrial remodeling comprising administering an amount of budiodarone effective to reduce AF episode duration and an effective amount of AC that is apixaban, wherein the maximum AF episode duration is reduced to less than about 20 hours, less than about 10 hours, or less than about 5 hours, and wherein the effective amount of budiodarone is 400 mg BID or more preferably 600 mg BID.

In another aspect, the invention provides methods for reversing atrial remodeling comprising administering an amount of budiodarone effective to reduce AF episode duration and an effective amount of AC that is rivaroxaban, wherein the effective amount of budiodarone is 400 mg BID or more preferably 600 mg BID.

In another aspect, the invention provides methods for reversing atrial remodeling comprising administering an amount of budiodarone effective to reduce AF episode duration and an effective amount of AC that is rivaroxaban, wherein the average AF episode duration is reduced to less than about 24 hours, less than about 5 hours, less than about 3 hours, or less than about 1 hour, and wherein the effective amount of budiodarone is 400 mg BID or more preferably 600 mg BID.

In another aspect, the invention provides methods for reversing atrial remodeling comprising administering an amount of budiodarone effective to reduce AF episode duration and an effective amount of AC that is rivaroxaban, wherein the maximum AF episode duration is reduced to less than about 20 hours, less than about 10 hours, or less than about 5 hours, and wherein the effective amount of budiodarone is 400 mg BID or more preferably 600 mg BID.

In another aspect, the invention provides methods for reversing atrial remodeling comprising administering an amount of budiodarone effective to reduce AF episode duration and an effective amount of AC that is tecarfarin, wherein the effective amount of budiodarone is 400 mg BID or more preferably 600 mg BID.

In another aspect, the invention provides methods for reversing atrial remodeling comprising administering an amount of budiodarone effective to reduce AF episode duration and an effective amount of AC that is tecarfarin, wherein the average AF episode duration is reduced to less than about 24 hours, less than about 5 hours, less than about 3 hours, or less than about 1 hour, and wherein the effective amount of budiodarone is 400 mg BID or more preferably 600 mg BID.

In another aspect, the invention provides methods for reversing atrial remodeling comprising administering an amount of budiodarone effective to reduce AF episode duration and an effective amount of AC that is tecarfarin, wherein the maximum AF episode duration is reduced to less than about 20 hours, less than about 10 hours, or less than about 5 hours, and wherein the effective amount of budiodarone is 400 mg BID or more preferably 600 mg BID.

In another aspect, the invention provides methods for reversing atrial remodeling comprising administering an amount of budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the reversal of atrial remodeling is defined as a measured increase in AFCL at the right atrial appendage or distal coronary sinus of at least 6 milliseconds.

In another aspect, the invention provides methods for reversing atrial remodeling comprising administering an amount of budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the average AF episode duration is reduced to less than about 24 hours, less than about 5 hours, less than about 3 hours, or less than about 1 hour, and wherein the reversal of atrial remodeling is defined as a measured increase in AFCL at the right atrial appendage or distal coronary sinus of at least 6 milliseconds.

In another aspect, the invention provides methods for reversing atrial remodeling comprising administering an amount of budiodarone effective to reduce AF episode duration and an effective amount of AC selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin, wherein the maximum AF episode duration is reduced to less than about 20 hours, less than about 10 hours, or less than about 5 hours, and wherein the reversal of atrial remodeling is defined as a measured increase in AFCL at the right atrial appendage or distal coronary sinus of at least 6 milliseconds.

In another aspect, the invention provides methods for reversing atrial remodeling comprising administering an amount of budiodarone effective to reduce AF episode duration and an effective amount of AC selected from the group consisting of tecarfarin, dabigatran etexilate, ximelagatran, AZD0837, apixaban and rivaroxaban, wherein the reversal of atrial remodeling is defined as a measured increase in AFCL at the right atrial appendage or distal coronary sinus of at least 6 milliseconds.

In another aspect, the invention provides methods for reversing atrial remodeling comprising administering an amount of budiodarone effective to reduce AF episode duration and an effective amount of AC selected from the group consisting of tecarfarin, dabigatran etexilate, ximelagatran, AZD0837, apixaban or rivaroxaban, wherein the average AF episode duration is reduced to less than about 24 hours, less than about 5 hours, less than about 3 hours, or less than about 1 hour, and wherein the reversal of atrial remodeling is defined as a measured increase in AFCL at the right atrial appendage or distal coronary sinus of at least 6 milliseconds.

In another aspect, the invention provides methods for reversing atrial remodeling comprising administering an amount of budiodarone effective to reduce AF episode duration and an effective amount of AC selected from the group consisting of tecarfarin, dabigatran etexilate, ximelagatran, AZD0837, apixaban or rivaroxaban, wherein the maximum AF episode duration is reduced to less than about 20 hours, less than about 10 hours, or less than about 5 hours, and wherein the reversal of atrial remodeling is defined as a measured increase in AFCL at the right atrial appendage or distal coronary sinus of at least 6 milliseconds.

315. A method for reversing atrial remodeling comprising administering an amount of budiodarone effective to reduce AF episode duration and an effective amount of AC that is dabigatran etexilate, wherein the reversal of atrial remodeling is defined as a measured increase in AFCL at the right atrial appendage or distal coronary sinus of at least 6 milliseconds.

In another aspect, the invention provides methods for reversing atrial remodeling comprising administering an amount of budiodarone effective to reduce AF episode duration and an effective amount of AC that is dabigatran etexilate, wherein the average AF episode duration is reduced to less than about 24 hours, less than about 5 hours, less than about 3 hours, or less than about 1 hour, and wherein the reversal of atrial remodeling is defined as a measured increase in AFCL at the right atrial appendage or distal coronary sinus of at least 6 milliseconds.

In another aspect, the invention provides methods for reversing atrial remodeling comprising administering an amount of budiodarone effective to reduce AF episode duration and an effective amount of AC that is dabigatran etexilate, wherein the maximum AF episode duration is reduced to less than about 20 hours, less than about 10 hours, or less than about 5 hours, and wherein the reversal of atrial remodeling is defined as a measured increase in AFCL at the right atrial appendage or distal coronary sinus of at least 6 milliseconds.

In another aspect, the invention provides methods for reversing atrial remodeling comprising administering an amount of budiodarone effective to reduce AF episode duration and an effective amount of AC selected from the group consisting of ximelagatran and AZD0837, wherein the reversal of atrial remodeling is defined as a measured increase in AFCL at the right atrial appendage or distal coronary sinus of at least 6 milliseconds.

In another aspect, the invention provides methods for reversing atrial remodeling comprising administering an amount of budiodarone effective to reduce AF episode duration and an effective amount of AC selected from the group consisting of ximelagatran and AZD0837, wherein the average AF episode duration is reduced to less than about 24 hours, less than about 5 hours, less than about 3 hours, or less than about 1 hour, and wherein the reversal of atrial remodeling is defined as a measured increase in AFCL at the right atrial appendage or distal coronary sinus of at least 6 milliseconds.

In another aspect, the invention provides methods for reversing atrial remodeling comprising administering an amount of budiodarone effective to reduce AF episode duration and an effective amount of AC selected from the group consisting of ximelagatran and AZD0837, wherein the maximum AF episode duration is reduced to less than about 20 hours, less than about 10 hours, or less than about 5 hours, and wherein the reversal of atrial remodeling is defined as a measured increase in AFCL at the right atrial appendage or distal coronary sinus of at least 6 milliseconds.

In another aspect, the invention provides methods for reversing atrial remodeling comprising administering an amount of budiodarone effective to reduce AF episode duration and an effective amount of AC that is apixaban, wherein the reversal of atrial remodeling is defined as a measured increase in AFCL at the right atrial appendage or distal coronary sinus of at least 6 milliseconds.

In another aspect, the invention provides methods for reversing atrial remodeling comprising administering an amount of budiodarone effective to reduce AF episode duration and an effective amount of AC that is apixaban, wherein the average AF episode duration is reduced to less than about 24 hours, less than about 5 hours, less than about 3 hours, or less than about 1 hour, and wherein the reversal of atrial remodeling is defined as a measured increase in AFCL at the right atrial appendage or distal coronary sinus of at least 6 milliseconds.

In another aspect, the invention provides methods for reversing atrial remodeling comprising administering an amount of budiodarone effective to reduce AF episode duration and an effective amount of AC that is apixaban, wherein the maximum AF episode duration is reduced to less than about 20 hours, less than about 10 hours, or less than about 5 hours, and wherein the reversal of atrial remodeling is defined as a measured increase in AFCL at the right atrial appendage or distal coronary sinus of at least 6 milliseconds.

In another aspect, the invention provides methods for reversing atrial remodeling comprising administering an amount of budiodarone effective to reduce AF episode duration and an effective amount of AC that is rivaroxaban, wherein the reversal of atrial remodeling is defined as a measured increase in AFCL at the right atrial appendage or distal coronary sinus of at least 6 milliseconds.

In another aspect, the invention provides methods for reversing atrial remodeling comprising administering an amount of budiodarone effective to reduce AF episode duration and an effective amount of AC that is rivaroxaban, wherein the average AF episode duration is reduced to less than about 24 hours, less than about 5 hours, less than about 3 hours, or less than about 1 hour, and wherein the reversal of atrial remodeling is defined as a measured increase in AFCL at the right atrial appendage or distal coronary sinus of at least 6 milliseconds.

In another aspect, the invention provides methods for reversing atrial remodeling comprising administering an amount of budiodarone effective to reduce AF episode duration and an effective amount of AC that is rivaroxaban, wherein the maximum AF episode duration is reduced to less than about 20 hours, less than about 10 hours, or less than about 5 hours, and wherein the reversal of atrial remodeling is defined as a measured increase in AFCL at the right atrial appendage or distal coronary sinus of at least 6 milliseconds.

In another aspect, the invention provides methods for reversing atrial remodeling comprising administering an amount of budiodarone effective to reduce AF episode duration and an effective amount of AC that is tecarfarin, and wherein the reversal of atrial remodeling is defined as a measured increase in AFCL at the right atrial appendage or distal coronary sinus of at least 6 milliseconds.

In another aspect, the invention provides methods for reversing atrial remodeling comprising administering an amount of budiodarone effective to reduce AF episode duration and an effective amount of AC that is tecarfarin, wherein the average AF episode duration is reduced to less than about 24 hours, less than about 5 hours, less than about 3 hours, or less than about 1 hour, and wherein the reversal of atrial remodeling is defined as a measured increase in AFCL at the right atrial appendage or distal coronary sinus of at least 6 milliseconds.

In another aspect, the invention provides methods for reversing atrial remodeling comprising administering an amount of budiodarone effective to reduce AF episode duration and an effective amount of AC that is tecarfarin, wherein the maximum AF episode duration is reduced to less than about 20 hours, less than about 10 hours, or less than about 5 hours, and wherein the reversal of atrial remodeling is defined as a measured increase in AFCL at the right atrial appendage or distal coronary sinus of at least 6 milliseconds.

In yet other aspects, the invention provides for all of the above methods in patients with severe heart failure.

The term "effective amount" for a direct thrombin inhibitor (DTI) refers to an amount effective to provide adequate anticoagulation according to the common coagulation tests activated partial thromboplastin time (aPTT) and activated clotting time (ACT). The aPTT is a measure of the intrinsic or "contact activation" pathway and the common coagulation pathway. Under common test conditions, clotting times below about 25 seconds or above about 39 seconds are considered abnormal. The ACT is a test of the intrinsic or common pathway of coagulation, using diatomaceous earth as an activating agent to hasten coagulation of whole blood, the time being measured.

Alternatively, for fixed or one-size-fits-most DTIs like dabigatran etexilate and dabigatran, about 110 to 300 mg daily can comprise an effective amount. For ximelagatran and melagatran, about 40 to 120 mg daily can comprise an effective amount. For AZD0837, about 100 to 500 mg daily can comprise an effective amount. For argatroban, about 2 mcg/kg/min infused for 1 minute per every 10 kg body mass, starting at 6 minutes for 50 kg patient can comprise an effective amount.

For a Factor Xa inhibitor, the term refers to an amount effective to reduce coagulation according to U.S. Pat. No. 7,220,553. Alternatively, for fixed or one-size-fits-most Xa inhibitors like apixaban, about 2.5 to 20 mg daily can comprise an effective amount. For rivaroxaban, about 5 to 60 mg daily can comprise an effective amount. For betrixaban, about 20 to 120 mg daily can comprise an effective amount. For edoxaban, about 15 to 120 mg daily can comprise an effective amount. For YM466, about 2 to 300 mg daily can comprise an effective amount. For otamixaban, about 0.05 to 0.20 mg/kg bolus followed by infusions of about 0.050 to 0.180 mg/kg/h can comprise an effective amount.

For VKOR inhibitors, like tecarfarin and warfarin, an effective amount refers to an amount of drug sufficient to maintain an International Normalized Ratio (INR) between 2-3.

The term "International Normalized Ratio" or INR refers to the ratio of a patient's prothrombin time to a normal (control) sample, raised to the power of the International Sensitivity Index (ISI) value for the analytical system used. The ISI value indicates how a particular batch of tissue factor compares to an internationally standardized sample, and is usually between 1.0 and 2.0. Prothrombin time is a measure of the extrinsic pathway of coagulation, and it is used to determine the clotting tendency of blood. Prothrombin time indirectly measures factors II, V, VII, X and fibrinogen.

The terms "AF episode" refers to a period wherein the heart in not in normal sinus rhythm (NSR) but is in atrial fibrillation. The term "AF episode duration" refers to the length of time, typically in hours, that an AF episode persists before reverting to NSR. "Average episode duration" is the mean length of a patient's AF episodes, typically in hours.

The term "refractory to one or more anti-arrhythmic drugs" refers to the failure of a non-budiodarone anti-arrhythmic drug, for example, amiodarone, sotalol, ibutilide, dofetilide, flecainide, propafenone, dronedarone, vernakalant, celivarone, AZ1305 and quinidine, to restore and/or maintain NSR in an AF patient.

The term "age-adjusted overall stroke rate" refers to the annual, age-adjusted stroke rates as defined in Lloyd-Jones D, et al., "Heart disease and stroke statistics—2009 update" Circulation. 2009 Jan. 27; 119(3):480-6. According to Chart 5-2 of page 65, for ages 65-74, the overall (annual) stroke rates for white females, white males, black females and black makes are 0.56%, 0.76%, 0.56% and 0.72%, respectively. For ages 75-84, the overall (annual) stroke rates for white females, white males, black females and black makes are 1.24%, 1.25%, 1.25% and 0.84%, respectively. For ages 85+, the overall (annual) stroke rates for white females, white males, black females and black makes are 1.96%, 3.21%, 2.02% and 1.47%, respectively.

Examplary Embodiments

I-1. In one embodiment, the invention provides a method for reducing atrial fibrillation (AF) episode duration comprising administering an amount of budiodarone effective to reduce AF episode duration.

I-2. In a further embodiment of embodiment I-1, the average AF episode duration is reduced to less than about 24 hours.

I-3. In a further embodiment of embodiment I-1, the average AF episode duration is reduced to less than about 5 hours.

I-4. In a further embodiment of embodiment I-1, the average AF episode duration is reduced to less than about 3 hours.

I-5. In a further embodiment of embodiment I-1, the average AF episode duration is reduced to less than about 1 hour.

I-6. In a further embodiment of embodiment I-1, the maximum AF episode duration is reduced to less than about 20 hours.

I-7. In a further embodiment of embodiment I-1, the maximum AF episode duration is reduced to less than about 10 hours.

I-8. In a further embodiment of embodiment I-1, the maximum AF episode duration is reduced to less than about 5 hours.

I-9. In one embodiment, the invention provides a method for reducing stroke rate comprising administering an amount of budiodarone effective to reduce AF episode duration.

I-10. In a further embodiment of embodiment I-9, the average AF episode duration is reduced to less than about 24 hours.

I-11. In a further embodiment of embodiment I-9, the average AF episode duration is reduced to less than about 5 hours.

I-12. In a further embodiment of embodiment I-9, the average AF episode duration is reduced to less than 3 hours.

I-13. In a further embodiment of embodiment I-9, the average AF episode duration is reduced to less than about 1 hour.

I-14. In a further embodiment of embodiment I-9, the maximum AF episode duration is reduced to less than about 20 hours.

I-15. In a further embodiment of embodiment I-9, the maximum AF episode duration is reduced to less than about 10 hours.

I-16. In a further embodiment of embodiment I-9, the maximum AF episode duration is reduced to less than about 5 hours.

I-17. In one embodiment, the invention provides a method for increasing time in normal sinus rhythm (NSR) comprising administering an amount of budiodarone effective to reduce AF episode duration.

I-18. In a further embodiment of embodiment I-17, the average AF episode duration is reduced to less than about 24 hours.

I-19. In a further embodiment of embodiment I-17, the average AF episode duration is reduced to less than about 5 hours.

I-20. In a further embodiment of embodiment I-17, the average AF episode duration is reduced to less than 3 hours.

I-21. In a further embodiment of embodiment I-17, the average AF episode duration is reduced to less than about 1 hour.

I-22. In a further embodiment of embodiment I-17, the maximum AF episode duration is reduced to less than about 20 hours.

I-23. In a further embodiment of embodiment I-17, the maximum AF episode duration is reduced to less than about 10 hours.

I-24. In a further embodiment of embodiment I-17, the maximum AF episode duration is reduced to less than about 5 hours.

I-25. In one embodiment, the invention provides a method for preventing atrial remodeling comprising administering an amount of budiodarone effective to reduce AF episode duration.

I-26. In a further embodiment of embodiment I-25, the average AF episode duration is reduced to less than about 24 hours.

I-27. In a further embodiment of embodiment I-25, the average AF episode duration is reduced to less than about 5 hours.

I-28. In a further embodiment of embodiment I-25, the average AF episode duration is reduced to less than 3 hours.

I-29. In a further embodiment of embodiment I-25, the average AF episode duration is reduced to less than about 1 hour.

I-30. In a further embodiment of embodiment I-25, the maximum AF episode duration is reduced to less than about 20 hours.

I-31. In a further embodiment of embodiment I-25, the maximum AF episode duration is reduced to less than about 10 hours.

I-32. In a further embodiment of embodiment I-25, the maximum AF episode duration is reduced to less than about 5 hours.

I-33. In one embodiment, the invention provides a method for reversing atrial remodeling comprising administering an amount of budiodarone effective to reduce AF episode duration.

I-34. In a further embodiment of embodiment I-33, the average AF episode duration is reduced to less than about 24 hours.

I-35. In a further embodiment of embodiment I-33, the average AF episode duration is reduced to less than about 5 hours.

I-36. In a further embodiment of embodiment I-33, the average AF episode duration is reduced to less than 3 hours.

I-37. In a further embodiment of embodiment I-33, the average AF episode duration is reduced to less than about 1 hour.

I-38. In a further embodiment of embodiment I-33, the maximum AF episode duration is reduced to less than about 20 hours.

I-39. In a further embodiment of embodiment I-33, the maximum AF episode duration is reduced to less than about 10 hours.

I-40. In a further embodiment of embodiment I-33, the maximum AF episode duration is reduced to less than about 5 hours.

I-41. In a further embodiment of embodiment I-33, the reversal of atrial remodeling is defined as a measured increase in AFCL at the right atrial appendage or distal coronary sinus of at least 6 milliseconds.

I-42. In a further embodiment of embodiment I-34, the reversal of atrial remodeling is defined as a measured increase in AFCL at the right atrial appendage or distal coronary sinus of at least 6 milliseconds.

I-43. In a further embodiment of embodiment I-35, the reversal of atrial remodeling is defined as a measured increase in AFCL at the right atrial appendage or distal coronary sinus of at least 6 milliseconds.

I-44. In a further embodiment of embodiment I-36, the reversal of atrial remodeling is defined as a measured increase in AFCL at the right atrial appendage or distal coronary sinus of at least 6 milliseconds.

I-45. In a further embodiment of embodiment I-37, the reversal of atrial remodeling is defined as a measured increase in AFCL at the right atrial appendage or distal coronary sinus of at least 6 milliseconds.

I-46. In a further embodiment of embodiment I-38, the reversal of atrial remodeling is defined as a measured increase in AFCL at the right atrial appendage or distal coronary sinus of at least 6 milliseconds.

I-47. In a further embodiment of embodiment I-39, the reversal of atrial remodeling is defined as a measured increase in AFCL at the right atrial appendage or distal coronary sinus of at least 6 milliseconds.

I-48. In a further embodiment of embodiment I-40, the reversal of atrial remodeling is defined as a measured increase in AFCL at the right atrial appendage or distal coronary sinus of at least 6 milliseconds.

I-49. In a further embodiment of embodiment I-1, the patient was refractory to one or more anti-arrhythmic drugs.

I-50. In a further embodiment of embodiment I-9, the patient was refractory to one or more anti-arrhythmic drugs.

I-51. In a further embodiment of embodiment I-17, the patient was refractory to one or more anti-arrhythmic drugs.

I-52. In a further embodiment of embodiment I-25, the patient was refractory to one or more anti-arrhythmic drugs.

I-53. In a further embodiment of embodiment I-33, the patient was refractory to one or more anti-arrhythmic drugs.

I-54. In a further embodiment of embodiment I-41, the patient was refractory to one or more anti-arrhythmic drugs.

I-55. In a further embodiment of embodiment I-1, the effective amount of budiodarone is 400 mg BID or 600 mg BID.

I-56. In a further embodiment of embodiment I-55, the effective amount of budiodarone is 600 mg BID.

I-57. In a further embodiment of embodiment I-9, the effective amount of budiodarone is 400 mg BID or 600 mg BID.

I-58. In a further embodiment of embodiment I-57, the effective amount of budiodarone is 600 mg BID.

I-59. In a further embodiment of embodiment I-17, the effective amount of budiodarone is 400 mg BID or 600 mg BID.

I-60. In a further embodiment of embodiment I-59, the effective amount of budiodarone is 600 mg BID.

I-61. In a further embodiment of embodiment I-25, the effective amount of budiodarone is 400 mg BID or 600 mg BID.

I-62. In a further embodiment of embodiment I-61, the effective amount of budiodarone is 600 mg BID.

I-63. In a further embodiment of embodiment I-33, the effective amount of budiodarone is 400 mg BID or 600 mg BID.

I-64. In a further embodiment of embodiment I-64, the effective amount of budiodarone is 600 mg BID.

I-65. In a further embodiment of embodiment I-41, the effective amount of budiodarone is 400 mg BID or 600 mg BID.

I-66. In a further embodiment of embodiment I-65, the effective amount of budiodarone is 600 mg BID.

II-1. In one embodiment, the invention provides a method for reducing stroke rate comprising administering an amount of budiodarone effective to reduce atrial fibrillation (AF) episode duration and an effective amount of anticoagulant (AC) selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin.

II-2. In a further embodiment of embodiment II-1, the average AF episode duration is reduced to less than about 24 hours.

II-3. In a further embodiment of embodiment II-1, the average AF episode duration is reduced to less than about 5 hours.

II-4. In a further embodiment of embodiment II-1, the average AF episode duration is reduced to less than 3 hours.

II-5. In a further embodiment of embodiment II-1, the average AF episode duration is reduced to less than about 1 hour.

II-6. In a further embodiment of embodiment II-1, the maximum AF episode duration is reduced to less than about 20 hours.

II-7. In a further embodiment of embodiment II-1, the maximum AF episode duration is reduced to less than about 10 hours.

II-8. In a further embodiment of embodiment II-1, the maximum AF episode duration is reduced to less than about 5 hours.

II-9. In a further embodiment of embodiment II-1, the AC is tecarfarin, dabigatran etexilate, ximelagatran, AZD0837, apixaban or rivaroxaban.

II-10. In a further embodiment of embodiment II-2, the AC is tecarfarin, dabigatran etexilate, ximelagatran, AZD0837, apixaban or rivaroxaban.

II-11. In a further embodiment of embodiment II-3, the AC is tecarfarin, dabigatran etexilate, ximelagatran, AZD0837, apixaban or rivaroxaban.

II-12. In a further embodiment of embodiment II-4, the AC is tecarfarin, dabigatran etexilate, ximelagatran, AZD0837, apixaban or rivaroxaban.

II-13. In a further embodiment of embodiment II-5, the AC is tecarfarin, dabigatran etexilate, ximelagatran, AZD0837, apixaban or rivaroxaban.

II-14. In a further embodiment of embodiment II-6, the AC is tecarfarin, dabigatran etexilate, ximelagatran, AZD0837, apixaban or rivaroxaban.

II-15. In a further embodiment of embodiment II-7, the AC is tecarfarin, dabigatran etexilate, ximelagatran, AZD0837, apixaban or rivaroxaban.

II-16. In a further embodiment of embodiment II-8, the AC is tecarfarin, dabigatran etexilate, ximelagatran, AZD0837, apixaban or rivaroxaban.

II-17. In a further embodiment of embodiment II-10, the AC is dabigatran etexilate.

II-18. In a further embodiment of embodiment II-11, the AC is dabigatran etexilate.

II-19. In a further embodiment of embodiment II-12, the AC is dabigatran etexilate.

II-20. In a further embodiment of embodiment II-13, the AC is dabigatran etexilate.

II-21. In a further embodiment of embodiment II-14, the AC is dabigatran etexilate.

II-22. In a further embodiment of embodiment II-15, the AC is dabigatran etexilate.

II-23. In a further embodiment of embodiment II-16, the AC is dabigatran etexilate.

II-24. In a further embodiment of embodiment II-10, the AC is ximelagatran or AZD0837.

II-25. In a further embodiment of embodiment II-11, the AC is ximelagatran or AZD0837.

II-26. In a further embodiment of embodiment II-12, the AC is ximelagatran or AZD0837.

II-27. In a further embodiment of embodiment II-13, the AC is ximelagatran or AZD0837.

II-28. In a further embodiment of embodiment II-14, the AC is ximelagatran or AZD0837.

II-29. In a further embodiment of embodiment II-15, the AC is ximelagatran or AZD0837.

II-30. In a further embodiment of embodiment II-16, the AC is ximelagatran or AZD0837.

II-31. In a further embodiment of embodiment II-10, the AC is apixaban.

II-32. In a further embodiment of embodiment II-11, the AC is apixaban.

II-33. In a further embodiment of embodiment II-12, the AC is apixaban.

II-34. In a further embodiment of embodiment II-13, the AC is apixaban.

II-35. In a further embodiment of embodiment II-14, the AC is apixaban.

II-36. In a further embodiment of embodiment II-15, the AC is apixaban.

II-37. In a further embodiment of embodiment II-16, the AC is apixaban.

II-38. In a further embodiment of embodiment II-10, the AC is rivaroxaban.

II-39. In a further embodiment of embodiment II-11, the AC is rivaroxaban.

II-40. In a further embodiment of embodiment II-12, the AC is rivaroxaban.

II-41. In a further embodiment of embodiment II-13, the AC is rivaroxaban.

II-42. In a further embodiment of embodiment II-14, the AC is rivaroxaban.

II-43. In a further embodiment of embodiment II-15, the AC is rivaroxaban.

II-44. In a further embodiment of embodiment II-16, the AC is rivaroxaban.

II-45. In a further embodiment of embodiment II-10, the AC is tecarfarin.

II-46. In a further embodiment of embodiment II-11, the AC is tecarfarin.

II-47. In a further embodiment of embodiment II-12, the AC is tecarfarin.

II-48. In a further embodiment of embodiment II-13, the AC is tecarfarin.

II-49. In a further embodiment of embodiment II-14, the AC is tecarfarin.

II-50. In a further embodiment of embodiment II-15, the AC is tecarfarin.

II-51. In a further embodiment of embodiment II-16, the AC is tecarfarin.

II-52. In a further embodiment of embodiment II-1, the reduced stroke rate is less than the age-adjusted overall stroke rate.

II-53. In a further embodiment of embodiment II-10, the reduced stroke rate is less than the age-adjusted overall stroke rate.

II-54. In a further embodiment of embodiment II-11, the reduced stroke rate is less than the age-adjusted overall stroke rate.

II-55. In a further embodiment of embodiment II-12, the reduced stroke rate is less than the age-adjusted overall stroke rate.

II-56. In a further embodiment of embodiment II-13, the reduced stroke rate is less than the age-adjusted overall stroke rate.

II-57. In a further embodiment of embodiment II-14, the reduced stroke rate is less than the age-adjusted overall stroke rate.

II-58. In a further embodiment of embodiment II-15, the reduced stroke rate is less than the age-adjusted overall stroke rate.

II-59. In a further embodiment of embodiment II-16, the reduced stroke rate is less than the age-adjusted overall stroke rate.

II-60. In a further embodiment of embodiment II-17, the reduced stroke rate is less than the age-adjusted overall stroke rate.

II-61. In a further embodiment of embodiment II-18, the reduced stroke rate is less than the age-adjusted overall stroke rate.

II-62. In a further embodiment of embodiment II-19, the reduced stroke rate is less than the age-adjusted overall stroke rate.

II-63. In a further embodiment of embodiments II-20-II-22, the reduced stroke rate is less than the age-adjusted overall stroke rate.

II-64. In a further embodiment of embodiment II-23, the reduced stroke rate is less than the age-adjusted overall stroke rate.

II-65. In a further embodiment of embodiment II-24, the reduced stroke rate is less than the age-adjusted overall stroke rate.

II-66. In a further embodiment of embodiment II-25, the reduced stroke rate is less than the age-adjusted overall stroke rate.

II-67. In a further embodiment of embodiment II-26, the reduced stroke rate is less than the age-adjusted overall stroke rate.

II-68. In a further embodiment of embodiments II-27-II-29, the reduced stroke rate is less than the age-adjusted overall stroke rate.

II-69. In a further embodiment of embodiment II-30, the reduced stroke rate is less than the age-adjusted overall stroke rate.

II-70. In a further embodiment of embodiment II-31, the reduced stroke rate is less than the age-adjusted overall stroke rate.

II-71. In a further embodiment of embodiment II-32, the reduced stroke rate is less than the age-adjusted overall stroke rate.

II-72. In a further embodiment of embodiment II-33, the reduced stroke rate is less than the age-adjusted overall stroke rate.

II-73. In a further embodiment of embodiments II-34-II-36, the reduced stroke rate is less than the age-adjusted overall stroke rate.

II-74. In a further embodiment of embodiment II-37, the reduced stroke rate is less than the age-adjusted overall stroke rate.

II-75. In a further embodiment of embodiment II-38, the reduced stroke rate is less than the age-adjusted overall stroke rate.

II-76. In a further embodiment of embodiment II-39, the reduced stroke rate is less than the age-adjusted overall stroke rate.

II-77. In a further embodiment of embodiment II-40, the reduced stroke rate is less than the age-adjusted overall stroke rate.

II-78. In a further embodiment of embodiments II-41-II-43, the reduced stroke rate is less than the age-adjusted overall stroke rate.

II-79. In a further embodiment of embodiment II-44, the reduced stroke rate is less than the age-adjusted overall stroke rate.

II-80. In a further embodiment of embodiment II-45, the reduced stroke rate is less than the age-adjusted overall stroke rate.

II-81. In a further embodiment of embodiment II-46, the reduced stroke rate is less than the age-adjusted overall stroke rate.

II-82. In a further embodiment of embodiment II-47, the reduced stroke rate is less than the age-adjusted overall stroke rate.

II-83. In a further embodiment of embodiment II-48, the reduced stroke rate is less than the age-adjusted overall stroke rate.

II-84. In a further embodiment of embodiment II-51, the reduced stroke rate is less than the age-adjusted overall stroke rate.

II-85. In a further embodiment of embodiment II-1, the patient was refractory to one or more anti-arrhythmic drugs.

II-86. In a further embodiment of any of embodiments II-2-II-5, the patient was refractory to one or more anti-arrhythmic drugs.

II-87. In a further embodiment of any of embodiments II-6-II-9, the patient was refractory to one or more anti-arrhythmic drugs.

II-88. In a further embodiment of any of embodiments II-10-II-13, the patient was refractory to one or more anti-arrhythmic drugs.

II-89. In a further embodiment of any of embodiments II-14-II-16, the patient was refractory to one or more anti-arrhythmic drugs.

II-90. In a further embodiment of any of embodiments II-17-II-20, the patient was refractory to one or more anti-arrhythmic drugs.

II-91. In a further embodiment of any of embodiments II-21-II-23, the patient was refractory to one or more anti-arrhythmic drugs.

II-92. In a further embodiment of any of embodiments II-24-II-27, the patient was refractory to one or more anti-arrhythmic drugs.

II-93. In a further embodiment of any of embodiments II-28-II-30, the patient was refractory to one or more anti-arrhythmic drugs.

II-94. In a further embodiment of any of embodiments II-31-II-34, the patient was refractory to one or more anti-arrhythmic drugs.

II-95. In a further embodiment of any of embodiments II-35-II-37, the patient was refractory to one or more anti-arrhythmic drugs.

II-96. In a further embodiment of any of embodiments II-38-II-41, the patient was refractory to one or more anti-arrhythmic drugs.

II-97. In a further embodiment of any of embodiments II-42-II-44, the patient was refractory to one or more anti-arrhythmic drugs.

II-98. In a further embodiment of any of embodiments II-45-II-48, the patient was refractory to one or more anti-arrhythmic drugs.

II-99. In a further embodiment of any of embodiments II-49-II-51, the patient was refractory to one or more anti-arrhythmic drugs.

II-100. In one embodiment, the invention provides a method for preventing atrial remodeling comprising administering an amount of budiodarone effective to reduce atrial fibrillation (AF) episode duration and an effective amount of anticoagulant (AC) selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin.

II-101. In a further embodiment of embodiment II-100, the average AF episode duration is reduced to less than about 24 hours.

II-102. In a further embodiment of embodiment II-100, the average AF episode duration is reduced to less than about 5 hours.

II-103. In a further embodiment of embodiment II-100, the average AF episode duration is reduced to less than 3 hours.

II-104. In a further embodiment of embodiment II-100, the average AF episode duration is reduced to less than about 1 hour.

II-105. In a further embodiment of embodiment II-100, the maximum AF episode duration is reduced to less than about 20 hours.

II-106. In a further embodiment of embodiment II-100, the maximum AF episode duration is reduced to less than about 10 hours.

II-107. In a further embodiment of embodiment II-100, the maximum AF episode duration is reduced to less than about 5 hours.

II-108. In a further embodiment of embodiment II-100, the AC is tecarfarin, dabigatran etexilate, ximelagatran, AZD0837, apixaban or rivaroxaban.

II-109. In a further embodiment of any of embodiments II-101-II-104, the AC is tecarfarin, dabigatran etexilate, ximelagatran, AZD0837, apixaban or rivaroxaban.

II-110. In a further embodiment of any of embodiments II-105-II-107, the AC is tecarfarin, dabigatran etexilate, ximelagatran, AZD0837, apixaban or rivaroxaban.

II-111. In a further embodiment of embodiment II-107, the AC is tecarfarin, dabigatran etexilate, ximelagatran, AZD0837, apixaban or rivaroxaban.

II-112. In a further embodiment of embodiment II-100, the AC is dabigatran etexilate.

II-113. In a further embodiment of any of embodiments II-101-II-104, the AC is dabigatran etexilate.

II-114. In a further embodiment of any of embodiments II-105-II-107, the AC is dabigatran etexilate.

II-115. In a further embodiment of embodiment II-107, the AC is dabigatran etexilate.

II-116. In a further embodiment of embodiment II-100, the AC is ximelagatran or AZD0837.

II-117. In a further embodiment of any of embodiments II-101-II-104, the AC is ximelagatran or AZD0837.

II-118. In a further embodiment of any of embodiments II-105-II-107, the AC is ximelagatran or AZD0837.

II-119. In a further embodiment of embodiment II-107, the AC is ximelagatran or AZD0837.

II-120. In a further embodiment of embodiment II-100, the AC is apixaban.

II-121. In a further embodiment of any of embodiments II-101-II-104, the AC is apixaban.

II-122. In a further embodiment of any of embodiments II-105-II-107, the AC is apixaban.

II-123. In a further embodiment of embodiment II-107, the AC is apixaban.

II-124. In a further embodiment of embodiment II-100, the AC is rivaroxaban.

II-125. In a further embodiment of any of embodiments II-101-II-104, the AC is rivaroxaban.

II-126. In a further embodiment of any of embodiments II-105-II-107, the AC is rivaroxaban.

II-127. In a further embodiment of embodiment II-107, the AC is rivaroxaban.

II-128. In a further embodiment of embodiment II-100, the AC is tecarfarin.

II-129. In a further embodiment of any of embodiments II-101-II-104, the AC is tecarfarin.

II-130. In a further embodiment of any of embodiments II-105-II-107, the AC is tecarfarin.

II-131. In a further embodiment of embodiment II-107, the AC is tecarfarin.

II-132. In a further embodiment of embodiment II-100, the patient was refractory to one or more anti-arrhythmic drugs.

II-133. In a further embodiment of any of embodiments II-101-II-104, the patient was refractory to one or more anti-arrhythmic drugs.

II-134. In a further embodiment of any of embodiments II-105-II-107, the patient was refractory to one or more anti-arrhythmic drugs.

II-135. In a further embodiment of embodiment II-107, the patient was refractory to one or more anti-arrhythmic drugs.

II-136. In a further embodiment of embodiment II-108, the patient was refractory to one or more anti-arrhythmic drugs.

II-137. In a further embodiment of embodiment II-109, the patient was refractory to one or more anti-arrhythmic drugs.

II-138. In a further embodiment of embodiment II-110, the patient was refractory to one or more anti-arrhythmic drugs.

II-139. In a further embodiment of embodiment II-111, the patient was refractory to one or more anti-arrhythmic drugs.

II-140. In a further embodiment of embodiment II-113, the patient was refractory to one or more anti-arrhythmic drugs.

II-141. In a further embodiment of embodiment II-114, the patient was refractory to one or more anti-arrhythmic drugs.

II-142. In a further embodiment of embodiment II-117, the patient was refractory to one or more anti-arrhythmic drugs.

II-143. In a further embodiment of embodiment II-118, the patient was refractory to one or more anti-arrhythmic drugs.

II-144. In a further embodiment of embodiment II-121, the patient was refractory to one or more anti-arrhythmic drugs.

II-145. In a further embodiment of embodiment II-122, the patient was refractory to one or more anti-arrhythmic drugs.

II-146. In a further embodiment of embodiment II-125, the patient was refractory to one or more anti-arrhythmic drugs.

II-147. In a further embodiment of embodiment II-126, the patient was refractory to one or more anti-arrhythmic drugs.

II-148. In a further embodiment of embodiment II-129, the patient was refractory to one or more anti-arrhythmic drugs.

II-149. In a further embodiment of embodiment II-130, the patient was refractory to one or more anti-arrhythmic drugs.

II-150. In one embodiment, the invention provides a method for reversing atrial remodeling comprising administering an amount of budiodarone effective to reduce atrial fibrillation (AF) episode duration and an effective amount of anticoagulant (AC) selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin.

II-151. In a further embodiment of embodiment II-150, the average AF episode duration is reduced to less than about 24 hours.

II-152. In a further embodiment of embodiment II-150, the average AF episode duration is reduced to less than about 5 hours.

II-153. In a further embodiment of embodiment II-150, the average AF episode duration is reduced to less than 3 hours.

II-154. In a further embodiment of embodiment II-150, the average AF episode duration is reduced to less than about 1 hour.

II-155. In a further embodiment of embodiment II-150, the maximum AF episode duration is reduced to less than about 20 hours.

II-156. In a further embodiment of embodiment II-150, the maximum AF episode duration is reduced to less than about 10 hours.

II-157. In a further embodiment of embodiment II-150, the maximum AF episode duration is reduced to less than about 5 hours.

II-158. In a further embodiment of embodiment II-150, the AC is tecarfarin, dabigatran etexilate, ximelagatran, AZD0837, apixaban or rivaroxaban.

II-159. In a further embodiment of any of embodiments II-151-II-154, the AC is tecarfarin, dabigatran etexilate, ximelagatran, AZD0837, apixaban or rivaroxaban.

II-160. In a further embodiment of any of embodiments II-154-II-157, the AC is tecarfarin, dabigatran etexilate, ximelagatran, AZD0837, apixaban or rivaroxaban.

II-161. In a further embodiment of embodiment II-157, the AC is tecarfarin, dabigatran etexilate, ximelagatran, AZD0837, apixaban or rivaroxaban.

II-162. In a further embodiment of embodiment II-150, the AC is dabigatran etexilate.

II-163. In a further embodiment of any of embodiments II-151-II-154, the AC is dabigatran etexilate.

II-164. In a further embodiment of any of embodiments II-155-II-157, the AC is dabigatran etexilate.

II-165. In a further embodiment of embodiment II-157, the AC is dabigatran etexilate.

II-166. In a further embodiment of embodiment II-150, the AC is ximelagatran or AZD0837.

II-167. In a further embodiment of any of embodiments II-151-II-154, the AC is ximelagatran or AZD0837.

II-168. In a further embodiment of any of embodiments II-155-II-157, the AC is ximelagatran or AZD0837.

II-169. In a further embodiment of embodiment II-157, the AC is ximelagatran or AZD0837.

II-170. In a further embodiment of embodiment II-150, the AC is apixaban.

II-171. In a further embodiment of any of embodiments II-151-II-154, the AC is apixaban.

II-172. In a further embodiment of any of embodiments II-155-II-157, the AC is apixaban.

II-173. In a further embodiment of embodiment II-157, the AC is apixaban.

II-174. In a further embodiment of embodiment II-150, the AC is rivaroxaban.

II-175. In a further embodiment of any of embodiments II-151-154, the AC is rivaroxaban.

II-176. In a further embodiment of any of embodiments II-155-II-157, the AC is rivaroxaban.

II-177. In a further embodiment of embodiment II-157, the AC is rivaroxaban.

II-178. In a further embodiment of embodiment II-150, the AC is tecarfarin.

II-179. In a further embodiment of any of embodiments II-151-II-154, the AC is tecarfarin.

II-180. In a further embodiment of any of embodiments II-155-II-157, the AC is tecarfarin.

II-181. In a further embodiment of embodiment II-157, the AC is tecarfarin.

II-182. In a further embodiment of embodiment II-150, the patient was refractory to one or more anti-arrhythmic drugs.

II-183. In a further embodiment of any of embodiments II-151-II-154, the patient was refractory to one or more anti-arrhythmic drugs.

II-184. In a further embodiment of any of embodiments II-155-II-157, the patient was refractory to one or more anti-arrhythmic drugs.

II-185. In a further embodiment of embodiment II-157, the patient was refractory to one or more anti-arrhythmic drugs.

II-186. In a further embodiment of embodiment II-158, the patient was refractory to one or more anti-arrhythmic drugs.

II-187. In a further embodiment of embodiment II-159, the patient was refractory to one or more anti-arrhythmic drugs.

II-188. In a further embodiment of embodiment II-160, the patient was refractory to one or more anti-arrhythmic drugs.

II-189. In a further embodiment of any of embodiments II-161-II-163, the patient was refractory to one or more anti-arrhythmic drugs.

II-190. In a further embodiment of any of embodiments II-164-II-167, the patient was refractory to one or more anti-arrhythmic drugs.

II-191. In a further embodiment of embodiment II-167, the patient was refractory to one or more anti-arrhythmic drugs.

II-192. In a further embodiment of embodiment II-168, the patient was refractory to one or more anti-arrhythmic drugs.

II-193. In a further embodiment of any of embodiments II-169-II-170, the patient was refractory to one or more anti-arrhythmic drugs.

II-194. In a further embodiment of embodiment II-171, the patient was refractory to one or more anti-arrhythmic drugs.

II-195. In a further embodiment of any of embodiments II-172-II-174, the patient was refractory to one or more anti-arrhythmic drugs.

II-196. In a further embodiment of embodiment II-175, the patient was refractory to one or more anti-arrhythmic drugs.

II-197. In a further embodiment of any of embodiments II-176-II-178, the patient was refractory to one or more anti-arrhythmic drugs.

II-198. In a further embodiment of embodiment II-179, the patient was refractory to one or more anti-arrhythmic drugs.

II-199. In a further embodiment of embodiment II-180, the patient was refractory to one or more anti-arrhythmic drugs.

II-200. In a further embodiment of embodiment II-1, the effective amount of budiodarone is 400 mg BID or 600 mg BID.

II-201. In a further embodiment of embodiment II-2, the effective amount of budiodarone is 600 mg BID.

II-202. In a further embodiment of embodiment II-3, the effective amount of budiodarone is 400 mg BID or 600 mg BID.

II-203. In a further embodiment of embodiment II-4, the effective amount of budiodarone is 600 mg BID.

II-204. In a further embodiment of embodiment II-5, the effective amount of budiodarone is 400 mg BID or 600 mg BID.

II-205. In a further embodiment of embodiment II-6, the effective amount of budiodarone is 600 mg BID.

II-206. In a further embodiment of embodiment II-7, the effective amount of budiodarone is 400 mg BID or 600 mg BID.

II-207. In a further embodiment of embodiment II-8, the effective amount of budiodarone is 600 mg BID.

II-208. In a further embodiment of embodiment II-9, the effective amount of budiodarone is 400 mg BID or 600 mg BID.

II-209. In a further embodiment of any of embodiments II-10-II-12, the effective amount of budiodarone is 600 mg BID.

II-210. In a further embodiment of any of embodiments II-13-II-15, the effective amount of budiodarone is 400 mg BID or 600 mg BID.

II-211. In a further embodiment of embodiment II-16, the effective amount of budiodarone is 600 mg BID.

II-212. In a further embodiment of any of embodiments II-17-II-19, the effective amount of budiodarone is 400 mg BID or 600 mg BID.

II-213. In a further embodiment of any of embodiments II-20-II-22, the effective amount of budiodarone is 600 mg BID.

II-214. In a further embodiment of embodiment II-23, the effective amount of budiodarone is 400 mg BID or 600 mg BID.

II-215. In a further embodiment of any of embodiments II-24-II-26, the effective amount of budiodarone is 600 mg BID.

II-216. In a further embodiment of any of embodiments II-27-II-29, the effective amount of budiodarone is 400 mg BID or 600 mg BID.

II-217. In a further embodiment of embodiment II-30, the effective amount of budiodarone is 600 mg BID.

II-218. In a further embodiment of any of embodiments II-31-II-33, the effective amount of budiodarone is 400 mg BID or 600 mg BID.

II-219. In a further embodiment of any of embodiments II-34-II-36, the effective amount of budiodarone is 600 mg BID.

II-220. In a further embodiment of embodiment II-37, the effective amount of budiodarone is 400 mg BID or 600 mg BID.

II-221. In a further embodiment of any of embodiments II-38-II-40, the effective amount of budiodarone is 600 mg BID.

II-222. In a further embodiment of any of embodiments II-41-II-43, the effective amount of budiodarone is 400 mg BID or 600 mg BID.

II-223. In a further embodiment of embodiment II-44, the effective amount of budiodarone is 600 mg BID.

II-224. In a further embodiment of any of embodiments II-45-II-47, the effective amount of budiodarone is 400 mg BID or 600 mg BID.

II-225. In a further embodiment of any of embodiments II-48-II-50, the effective amount of budiodarone is 600 mg BID.

II-226. In a further embodiment of embodiment II-51, the effective amount of budiodarone is 400 mg BID or 600 mg BID.

II-227. In a further embodiment of embodiment II-52, the effective amount of budiodarone is 600 mg BID.

II-228. In a further embodiment of any of embodiments II-53-II-55, the effective amount of budiodarone is 400 mg BID or 600 mg BID.

II-229. In a further embodiment of any of embodiments II-56-II-58, the effective amount of budiodarone is 600 mg BID.

II-230. In a further embodiment of embodiment II-59, the effective amount of budiodarone is 400 mg BID or 600 mg BID.

II-231. In a further embodiment of any of embodiments II-60-II-62, the effective amount of budiodarone is 600 mg BID.

II-232. In a further embodiment of embodiment II-63, the effective amount of budiodarone is 400 mg BID or 600 mg BID.

II-233. In a further embodiment of embodiment II-64, the effective amount of budiodarone is 600 mg BID.

II-234. In a further embodiment of any of embodiments II-65-II-67, the effective amount of budiodarone is 400 mg BID or 600 mg BID.

II-235. In a further embodiment of embodiment II-68, the effective amount of budiodarone is 600 mg BID.

II-236. In a further embodiment of embodiment II-69, the effective amount of budiodarone is 400 mg BID or 600 mg BID.

II-237. In a further embodiment of any of embodiments II-70-II-72, the effective amount of budiodarone is 600 mg BID.

II-238. In a further embodiment of embodiment II-73, the effective amount of budiodarone is 400 mg BID or 600 mg BID.

II-239. In a further embodiment of embodiment II-74, the effective amount of budiodarone is 600 mg BID.

II-240. In a further embodiment of any of embodiments II-75-II-77, the effective amount of budiodarone is 400 mg BID or 600 mg BID.

II-241. In a further embodiment of embodiment II-78, the effective amount of budiodarone is 600 mg BID.

II-242. In a further embodiment of embodiment II-79, the effective amount of budiodarone is 400 mg BID or 600 mg BID.

II-243. In a further embodiment of any of embodiments II-80-II-82, the effective amount of budiodarone is 600 mg BID.

II-244. In a further embodiment of embodiment II-83, the effective amount of budiodarone is 400 mg BID or 600 mg BID.

II-245. In a further embodiment of embodiment II-84, the effective amount of budiodarone is 600 mg BID.

II-246. In a further embodiment of embodiment II-100, the effective amount of budiodarone is 400 mg BID or 600 mg BID.

II-247. In a further embodiment of embodiment II-101, the effective amount of budiodarone is 600 mg BID.

II-248. In a further embodiment of embodiment II-102, the effective amount of budiodarone is 400 mg BID or 600 mg BID.

II-249. In a further embodiment of embodiment II-103, the effective amount of budiodarone is 600 mg BID.

II-250. In a further embodiment of embodiment II-104, the effective amount of budiodarone is 400 mg BID or 600 mg BID.

II-251. In a further embodiment of embodiment II-105, the effective amount of budiodarone is 600 mg BID.

II-252. In a further embodiment of embodiment II-106, the effective amount of budiodarone is 400 mg BID or 600 mg BID.

II-253. In a further embodiment of embodiment II-107, the effective amount of budiodarone is 600 mg BID.

II-254. In a further embodiment of embodiment II-109, the effective amount of budiodarone is 400 mg BID or 600 mg BID.

II-255. In a further embodiment of embodiment II-110, the effective amount of budiodarone is 600 mg BID.

II-256. In a further embodiment of embodiment II-111, the effective amount of budiodarone is 400 mg BID or 600 mg BID.

II-257. In a further embodiment of embodiment II-112, the effective amount of budiodarone is 600 mg BID.

II-258. In a further embodiment of embodiment II-113, the effective amount of budiodarone is 400 mg BID or 600 mg BID.

II-259. In a further embodiment of embodiment II-114, the effective amount of budiodarone is 600 mg BID.

II-260. In a further embodiment of embodiment II-115, the effective amount of budiodarone is 400 mg BID or 600 mg BID.

II-261. In a further embodiment of embodiment II-116, the effective amount of budiodarone is 600 mg BID.

II-262. In a further embodiment of embodiment II-117, the effective amount of budiodarone is 400 mg BID or 600 mg BID.

II-263. In a further embodiment of embodiment II-118, the effective amount of budiodarone is 600 mg BID.

II-264. In a further embodiment of embodiment II-119, the effective amount of budiodarone is 400 mg BID or 600 mg BID.

II-265. In a further embodiment of embodiment II-120, the effective amount of budiodarone is 600 mg BID.

II-266. In a further embodiment of embodiment II-121, the effective amount of budiodarone is 400 mg BID or 600 mg BID.

II-267. In a further embodiment of embodiment II-122, the effective amount of budiodarone is 600 mg BID.

II-268. In a further embodiment of embodiment II-123, the effective amount of budiodarone is 400 mg BID or 600 mg BID.

II-269. In a further embodiment of embodiment II-124, the effective amount of budiodarone is 600 mg BID.

II-270. In a further embodiment of embodiment II-125, the effective amount of budiodarone is 400 mg BID or 600 mg BID.

II-271. In a further embodiment of embodiment II-126, the effective amount of budiodarone is 600 mg BID.

II-272. In a further embodiment of embodiment II-127, the effective amount of budiodarone is 400 mg BID or 600 mg BID.

II-273. In a further embodiment of embodiment II-128, the effective amount of budiodarone is 600 mg BID.

II-274. In a further embodiment of embodiment II-129, the effective amount of budiodarone is 400 mg BID or 600 mg BID.

II-275. In a further embodiment of embodiment II-130, the effective amount of budiodarone is 600 mg BID.

II-276. In a further embodiment of embodiment II-131, the effective amount of budiodarone is 400 mg BID or 600 mg BID.

II-277. In a further embodiment of embodiment II-150, the effective amount of budiodarone is 600 mg BID.

II-278. In a further embodiment of embodiment II-151, the effective amount of budiodarone is 400 mg BID or 600 mg BID.

II-279. In a further embodiment of embodiment II-152, the effective amount of budiodarone is 600 mg BID.

III-280. In a further embodiment of embodiment II-153, the effective amount of budiodarone is 400 mg BID or 600 mg BID.

II-281. In a further embodiment of embodiment II-154, the effective amount of budiodarone is 600 mg BID.

II-282. In a further embodiment of embodiment II-155, the effective amount of budiodarone is 400 mg BID or 600 mg BID.

II-283. In a further embodiment of embodiment II-156, the effective amount of budiodarone is 600 mg BID.

II-284. In a further embodiment of embodiment II-157, the effective amount of budiodarone is 400 mg BID or 600 mg BID.

II-285. In a further embodiment of embodiment II-159, the effective amount of budiodarone is 600 mg BID.

II-286. In a further embodiment of embodiment II-160, the effective amount of budiodarone is 400 mg BID or 600 mg BID.

II-287. In a further embodiment of embodiment II-161, the effective amount of budiodarone is 600 mg BID.

II-288. In a further embodiment of embodiment II-162, the effective amount of budiodarone is 400 mg BID or 600 mg BID.

II-289. In a further embodiment of embodiment II-163, the effective amount of budiodarone is 600 mg BID.

II-290. In a further embodiment of embodiment II-164, the effective amount of budiodarone is 400 mg BID or 600 mg BID.

II-291. In a further embodiment of embodiment II-165, the effective amount of budiodarone is 600 mg BID.

II-292. In a further embodiment of embodiment II-166, the effective amount of budiodarone is 400 mg BID or 600 mg BID.

II-293. In a further embodiment of embodiment II-167, the effective amount of budiodarone is 600 mg BID.

II-294. In a further embodiment of embodiment II-168, the effective amount of budiodarone is 400 mg BID or 600 mg BID.

II-295. In a further embodiment of embodiment II-169, the effective amount of budiodarone is 600 mg BID.

II-296. In a further embodiment of embodiment II-170, the effective amount of budiodarone is 400 mg BID or 600 mg BID.

II-297. In a further embodiment of embodiment II-171, the effective amount of budiodarone is 600 mg BID.

II-298. In a further embodiment of embodiment II-172, the effective amount of budiodarone is 400 mg BID or 600 mg BID.

II-299. In a further embodiment of embodiment II-173, the effective amount of budiodarone is 600 mg BID.

II-300. In a further embodiment of embodiment II-174, the effective amount of budiodarone is 400 mg BID or 600 mg BID.

II-301. In a further embodiment of embodiment II-175, the effective amount of budiodarone is 600 mg BID.

II-302. In a further embodiment of embodiment II-176, the effective amount of budiodarone is 400 mg BID or 600 mg BID.

II-303. In a further embodiment of embodiment II-177, the effective amount of budiodarone is 600 mg BID.

II-304. In a further embodiment of embodiment II-178, the effective amount of budiodarone is 400 mg BID or 600 mg BID.

II-305. In a further embodiment of embodiment II-179, the effective amount of budiodarone is 600 mg BID.

II-306. In a further embodiment of embodiment II-180, the effective amount of budiodarone is 400 mg BID or 600 mg BID.

II-307. In a further embodiment of embodiment II-181, the effective amount of budiodarone is 600 mg BID.

II-308. In a further embodiment of embodiment II-150, the reversal of atrial remodeling is defined as a measured increase in AFCL at the right atrial appendage or distal coronary sinus of at least 6 milliseconds.

II-309. In a further embodiment of any of embodiments II-151-II-154, the reversal of atrial remodeling is defined as a measured increase in AFCL at the right atrial appendage or distal coronary sinus of at least 6 milliseconds.

II-310. In a further embodiment of any of embodiments II-155-II-157, the reversal of atrial remodeling is defined as a measured increase in AFCL at the right atrial appendage or distal coronary sinus of at least 6 milliseconds.

II-311. In a further embodiment of embodiment II-157, the reversal of atrial remodeling is defined as a measured increase in AFCL at the right atrial appendage or distal coronary sinus of at least 6 milliseconds.

II-312. In a further embodiment of embodiment II-158, the reversal of atrial remodeling is defined as a measured increase in AFCL at the right atrial appendage or distal coronary sinus of at least 6 milliseconds.

II-313. In a further embodiment of embodiment II-159, the reversal of atrial remodeling is defined as a measured increase in AFCL at the right atrial appendage or distal coronary sinus of at least 6 milliseconds.

II-314. In a further embodiment of embodiment II-160, the reversal of atrial remodeling is defined as a measured increase in AFCL at the right atrial appendage or distal coronary sinus of at least 6 milliseconds.

II-315. In a further embodiment of any of embodiments II-161-II-162, the reversal of atrial remodeling is defined as a measured increase in AFCL at the right atrial appendage or distal coronary sinus of at least 6 milliseconds.

II-316. In a further embodiment of embodiment II-163, the reversal of atrial remodeling is defined as a measured increase in AFCL at the right atrial appendage or distal coronary sinus of at least 6 milliseconds.

II-317. In a further embodiment of any of embodiments II-164-II-167, the reversal of atrial remodeling is defined as a measured increase in AFCL at the right atrial appendage or distal coronary sinus of at least 6 milliseconds.

II-318. In a further embodiment of any of embodiments II-165-II-168, the reversal of atrial remodeling is defined as a measured increase in AFCL at the right atrial appendage or distal coronary sinus of at least 6 milliseconds.

II-319. In a further embodiment of embodiment II-168, the reversal of atrial remodeling is defined as a measured increase in AFCL at the right atrial appendage or distal coronary sinus of at least 6 milliseconds.

II-320. In a further embodiment of embodiment II-171, the reversal of atrial remodeling is defined as a measured increase in AFCL at the right atrial appendage or distal coronary sinus of at least 6 milliseconds.

II-321. In a further embodiment of embodiment II-172, the reversal of atrial remodeling is defined as a measured increase in AFCL at the right atrial appendage or distal coronary sinus of at least 6 milliseconds.

II-322. In a further embodiment of embodiment II-175, the reversal of atrial remodeling is defined as a measured increase in AFCL at the right atrial appendage or distal coronary sinus of at least 6 milliseconds.

II-323. In a further embodiment of embodiment II-176, the reversal of atrial remodeling is defined as a measured increase in AFCL at the right atrial appendage or distal coronary sinus of at least 6 milliseconds.

II-324. In a further embodiment of embodiment II-179, the reversal of atrial remodeling is defined as a measured increase in AFCL at the right atrial appendage or distal coronary sinus of at least 6 milliseconds.

II-325. In a further embodiment of embodiment II-180, reversal of atrial remodeling is defined as a measured increase in AFCL at the right atrial appendage or distal coronary sinus of at least 6 milliseconds.

III-1. In one embodiment, the invention provides a method for reducing stroke rate comprising administering an amount of multiple ion channel blocker selected from the group consisting of amiodarone, dronedarone, budiodarone, vernakalant, celivarone, and AZD1305 effective to reduce atrial fibrillation (AF) episode duration and an effective amount of anticoagulant (AC) selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin.

III-2. In a further embodiment of embodiment III-1, the average AF episode duration is reduced to less than about 24 hours.

III-3. In a further embodiment of embodiment III-1, the average AF episode duration is reduced to less than about 5 hours.

III-4. In a further embodiment of embodiment III-1, the average AF episode duration is reduced to less than 3 hours.

III-5. In a further embodiment of embodiment III-1, the average AF episode duration is reduced to less than about 1 hour.

III-6. In a further embodiment of embodiment III-1, the maximum AF episode duration is reduced to less than about 20 hours.

III-7. In a further embodiment of embodiment III-1, the maximum AF episode duration is reduced to less than about 10 hours.

III-8. In a further embodiment of embodiment III-1, the maximum AF episode duration is reduced to less than about 5 hours.

III-9. In a further embodiment of embodiment III-1, the multiple ion channel blocker is budiodarone, dronedarone, celivarone, AZD1305 or vernakalant.

III-10. In a further embodiment of embodiment III-2, the multiple ion channel blocker is budiodarone, dronedarone, celivarone, AZD1305 or vernakalant.

III-11. In a further embodiment of embodiment III-3, the multiple ion channel blocker is budiodarone, dronedarone, celivarone, AZD1305 or vernakalant.

III-12. In a further embodiment of embodiment III-4, the multiple ion channel blocker is budiodarone, dronedarone, celivarone, AZD1305 or vernakalant.

III-13. In a further embodiment of embodiment III-5, the multiple ion channel blocker is budiodarone, dronedarone, celivarone, AZD1305 or vernakalant.

III-14. In a further embodiment of embodiment III-6, the multiple ion channel blocker is budiodarone, dronedarone, celivarone, AZD1305 or vernakalant.

III-15. In a further embodiment of embodiment III-7, the multiple ion channel blocker is budiodarone, dronedarone, celivarone, AZD1305 or vernakalant.

III-16. In a further embodiment of embodiment III-8, the multiple ion channel blocker is budiodarone, dronedarone, celivarone, AZD1305 or vernakalant.

III-17. In a further embodiment of embodiment III-1, the multiple ion channel blocker is budiodarone.

III-18. In a further embodiment of embodiment III-2, the multiple ion channel blocker is budiodarone.

III-19. In a further embodiment of embodiment III-3, the multiple ion channel blocker is budiodarone.

III-20. In a further embodiment of embodiment III-4, the multiple ion channel blocker is budiodarone.

III-21. In a further embodiment of embodiment III-5, the multiple ion channel blocker is budiodarone.

III-22. In a further embodiment of embodiment III-6, the multiple ion channel blocker is budiodarone.

III-23. In a further embodiment of embodiment III-7, the multiple ion channel blocker is budiodarone.

III-24. In a further embodiment of embodiment III-8, the multiple ion channel blocker is budiodarone.

III-25. In a further embodiment of embodiment III-1, the AC is tecarfarin, dabigatran etexilate, ximelagatran, AZD0837, apixaban or rivaroxaban.

III-26. In a further embodiment of any of embodiments III-2-III-5, the AC is tecarfarin, dabigatran etexilate, ximelagatran, AZD0837, apixaban or rivaroxaban.

III-27. In a further embodiment of embodiment III-5, the AC is tecarfarin, dabigatran etexilate, ximelagatran, AZD0837, apixaban or rivaroxaban.

III-28. In a further embodiment of any of embodiments III-6-III-8, the AC is tecarfarin, dabigatran etexilate, ximelagatran, AZD0837, apixaban or rivaroxaban.

III-29. In a further embodiment of embodiment III-8, the AC is tecarfarin, dabigatran etexilate, ximelagatran, AZD0837, apixaban or rivaroxaban.

III-30. In a further embodiment of embodiment III-9, the AC is tecarfarin, dabigatran etexilate, ximelagatran, AZD0837, apixaban or rivaroxaban.

III-31. In a further embodiment of any of embodiments III-10-III-12, the AC is tecarfarin, dabigatran etexilate, ximelagatran, AZD0837, apixaban or rivaroxaban.

III-32. In a further embodiment of embodiment III-13, the AC is tecarfarin, dabigatran etexilate, ximelagatran, AZD0837, apixaban or rivaroxaban.

III-33. In a further embodiment of any of embodiments III-14-III-16, the AC is tecarfarin, dabigatran etexilate, ximelagatran, AZD0837, apixaban or rivaroxaban.

III-34. In a further embodiment of embodiment III-16, the AC is tecarfarin, dabigatran etexilate, ximelagatran, AZD0837, apixaban or rivaroxaban.

III-35. In a further embodiment of embodiment III-17, the AC is tecarfarin, dabigatran etexilate, ximelagatran, AZD0837, apixaban or rivaroxaban.

III-36. In a further embodiment of embodiment III-18, the AC is tecarfarin, dabigatran etexilate, ximelagatran, AZD0837, apixaban or rivaroxaban.

III-37. In a further embodiment of any of embodiments III-19-III-20, the AC is tecarfarin, dabigatran etexilate, ximelagatran, AZD0837, apixaban or rivaroxaban.

III-38. In a further embodiment of embodiment III-21, the AC is tecarfarin, dabigatran etexilate, ximelagatran, AZD0837, apixaban or rivaroxaban.

III-39. In a further embodiment of any of embodiments III-22-III-24, the AC is tecarfarin, dabigatran etexilate, ximelagatran, AZD0837, apixaban or rivaroxaban.

III-40. In a further embodiment of any of embodiments III-26-III-27, the AC is dabigatran etexilate.

III-41. In a further embodiment of embodiment III-28, the AC is dabigatran etexilate.

III-42. In a further embodiment of any of embodiments III-29-III-30, the AC is dabigatran etexilate.

III-43. In a further embodiment of embodiment III-31, the AC is dabigatran etexilate.

III-44. In a further embodiment of embodiment III-33, the AC is dabigatran etexilate.

III-45. In a further embodiment of embodiment III-34, the AC is dabigatran etexilate.

III-46. In a further embodiment of embodiment III-36, the AC is dabigatran etexilate.

III-47. In a further embodiment of embodiment III-38, the AC is dabigatran etexilate.

III-48. In a further embodiment of embodiment III-39, the AC is dabigatran etexilate.

III-49. In a further embodiment of embodiment III-26, the AC is ximelagatran or AZD0837.

III-50. In a further embodiment of embodiment III-28, the AC is ximelagatran or AZD0837.

III-51. In a further embodiment of embodiment III-29, the AC is ximelagatran or AZD0837.

III-52. In a further embodiment of embodiment III-31, the AC is ximelagatran or AZD0837.

III-53. In a further embodiment of embodiment III-33, the AC is ximelagatran or AZD0837.

III-54. In a further embodiment of embodiment III-34, the AC is ximelagatran or AZD0837.

III-55. In a further embodiment of embodiment III-36, the AC is ximelagatran or AZD0837.

III-56. In a further embodiment of embodiment III-38, the AC is ximelagatran or AZD0837.

III-57. In a further embodiment of embodiment III-39, the AC is ximelagatran or AZD0837.

III-58. In a further embodiment of embodiment III-26, the AC is apixaban.

III-59. In a further embodiment of embodiment III-28, the AC is apixaban.

III-60. In a further embodiment of embodiment III-29, the AC is apixaban.

III-61. In a further embodiment of embodiment III-31, the AC is apixaban.

III-62. In a further embodiment of embodiment III-33, the AC is apixaban.

III-63. In a further embodiment of embodiment III-34, the AC is apixaban.

III-64. In a further embodiment of embodiment III-36, the AC is apixaban.

III-65. In a further embodiment of embodiment III-38, the AC is apixaban.

III-66. In a further embodiment of embodiment III-39, the AC is apixaban.

III-67. In a further embodiment of embodiment III-26, the AC is rivaroxaban.

III-68. In a further embodiment of embodiment III-28, the AC is rivaroxaban.

III-69. In a further embodiment of embodiment III-29, the AC is rivaroxaban.

III-70. In a further embodiment of embodiment III-31, the AC is rivaroxaban.

III-71. In a further embodiment of embodiment III-33, the AC is rivaroxaban.

III-72. In a further embodiment of embodiment III-34, the AC is rivaroxaban.

III-73. In a further embodiment of embodiment III-36, the AC is rivaroxaban.

III-74. In a further embodiment of embodiment III-38, the AC is rivaroxaban.

III-75. In a further embodiment of embodiment III-39, the AC is rivaroxaban.

III-76. In a further embodiment of embodiment III-26, the AC is tecarfarin.

III-77. In a further embodiment of embodiment III-28, the AC is tecarfarin.

III-78. In a further embodiment of embodiment III-29, the AC is tecarfarin.

III-79. In a further embodiment of embodiment III-31, the AC is tecarfarin.

III-80. In a further embodiment of embodiment III-33, the AC is tecarfarin.

III-81. In a further embodiment of embodiment III-34, the AC is tecarfarin.

III-82. In a further embodiment of embodiment III-36, the AC is tecarfarin.

III-83. In a further embodiment of embodiment III-38, the AC is tecarfarin.

III-84. In a further embodiment of embodiment III-39, the AC is tecarfarin.

III-85. In a further embodiment of embodiment III-1, the reduced stroke rate is less than the age-adjusted overall stroke rate.

III-86. In a further embodiment of embodiment III-2, the reduced stroke rate is less than the age-adjusted overall stroke rate.

III-87. In a further embodiment of embodiment III-3, the reduced stroke rate is less than the age-adjusted overall stroke rate.

III-88. In a further embodiment of embodiment III-4, the reduced stroke rate is less than the age-adjusted overall stroke rate.

III-89. In a further embodiment of embodiment III-5, the reduced stroke rate is less than the age-adjusted overall stroke rate.

III-90. In a further embodiment of embodiment III-6, the reduced stroke rate is less than the age-adjusted overall stroke rate.

III-91. In a further embodiment of embodiment III-7, the reduced stroke rate is less than the age-adjusted overall stroke rate.

III-92. In a further embodiment of embodiment III-8, the reduced stroke rate is less than the age-adjusted overall stroke rate.

III-93. In a further embodiment of embodiment III-10, the reduced stroke rate is less than the age-adjusted overall stroke rate.

III-94. In a further embodiment of embodiment III-13, the reduced stroke rate is less than the age-adjusted overall stroke rate.

III-95. In a further embodiment of embodiment III-16, the reduced stroke rate is less than the age-adjusted overall stroke rate.

III-96. In a further embodiment of embodiment III-18, the reduced stroke rate is less than the age-adjusted overall stroke rate.

III-97. In a further embodiment of embodiment III-21, the reduced stroke rate is less than the age-adjusted overall stroke rate.

III-98. In a further embodiment of embodiment III-24, the reduced stroke rate is less than the age-adjusted overall stroke rate.

III-99. In a further embodiment of embodiment III-25, the reduced stroke rate is less than the age-adjusted overall stroke rate.

III-100. In a further embodiment of embodiment III-26, the reduced stroke rate is less than the age-adjusted overall stroke rate.

III-101. In a further embodiment of embodiment III-27, the reduced stroke rate is less than the age-adjusted overall stroke rate.

III-102. In a further embodiment of embodiment III-28, the reduced stroke rate is less than the age-adjusted overall stroke rate.

III-103. In a further embodiment of embodiment III-29, the reduced stroke rate is less than the age-adjusted overall stroke rate.

III-104. In a further embodiment of embodiment III-30, the reduced stroke rate is less than the age-adjusted overall stroke rate.

III-105. In a further embodiment of embodiment III-31, the reduced stroke rate is less than the age-adjusted overall stroke rate.

III-106. In a further embodiment of embodiment III-32, the reduced stroke rate is less than the age-adjusted overall stroke rate.

III-107. In a further embodiment of embodiment III-33, the reduced stroke rate is less than the age-adjusted overall stroke rate.

III-108. In a further embodiment of embodiment III-34, the reduced stroke rate is less than the age-adjusted overall stroke rate.

III-109. In a further embodiment of embodiment III-35, the reduced stroke rate is less than the age-adjusted overall stroke rate.

III-110. In a further embodiment of embodiment III-36, the reduced stroke rate is less than the age-adjusted overall stroke rate.

III-111. In a further embodiment of embodiment III-37, the reduced stroke rate is less than the age-adjusted overall stroke rate.

III-112. In a further embodiment of embodiment III-38, the reduced stroke rate is less than the age-adjusted overall stroke rate.

III-113. In a further embodiment of embodiment III-39, the reduced stroke rate is less than the age-adjusted overall stroke rate.

III-114. In a further embodiment of embodiment III-40, the reduced stroke rate is less than the age-adjusted overall stroke rate.

III-115. In a further embodiment of embodiment III-41, the reduced stroke rate is less than the age-adjusted overall stroke rate.

III-116. In a further embodiment of embodiment III-42, the reduced stroke rate is less than the age-adjusted overall stroke rate.

III-117. In a further embodiment of embodiment III-43, the reduced stroke rate is less than the age-adjusted overall stroke rate.

III-118. In a further embodiment of embodiment III-44, the reduced stroke rate is less than the age-adjusted overall stroke rate.

III-119. In a further embodiment of embodiment III-45, the reduced stroke rate is less than the age-adjusted overall stroke rate.

III-120. In a further embodiment of embodiment III-46, the reduced stroke rate is less than the age-adjusted overall stroke rate.

III-121. In a further embodiment of embodiment III-47, the reduced stroke rate is less than the age-adjusted overall stroke rate.

III-122. In a further embodiment of embodiment III-48, the reduced stroke rate is less than the age-adjusted overall stroke rate.

III-123. In a further embodiment of embodiment III-49, the reduced stroke rate is less than the age-adjusted overall stroke rate.

III-124. In a further embodiment of embodiment III-50, the reduced stroke rate is less than the age-adjusted overall stroke rate.

III-125. In a further embodiment of embodiment III-51, the reduced stroke rate is less than the age-adjusted overall stroke rate.

III-126. In a further embodiment of embodiment III-52, the reduced stroke rate is less than the age-adjusted overall stroke rate.

III-127. In a further embodiment of embodiment III-53, the reduced stroke rate is less than the age-adjusted overall stroke rate.

III-128. In a further embodiment of embodiment III-54, the reduced stroke rate is less than the age-adjusted overall stroke rate.

III-129. In a further embodiment of embodiment III-55, the reduced stroke rate is less than the age-adjusted overall stroke rate.

III-130. In a further embodiment of embodiment III-56, the reduced stroke rate is less than the age-adjusted overall stroke rate.

III-131. In a further embodiment of embodiment III-57, the reduced stroke rate is less than the age-adjusted overall stroke rate.

III-132. In a further embodiment of embodiment III-58, the reduced stroke rate is less than the age-adjusted overall stroke rate.

III-133. In a further embodiment of embodiment III-59, the reduced stroke rate is less than the age-adjusted overall stroke rate.

III-134. In a further embodiment of embodiment III-60, the reduced stroke rate is less than the age-adjusted overall stroke rate.

III-135. In a further embodiment of embodiment III-61, the reduced stroke rate is less than the age-adjusted overall stroke rate.

III-136. In a further embodiment of embodiment III-62, the reduced stroke rate is less than the age-adjusted overall stroke rate.

III-137. In a further embodiment of embodiment III-63, the reduced stroke rate is less than the age-adjusted overall stroke rate.

III-138. In a further embodiment of embodiment III-64, the reduced stroke rate is less than the age-adjusted overall stroke rate.

III-139. In a further embodiment of embodiment III-65, the reduced stroke rate is less than the age-adjusted overall stroke rate.

III-140. In a further embodiment of embodiment III-66, the reduced stroke rate is less than the age-adjusted overall stroke rate.

III-141. In a further embodiment of embodiment III-67, the reduced stroke rate is less than the age-adjusted overall stroke rate.

III-142. In a further embodiment of embodiment III-68, the reduced stroke rate is less than the age-adjusted overall stroke rate.

III-143. In a further embodiment of embodiment III-69, the reduced stroke rate is less than the age-adjusted overall stroke rate.

III-144. In a further embodiment of embodiment III-70, the reduced stroke rate is less than the age-adjusted overall stroke rate.

III-145. In a further embodiment of embodiment III-71, the reduced stroke rate is less than the age-adjusted overall stroke rate.

III-146. In a further embodiment of embodiment III-72, the reduced stroke rate is less than the age-adjusted overall stroke rate.

III-147. In a further embodiment of embodiment III-73, the reduced stroke rate is less than the age-adjusted overall stroke rate.

III-148. In a further embodiment of embodiment III-74, the reduced stroke rate is less than the age-adjusted overall stroke rate.

III-149. In a further embodiment of embodiment III-75, the reduced stroke rate is less than the age-adjusted overall stroke rate.

III-150. In a further embodiment of embodiment III-76, the reduced stroke rate is less than the age-adjusted overall stroke rate.

III-151. In a further embodiment of embodiment III-77, the reduced stroke rate is less than the age-adjusted overall stroke rate.

III-152. In a further embodiment of embodiment III-78, the reduced stroke rate is less than the age-adjusted overall stroke rate.

III-153. In a further embodiment of embodiment III-79, the reduced stroke rate is less than the age-adjusted overall stroke rate.

III-154. In a further embodiment of embodiment III-80, the reduced stroke rate is less than the age-adjusted overall stroke rate.

III-155. In a further embodiment of embodiment III-81, the reduced stroke rate is less than the age-adjusted overall stroke rate.

III-156. In a further embodiment of embodiment III-82, the reduced stroke rate is less than the age-adjusted overall stroke rate.

III-157. In a further embodiment of embodiment III-83, the reduced stroke rate is less than the age-adjusted overall stroke rate.

III-158. In a further embodiment of embodiment III-84, the reduced stroke rate is less than the age-adjusted overall stroke rate.

III-159. In a further embodiment of embodiment III-2, the patient was refractory to one or more anti-arrhythmic drugs.

III-160. In a further embodiment of embodiment III-5, the patient was refractory to one or more anti-arrhythmic drugs.

III-161. In a further embodiment of embodiment III-10, the patient was refractory to one or more anti-arrhythmic drugs.

III-162. In a further embodiment of embodiment III-13, the patient was refractory to one or more anti-arrhythmic drugs.

III-163. In a further embodiment of embodiment III-18, the patient was refractory to one or more anti-arrhythmic drugs.

III-164. In a further embodiment of embodiment III-21, the patient was refractory to one or more anti-arrhythmic drugs.

III-165. In a further embodiment of embodiment III-41, the patient was refractory to one or more anti-arrhythmic drugs.

III-166. In a further embodiment of embodiment III-44, the patient was refractory to one or more anti-arrhythmic drugs.

III-167. In a further embodiment of embodiment III-47, the patient was refractory to one or more anti-arrhythmic drugs.

III-168. In a further embodiment of embodiment III-50, the patient was refractory to one or more anti-arrhythmic drugs.

III-169. In a further embodiment of embodiment III-53, the patient was refractory to one or more anti-arrhythmic drugs.

III-170. In a further embodiment of embodiment III-56, the patient was refractory to one or more anti-arrhythmic drugs.

III-171. In a further embodiment of embodiment III-59, the patient was refractory to one or more anti-arrhythmic drugs.

III-172. In a further embodiment of embodiment III-62, the patient was refractory to one or more anti-arrhythmic drugs.

III-173. In a further embodiment of embodiment III-65, the patient was refractory to one or more anti-arrhythmic drugs.

III-174. In a further embodiment of embodiment III-68, the patient was refractory to one or more anti-arrhythmic drugs.

III-175. In a further embodiment of embodiment III-71, the patient was refractory to one or more anti-arrhythmic drugs.

III-176. In a further embodiment of embodiment III-74, the patient was refractory to one or more anti-arrhythmic drugs.

III-177. In a further embodiment of embodiment III-77, the patient was refractory to one or more anti-arrhythmic drugs.

III-178. In a further embodiment of embodiment III-80, the patient was refractory to one or more anti-arrhythmic drugs.

III-179. In a further embodiment of embodiment III-83, the patient was refractory to one or more anti-arrhythmic drugs.

III-180. In a further embodiment of embodiment III-85, the patient was refractory to one or more anti-arrhythmic drugs.

III-181. In a further embodiment of embodiment III-86, the patient was refractory to one or more anti-arrhythmic drugs.

III-182. In a further embodiment of embodiment III-87, the patient was refractory to one or more anti-arrhythmic drugs.

III-183. In a further embodiment of embodiment III-88, the patient was refractory to one or more anti-arrhythmic drugs.

III-184. In a further embodiment of embodiment III-89, the patient was refractory to one or more anti-arrhythmic drugs.

III-185. In a further embodiment of embodiment III-90, the patient was refractory to one or more anti-arrhythmic drugs.

III-186. In a further embodiment of embodiment III-91, the patient was refractory to one or more anti-arrhythmic drugs.

III-187. In a further embodiment of embodiment III-92, the patient was refractory to one or more anti-arrhythmic drugs.

III-188. In a further embodiment of embodiment III-93, the patient was refractory to one or more anti-arrhythmic drugs.

III-189. In a further embodiment of embodiment III-94, the patient was refractory to one or more anti-arrhythmic drugs.

III-190. In a further embodiment of embodiment III-97, the patient was refractory to one or more anti-arrhythmic drugs.

III-191. In a further embodiment of embodiment III-102, the patient was refractory to one or more anti-arrhythmic drugs.

III-192. In a further embodiment of embodiment III-107, the patient was refractory to one or more anti-arrhythmic drugs.

III-193. In a further embodiment of embodiment III-112, the patient was refractory to one or more anti-arrhythmic drugs.

III-194. In a further embodiment of embodiment III-115, the patient was refractory to one or more anti-arrhythmic drugs.

III-195. In a further embodiment of embodiment III-118, the patient was refractory to one or more anti-arrhythmic drugs.

III-196. In a further embodiment of embodiment III-121, the patient was refractory to one or more anti-arrhythmic drugs.

III-197. In a further embodiment of embodiment III-124, the patient was refractory to one or more anti-arrhythmic drugs.

III-198. In a further embodiment of embodiment III-127, the patient was refractory to one or more anti-arrhythmic drugs.

III-199. In a further embodiment of embodiment III-130, the patient was refractory to one or more anti-arrhythmic drugs.

III-200. In a further embodiment of embodiment III-133, the patient was refractory to one or more anti-arrhythmic drugs.

III-201. In a further embodiment of embodiment III-136, the patient was refractory to one or more anti-arrhythmic drugs.

III-202. In a further embodiment of embodiment III-139, the patient was refractory to one or more anti-arrhythmic drugs.

III-203. In a further embodiment of embodiment III-142, the patient was refractory to one or more anti-arrhythmic drugs.

III-204. In a further embodiment of embodiment III-145, the patient was refractory to one or more anti-arrhythmic drugs.

III-205. In a further embodiment of embodiment III-148, the patient was refractory to one or more anti-arrhythmic drugs.

III-206. In a further embodiment of embodiment III-151, the patient was refractory to one or more anti-arrhythmic drugs.

III-207. In a further embodiment of embodiment III-154, the patient was refractory to one or more anti-arrhythmic drugs.

III-208. In a further embodiment of embodiment III-157, the patient was refractory to one or more anti-arrhythmic drugs.

III-209. In one embodiment, the invention provides a method for preventing atrial remodeling comprising administering an amount of multiple ion channel blocker selected from the group consisting of amiodarone, dronedarone, budiodarone, vernakalant, celivarone, and AZD1305 effective to reduce atrial fibrillation (AF) episode duration and an effective amount of anticoagulant (AC) selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin.

III-210. In a further embodiment of embodiment III-209, the average AF episode duration is reduced to less than about 24 hours.

III-211. In a further embodiment of embodiment III-209, the average AF episode duration is reduced to less than about 5 hours.

III-212. In a further embodiment of embodiment III-209, the average AF episode duration is reduced to less than 3 hours.

III-213. In a further embodiment of embodiment III-209, the average AF episode duration is reduced to less than about 1 hour.

III-214. In a further embodiment of embodiment III-209, the maximum AF episode duration is reduced to less than about 20 hours.

III-215. In a further embodiment of embodiment III-209, the maximum AF episode duration is reduced to less than about 10 hours.

III-216. In a further embodiment of embodiment III-209, the maximum AF episode duration is reduced to less than about 5 hours.

III-217. In a further embodiment of embodiment III-209, the multiple ion channel blocker is budiodarone, dronedarone, celivarone, AZD1305 or vernakalant.

III-218. In a further embodiment of embodiment III-210, the multiple ion channel blocker is budiodarone, dronedarone, celivarone, AZD1305 or vernakalant.

III-219. In a further embodiment of embodiment III-211, the multiple ion channel blocker is budiodarone, dronedarone, celivarone, AZD1305 or vernakalant.

III-220. In a further embodiment of embodiment III-212, the multiple ion channel blocker is budiodarone, dronedarone, celivarone, AZD1305 or vernakalant.

III-221. In a further embodiment of embodiment III-213, the multiple ion channel blocker is budiodarone, dronedarone, celivarone, AZD1305 or vernakalant.

III-222. In a further embodiment of embodiment III-214, the multiple ion channel blocker is budiodarone, dronedarone, celivarone, AZD1305 or vernakalant.

III-223. In a further embodiment of embodiment III-215, the multiple ion channel blocker is budiodarone, dronedarone, celivarone, AZD1305 or vernakalant.

III-224. In a further embodiment of embodiment III-216, the multiple ion channel blocker is budiodarone, dronedarone, celivarone, AZD1305 or vernakalant.

III-225. In a further embodiment of embodiment III-209, the multiple ion channel blocker is budiodarone.

III-226. In a further embodiment of embodiment III-210, the multiple ion channel blocker is budiodarone.

III-227. In a further embodiment of embodiment III-211, the multiple ion channel blocker is budiodarone.

III-228. In a further embodiment of embodiment III-212, the multiple ion channel blocker is budiodarone.

III-229. In a further embodiment of embodiment III-213, the multiple ion channel blocker is budiodarone.

III-230. In a further embodiment of embodiment III-214, the multiple ion channel blocker is budiodarone.

III-231. In a further embodiment of embodiment III-215, the multiple ion channel blocker is budiodarone.

III-232. In a further embodiment of embodiment III-216, the multiple ion channel blocker is budiodarone.

III-233. In a further embodiment of embodiment III-209, the AC is tecarfarin, dabigatran etexilate, ximelagatran, AZD0837, apixaban or rivaroxaban.

III-234. In a further embodiment of embodiment III-210, the AC is tecarfarin, dabigatran etexilate, AZD0837, apixaban or rivaroxaban.

III-235. In a further embodiment of embodiment III-211, the AC is tecarfarin, dabigatran etexilate, ximelagatran, AZD0837, apixaban or rivaroxaban.

III-236. In a further embodiment of embodiment III-213, the AC is tecarfarin, dabigatran etexilate, ximelagatran, AZD0837, apixaban or rivaroxaban.

III-237. In a further embodiment of any of embodiments III-214-III-216, the AC is tecarfarin, dabigatran etexilate, ximelagatran, AZD0837, apixaban or rivaroxaban.

III-238. In a further embodiment of embodiment III-217, the AC is tecarfarin, dabigatran etexilate, ximelagatran, AZD0837, apixaban or rivaroxaban.

III-239. In a further embodiment of embodiment III-218, the AC is tecarfarin, dabigatran etexilate, ximelagatran, AZD0837, apixaban or rivaroxaban.

III-240. In a further embodiment of embodiment III-219, the AC is tecarfarin, dabigatran etexilate, ximelagatran, AZD0837, apixaban or rivaroxaban.

III-241. In a further embodiment of embodiment III-221, the AC is tecarfarin, dabigatran etexilate, ximelagatran, AZD0837, apixaban or rivaroxaban.

III-242. In a further embodiment of any of embodiments III-222-III-224, the AC is tecarfarin, dabigatran etexilate, ximelagatran, AZD0837, apixaban or rivaroxaban.

III-243. In a further embodiment of embodiment III-225, the AC is tecarfarin, dabigatran etexilate, ximelagatran, AZD0837, apixaban or rivaroxaban.

III-244. In a further embodiment of embodiment III-226, the AC is tecarfarin, dabigatran etexilate, ximelagatran, AZD0837, apixaban or rivaroxaban.

III-245. In a further embodiment of embodiment III-227, the AC is tecarfarin, dabigatran etexilate, ximelagatran, AZD0837, apixaban or rivaroxaban.

III-246. In a further embodiment of embodiment III-229, the AC is tecarfarin, dabigatran etexilate, ximelagatran, AZD0837, apixaban or rivaroxaban.

III-247. In a further embodiment of embodiment III-232, the AC is tecarfarin, dabigatran etexilate, ximelagatran, AZD0837, apixaban or rivaroxaban.

III-248. In a further embodiment of embodiment III-234, the AC is dabigatran etexilate.

III-249. In a further embodiment of embodiment III-236, the AC is dabigatran etexilate.

III-250. In a further embodiment of embodiment III-237, the AC is dabigatran etexilate.

III-251. In a further embodiment of embodiment III-239, the AC is dabigatran etexilate.

III-252. In a further embodiment of embodiment III-241, the AC is dabigatran etexilate.

III-253. In a further embodiment of embodiment III-242, the AC is dabigatran etexilate.

III-254. In a further embodiment of embodiment III-244, the AC is dabigatran etexilate.

III-255. In a further embodiment of embodiment III-246, the AC is dabigatran etexilate.

III-256. In a further embodiment of embodiment III-247, the AC is dabigatran etexilate.

III-257. In a further embodiment of embodiment III-234, the AC is ximelagatran or AZD0837.

III-258. In a further embodiment of embodiment III-236, the AC is ximelagatran or AZD0837.

III-259. In a further embodiment of embodiment III-237, the AC is ximelagatran or AZD0837.

III-260. In a further embodiment of embodiment III-239, the AC is ximelagatran or AZD0837.

III-261. In a further embodiment of embodiment III-241, the AC is ximelagatran or AZD0837.

III-262. In a further embodiment of embodiment III-242, the AC is ximelagatran or AZD0837.

III-263. In a further embodiment of embodiment III-244, the AC is ximelagatran or AZD0837.

III-264. In a further embodiment of embodiment III-246, the AC is ximelagatran or AZD0837.

III-265. In a further embodiment of embodiment III-247, the AC is ximelagatran or AZD0837.

III-266. In a further embodiment of embodiment III-234, the AC is apixaban.

III-267. In a further embodiment of embodiment III-236, the AC is apixaban.

III-268. In a further embodiment of embodiment III-237, the AC is apixaban.

III-269. In a further embodiment of embodiment III-239, the AC is apixaban.

III-270. In a further embodiment of embodiment III-241, the AC is apixaban.

III-271. In a further embodiment of embodiment III-242, the AC is apixaban.

III-272. In a further embodiment of embodiment III-244, the AC is apixaban.

III-273. In a further embodiment of embodiment III-246, the AC is apixaban.

III-274. In a further embodiment of embodiment III-247, the AC is apixaban.

III-275. In a further embodiment of embodiment III-234, the AC is rivaroxaban.

III-276. In a further embodiment of embodiment III-236, the AC is rivaroxaban.

III-277. In a further embodiment of embodiment III-237, the AC is rivaroxaban.

III-278. In a further embodiment of embodiment III-239, the AC is rivaroxaban.

III-279. In a further embodiment of embodiment III-241, the AC is rivaroxaban.

III-280. In a further embodiment of embodiment III-242, the AC is rivaroxaban.

III-281. In a further embodiment of embodiment III-244, the AC is rivaroxaban.

III-282. In a further embodiment of embodiment III-246, the AC is rivaroxaban.

III-283. In a further embodiment of embodiment III-247, the AC is rivaroxaban.

III-284. In a further embodiment of embodiment III-234, the AC is tecarfarin.

III-285. In a further embodiment of embodiment III-236, the AC is tecarfarin.

III-286. In a further embodiment of embodiment III-237, the AC is tecarfarin.

III-287. In a further embodiment of embodiment III-239, the AC is tecarfarin.

III-288. In a further embodiment of embodiment III-241, the AC is tecarfarin.

III-289. In a further embodiment of embodiment III-242, the AC is tecarfarin.

III-290. In a further embodiment of embodiment III-244, the AC is tecarfarin.

III-291. In a further embodiment of embodiment III-246, the AC is tecarfarin.

III-292. In a further embodiment of embodiment III-247, the AC is tecarfarin.

III-293. In a further embodiment of embodiment III-210, the patient was refractory to one or more anti-arrhythmic drugs.

III-294. In a further embodiment of any of embodiments III-213-216, the patient was refractory to one or more anti-arrhythmic drugs.

III-295. In a further embodiment of embodiment III-218, the patient was refractory to one or more anti-arrhythmic drugs.

III-295. In a further embodiment of embodiment III-221, the patient was refractory to one or more anti-arrhythmic drugs.

III-297. In a further embodiment of embodiment III-226, the patient was refractory to one or more anti-arrhythmic drugs.

III-298. In a further embodiment of any of embodiments III-229-III-232, the patient was refractory to one or more anti-arrhythmic drugs.

III-299. In a further embodiment of embodiment III-249, the patient was refractory to one or more anti-arrhythmic drugs.

III-300. In a further embodiment of embodiment III-252, the patient was refractory to one or more anti-arrhythmic drugs.

III-301. In a further embodiment of embodiment III-255, the patient was refractory to one or more anti-arrhythmic drugs.

III-302. In a further embodiment of embodiment III-258, the patient was refractory to one or more anti-arrhythmic drugs.

III-303. In a further embodiment of embodiment III-261, the patient was refractory to one or more anti-arrhythmic drugs.

III-304. In a further embodiment of embodiment III-264, the patient was refractory to one or more anti-arrhythmic drugs.

III-305. In a further embodiment of embodiment III-267, the patient was refractory to one or more anti-arrhythmic drugs.

III-306. In a further embodiment of embodiment III-270, the patient was refractory to one or more anti-arrhythmic drugs.

III-307. In a further embodiment of embodiment III-273, the patient was refractory to one or more anti-arrhythmic drugs.

III-308. In a further embodiment of embodiment III-276, the patient was refractory to one or more anti-arrhythmic drugs.

III-309. In a further embodiment of embodiment III-279, the patient was refractory to one or more anti-arrhythmic drugs.

III-310. In a further embodiment of embodiment III-282, the patient was refractory to one or more anti-arrhythmic drugs.

III-311. In a further embodiment of embodiment III-285, the patient was refractory to one or more anti-arrhythmic drugs.

III-312. In a further embodiment of embodiment III-288, the patient was refractory to one or more anti-arrhythmic drugs.

III-313. In a further embodiment of embodiment III-291, the patient was refractory to one or more anti-arrhythmic drugs.

III-314. In one embodiment, the invention provides a method for reversing atrial remodeling comprising administering an amount of multiple ion channel blocker selected from the group consisting of amiodarone, dronedarone, budiodarone, vernakalant, celivarone, and AZD1305 effective to reduce atrial fibrillation (AF) episode duration and an effective amount of anticoagulant (AC) selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin.

III-315. In a further embodiment of embodiment III-314, the average AF episode duration is reduced to less than about 24 hours.

III-316. In a further embodiment of embodiment III-314, the average AF episode duration is reduced to less than about 5 hours.

III-317. In a further embodiment of embodiment III-314, the average AF episode duration is reduced to less than 3 hours.

III-318. In a further embodiment of embodiment III-314, the average AF episode duration is reduced to less than about 1 hour.

III-319. In a further embodiment of embodiment III-314, the maximum AF episode duration is reduced to less than about 20 hours.

III-320. In a further embodiment of embodiment III-314, the maximum AF episode duration is reduced to less than about 10 hours.

III-321. In a further embodiment of embodiment III-314, the maximum AF episode duration is reduced to less than about 5 hours.

III-322. In a further embodiment of embodiment III-314, the multiple ion channel blocker is budiodarone, dronedarone, celivarone, AZD1305 or vernakalant.

III-323. In a further embodiment of embodiment III-315, the multiple ion channel blocker is budiodarone, dronedarone, celivarone, AZD1305 or vernakalant.

III-324. In a further embodiment of embodiment III-316, the multiple ion channel blocker is budiodarone, dronedarone, celivarone, AZD1305 or vernakalant.

III-325. In a further embodiment of embodiment III-317, the multiple ion channel blocker is budiodarone, dronedarone, celivarone, AZD1305 or vernakalant.

III-326. In a further embodiment of embodiment III-318, the multiple ion channel blocker is budiodarone, dronedarone, celivarone, AZD1305 or vernakalant.

III-327. In a further embodiment of embodiment III-319, the multiple ion channel blocker is budiodarone, dronedarone, celivarone, AZD1305 or vernakalant.

III-328. In a further embodiment of embodiment III-320, the multiple ion channel blocker is budiodarone, dronedarone, celivarone, AZD1305 or vernakalant.

III-329. In a further embodiment of embodiment III-321, the multiple ion channel blocker is budiodarone, dronedarone, celivarone, AZD1305 or vernakalant.

III-330. In a further embodiment of embodiment III-314, the multiple ion channel blocker is budiodarone.

III-331. In a further embodiment of embodiment III-315, the multiple ion channel blocker is budiodarone.

III-332. In a further embodiment of embodiment III-316, the multiple ion channel blocker is budiodarone.

III-333. In a further embodiment of embodiment III-317, the multiple ion channel blocker is budiodarone.

III-334. In a further embodiment of embodiment III-318, the multiple ion channel blocker is budiodarone.

III-335. In a further embodiment of embodiment III-319, the multiple ion channel blocker is budiodarone.

III-336. In a further embodiment of embodiment III-320, the multiple ion channel blocker is budiodarone.

III-337. In a further embodiment of embodiment III-321, the multiple ion channel blocker is budiodarone.

III-338. In a further embodiment of embodiment III-314, the AC is tecarfarin, dabigatran etexilate, ximelagatran, AZD0837, apixaban or rivaroxaban.

III-339. In a further embodiment of embodiment III-315, the AC is tecarfarin, dabigatran etexilate, ximelagatran, AZD0837, apixaban or rivaroxaban.

III-340. In a further embodiment of any of embodiments III-316-317, the AC is tecarfarin, dabigatran etexilate, ximelagatran, AZD0837, apixaban or rivaroxaban.

III-341. In a further embodiment of embodiment III-318, the AC is tecarfarin, dabigatran etexilate, ximelagatran, AZD0837, apixaban or rivaroxaban.

III-342. In a further embodiment of any of embodiments III-319-321, the AC is tecarfarin, dabigatran etexilate, ximelagatran, AZD0837, apixaban or rivaroxaban.

III-343. In a further embodiment of embodiment III-322, the AC is tecarfarin, dabigatran etexilate, ximelagatran, AZD0837, apixaban or rivaroxaban.

III-344. In a further embodiment of embodiment III-323, the AC is tecarfarin, dabigatran etexilate, ximelagatran, AZD0837, apixaban or rivaroxaban.

III-345. In a further embodiment of any of embodiments III-324-325, the AC is tecarfarin, dabigatran etexilate, ximelagatran, AZD0837, apixaban or rivaroxaban.

III-346. In a further embodiment of any of embodiments III-326-328, the AC is tecarfarin, dabigatran etexilate, ximelagatran, AZD0837, apixaban or rivaroxaban.

III-347. In a further embodiment of embodiment III-329, the AC is tecarfarin, dabigatran etexilate, ximelagatran, AZD0837, apixaban or rivaroxaban.

III-348. In a further embodiment of embodiment III-330, the AC is tecarfarin, dabigatran etexilate, ximelagatran, AZD0837, apixaban or rivaroxaban.

III-349. In a further embodiment of embodiment III-331, the AC is tecarfarin, dabigatran etexilate, ximelagatran, AZD0837, apixaban or rivaroxaban.

III-350. In a further embodiment of any of embodiments III-332-III-333, the AC is tecarfarin, dabigatran etexilate, ximelagatran, AZD0837, apixaban or rivaroxaban.

III-351. In a further embodiment of any of embodiments III-334-III-336, the AC is tecarfarin, dabigatran etexilate, ximelagatran, AZD0837, apixaban or rivaroxaban.

III-352. In a further embodiment of embodiment III-337, the AC is tecarfarin, dabigatran etexilate, ximelagatran, AZD0837, apixaban or rivaroxaban.

III-353. In a further embodiment of embodiment III-339, the AC is dabigatran etexilate.

III-354. In a further embodiment of embodiment III-341, the AC is dabigatran etexilate.

III-355. In a further embodiment of embodiment III-342, the AC is dabigatran etexilate.

III-356. In a further embodiment of embodiment III-344, the AC is dabigatran etexilate.

III-357. In a further embodiment of embodiment III-346, the AC is dabigatran etexilate.

III-358. In a further embodiment of embodiment III-347, the AC is dabigatran etexilate.

III-359. In a further embodiment of embodiment III-349, the AC is dabigatran etexilate.

III-360. In a further embodiment of embodiment III-351, the AC is dabigatran etexilate.

III-361. In a further embodiment of embodiment III-352, the AC is dabigatran etexilate.

III-362. In a further embodiment of embodiment III-339, the AC is ximelagatran or AZD0837.

III-363. In a further embodiment of embodiment III-341, the AC is ximelagatran or AZD0837.

III-364. In a further embodiment of embodiment III-342, the AC is ximelagatran or AZD0837.

III-365. In a further embodiment of embodiment III-344, the AC is ximelagatran or AZD0837.

III-366. In a further embodiment of embodiment III-346, the AC is ximelagatran or AZD0837.

III-367. In a further embodiment of embodiment III-347, the AC is ximelagatran or AZD0837.

III-368. In a further embodiment of embodiment III-349, the AC is ximelagatran or AZD0837.

III-369. In a further embodiment of embodiment III-351, the AC is ximelagatran or AZD0837.

III-370. In a further embodiment of embodiment III-352, the AC is ximelagatran or AZD0837.

III-371. In a further embodiment of embodiment III-339, the AC is apixaban.

III-372. In a further embodiment of embodiment III-341, the AC is apixaban.

III-373. In a further embodiment of embodiment III-342, the AC is apixaban.

III-374. In a further embodiment of embodiment III-344, the AC is apixaban.

III-375. In a further embodiment of embodiment III-346, the AC is apixaban.

III-376. In a further embodiment of embodiment III-347, the AC is apixaban.

III-377. In a further embodiment of embodiment III-349, the AC is apixaban.

III-378. In a further embodiment of embodiment III-351, the AC is apixaban.

III-379. In a further embodiment of embodiment III-352, the AC is apixaban.

III-380. In a further embodiment of embodiment III-339, the AC is rivaroxaban.

III-381. In a further embodiment of embodiment III-341, the AC is rivaroxaban.

III-382. In a further embodiment of embodiment III-342, the AC is rivaroxaban.

III-383. In a further embodiment of embodiment III-344, the AC is rivaroxaban.

III-384. In a further embodiment of embodiment III-346, the AC is rivaroxaban.

III-385. In a further embodiment of embodiment III-347, the AC is rivaroxaban.

III-386. In a further embodiment of embodiment III-349, the AC is rivaroxaban.

III-387. In a further embodiment of embodiment III-351, the AC is rivaroxaban.

III-388. In a further embodiment of embodiment III-352, the AC is rivaroxaban.

III-389. In a further embodiment of embodiment III-339, the AC is tecarfarin.

III-390. In a further embodiment of embodiment III-341, the AC is tecarfarin.

III-391. In a further embodiment of embodiment III-342, the AC is tecarfarin.

III-392. In a further embodiment of embodiment III-344, the AC is tecarfarin.

III-393. In a further embodiment of embodiment III-346, the AC is tecarfarin.

III-394. In a further embodiment of embodiment III-347, the AC is tecarfarin.

III-395. In a further embodiment of embodiment III-349, the AC is tecarfarin.

III-396. In a further embodiment of embodiment III-351, the AC is tecarfarin.

III-397. In a further embodiment of embodiment III-352, the AC is tecarfarin.

III-398. In a further embodiment of embodiment III-315, the patient was refractory to one or more anti-arrhythmic drugs.

III-399. In a further embodiment of embodiment III-318, the patient was refractory to one or more anti-arrhythmic drugs.

III-400. In a further embodiment of embodiment III-323, the patient was refractory to one or more anti-arrhythmic drugs.

III-401. In a further embodiment of embodiment III-326, the patient was refractory to one or more anti-arrhythmic drugs.

III-402. In a further embodiment of embodiment III-331, the patient was refractory to one or more anti-arrhythmic drugs.

III-403. In a further embodiment of embodiment III-334, the patient was refractory to one or more anti-arrhythmic drugs.

III-404. In a further embodiment of embodiment III-354, the patient was refractory to one or more anti-arrhythmic drugs.

III-405. In a further embodiment of embodiment III-357, the patient was refractory to one or more anti-arrhythmic drugs.

III-406. In a further embodiment of embodiment III-360, the patient was refractory to one or more anti-arrhythmic drugs.

III-407. In a further embodiment of embodiment III-363, the patient was refractory to one or more anti-arrhythmic drugs.

III-408. In a further embodiment of embodiment III-366, the patient was refractory to one or more anti-arrhythmic drugs.

III-409. In a further embodiment of embodiment III-369, the patient was refractory to one or more anti-arrhythmic drugs.

III-410. In a further embodiment of embodiment III-372, the patient was refractory to one or more anti-arrhythmic drugs.

III-411. In a further embodiment of embodiment III-375, the patient was refractory to one or more anti-arrhythmic drugs.

III-412. In a further embodiment of embodiment III-378, the patient was refractory to one or more anti-arrhythmic drugs.

III-413. In a further embodiment of embodiment III-381, the patient was refractory to one or more anti-arrhythmic drugs.

III-414. In a further embodiment of embodiment III-384, the patient was refractory to one or more anti-arrhythmic drugs.

III-415. In a further embodiment of embodiment III-387, the patient was refractory to one or more anti-arrhythmic drugs.

III-416. In a further embodiment of embodiment III-390, the patient was refractory to one or more anti-arrhythmic drugs.

III-417. In a further embodiment of embodiment III-393, the patient was refractory to one or more anti-arrhythmic drugs.

III-418. In a further embodiment of embodiment III-396, the patient was refractory to one or more anti-arrhythmic drugs.

III-419. In a further embodiment of embodiment III-315, the reversal of atrial remodeling is defined as a measured increase in AFCL at the right atrial appendage or distal coronary sinus of at least 6 milliseconds.

III-420. In a further embodiment of embodiment III-318, the reversal of atrial remodeling is defined as a measured increase in AFCL at the right atrial appendage or distal coronary sinus of at least 6 milliseconds.

III-421. In a further embodiment of embodiment III-323, the reversal of atrial remodeling is defined as a measured increase in AFCL at the right atrial appendage or distal coronary sinus of at least 6 milliseconds.

III-422. In a further embodiment of embodiment III-326, the reversal of atrial remodeling is defined as a measured increase in AFCL at the right atrial appendage or distal coronary sinus of at least 6 milliseconds.

III-423. In a further embodiment of embodiment III-331, the reversal of atrial remodeling is defined as a measured increase in AFCL at the right atrial appendage or distal coronary sinus of at least 6 milliseconds.

III-424. In a further embodiment of embodiment III-334, the reversal of atrial remodeling is defined as a measured increase in AFCL at the right atrial appendage or distal coronary sinus of at least 6 milliseconds.

III-425. In a further embodiment of embodiment III-354, the reversal of atrial remodeling is defined as a measured increase in AFCL at the right atrial appendage or distal coronary sinus of at least 6 milliseconds.

III-426. In a further embodiment of embodiment III-357, the reversal of atrial remodeling is defined as a measured increase in AFCL at the right atrial appendage or distal coronary sinus of at least 6 milliseconds.

III-427. In a further embodiment of embodiment III-360, the reversal of atrial remodeling is defined as a measured increase in AFCL at the right atrial appendage or distal coronary sinus of at least 6 milliseconds.

III-428. In a further embodiment of embodiment III-363, the reversal of atrial remodeling is defined as a measured increase in AFCL at the right atrial appendage or distal coronary sinus of at least 6 milliseconds.

III-429. In a further embodiment of embodiment III-366, the reversal of atrial remodeling is defined as a measured increase in AFCL at the right atrial appendage or distal coronary sinus of at least 6 milliseconds.

III-430. In a further embodiment of embodiment III-369, the reversal of atrial remodeling is defined as a measured increase in AFCL at the right atrial appendage or distal coronary sinus of at least 6 milliseconds.

III-431. In a further embodiment of embodiment III-372, the reversal of atrial remodeling is defined as a measured increase in AFCL at the right atrial appendage or distal coronary sinus of at least 6 milliseconds.

III-432. In a further embodiment of embodiment III-375, the defined as a measured increase in AFCL at the right atrial appendage or distal coronary sinus of at least 6 milliseconds.

III-433. In a further embodiment of embodiment III-378, the reversal of atrial remodeling is defined as a measured increase in AFCL at the right atrial appendage or distal coronary sinus of at least 6 milliseconds.

III-434. In a further embodiment of embodiment III-381, the reversal of atrial remodeling is defined as a measured increase in AFCL at the right atrial appendage or distal coronary sinus of at least 6 milliseconds.

III-435. In a further embodiment of embodiment III-384, the reversal of atrial remodeling is defined as a measured increase in AFCL at the right atrial appendage or distal coronary sinus of at least 6 milliseconds.

III-436. In a further embodiment of embodiment III-387, the reversal of atrial remodeling is defined as a measured increase in AFCL at the right atrial appendage or distal coronary sinus of at least 6 milliseconds.

III-437. In a further embodiment of embodiment III-390, the reversal of atrial remodeling is defined as a measured increase in AFCL at the right atrial appendage or distal coronary sinus of at least 6 milliseconds.

III-438. In a further embodiment of embodiment III-393, the reversal of atrial remodeling is defined as a measured increase in AFCL at the right atrial appendage or distal coronary sinus of at least 6 milliseconds.

III-439. In a further embodiment of embodiment III-396, the reversal of atrial remodeling is defined as a measured increase in AFCL at the right atrial appendage or distal coronary sinus of at least 6 milliseconds.

EXAMPLE 1

Budiodarone (ATI-2042) and AF

The primary objective of the study was to assess the efficacy of budiodarone, (S)-sec-butyl 2-(3-(4-(2-(diethylamino)ethoxy)-3,5-diiodobenzoyl)benzofuran-2-yl)acetate, in treating AF, as measured by a reduction in AF burden (AFB) in subjects with paroxysmal atrial fibrillation who had implanted pacemakers (Arya A, et al., Europace. 2009 April; 11(4):458-64. Epub 2009 Jan. 26).

This study was a proof of concept design seeking preliminary information on the pharmacodynamic effects, safety, and tolerability of the investigational drug ATI-2042 at a variety of doses, in patients with PAF. Patients with advanced DDDRP pacemakers were selected because of the pacemaker's sophisticated diagnostics and the ability to record continuously and log asymptomatic as well as symptomatic episodes.

The molecular structure of budiodarone is identical to that of amiodarone, except for the presence of a sec-butyl acetate side chain at position 2 of the benzofuran moiety. The core of the molecule is a benzofuranyl ring system, to which an iodinated diiodophenyl group, a tertiary amine, and the chiral centre of the molecule, an (S)-2-butanyl group, are added over the course of the synthesis. The final drug substance is provided as a tartrate salt.

ATI-2042 is not a prodrug of amiodarone, nor is amiodarone a metabolite of ATI-2042. The electrophysiological activity of ATI-2042 in animals includes inhibition comparable with amiodarone of sodium, potassium, and calcium ion channels, increased left and right atrial refractoriness comparable with amiodarone, atrial effects (increased St-A and A-H intervals), and ventricular effects (increased MAPD90 and QT-interval). The major metabolite (ATI-2000) is electrophysiologically inactive.

Only post-menopausal or surgically sterile females with a significant PAF burden and pacemakers were included in this study. The pacemakers had to have been in situ for at least 1 month prior to the study and have appropriate arrhythmia diagnostics. In this study, Vitatron pacemakers, models Selection 9000 or T70 pacemakers, were used. Non-specific but potentially toxic findings were observed in canine testes during pre-clinical safety testing. Although this finding was explored further, it was prudent to commence clinical testing in a population not at risk for this effect. Hence, the study described in Example 1 was limited to post-menopausal or surgically sterile females; the use of the drug in males has been addressed in the study described in Example 2.

The patients underwent screening assessments to assess suitability for the study and to obtain a baseline medical history and examination. The value of this cohort was that the pacemaker was not inserted for bradycardia but for the treatment of AF using various prevention pacing and rate control techniques. The inclusion criteria were as follows: age 18-85 years; AF burden (AFB) of 1-50%; able to have pacemaker anti-arrhythmic algorithms turned off or remain at a stable setting; stable warfarin regimen; be generally healthy and free from significant comorbid illnesses; and able to understand study requirements.

The exclusion criteria were significant structural heart disease (ejection fraction <45% and congestive heart failure); abnormal QTc interval (i.e. >470 ms); an abnormal 12-lead electrocardiogram (ECG); known hypersensitivity to amiodarone or iodine; chronic treatment with amiodarone within 3 months; demonstrated lack of efficacy with amiodarone treatment; treatment with any other investigational drug within 30 days; treatment with any anti-arrhythmic medication (exclusive of a stable dose of digoxin or a beta-blocker or calcium blocker) within five half-lives prior to study entry; major surgery within 3 months prior to study entry or any surgery within 2 weeks prior to study entry; or any laboratory assay result that was out of the normal reference range at screening from a standard battery of blood chemistry, haematology, and urinalysis tests.

Patients were enrolled within 8 weeks of screening. During the study, they were reviewed on days 1, 2, and 8 of each study period. ATI-2042 was increased on day 1 of each 2-week study period, following routine bloods for haematology, biochemistry, and coagulation screens. Plasma samples for pharmacokinetic analysis of ATI-2042 and its metabolites were taken at steady state at the end of each study period just prior to the first escalated dose of the subsequent period and within 15 min prior to the pre-dose ECG for that dose.

Patients were then monitored for at least 3 h continuously post-dose; this included telemetry, vital signs, and oxygen saturations. Electrocardiograms were taken, and the pacemaker data were downloaded prior to drug administration on day 8 and day 14 of each study period.

Criteria for drug discontinuation included a fall in systolic blood pressure (BP) to <90 mmHg systolic, an increase in BP>200 mmHg, intolerable side-effects, a change in rhythm that in the opinion of the investigator constituted a risk to safety, or a QRS increase >50%. Where possible, ECGs of intrinsic rhythm rather than ventricular-paced rhythm were obtained, as paced complexes can be difficult to interpret for QT prolongation. An increase in QT interval >470 ms for intrinsic and >550 ms for paced beats or an increase of 30% was considered significant.

The study consisted of six 2-week periods: a baseline period (p1), four treatment periods (p2-p5), and a washout period where return to baseline was observed (p6).

The initial ATI-2042 dosage for all subjects was 200 mg orally bid, and it was then increased by 200 mg bid for each subsequent study period. Patients received 200 mg bid of ATI-2042 during period 2, 400 mg bid during period 3, 600 mg bid during period 4 and 800 mg bid during period 5, and no drug was administered during baseline and washout periods.

"Selection 9000" and "T70" pacemakers (Vitatron, Arnhem, The Netherlands) are dual-chamber pacemakers with sophisticated and similar algorithms for AF detection and prevention. Atrial fibrillation detection is based on atrial rate; atrial tachyarrhythmias are detected when the median atrial cycle length is less than that programmed for AT or AF detection. In all patients, atrial fibrillation was detected if the atrial rate was >200 bpm for six consecutive beats, and its end logged if the atrial rate dropped below 200 bpm for 10 beats. An arrhythmia diary of up to 400 episodes and 15 detailed onset reports (DORs) were recorded with rate profile, interval plots, and electrograms to confirm diagnosis. Pacemaker anti-arrhythmic algorithms were turned off prior to entry into the baseline period and remained turned off until after washout.

Pacemaker data, for the primary outcome measure AFB, were downloaded on days 8 and 14 of each 2-week period to allow up to 800 episodes of AF to be recorded.

The primary outcome measure, AFB, was defined as the duration of time the subject's cardiac rhythm was AF divided by the total time recorded for that study period, expressed as percent. The total duration of time that the rhythm was AF is a function of the number of PAF episodes and the duration of each episode. Therefore, a reduction in AFB can occur through reduction in either or both of these variables. Atrial fibrillation burden was compared with baseline during the treatment periods. Secondary outcome measures were the number of AF episodes, the safety of ATI-2042, and the incidence and severity of adverse events (AEs).

The minimum study interval was 2 weeks; data were acquired from the pacemaker and averaged to give a final value. Atrial fibrillation burden is given as the percentage of total storage duration.

The sample size for this study was selected empirically. All patients who received any amount of study medication were included in the efficacy and safety analysis. Efficacy variables for the study group are described as mean and standard deviation for each study period. Due to the small number of subjects, comparisons of periods 2-6 with baseline were made using estimates from a mixed-effects regression model. This model had a fixed, categorical effect of period and a random patient effect to account for correlations over time. A P-value of <0.05 was considered significant.

Electrocardiogram parameters (ventricular HR, PR, QRS, QT, QTc interval) were summarized by baseline, dosing period, and washout using descriptive statistics. Changes from baseline in ECG values at day 8 of dosing and day 14 of washout were also summarized. Baseline values of ECG parameters are defined as the mean of three values recorded prior to the first dose of ATI-2042.

An AE was defined as any untoward medical occurrence in a study subject administered a medicinal product (either study drug or marketed product), whether or not the event had a causal relationship with this product.

Trough concentrations of ATI-2042 and its metabolites (ATI-2000, ATI-2100, and ATI-2142), measured at pre-dose on day 1 of each of the four treatment periods and on days 1 and 8 of the washout period, were summarized by time point. Spearman's rank correlation was used to examine the relationship between trough concentrations of ATI-2042 and AFB.

Levels of pacemaker malsensing of AF or over- and under-sensing were evaluated by the manual examination of each DOR; this was performed for all patients and or every pacemaker download throughout the study and confirmed by an independent observer.

Six females, mean age (SD) 70.8+7.1 years with PAF of mean duration 4.7+2.3 years, were recruited. One patient withdrew in period 3 due to gastric AEs (nausea, flatulence, and loose stools) and for logistical reasons.

Patients were treated with a mean of 1.8+1.0 AADs, range 1-3, for PAF prior to study entry. Three patients had Vitatron T70 pacemakers and three had Selection 9000s. All patients had echocardiographic assessments prior to the study; mean (SD) left atrial diameter 3.66+0.54 cm and mean fractional shortening 41.4+10.7%.

All patients were compliant with study medication. Mean trough levels of ATI-2042 were 0.0+0.0 ng/mL at baseline, 2.4+0.9 ng/mL at 200 mg bid, 5.2+1.7 ng/mL at 400 mg bid, 13.1+5.6 ng/mL at 600 mg bid, and 19.8+17.9 ng/mL at 800 mg bid, indicating some dose proportionality. In washout, trough levels of ATI-2042 were 0.3+0.4 ng/mL, and its metabolites were low or undetectable.

A summary of ATI-2042 efficacy measures is shown in FIG. 7. Mean AFB at baseline ranged from 4.6 to 45.3%, mean (SD) 20.3+14.6%. Absolute values of AFB decreased between baseline and all doses; mean AFB (SD) at 200 mg bid was 5.2+4.2%, at 400 mg bid 5.2+5.2%, at 600 mg bid 2.8+3.4%, and at 800 mg bid 1.5+0.5%. There was a 71.2+31.3% relative reduction (RR) in p2 from baseline (P=0.0045), 71.7+20.6% in p3 (P=0.0047), 79.9+26.4% in p4 (P=0.0023), and 86.8+9.8% in p5 (P=0.0013). Atrial fibrillation burden increased towards baseline in washout; mean (SD) 11.7+14.0%, range 0.8-38.4 (P=0.1880 compared with baseline).

The number of AF episodes increased initially with ATI-2042 and remained elevated in washout (FIG. 7). Mean episode duration (SD) decreased from baseline at 4.8+5.2 to 1.7+2.5 h in p2, to 0.6+0.7 h in p3, to 0.1+0.2 h in p4, to 0.5+0.7 h in p5. Mean episode duration increased in washout to 2.4+3.0 h, but did not reach baseline values.

There were no significant changes in HR, QRS, QT, or QTc between baseline and dosing or washout. There were no clinically significant changes in overall ECG interpretation. The PR interval showed a trend towards decreasing: reductions from baseline were 16.6+23.9% at 200 mg bid, 11.4+22.6% at 400 mg bid, 27.0+32.1% at 600 mg bid, 35.1+30.9% at 800 mg bid, and 30.7+24.3% at washout. There were no group or individual trends to QT or QTc prolongation with dosing. One patient exhibited a 30-60 ms change in QTc from baseline at 400 mg bid; this patient had had a previous atrioventricular (AV) node ablation and had permanently paced rhythm. A change in the paced QTc amounted to 15% from baseline. No patient exhibited >30% change from baseline QT or QTc with dosing, despite the presence or absence of pacing.

The drug was generally well tolerated. There were no serious AEs related to study drug. The number of subjects with AEs was similar in all groups, and most were of mild severity. The highest number of AEs was in period 5 (800 mg bid) and the fewest in period 4 (600 mg bid); gastric AEs, including transient nausea, flatulence, and loose stools, were more prevalent at 800 mg bid, clinically insignificant biochemical abnormalities at 400 mg bid, and cardiac AEs (transient palpitations) while taking 200 mg bid of ATI-2042.

There were no cases of proarrhythmia, clinical hypothyroidism, or hyperthyroidism. Three patients demonstrated dose-responsive increases in thyroid-stimulating hormone, which were outside the normal range. The level in one patient increased from 2.53 to 4.82 mU/L (normal range 0.27-4.2), another increased from 3.51 to 9.49 mU/L, and a third increased from 0.68 to 16.12 mU/L. None was associated with clinical abnormalities, and all returned towards normal after drug discontinuation in washout. There were minor fluctuations in free T4 and free T3, which were felt not to be clinically significant.

A total of 524 DORs were manually overread for accuracy, mean 87+69 per patient. A total of 10.9% of the DORs exhibited under- or over-sensing, and 6.3% of the DORs were undersensed almost exclusively due to blanking of P waves during AV delay as opposed to P wave fallout. Over-sensing was entirely due to farfield R sensing (4.6%) and was present in one patient; this patient had an excessive inter-electrode distance of 17 mm on the atrial pacing lead. The mean number of malsensed DORs/patient was 10+12.

During anti-arrhythmic drug (AAD) development, establishing human drug efficacy in phase Ito III studies is often hindered by problems of proarrhythmia and tolerability. In addition, arrhythmic conditions are challenging to treat and evaluate because of heterogeneous temporal patterns of arrhythmia behavior.

This study was novel in using the sophisticated data logs of pacemakers to monitor drug efficacy continuously throughout the study and to record all episodes of AF including those that were asymptomatic. Patients with refractory PAF, i.e., those who had failed at least one AAD therapy were included in this study. ATI-2042 was significantly effective in reducing AFB at all doses in this group of patients. The endpoint of AFB can be affected by a reduction in the number of episodes of AF, indicating an effect on AF initiation, or by a reduction in the duration of episodes, indicating an effect on the sustainability of the episodes. In this study, therapy with ATI-2042 was associated with a mild trend for the number of episodes to increase with doses up to 600 mg bid, but this was offset by a substantial shortening of mean AF episode duration at all doses that reached statistical significance. The overall effect was a clinically and statistically significant reduction in AFB.

It was also apparent that the effects of ATI-2042, despite its short half-life, have a prolonged cardiac effect after discontinuation of the drug. Even in washout, AF parameters did not completely return to baseline. Trough levels of ATI-2042 and its metabolite were low or negligible within days of drug discontinuation, making drug persistence unlikely. Results indicate that even relatively short courses of this drug may promote atrial reverse-remodeling, which have a carry-over effect longer than its metabolism.

Overall, the drug was well tolerated. The absence of the electrocardiographic changes that were seen in animal testing may be due to the small sample size and/or the inclusion of patients with prior AV nodal ablation procedures with paced rhythms. One patient withdrew due to moderate gastric side effects and logistical reasons. There were no serious AEs related to study drug and no cases of proarrhythmia. Minor changes in thyroid function studies were likely reflective of the iodine content of ATI-2042. These resolved during continued study drug administration or after discontinuing the study medication. This pattern of thyroid function study changes is consistent with those reported for amiodarone. These findings require additional evaluation in future studies.

Paroxysmal atrial fibrillation is a common, distressing arrhythmia, which is often difficult to treat due to its heterogeneity and the tendency for AADs with class III action to exhibit reverse-use dependency. Drugs with multiple classes of action rather than specific class action, such as amiodarone, are the most efficacious in treating AF, but many drugs are limited to low-risk patients because of concerns regarding proarrhythmia. Amiodarone has been shown to be superior to other AADs in the maintenance of sinus rhythm post-cardioversion, but it is less effective in preventing recurrence in PAF than chronic AF. It has a pharmacokinetic and metabolic profile that contributes to its slow onset and offset of action and its toxicity. Prescribing class I agents, such as flecanide and quinidine, tends to be limited to patients without ischemic heart disease, who have preserved left ventricular function. This is due to the observation of increased mortality of post-myocardial infarction patients in the Cardiac Arrhythmia Suppression Trial (CAST; Echt D S, et al. "Mortality and morbidity in patients receiving encainide, flecainide or placebo: the Cardiac Arrhythmia Suppression Trial."

N Engl J Med 1991; 324:781-8) and concerns regarding Torsades de Pointes extending to 'pure' class III agents such as dofetilide and ibutilide. New atrio-selective drugs that prolong atrial refractoriness without significant effects on ventricular refractoriness or the QT interval appear promising, but are early in development. In the present study, ATI-2042 was well tolerated and effective in reducing AFB, with decreases of at least 70% in AFB at all doses. Its short half-life, rapid onset and offset, small volume of distribution, and cytochrome P450-independent elimination represent attractive drug features of an AAD.

This study used the sophisticated monitoring capacity of pacemakers to record all episodes of AF and differed from the conventional means of assessing drug efficacy by the 'time to first recurrence' of AF. 'Time to first recurrence' is the time taken for an atrial tachyarrhythmia to recur post-chemical or electrical cardioversion. This measure makes the assumption that AF episodes are uniformly random, i.e. the risk of having an episode at any given time is uniform. However, recent data from pacemaker and defibrillator studies suggest a tendency to clustering of fibrillation episodes with the highest instantaneous risk of AF being immediately after termination. Human arrhythmia patterns vary between patients and the majority of episodes are asymptomatic, making assessment of drug efficacy in PAF patients challenging even with frequent study follow-up or trans-telephonic monitoring. Despite the complexities and heterogeneous nature of PAF, we propose that pacemaker data logs provide a comprehensive documentation of arrhythmia events. The degree of accuracy of the pacemaker diagnostics as determined by manual overreading supports the use of this method to measure AFB. Pacemaker logs may also monitor for proarrhythmia and can be used with hand-held activators to correlate symptoms with events.

This study suggests that ATI-2042 is safe, well tolerated and may reduce AFB in patients with PAF. It has a promising electrophysiological and pharmacokinetic profile that makes it an attractive alternative to amiodarone. This study provides support for further clinical trials that evaluate the use of this investigational drug in an expanded cohort of patients with PAF and supports the concept of using implanted pacemaker devices to monitor AAD efficacy. Such a randomized, double-blind, placebo-controlled clinical trial of ATI-2042 is described in Example 2.

EXAMPLE 2

Budiodarone (ATI-2042) and AF, Round 2

The objective of the study is to determine the efficacy of budiodarone in reducing atrial tachyarrhythmia (AT/AF) burden in patients with paroxysmal atrial fibrillation (PAF) compared to placebo, for 12 weeks of treatment, and the safety and tolerability of budiodarone for up to 12 weeks of treatment.

Secondary: to study the effect of budiodarone versus placebo on the number and duration of AT/AF episodes, duration of normal sinus rhythm (NSR) between episodes of AT/AF and on symptoms associated with PAF.

Example 2 describes a multicenter, multinational, randomized, double-blind, placebo-controlled, parallel-group study of the efficacy and safety of budiodarone in patients with PAF. Planned enrollment was up to 140 patients (with eventually 110 enrolled) with proven PAF who had permanently implanted pacemakers with appropriate AT/AF diagnostic and recording capabilities. Potential study participants underwent screening assessments, including the optimization of pacemaker programming for accurate AT/AF detection. Within 30 days after screening assessments began, eligible patients entered a 4-week baseline period (Period 1) when baseline atrial fibrillation burden (AFB) was established followed by randomization to one of three active treatment regimens or placebo for a 12-week treatment period (Period 2), followed by a 4-week washout period (Period 3). During the treatment period, patients received twice-daily (BID) oral doses of 200 mg ATI-2042, 400 mg ATI-2042, 600 mg ATI-2042, or placebo. No study drug was given during the baseline and washout periods.

110 patients were enrolled. Of 72 randomized and analyzed: 72 were treated and included in the intent-to-treat (ITT) and safety population; 60 were in the modified ITT (mITT) population; and 45 in the efficacy evaluable (EE) population Inclusion Criteria were the following: age 18 and above; proven PAF (electrocardiogram, Holter monitor, or pacemaker diagnosis obtained by the clinical site or patient's prior medical record documenting clear evidence of a diagnosis of PAF); pacemaker with appropriate AF diagnostic and recording capabilities implanted for at least 6 weeks (additional pacemaker requirements included: dual chamber with bipolar leads, able to diagnose and log AT/AF events, able to have AT/AF treatment algorithms turned off, capable of storing at least 4 weeks AT/AF data between downloads, and able to record and store electrograms); atrial P waves of adequate amplitude to allow accurate sensing and assessment of AT/AF episodes and no obvious indications of frequent oversensing or undersensing; Able to have pacemaker AT/AF treatment algorithms turned off for the duration of the study; able to understand study requirements and willing to follow instructions, attend all required study visits, and undergo all planned tests; women: unable to bear children, that is, post-menopausal (absence of vaginal bleeding or spotting) for at least one year or surgically sterile; men: starting at the time of study drug administration until completion of the 12-week treatment period, must have been willing to use an approved method of contraception (which included use of a condom with spermicide or use by partner of oral, implantable, or injectable contraceptives, intrauterine device (IUD), diaphragm with spermicide) or had a sterile sex partner.

To be randomized, study participant must have had: an AT/AF burden between 5% and 70% during the baseline period; no evidence of persistent AF (i.e., 7 or more consecutive days of AT/AF with episodes lasting >23 hours); able to have pacemaker atrial antitachyarrhythmia treatment algorithms turned off for the remaining duration of the study.

Efficacy outcome measures were AT/AF burden (total time spent in AT/AF as a percentage of total observation time), number and mean duration of AT/AF episodes, mean duration of NSR, patient global clinical impression (GCI) questionnaire, and University of Toronto Atrial Fibrillation Severity Scale (AFSS).

Safety: treatment-emergent adverse event (TEAE) type, severity, and incidence; clinical laboratory assessments, including thyroid function and testicular function (males); coagulation tests; vital signs; physical examinations; ECGs; eye examinations; chest X-rays; and pulmonary function tests.

Three analysis populations were used, which were: intent to treat (ITT; all randomized patients who had at least one assessment of AT/AF burden during the treatment period); modified intent to treat (mitt; all randomized patients who had a baseline AT/AF burden >3%, completed at least the first 4 weeks of treatment, and had been assessed as usable by the core lab and/or had over/undersensing detected by core lab adjudication but no gross violations of pacemaker programming guidelines); and efficacy evaluable (EE; all randomized patients who had a baseline AT/AF burden of 3% to 70%, completed at least the first 4 weeks of treatment, and had been assessed as usable by the core lab).

Statistical methods for efficacy: The primary efficacy analysis was the percent change in the AT/AF burden from baseline to the 12-week treatment period. Pairwise comparisons between each ATI-2042 dose group and the placebo group were performed using the Wilcoxon rank sum test. The primary analysis was based on the mITT population.

For all variables based on the pacemaker data, the Wilcoxon rank sum test was used to compare each ATI-2042 dose group to the placebo group. The Jonckheere-Terpstra test was used to test for a dose response. The Wilcoxon signed rank test was used to test for a significant change from baseline within each treatment group. An analysis of covariance (ANCOVA) was used to compare the percent change from baseline in AT/AF burden among the treatment groups after adjusting for the baseline AT/AF burden. The ANCOVA model contained effects for treatment group and baseline AT/AF burden.

For patient GCI, the Cochran-Mantel-Haenszel test was used to compare each ATI-2042 dose group to the placebo group. The Jonckheere-Terpstra test was used to test for a dose response.

Statistical methods for safety: Adverse events (AEs) were summarized by system organ class and preferred term. Laboratory parameters and vital signs were summarized by descriptive statistics and shift tables were also created for laboratory parameters. The percent of patients with physical examination findings that changed over the study, with ECG abnormalities by visit, and with corneal deposits were summarized. Chest X-rays and pulmonary function test results were provided in listings.

The ITT/safety population included 72 treated patients. Among the treated patients, 18 were randomized to placebo, 21 to 200 mg BID, 18 to 400 mg BID, and 15 to 600 mg BID. The mITT population was comprised of 60 patients and 45 patients comprised the EE population. Overall, 84.7% of the treated patients completed the study. The average age was 69.2 years (range, 51 to 88) and 98.6% of patients were white. Males comprised 56.9% and females 43.1% of the treated patients. Overall medical and cardiovascular history did not show notable differences among treatment groups. The mean AT/AF burden at screening was comparable across treatment groups and ranges from 17.8% to 23.4%.

ATI-2042 at 400 mg BID and 600 mg BID achieved a significant reduction in AT/AF burden compared to placebo over Treatment Months 1-3. The median percent reductions from baseline were 54% (p=0.015) and 75% (p=0.006) for the 400 mg BID and 600 mg BID groups, respectively, in the mITT population, and 54% (p=0.013) and 74% (p=0.001) in the ITT population (FIG. 1). A significant dose response (p<0.0001) was seen for the primary endpoint of the study for both the mITT and ITT populations. The reduction in AT/AF burden was statistically significant in each of the 3 months of treatment in both the 400 mg BID and 600 mg BID groups. As the dose and treatment duration increased the effect became more pronounced. The maximal effect was seen at Treatment Month 3 (16 weeks) for the 600 mg BID group, with a median percent reduction of 83% (p=0.010) in the mITT population and 80% (p=0.002) in the ITT population.

All secondary endpoints showed statistically significant improvement over Treatment Months 1-3 with 600 mg BID as shown by median percent changes from baseline in the number of AT/AF episodes (−62.1% in the mITT and −52.9% in the ITT population), duration of AT/AF episodes (−51.3% in the mITT population and −51.3% in the ITT population) and an increase in the duration of NSR (241.8% in the mITT population and 208.8% in the ITT population). See FIG. 3 through FIG. 6.

These are profound results that demonstrate how budiodarone can prevent or reverse atrial remodeling and reduce stroke risk. As mentioned above, AF is progressive, with PAF evolving to persistent and eventually permanent AF—a progression that occurs and accelerates with greater time spent in AF. That is, what is initially electrical and thrombotic remodeling on the hours and days timescale, eventually leads to structural remodeling on the months and years timescale, and with greater structural remodeling and greater electrical remodeling comes greater resistance to cardioversion. FIG. 3 shows that number and duration of AF episodes were reduced about 70% below baseline for patients on drug 600 mg drug. FIG. 4 shows that on 600 mg drug, patients' mean episode duration was reduced to less than 1 hour (down from nearly 24), and at month 3, the median AF episode duration was 0. More than half the patients had their AF eradicated during the study period. FIG. 6 shows that for the 600 mg dose group, no patients experienced an AF episode lasting 24 or more hours. The 400 mg dose cohort experienced only a single 24 hour episode. Less time in AF, particularly zero or only sporadic episodes of less than an hour, is much less likely to cause electrical, thrombotic and structural remodeling. Moreover, the concomitant increase in time in NSR enables the reversal of atrial remodeling. Thus, progression of AF should be retarded, halted or reversed, and stroke risk reduced. The concomitant administration of a potent anticoagulant on top of budiodarone will further reduce stroke risk, and likely below the age-adjusted overall stroke risk, i.e., lower than the general population not specifically diagnosed with AF. Since budiodarone is primarily metabolized by esterases, synergistic lowering of stroke rate with an effective anticoagulant should not be due to pharmacokinetic interactions raising the effective dose of anticoagulant (with coincident increase in bleeding risk and further drug-drug interactions in this patient group highly susceptible to polypharmacy), but rather pharmacodynamic synergy.

Patient GCI Scale showed significant dose responses, with 60.0% of the patients in the ITT population reporting that they were a lot or completely satisfied with the test medication and 46.7% of patients in the ITT population reporting a lot of improvement or complete relief in the mITT population. There were few significant findings for the AFSS survey. There was a positive trend in the more common AF symptoms of palpitations and shortness of breath during physical activity when analysis was restricted to symptomatic patients only.

All doses of ATI-2042 in this study were well tolerated with an acceptable overall TEAE profile. The most frequent TEAEs were changes in INR values. Increases in INR are expected given that ATI-2042 is an inhibitor of cytochrome P450 2C9 (CYP2C9), which is a primary metabolism pathway for warfarin, and decreased INR values were most likely caused by dose adjustments made to lower increased INRs. Thyroid function changes related to known effects of the drug were mild and reversible, and in only one case led to discontinuation of the study medication. There were no dose-related changes in hematological tests, testicular function tests and the great majority of chemistry tests. There was a reversible elevation in creatinine that is undoubtedly due to inhibition of tubular secretion and did not result in any reduction in glomerular filtration as evidenced by unchanged BUN levels. There was a mild, reversible increase in ALT that appeared to be dose related and was not associated with signs of cholestasis or other signs of liver injury. There were no notable changes in vital signs, physical examinations, ECGs, eye examinations, chest X-rays, and pulmonary function tests, and no safety concerns were identified with ATI-2042 treatment. No evidence of amiodarone-like end-organ toxicity was seen (pulmonary fibrosis, corneal deposits, neuropathy, photosensitivity). There was no evidence of budiodarone tissue accumulation based on lack of corneal microdeposits on slit lamp examination at the end of the treatment period.

The study achieved its primary objectives and demonstrated the efficacy of ATI-2042 at 400 mg BID and 600 mg BID in reducing AT/AF burden in patients with PAF, compared to placebo, for 12 weeks of treatment.

The primary statistical efficacy analysis in the mITT population showed significance for ATI-2042 at the 400 mg BID (p=0.015) and 600 mg BID (p=0.005) doses. The AT/AF burden in these two treatment groups was reduced from baseline by a median of 54% and 75%, respectively. Although the 200 mg BID dose decreased AFB by 10%, that did not reach statistical significance.

The analysis of primary endpoint adjusted for baseline burden confirmed that the drug was efficacious independently of the baseline AF burden.

The overall dose response effect was both robust and linear with p=0.0001. Randomization was balanced across all four treatment groups.

The benefit of ATI-2042 on the larger ITT population in reducing AFB was also highly significant. The percentage reduction in AFB for the 400 mg BID group was 54% (p=0.013) and for the 600 mg BID group it was 74% (p=0.001). A similarly marked dose response effect was seen (p<0.0001).

The efficacy of 600 mg BID in the ITT population was also demonstrated for the number and duration of AT/AF episodes, and the mean duration of NSR. There was a significant reduction in both the number and duration of AT/AF episodes and a corresponding increase in mean duration of NSR. These results are supportive of the primary endpoint.

The efficacy analysis also included a month-by-month assessment of the patients' burden. The reduction in AFB was statistically significant in each of the 3 months of treatment in both the 400 mg BID group and the 600 mg BID group in the ITT population. As the dose and duration of treatment of ATI-2042 was increased, the effect of the drug in reducing AFB became more pronounced. The maximal effect was seen in the third month on 600 mg BID when the median percentage reduction was 83% (p=0.009).

In each of the three ATI-2042 dose groups, the AFB returned to essentially the baseline values within the one-month washout period. The washout data showed no evidence of accumulation or of a rebound effect in the AFB (FIG. 2).

The ITT population achieved statistically significant satisfaction with test medication for all doses tested and reported statistically significant control of atrial fibrillation symptoms in the 400 mg BID and 600 mg BID groups.

The safety of ATI-2042 was demonstrated in this study by the mild TEAE profile. Only one SAE was possibly related to ATI-2042 (hematuria and high INR) and the discontinuation rate was low and balanced across the treatment groups.

The results on thyroid function were not unexpected since ATI-2042 shares the same iodinated chemical structure as amiodarone. Amiodarone inhibits the metabolic conversion of T4 to T3 and it is presumed that ATI-2042 acts in a similar fashion. Lowering levels of T3 and TSH elevations that were observed in the study were consistent with this mechanism and with findings from the previous studies. With the exception of one patient on 200 mg BID who discontinued due to hyperthyroidism (limited to changes in laboratory values only) the effects on thyroid function were considered mild and did not affect study participation.

INR was monitored closely in this study to allow adjustment of the warfarin dose as needed for patients on concomitant therapy. Time within normal range improved in all active drug groups as the initial dose adjustments were made during the first month of treatment. The early increase in INR is expected after start of dosing based on the ability of ATI-2042 to inhibit CYP2C9.

Chest X-ray and pulmonary function tests were performed during the study to monitor for the symptoms of amiodarone pulmonary toxicity. No safety concern was identified.

Because amiodarone is known to accumulate in the cornea and form microcrystalline deposits, slit-lamp examinations were performed. No patient treated with ATI-2042 developed corneal deposits during the study. Together with the washout period data, these findings provide evidence of the lack of tissue accumulation of ATI-2042 and its metabolites.

This, budiodarone significantly reduced AFB at doses of 400 mg BID and 600 mg BID, and appeared to be safe and tolerable at these doses. This was the first controlled study to use permanently implanted pacemakers to continuously record AFB. Use of AFB as a continuously recorded variable offers several advantages. It allows a patient to serve as his or her own control; it accounts for both symptomatic and asymptomatic episodes, thus providing a more accurate measure of clinical response than measurements triggered only by symptoms; and it allows establishment of a dose-response curve with fewer patients than, for example, traditional time to first symptomatic recurrence studies.

The patients recruited for this study had a mean AT/AF burden at screening that ranged from a 17.8% to 23.4%. This is a significant amount of time spent in atrial fibrillation as opposed to normal sinus rhythm. The time spent in atrial fibrillation, especially long duration episodes, has been correlated with increased risk of stroke. For a patient who is experiencing symptoms of atrial fibrillation, this amount of AF also may present a serious quality of life issue.

ATI-2042 was well tolerated, including in CHF NYHA Class I and II patients in this study, and did not exhibit any of the side effects associated with amiodarone accumulation in peripheral tissues. There were no corneal deposits, no evidence of pulmonary toxicity or photosensitivity.

The significant reduction of AFB, shortening of atrial fibrillation episodes and increase in duration of normal sinus rhythm achieved by ATI-2042 in this study thus suggests that budiodarone can offer a considerable advantage for the patient.

The ACs and anti-arrhythmic drugs described herein may be administered together in dosage unit form or as separate, independent dosages, and each, independently, can be administered orally or parenterally (and preferably orally or intravenously) in formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising an AC, an anti-arrhythmic and a pharmaceutically acceptable carrier. One or more AC and anti-arrhythmics described herein may be present in association with one or more non-toxic pharmaceutically acceptable carriers and/or diluents and/or adjuvants, and if desired other active ingredients. The pharmaceutical compositions containing compounds described herein may be in a form suitable for oral use, for example, as tablets, troches, lozenges, aqueous or oily suspensions, dispersible powders or granules, emulsion, hard or soft capsules, or syrups or elixirs.

Formulations are described in detail in a number of sources that are well known and readily available to those skilled in the art. For example, Remington's Pharmaceutical Science by E. W. Martin describes formulations that can be used in connection with the subject invention. In general, the compositions of the subject invention will be formulated such that an effective amount of the bioactive compound(s) is combined with at least one suitable carrier, solvent, excipient, and/or adjuvant in order to facilitate effective administration of the composition.

In accordance with the invention, pharmaceutical compositions comprising, as an active ingredient, an effective amount of one or more of the compounds described herein and one or more non-toxic, pharmaceutically acceptable carrier(s) and/or diluent(s). Examples of such carriers for use in the invention include ethanol, dimethylsulfoxide, glycerol, silica, alumina, starch, and equivalent carriers and diluents.

Further, acceptable carriers can be either solid or liquid. Solid form preparations include powders, tablets, pills, capsules, cachets, suppositories and dispersible granules. A solid carrier can be one or more substances that may act as diluents, flavoring agents, solubilizers, lubricants, suspending agents, binders, preservatives, tablet disintegrating agents or an encapsulating material.

The disclosed pharmaceutical compositions may be subdivided into unit doses containing appropriate quantities of the active component. The unit dosage form can be a packaged preparation, such as packeted tablets, capsules, and powders in paper or plastic containers or in vials or ampoules.

The terms "individual(s)" and "patient(s)" are defined as a mammal to which is administered a compound of the present invention. The mammal may be, for example, a pig, a horse, a rabbit, a goat, a cow, a cat, a dog, or can be a human. In a preferred embodiment, the individual is a human.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

The invention and the manner and process of making and using it, are now described in such full, clear, concise and exact terms as to enable any person skilled in the art to which it pertains, to make and use the same. It is to be understood that the foregoing describes preferred embodiments of the invention and that modifications may be made therein without departing from the spirit or scope of the invention as set forth in the claims. To particularly point out and distinctly claim the subject matter regarded as invention, the following claims conclude this specification.

The invention claimed is:

1. A method for reducing an average atrial fibrillation episode duration in a patient with refractory atrial fibrillation comprising
administering to the patient with refractory atrial fibrillation an amount of budiodarone effective to reduce the average atrial fibrillation episode duration; and
wherein said method does not comprise cardioversion of the patient with refractory atrial fibrillation.

2. The method of claim 1, further comprising administration of an effective amount of an anticoagulant (AC) selected from the group consisting of AZD0837, dabigatran etexilate, dabigatran, ximelagatran, melagatran, argatroban, apixaban, rivaroxaban, YM466, betrixaban, edoxaban, otamixaban, tecarfarin and warfarin.

3. The method of claim 1, wherein said patient with refractory atrial fibrillation has a $CHADS_2$ (Cardiac failure, Hypertension, Age, Diabetes, Stroke/transient ischemic event [doubled]) score of 1 or more.

4. The method of claim 1, wherein said refractory atrial fibrillation is paroxysmal atrial fibrillation (PAF).

5. The method of claim 1, wherein said refractory atrial fibrillation is persistent atrial fibrillation.

6. The method of claim 1, wherein the average atrial fibrillation episode duration is greater than 5 hours prior to administration of budiodarone.

7. The method of claim 1, wherein the average atrial fibrillation episode duration is reduced to less than 5 hours.

8. The method of claim 1, wherein the average atrial fibrillation episode duration is reduced to less than 3 hours.

9. The method of claim 1, wherein the average atrial fibrillation episode duration is reduced to less than 1 hour.

10. The method of claim 2, wherein the average atrial fibrillation episode duration is decreased by more than 50% after the budiodarone administration.

11. The method of claim 2, wherein the average atrial fibrillation episode duration is decreased by more than 70% after the budiodarone administration.

12. The method of claim 1, wherein the amount of budiodarone is 400 mg BID.

13. The method of claim 1, wherein the amount of budiodarone is 600 mg BID.

14. The method of claim 1, wherein the patient with refractory atrial fibrillation is refractory to one or more anti-arrhythmic drugs which is a class III anti-arrhythmic drug.

15. The method of claim 14, wherein said one or more class III anti-arrhythmic drug is dofetilide or ibutilide.

16. The method of claim 1, wherein the patient with refractory atrial fibrillation is refractory to one or more anti-arrhythmic drugs which is amiodarone or sotalol.

17. The method of claim 1, wherein the patient with refractory atrial fibrillation is refractory to one or more anti-arrhythmic drugs which is a class I anti-arrhythmic drug.

18. The method of claim 17, wherein said one or more class I anti-arrhythmic drug is flecainide or quinidine.

19. The method of claim 1, further comprising administration of an effective amount of an anticoagulant (AC).

20. The method of claim 1, further comprising administration of an effective amount of an anticoagulant (AC) selected from the group consisting of vitamin-K epoxide reductase inhibitor, direct thrombin inhibitor, and Factor Xa inhibitor.

21. The method of claim 1, wherein the one or more anti-arrhythmic drugs is amiodarone or dronedarone.

22. The method of claim 1, wherein the administration is oral.

23. The method of claim 19, wherein the budiodarone and the anticoagulant are administered together.

24. The method of claim 23, wherein the budiodarone and the anticoagulant are administered together in a dosage unit form.

25. The method of claim 24, wherein the budiodarone and the anticoagulant are administered together in a dosage unit form for oral administration.

26. The method of claim 19, wherein the amount of budiodarone is 400 mg or 600 mg.

27. The method of claim 26, wherein the amount of budiodarone is 400 mg.

28. The method of claim 26, wherein the amount of budiodarone is 600 mg.

29. The method of claim 19, wherein the anticoagulant is dabigatran.

30. The method of claim 19, wherein the anticoagulant is ximelagatran.

31. The method of claim 19, wherein the anticoagulant is apixaban.

32. The method of claim 19, wherein the anticoagulant is rivaroxaban.

33. The method of claim 19, wherein the anticoagulant is edoxaban.

34. The method of claim 19, wherein the anticoagulant is otamixaban.

35. The method of claim 19, wherein the anticoagulant is AZD0837.

36. The method of claim 19, wherein the anticoagulant is argatroban.

37. The method of claim 19, wherein the anticoagulant is YM466.

38. The method of claim 19, wherein the anticoagulant is betrixaban.

39. The method of claim 19, wherein the anticoagulant is tecarfarin.

40. The method of claim 19, wherein the anticoagulant is warfarin.

41. The method of claim 1, wherein a maximum atrial fibrillation episode duration is reduced to less than 20 hours.

42. The method of claim 1, wherein a maximum atrial fibrillation episode duration is reduced to less than 10 hours.

43. The method of claim 1, wherein a maximum atrial fibrillation episode duration is reduced to less than 5 hours.

* * * * *

UNITED STATES PATENT AND TRADEMARK OFFICE
CERTIFICATE OF CORRECTION

PATENT NO. : 9,549,912 B2  
APPLICATION NO. : 13/758687  
DATED : January 24, 2017  
INVENTOR(S) : Peter G. Milner et al.

Page 1 of 1

It is certified that error appears in the above-identified patent and that said Letters Patent is hereby corrected as shown below:

In the Claims

At Column 148, Claim number 21, Line numbers 10-11, replace "wherein the one or more anti-arrhythmic drugs is amiodarone or dronedarone" with:

-- wherein the patient with refractory atrial fibrillation is refractory to one or more anti-arrhythmic drugs which is amiodarone or dronedarone --.

Signed and Sealed this
Fifteenth Day of August, 2017

Joseph Matal
*Performing the Functions and Duties of the*
*Under Secretary of Commerce for Intellectual Property and*
*Director of the United States Patent and Trademark Office*